United States Patent
Cantrell et al.

(10) Patent No.: US 9,518,062 B2
(45) Date of Patent: *Dec. 13, 2016

(54) COMPOUNDS AND COMPOSITIONS FOR USE IN PHOTOTHERAPY AND IN TREATMENT OF OCULAR NEOVASCULAR DISEASE AND CANCERS

(71) Applicant: Mallinckrodt LLC, Hazelwood, MO (US)

(72) Inventors: Gary L. Cantrell, Hazelwood, MO (US); Raghavan Rajagopalan, Hazelwood, MO (US); Amolkumar Karwa, Hazelwood, MO (US); Richard B. Dorshow, Hazelwood, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/316,415

(22) Filed: Jun. 26, 2014

(65) Prior Publication Data

US 2014/0370005 A1 Dec. 18, 2014

Related U.S. Application Data

(63) Continuation of application No. 13/383,243, filed as application No. PCT/US2010/042218 on Jul. 16, 2010, now Pat. No. 8,829,020.

(60) Provisional application No. 61/226,032, filed on Jul. 16, 2009, provisional application No. 61/238,358, filed on Aug. 31, 2009, provisional application No. 61/226,015, filed on Jul. 16, 2009, provisional application No. 61/286,877, filed on Dec. 16, 2009.

(51) Int. Cl.

| | |
|---|---|
| *A61K 31/485* | (2006.01) |
| *C07D 489/02* | (2006.01) |
| *A61K 9/00* | (2006.01) |
| *A61K 9/02* | (2006.01) |
| *A61K 9/10* | (2006.01) |
| *A61K 9/14* | (2006.01) |
| *A61K 9/20* | (2006.01) |
| *A61K 9/48* | (2006.01) |
| *A61K 31/472* | (2006.01) |
| *A61K 41/00* | (2006.01) |
| *A61K 45/06* | (2006.01) |
| *A61K 47/26* | (2006.01) |
| *A61K 47/36* | (2006.01) |
| *A61K 47/38* | (2006.01) |
| *C07D 221/28* | (2006.01) |

(52) U.S. Cl.
CPC .......... *C07D 489/02* (2013.01); *A61K 9/0075* (2013.01); *A61K 9/02* (2013.01); *A61K 9/10* (2013.01); *A61K 9/145* (2013.01); *A61K 9/2009* (2013.01); *A61K 9/2022* (2013.01); *A61K 9/2027* (2013.01); *A61K 9/2054* (2013.01); *A61K 9/2059* (2013.01); *A61K 9/4858* (2013.01); *A61K 9/4866* (2013.01); *A61K 31/472* (2013.01); *A61K 31/485* (2013.01); *A61K 41/0057* (2013.01); *A61K 45/06* (2013.01); *A61K 47/26* (2013.01); *A61K 47/36* (2013.01); *A61K 47/38* (2013.01); *C07D 221/28* (2013.01)

(58) Field of Classification Search
None
See application file for complete search history.

(56) References Cited

U.S. PATENT DOCUMENTS

| | | |
|---|---|---|
| 4,521,601 A | 6/1985 | Rice |
| 4,649,151 A | 3/1987 | Dougherty et al. |
| 4,722,928 A | 2/1988 | Boswell et al. |
| 4,847,265 A | 7/1989 | Badorc et al. |
| 4,866,168 A | 9/1989 | Dougherty et al. |
| 4,883,790 A | 11/1989 | Levy et al. |
| 4,920,143 A | 4/1990 | Levy et al. |
| 4,968,715 A | 11/1990 | Dougherty et al. |
| 4,990,617 A | 2/1991 | Boswell et al. |
| 5,002,962 A | 3/1991 | Pandey et al. |
| 5,028,621 A | 7/1991 | Dougherty et al. |
| 5,079,262 A | 1/1992 | Kennedy et al. |
| 5,093,349 A | 3/1992 | Pandey et al. |
| 5,095,030 A | 3/1992 | Levy et al. |
| 5,166,197 A | 11/1992 | Kenney et al. |
| 5,171,741 A | 12/1992 | Dougherty |

(Continued)

FOREIGN PATENT DOCUMENTS

| | | |
|---|---|---|
| CH | 683 005 A5 | 12/1993 |
| CN | 1981763 * | 6/2007 .......... A61K 31/485 |

(Continued)

OTHER PUBLICATIONS

Machine translation of CN 1981763, obtained from <http://worldwide.espacenet.com/>, Accessed Mar. 10, 2014.*
Notice of Allowance regarding U.S. Appl. No. 13/383,243 issued May 7, 2014, 10 pages.
Augustin et al. (2007) "Triple Therapy for Choroidal Neovascularization Due to Age-Related Macular Degeneration. Vertportfrin PDT, Bevacizumab, and Dexamethsone," *Retina* 27(2):133-140.

(Continued)

*Primary Examiner* — Alicia L Otton

(57) ABSTRACT

The invention relates generally to anti-angiogenesis agents and related methods of using to anti-angiogenesis agents for biomedical applications including direct monotherapy and combination therapy for treatment of an angiogenesis related condition. In an embodiment, the invention provides a class of opioid compounds and structurally related opioid derivatives exhibiting anti-VEGF activity for use in therapeutic procedures, including phototherapy. Opioid compounds and structurally related opioid derivatives of the invention may be administered alone or in combination with administration of a phototherapy agent and/or other therapeutic agent.

49 Claims, 7 Drawing Sheets

(56) References Cited

U.S. PATENT DOCUMENTS

| | | |
|---|---|---|
| 5,173,504 A | 12/1992 | Dougherty et al. |
| 5,190,966 A | 3/1993 | Dougherty et al. |
| 5,198,460 A | 3/1993 | Pandey et al. |
| RE34,712 E | 8/1994 | Boegesoe et al. |
| 5,352,680 A | 10/1994 | Portoghese et al. |
| 5,405,957 A | 4/1995 | Tang et al. |
| 5,438,071 A | 8/1995 | Clauss et al. |
| 5,668,285 A | 9/1997 | Rice et al. |
| 5,739,145 A | 4/1998 | Nagase et al. |
| 5,919,826 A | 7/1999 | Caruso |
| 6,174,891 B1 | 1/2001 | Nagase et al. |
| 6,258,378 B1 | 7/2001 | Schneider et al. |
| 6,277,859 B1 | 8/2001 | Nagase et al. |
| 6,299,901 B1 | 10/2001 | DiSanto et al. |
| 6,406,713 B1 | 6/2002 | Janoff et al. |
| 6,485,704 B1 | 11/2002 | Rajagopalan et al. |
| 6,693,093 B2 | 2/2004 | Chowdhary et al. |
| 6,747,151 B2 | 6/2004 | Rajagopalan et al. |
| 7,011,817 B2 | 3/2006 | Achilefu et al. |
| 7,128,896 B2 | 10/2006 | Achilefu et al. |
| 7,198,778 B2 | 4/2007 | Achilefu et al. |
| 7,201,892 B2 | 4/2007 | Achilefu et al. |
| 7,230,088 B2 | 6/2007 | Rajagopalan et al. |
| 7,235,685 B2 | 6/2007 | Rajagopalan et al. |
| 7,303,926 B2 | 12/2007 | Rajagopalan et al. |
| 7,351,807 B2 | 4/2008 | Rajagopalan et al. |
| 7,427,657 B1 | 9/2008 | Rajagopalan et al. |
| 7,713,514 B2 | 5/2010 | Cantrell et al. |
| 7,758,861 B2 | 7/2010 | Rajagopalan et al. |
| 8,829,020 B2 | 9/2014 | Cantrell et al. |
| 2002/0026945 A1 | 3/2002 | Gomer et al. |
| 2002/0164287 A1 | 11/2002 | Rajagopalan et al. |
| 2002/0169107 A1 | 11/2002 | Rajagopalan et al. |
| 2003/0017164 A1 | 1/2003 | Rajagopalan et al. |
| 2003/0036538 A1 | 2/2003 | Rajagopalan et al. |
| 2003/0072763 A1 | 4/2003 | Rajagopalan et al. |
| 2003/0087889 A1 | 5/2003 | Strong et al. |
| 2003/0099596 A1 | 5/2003 | Strong et al. |
| 2003/0105300 A1 | 6/2003 | Achilefu et al. |
| 2003/0158127 A1 | 8/2003 | Rajagopalan et al. |
| 2003/0171320 A1 | 9/2003 | Gruyer |
| 2004/0077863 A1 | 4/2004 | Scammells et al. |
| 2004/0161430 A1 | 8/2004 | Rajagopalan et al. |
| 2004/0180864 A1 | 9/2004 | Rajagopalan et al. |
| 2004/0204434 A1 | 10/2004 | Shafer et al. |
| 2005/0107415 A1 | 5/2005 | Wu et al. |
| 2005/0182258 A1 | 8/2005 | Schmidhammer et al. |
| 2005/0261329 A1 | 11/2005 | Wu et al. |
| 2006/0177457 A1 | 8/2006 | Rajagopalan et al. |
| 2006/0258696 A1 | 11/2006 | Moss et al. |
| 2007/0128662 A1 | 6/2007 | Isacoff et al. |
| 2007/0265293 A1 | 11/2007 | Boyd et al. |
| 2008/0161570 A1 | 7/2008 | Perez et al. |
| 2008/0176884 A1 | 7/2008 | Perez et al. |
| 2008/0207669 A1 | 8/2008 | Perez et al. |
| 2008/0214817 A1 | 9/2008 | Dlubala |
| 2008/0234306 A1 | 9/2008 | Perez et al. |
| 2008/0274119 A1 | 11/2008 | Moss et al. |
| 2009/0062544 A1 | 3/2009 | Wakita et al. |
| 2009/0156815 A1 | 6/2009 | Wang et al. |
| 2009/0156816 A1 | 6/2009 | Wang et al. |
| 2009/0156817 A1 | 6/2009 | Wang et al. |
| 2009/0156818 A1 | 6/2009 | Wang et al. |
| 2009/0312552 A1 | 12/2009 | Bao et al. |
| 2010/0015219 A1 | 1/2010 | Berleur et al. |
| 2010/0041826 A1 | 2/2010 | Cantrell et al. |
| 2010/0041827 A1 | 2/2010 | Cantrell et al. |
| 2010/0081819 A1 | 4/2010 | Wang et al. |
| 2010/0197921 A1 | 8/2010 | Grote et al. |
| 2010/0216996 A1 | 8/2010 | Cantrell et al. |
| 2010/0216997 A1 | 8/2010 | Cantrell et al. |
| 2010/0222547 A1 | 9/2010 | Rajagopalan et al. |
| 2010/0280177 A1 | 11/2010 | Cantrell et al. |
| 2010/0280232 A1 | 11/2010 | Cantrell et al. |
| 2011/0015219 A1 | 1/2011 | Trawick et al. |
| 2011/0136845 A1 | 6/2011 | Trawick et al. |
| 2011/0288033 A1 | 11/2011 | Rajagopalan et al. |

FOREIGN PATENT DOCUMENTS

| | | |
|---|---|---|
| CN | 101 066 948 | 11/2007 |
| CN | 101 265 266 | 9/2008 |
| DE | 1119284 | 12/1961 |
| EP | 0 418 591 | 3/1991 |
| EP | 1 390 080 | 2/2004 |
| EP | 1 406 516 | 4/2004 |
| EP | 1 409 482 | 4/2004 |
| EP | 1 409 516 | 4/2004 |
| EP | 1 427 712 | 6/2004 |
| EP | 1 443 861 | 8/2004 |
| EP | 1 551 461 | 7/2005 |
| EP | 1 595 541 | 11/2005 |
| EP | 1 680 472 | 7/2006 |
| EP | 2 001 893 | 12/2008 |
| EP | 2 227 474 | 12/2009 |
| EP | 2 149 372 | 2/2010 |
| EP | 2 201 897 | 6/2010 |
| EP | 2 226 318 | 9/2010 |
| EP | 1 465 666 | 5/2011 |
| FR | 2923484 | 5/2009 |
| GB | 624391 | 6/1949 |
| GB | 797954 | 7/1958 |
| JP | 1068376 | 3/1989 |
| JP | 2001-163784 | 6/2001 |
| JP | 2001-302668 | 10/2001 |
| KR | 2009034787 | 8/2009 |
| WO | WO 92/03137 | 3/1992 |
| WO | WO 93/15081 | 8/1993 |
| WO | WO 94/13275 | 6/1994 |
| WO | WO 95/01178 | 1/1995 |
| WO | WO 98/23290 | 6/1998 |
| WO | WO 98/31684 | 7/1998 |
| WO | WO 99/00129 | 1/1999 |
| WO | WO 01/05250 | 1/2001 |
| WO | WO 01/14382 | 3/2001 |
| WO | WO 01/74819 | 4/2001 |
| WO | WO 01/70031 | 9/2001 |
| WO | WO 02/16367 | 2/2002 |
| WO | WO 02/089858 | 11/2002 |
| WO | WO 03/003806 | 1/2003 |
| WO | WO 03/004091 | 1/2003 |
| WO | WO 03/004466 | 1/2003 |
| WO | WO 03/015606 | 2/2003 |
| WO | WO 03/032900 | 4/2003 |
| WO | WO 03/032902 | 4/2003 |
| WO | WO 03/097608 | 11/2003 |
| WO | WO 2004/005294 | 1/2004 |
| WO | WO 2004/035536 | 4/2004 |
| WO | WO 2004/043964 | 5/2004 |
| WO | WO 2004/091622 | 10/2004 |
| WO | WO 2004/091665 | 10/2004 |
| WO | WO 2005/028483 | 3/2005 |
| WO | WO 2005/037928 | 4/2005 |
| WO | WO 2005/051356 | 6/2005 |
| WO | WO 2005/089813 | 9/2005 |
| WO | WO 2005/107726 | 11/2005 |
| WO | WO 2006/016143 | 2/2006 |
| WO | WO 2006/023669 | 3/2006 |
| WO | WO 2006/039691 | 4/2006 |
| WO | WO 2006/052430 | 5/2006 |
| WO | WO 2006/073419 | 7/2006 |
| WO | WO 2006/096626 | 9/2006 |
| WO | WO 2006/098855 | 9/2006 |
| WO | WO 2006/109671 | 10/2006 |
| WO | WO 2006/127898 | 11/2006 |
| WO | WO 2006/127899 | 11/2006 |
| WO | WO 2007/072503 | 6/2007 |
| WO | WO 2007/088489 | 8/2007 |
| WO | WO 2007/103250 | 9/2007 |
| WO | WO 2007/121447 | 10/2007 |
| WO | WO 2008/034973 | 3/2008 |
| WO | WO 2008/036172 | 3/2008 |
| WO | WO 2008/060764 | 5/2008 |

(56) References Cited

FOREIGN PATENT DOCUMENTS

| | | |
|---|---|---|
| WO | WO 2008/064150 | 5/2008 |
| WO | WO 2008/064351 | 5/2008 |
| WO | WO 2008/064353 | 5/2008 |
| WO | WO 2008/069632 | 6/2008 |
| WO | WO 2008/070462 | 6/2008 |
| WO | WO 2008/073381 | 6/2008 |
| WO | WO 2008/073389 | 6/2008 |
| WO | WO 2008/073390 | 6/2008 |
| WO | WO 2008/108941 | 9/2008 |
| WO | WO 2008/108944 | 9/2008 |
| WO | WO 2008/108957 | 9/2008 |
| WO | WO 2008/108958 | 9/2008 |
| WO | WO 2008/109156 | 9/2008 |
| WO | WO 2008/137474 | 11/2008 |
| WO | WO 2008/137672 | 11/2008 |
| WO | WO 2009/009292 | 1/2009 |
| WO | WO 2009/012005 | 1/2009 |
| WO | WO 2009/059048 | 5/2009 |
| WO | WO 2009/061473 | 5/2009 |
| WO | WO 2009/067275 | 5/2009 |
| WO | WO 2009/092912 | 7/2009 |
| WO | WO 2009/117669 | 9/2009 |
| WO | WO 2009/141823 | 11/2009 |
| WO | WO 2009/152577 | 12/2009 |
| WO | WO 2010/000073 | 1/2010 |
| WO | WO 2010/002576 | 1/2010 |
| WO | WO 2010/033801 | 3/2010 |
| WO | WO 2010/039209 | 4/2010 |
| WO | WO 2010/060018 | 5/2010 |
| WO | WO 2010/096788 | 8/2010 |
| WO | WO 2010/096790 | 8/2010 |
| WO | WO 2010/096791 | 8/2010 |
| WO | WO 2010/132515 | 11/2010 |
| WO | WO 2010/132525 | 11/2010 |
| WO | WO 2010/132547 | 11/2010 |
| WO | WO 2010/132554 | 11/2010 |
| WO | WO 2010/144641 | 12/2010 |
| WO | WO 2011/009015 | 1/2011 |
| WO | WO 2011/009020 | 1/2011 |
| WO | WO 2011/060113 | 5/2011 |
| WO | WO 2011/084571 | 7/2011 |
| WO | WO 2011/108944 | 9/2011 |

OTHER PUBLICATIONS

Balikova (Mar. 5, 2001) "Evaluation of Urinary Dihydrocodeine Excretion in Human by Gas Chromatography—Mass Spectrometry," *J. Chromatog. B* 752(1):179-186.
Bao et al. (2005) "Morphine Alkaloids with Cell Protective Effects from *Sinomenium actum*," *J. Nat. Prod.* 68:1128-1130.
Barenholz, Y. (1992) "Liposome Production: Historic Aspects," In; *Griesbach Conference, Liposome Dermantics*, Braun-Falco et al. Eds Springer-Verlag, Berlin, pp. 69-81, 91-117.
Benaron et al. (Mar. 5, 1993) "Optical Time-of-Flight and Absorbance Imaging of Biological Media," *Science* 259:1463-1466.
Bhuvaneswari et al. (2007) "Effect of Hypericin-Mediated Photodynamic Therapy on the Expression of Vascular Endothelial Growth Factor in Human Nasopharyngeal Carcinoma," *Int. J. Mol. Med.* 20:421-428.
Brasch et al. (1986) "Influence of the Optical Isomers (+)- and (_)-Naloxone on Beating Frequency, Contractile Force and Action Potentials of Guinea-Pig Isolated Cardiac Preparations," *Br. J. Pharmac.* 88:733-740.
Brossi, A. (1979) "Unnatural Alkaloids," *Pure Appl. Chem.* 51(4):681-688.
Bundgaard et al. (1992) "(C) Means to Enhance Penetration: (1) Prodrugs as a Means to Improve the Delivery of Peptide Drugs," *Adv. Drug Deliv. Rev.* 8(1):1-38.
Bundgaard, H.(1991) "Design and Application of Prodrugs," In; *A Textbook of Drug Design and Development*, Krosgaard-Larsen et al. Eds., Ch. 5, pp. 113-191.
Chang et al. (2003) "Cytotoxic Banzophenanthridine and Benzylisoquinoline Alkaloids from *Argemone mexicana*," *Z. Naturforsch.* 58C:521-526.

Cui et al. (Web Release Nov. 28, 2005) "Potential Cancer Chemopreventive Activity of Simple Isoquinolines 1-Benzylisoquinolines, and Protoberberines," *Phytochemistry* 67:70-79.
Dvorak et al. (1995) "Vascular Permeability Factor/Vascular Endothelial Growth Factor, Microvascular Hyperpermeability and Angiogenesis," *Am. J. Pathol.* 146(5):1029-1039.
Eugui et al. (1994) "Some Antioxidants Inhibit, in a Co-Ordinate Fashion, the Production of Tumor Necrosis Factor-α, IL-β, and IL-6 by Human Peripheral Blood Mononuclear Cells," *Int. Immunol.* 6(3):409-422.
Fan et al. (2008) "Effect of Chemotherapeutic Stress on Induction of Vascular Endothelial Growth Factor Family Members and Receptors in Human Colorectal Cancer Cells," *Mol. Cancer Ther.* 7(9):3064-3070.
Fantini et al. (1998) "Assessment of the Size, Position, and Optical Properties of Breast Tumors in Vivo by Noninvasive Optical Methods," *Appl. Opt.* 37(1):1982-1989.
Ferrara, N. (2004) "Vascular Endothelial Growth Factor as a Target for Anticancer Therapy," *Oncologist* 9:2-10.
Ferrario et al. (2006) "Avastin Enhances Photodynamic Therapy Treatment of Kaposi's Sarcoma in a Mouse Tumor Model," *J. Environ Pathol. Toxicol. Oncol.* 25(1-2):251-259.
Ferrario et al. (Aug. 1, 2000) "Antiangiogenic Treatment Enhances Photodynamic Therapy Responsiveness in a Mouse Mammary Carcinoma," *Cancer Res.* 60:4066-4069.
Fialip et al. (1996) "Study of the Antinociceptive Effect of Tetrahydro-Papaveroline Derivatives: Interactions with Opiods," *Life Sci.* 59(11):133-139.
Folkman, J. (1995) "Angiogenesis in Cancer, Vascular, Rheumatoid and Other Diseases," *Nat. Med.* 1(1):27-33.
Foppoli et al. (2005) "Biological Response of Human Diploid Keratinocytes to Quinone-Producing Compounds: Role od NAD(P)H: Quinone Oxidereductase 1," *Int. J. Biochem. Cell. Bio.* 37:852-863.
Giannis et al. (1993) "Peptidomimetics for Receptor Ligands— Discovery, Development, and Medical Perspectives," *Angew. Chem. Int. Ed. Eng.* 32:1244-1267.
Gomez-Flores et al. (2006) "Selective Lymphocyte Activation and Inhibition of In Vitro Tumor Cell Growth by Novel Morphinans," *Am. J. Immunol.* 2(1):1-7.
Grosjean et al. (1998) "Clinical Phototherapy for Superficial Cancer in the Esophagus and the Bronchi: n514nm Compared to 630nm Light Irradiation after Sensitization with Photofrin II," *British J. Cancer* 77(11):1989-1955.
Heiskanen (2000) "Morphine or Oxycodone in Cancer Pain," *Acta Oncologica* 39(8):941-947.
Hellewell et al. (1990) "A Sigma-Like Binding Site in Rat Pheochromocytome (PC12) Cells: Decreased Affinity for )+)-Benzomorphans and Lower Molecular Weight Suggests a Different Sigma Receptor form from that of Guinea Pig Brain," *Brain Res.* 527(2):244-253.
Heumans et al. (1971) "Some Aspects of the Metabolism of Morphine-N-Oxide," *J. Pharm. Pharmac.* 23:831-836.
Hutchinson (Mar. 2004) "CYP2D6 and CYP3A4 Involvement in the Primary Oxidative Metabolism of Hydrocodone by Human Liver Microsomes," *Br. J. Clin. Pharmacol.* 57(3):287-297.
Hutchinson et al. (2007) "Opiod Induced Glial Activation: Mechanisms of Activation and Implications for Opiod Analgesia, Dependence, and Reward," *The Scientific World J.* 7(S2):98-111.
Hutchinson et al. (2008) "Non-Stereoselective Reversal of Neuropathic Pain by Naloxone and Naltrexone: Involvement of Toll-Like Receptor 4 (TLR4)," *Eur. J. Neurosci.* 28(1):20-29.
Iijima et al. (1978) "Studies in the (+)-Morphinan Series. 5. Synthesis and Biological Properties of (+)-Naloxone," *J. Med. Chem.* 21(4):398-400.
Iliev et al. (2004) "Neuronal Injury Mediated via Stimulation of Microglial Toll-Like Receptor-9 (TLR9)1," *The FASEB J.* 18:412-414.
Iljima et al. (1978) "Studies in the (+)-Morphine Series. 4. A Markedly Improved Synthesis of (+)-Morphine," *J. Org. Chem.* 43(7):1462-1463.

(56) References Cited

OTHER PUBLICATIONS

Iljima et al. (1978) "Studies in the (+)-Morphine Series. V. Synthesis and Biological Properties of (+)Naloxone," *J. Med. Chem.* 21(4):398-400.

International Search Report and Written Opinion, Corresponding to International Application No. PCT/US2010/042218, Mailed Jan. 4, 2011.

Jacquet et al. (1977) "Stereospecific and Nonstereospecific Effects of (+)- and (−)-Morphine: Evidence for a New Class of Receptors," *Science* 198(4319):842-845.

Kang et al. (1999) Inhibition of Activation of Nuclear Factor κB is Responsible for Inhibition of Inducible Nitric Synthase Expression by Higenamine, and Active Component of Aconite Root, *J. Pharmacol. Exp. Ther.* 291(1):314-320.

Kelentey et al. (1957) "Preparation and Pharmacological Studies of N-Oxides of Opium Alaloids," *Arzneimittel-Forschung* 7:594-597.

Kelentey et al. (1958) "Preparation and Pharmacological Properties of N-Oxides of Opium Alkaloids," *Kiserletes Orvostudomany* 10(1):70-77.

Kielian (Web Release Feb. 14, 2006) "Toll-Like Receptors in Central Nervous System Glial Inflammation and Homeostasis," *J. Neurosci. Res.* 83:711-730.

Kigoshi et al. (1987) "Effect of Several d-Morphinans on Ascites Tumors in Mice," *Jpn. J. Pharmacol.* 44:293-302.

Kitamura et al. (1994) "General Asymmetric Synthesis of Isoquinoline Alkaloids. Enantioselective Hydrogenation of Enamides Catalyzed by Binap-Ruthenium(II) Complexes," *J. Org. Chem.* 59(2):297-310.

Kobayashi et al. (2010) "Z-360, a Novel Cholecystokinin-2/Gastrin Receptor Antagonist, Inhibits Gemcitabine-Induced Expression of the Vascular Endothelial Growth Factor Gene in Human Pancreatic Cancer Cells," *Biol. Pharm. Bull.* 33(2):216-222.

Kosharskyy et al. (Nov. 15, 2006) "A Mechanism-Based Combination Therapy Reduces Local Tumor Growth and Metastasis in an Orthotropic Model of Prostate Cancer," *Cancer Res.* 66(22):10953-10958.

Kriftner, R.W. (1992) "Liposome Production: The Ethanol Injection Technique and the Development of the First Approced Liposome Dermatic," In; *Griesbach Conference, Liposome Dermantics*, Braun-Falco et al. Eds Springer-Verlag, Berlin, pp. 9.

Lee (2005) "Measurements of Plasma Oxycodone, Noroxycodone and Oxymorphone levels in a Patient with Bilateral Nephrectomy Who is Undergoing Haemodialysis," *Pallative Med.* 19(3):259-260.

Li et al. (2006) "Clinical Study of Photofrin Phototherapy for the Treatment of Relapse Nasopharyngeal Carcinoma," *Photodiag. Photother.* 3:266-271.

Li et al. (Jul. 10, 2006) "Effect of Sinomenine on Gene Expression of the IL-1Beta-Activated Human Synovial Sarcoma," *Life Sci.* 79(7):665-673.

Lin et al. (2004) "Berberine Inhibits HIF-1α Expression via Enhanced Preteolysis," *Mol. Pharmacol.* 66(3):612-619.

Liu et al. (2000) "Nalozone Protects Rat Dopaminergic Neurons Against Inflammatory Damage Through Inhibition of Microglia Activation and Superoxide Generation," *J. Pharmacol. Exp. Ther.* 298(2)607-617.

Liu et al. (2003) "Role of Microglia in Inflammation-Mediated Neurodegenerative Diseases: Mechanisms and Strategies for Therapeutic Intervention," *J. Pharmacol. Exp. Ther.* 304(1):1-7.

Liu et al. (2006) "Inhibition of (S)-Armepavine from *Nelumbo nucifera* on Autoimmune Disease of MRL/MpJ-1pr/1pr Mice," *Eur. J. Pharmacol.* 531(1-3):270-279.

Loidl et al. (2000) "Synthesis of β-(1-Azulenyl)-L-Alanine as a Potential Blue-Colored Florescent Tryptophan Analog and its Use in Peptide Synthesis," *J. Peptide Sci.* 6:139-144.

Makareviche et al. (2006) "Quaternary Salts of Alkaloids," *Chem. Nat. Compounds* 42(4):473-476.

Malazdrewich et al. (2004) "Pharmacological Inhibition of *Mannheimia haemolytica* Lipopolysaccharide and Leukotoxin-Induced Cytokine Expression in Bovine Alveolar Macrophages," *Microbial Pathogenesis* 36:159-169.

Merz et al. (Jun. 1997) "Diastereoisomeric N-Tetrahydrofurfurylnoroxymorphones with Opioid Agonist-Antagonist Properties," *J. Med. Chem.* 20(6):844-846.

Miller et al. (Web Release Feb. 15, 2007) "Photodynamic Therapy with the Phthalocyanine Photosensitizer Pc4," *Toxicol. Appl. Pharmacol.* 224(3):290-299.

Mitton et al. (Web Release May 2, 2006) "Photodynamic Therapy of Barrett's Oesophagus and Oesophageal Carcinoma—How I do it," *Photodiag. Photother.* 3:96-98.

Mlkvy et al. (1998) "Phototherapy for Gastrointestinal Tumors Using Three Photosensitizers—ALA Induced PPIX, Photofrin, and MTHPC," *Neoplasma* 45(3):157-161.

Momma et al. (Dec. 1, 1998) Phototdynamic Therapy of Orthotropic Prostate Cancer with Benzoporphyrin Derivative: Local Control and Distant Metastasis, *Cancer Res.* 58:5425-5431.

Nairn (1985) "Solutions, Emulsions, Suspensions and Extractives," In; *Remington's Pharmaceutical Science*, Gennaro, ed., Mack Publishing Co., Easton, Pa., pp. 1492-1517.

Neuvonen (Jun. 2008) "Determination of Oxycodone, Noroxycodone, Oxymorphone, and Noroxymorphone in Human Plasma by Liquid Chromatography-Electrospray-Tandem Mass Spectrometry," *Therapeutic Drug Monitoring* 30(3):333-340.

Norgrady (1985) "4. Pro-drugs and "soft" Drugs," In; *Medicinal Chemistry a Biochemical Approach*, Oxford University Press, New York, pp. 388-394.

Park et al. (Aug. 2005) "A Case of Prurigo Nodularis Treated with Narrow-Band UVB and Naltrexone," *Korean J. Dermatol.* 43(8):1113-1115.

Presta et al. (Oct. 15, 1997) "Humanization of an Anti-Vascular Endothelial Growth Factor Monoclonal Antibody for the Therapy of Solid Tumors and Other Disorders," *Cancer Res.* 57:4593-4599.

Pugh et al. (Jun. 2003) "Regulation of Angiogenesis by Hypoxia: Role of the HIF System," *Nat. Med.* 9(6):677-684.

Redman et al. (Web Release Sep. 30, 2002) "Synthesis of Photoactive p-Azidotetraflurorphenylalanine Containing Peptide by Solid-Phase Fmoc Methodology," *Org. Lett.* 4(25):4467-4469.

Renno et al. (Jul. 2004) "Selective Photodynamic Therapy by Targeted Verteporfin Delivery to Experimental Choroidal Neovascularization Mediated by a Homing Peptide to Vascular Endothelial Growth Factor Receptor-2," *Arch Ophthalmol.* 122:1002-1011.

Riedel et al. (Jul. 1, 2004) "Targeting Chemotherapy-Induced VEGF Up-Regulation by VEGF Antisense Oligonucleotides in HNSCC Cell Lines," *Anticancer Res.* 24(4):2179-2184.

Röding, J. (1992) "Properties and Characterization of Pre-Liposome Systems," *Griesbach Conference, Liposome Dermantics*, Braun-Falco et al. Eds Springer-Verlag, Berlin, pp. 110-117.

Schmidt (2002) "Affinities of Dihydrocodeine and its Metabolites to Opioid Receptors," *Pharmacol. Toxicol.* 91(2):57-63.

Schmidt-Drfurth et al. (Dec. 1996) "Phototherapy in Ocular Vascular Disease," *IEEE J. Selected Topic Quantum Electron.* 2(4):988-996.

She et al. (Nov. 2008) "Photoreceptor Protection after Phtotdynamic Therapy Using Dexamethasone in a Rat Model of Choroidal Neovascularization," *IOVS* 49(11):5008-5014.

Shen et al. (Sep. 29, 2005) "Suppression of Ocular Neovascularization with siRNA Targeting VEGF Receptor 1," *Gene Ther.* 13(3):225-234.

Shin (May 1, 2004) "Potential Roles of NF-κB and ERK1/2 in Cytoprotection Against Oxidative Cell Death Induced by Tetrahydropapaveroline," *Free Radical Biol. Med.* 36(9):1185-1194.

Singleton et al. (2007) "Attenuation of Vascular Permeability by Methylnaltrexone: Role of mOP-R and S1P3 Transactivation," *Am. J. Resp. Cell Mol. Biol.* 37(2):222-231.

Singleton et al. (2008) "Synergistic Effects of Methylnaltrexone with 5-Fluorouracil and Bevacizumab on Inhibition of Vascular Endothelial Growth Factor-Induced Angiogenesis," *J. Mol. Cancer Ther.* 7(6):1669-1679.

Singleton et al. (Web Release Jul. 3, 2006) "Methylnaltrexone Inhibits Opiate and VEGF-Induced Angiogenesis: Role of Receptor Transactivation," *Microvascular Res.* 72(1-2):3-11.

(56) References Cited

OTHER PUBLICATIONS

Skopp (1998) "Postmortem Distribution of Dihydrocodeine and Metabolites in a Fatal Case of Dihydrocodeine," *Forensic Sci. Int.* 95(2):99-107.
Solban et al. (Jun. 1, 2006) "Mechanistic Investigation and Implications of Photodynamic Therapy Induction of Vascular Endothelial Growth Factor in Prostate Cancer," *Cancer Res.* 66(11):5633-5640.
Song et al. (2001) "The Involvement of Glial Cells in the Development of Morphine Tolerance," *Neurosci Res.* 39:281-286.
Stambugh (May 1, 2001) "Double-Blind, Randmoized Comparison of the Analgesic and Pharmacokinetic Profiles of Controlled- and Immediate-Release Oral Oxycodone in Cancer Pain Patients," *J. Clin. Pharmacol.* 41(5):500-506.
Stingl et al. (1992) "In Vitro Screening of Crude Extracts and Pure Metabolites Obtained from Marine Invertebrates for the Treatment of Breast Cancer," *Cancer. Chemother. Pharmacol.* 30:401-406.
Stolba et al. (2006) "Long Term Results after Transpupillary in Eyes with Occult Choroidal Neovascularisation Associated with Age Related Macular Degeneration: A Prospective Trial," *Br. J. Ophthalmol.* 90:158-161.
Takagi et al. (1960) "Studies on Antitussives. II. Opium Alkaloids and their N-Oxides," *J. Pharm. Soc. Jpn.* 80(10):1501-1506.
Takagi et al. (Nov. 1957) "Antitussive Activity of the N-Oxides of Opium Alkaloids," *J. Pharm. Soc. Jpn.* 77(11):1358-1359.
Tanabe et al. (May 2004) "Fluorescence Detection of a New Photosensitizer, PAD-S31, in Tumour Tissues and its use as a Photodynamic Treatment for Skin Tumours in Dogs and a Cat: A Preliminary Report," *Vet. J.* 167(3):286-293.
Tatsu et al. (1996) "Solid-Phase Synthesis of Caged Peptides Using Tyrosine Modified with a Photocleavable Protecting Group: Application to the Synthesis of Caged Neuropeptide Y," *Biochem. Biophys. Res. Commun.* 227:688-693.
Taylor (May 30, 2009) "A Validated Hrbrid Quadrupole Linear Ion-Trap LC-MS Method for the Analysis of Morphine and Morphine Glucuronides Applied to Opiate Deaths," *Forensic Science International* 187(1-3):34-41.
Tearney et al. (Jun. 27, 1997) "In Vivo Endoscopic Optical Biopsy with Optical Coherence Tomography," *Science* 276:2037-2039.
Tromberg et al. (1997) "Non-Invasive Measurements of Breast Tissue Optical Properties Using Frequency-Domain Photon Migration," *Phil. Trans. Royal Soc. London B* 352:661-668.
Watkins et al. (Feb. 2007) "Glia as the 'Bad Guys': Implications for Improving Clinical Pain Control and the Clinical Utility of Opiods," *Brain Behavior Immunity* 21(2):131-146.
Watkins et al. (Nov. 2009) "The 'Toll' of Opiod-Induced Glial Activation: Improving the Clinical Efficacy of Opiods by Targeting Glia," *Trends Pharmacol. Sci* 30(11):581-591.
Weder, H.G. (1992) "Liposome Production: The Sizing-Up Technology Starting from Mices Micelled and the Scaling-Up Procedure for the Topical Glucocorticoid Beta-Methasone Dipropionate and Betamethasone," In; *Griesbach Conference, Liposome Dermantics*, Braun-Falco et al. Eds Springer-Verlag, Berlin, pp. 101-109.
Wu et al. (2007) "Antianalgesia: Stereoselective Action of Dextro-Morphine over Levo-Morhine on Glia in the Mouse Spinal Cord," *J. Pharm. Exp. Ther.* 314(3):1101-1108.

Zhao et al. (Web Release Mar. 2, 2006) "Antiociceptive and Free Radical Scavenging Activities of Alkaloids Isolated from *Lindera angustifolia* Chen," *J. Ethnopharmacology* 106(3):408-413.
Zuluaga et al. (Apr. 2007) "Synergies of VEGF Inhibition and Photodynamic Therapy in the Treatment of Age-Related Macular Degeneration," *IOVS* 48(4):1767-1772.
Baldessarini et al. (2001) "Drugs and the Treatment of Psychiatric Disorders, Psychosis and Mania," In; *Goodman & Gilman's the Pharmacological Basis of Therapeutics*, 10th ed., Ch. 20, pp. 485-520.
Baldessarini et al. (2001) "Drugs and the Treatment of Psychiatric Disorders, Depression and Anxiety Disorders," In; *Goodman & Gilman's the Pharmacological Basis of Therapeutics*, 10th ed., Ch. 19, pp. 447-483.
Bundgaard, H. (1987) "Design of Bioreversible Drug Derivatives and the Utility of the Double Prodrug Concept," In; *Bioreversible Carriers in Drug Design*, Roche, E.B. ed. American Pharmaceutical Association and Pergamon Press, Ch. 2, pp. 13-94.
Chang et al. (Jul. 2002) "The Capabilities of Benzoporphyrin: In Vivo Study of Canine Malignant Melanomas with Photodynamic Therapy," *Formosan J. Surg.* 35(4):166-172.
Folkman, J. (1992) "The Role of Angiogenesis in Tumor Growth," *Cancer Biol.* 3:65-71.
Hälfinger et al. (1956) "Hydroxy-Morphinane. Mitteilung. Über ein Photooxydationsprodukt von (+)-3-Methoxy-N-Methyl-Morphinan," *Helvetica Chimica Acta* 39(7):2053-2062.
Higuchi, T. (1987) "Prodrug and Drug Delivery—An Overview," In; *Bioreversible Carriers in Drug Design*, Roche, E.B. ed. American Pharmaceutical Association and Pergamon Press, Ch. 1. pp. 1-12.
Lingen, M.W. (2002) "Endothelial Cell Migration Assay: A Quantitative Assay for Prediction of in Vivo Biology," In; *Methods Molecular Medicine*, vol. 78, Humana Press, Inc. pp. 337-347.
Marshall, K. (1979) "Solid Oral Dosage Forms," In; *Modern Pharmaceutics*, Banker and Rhodes Eds., Ch. 10, 359-427.
Patch et al. (2004) "Versatile Oligo(N-Substituted)glycines: The Many Roles of Peptoids in Drug Discovery," *Pseudo-Peptides in Drug Discovery* :1-31.
Pelegrin et al. (1992) "Photoimmunodiagnosis with Antibody-Fluorescein Conjugates: in Vitro and in Vivo Preclinical Studies," *J. Cell. Pharmacol.* 3:141-145 Abstract Only.
Rhodes, C.T. (1979) "Disperse Systems: Solubilized Products, Suspensions, and Emulsions," In; *Modern Pharmaceutics*, Banker and Rhodes Eds., Ch 9, pp. 329-357.
Sanderson (May 1989) "Iontophoretic Delivery of Nonpeptide Drugs: Formulation Optimization for Maximum Skin Permeability," *J. Pharm. Sci.* 78(5):361-364.
Solans (Mar./Apr. 1995) "Comprehensive Screening Procedure for Detection of Stimulants, Narcotics, Adrenergic Drugs, and Their Metabolites in Human Urine," *J. Analytical Toxicol.* 19(2):104-114.
Spiegel et al. (Oct. 1963) "Use of Nonaqueous Solvents in Parenteral Products," *J. Pharma Sci.* 52(10):917-927.
Office Action dated Feb. 19, 2016 in related U.S. Appl. No. 14/316,443, 15 pgs.
"Treatment." (2009) Mosby's Dictionary of Medicine, Nursing, & Health Professions. Retreived from <http://www.credoreference.com/entry/ehsmosbymed/treatment> on Nov. 18, 2010.

\* cited by examiner

PBS, IP

MNTX1, IP

COMPOUNDS AND COMPOSITIONS FOR USE IN PHOTOTHERAPY AND IN TREATMENT OF OCULAR NEOVASCULAR DISEASE AND CANCERS

CROSS-REFERENCE TO RELATED APPLICATIONS

This application claims the priority of U.S. National application Ser. No. 13/383,243, filed Jan. 10, 2012, which claims the priority of PCT Application No. PCT/US10/42218, filed Jul. 16, 2010, which claims the benefit of U.S. Provisional Application No. 61/226,032, filed Jul. 16, 2009, U.S. Provisional Application No. 61/238,358, filed Aug. 31, 2009, U.S. Provisional Patent Application No. 61/226,015, filed on Jul. 16, 2009, and U.S. Provisional Patent Application No. 61/286,877, filed on Dec. 16, 2009, each of which is hereby incorporated by reference to the extent not inconsistent herewith.

BACKGROUND

Optical agents play a central role in a large number of in vivo, in vitro and ex vivo clinical procedures including important diagnostic and therapeutic procedures. Photodiagnostic and phototherapy agents, for example, include a class of molecules capable of absorbing, emitting, or scattering electromagnetic radiation applied to a biological material, particularly in the visible and near infrared regions of the electromagnetic spectrum. This property of optical agents is used in a range of biomedical applications for visualizing, imaging or otherwise characterizing biological materials and/or achieving a desired therapeutic outcome. Recent developments in targeted administration and delivery of optical agents, and advanced systems and methods for applying and detecting electromagnetic radiation in biological environments, has considerably expanded the applicability and effectiveness of optical agents for many clinical applications.

Important applications of optical agents that absorb and/or emit in the visible and near-infrared (NIR) region of the electromagnetic spectrum include their use in biomedical imaging and visualization. Imaging and visualization using such optical agents has potential to provide a less invasive and safer imaging technology, as compared to X-ray, and other widely used nuclear medicine technologies. Applications of optical imaging for diagnosis and monitoring of the onset, progression and treatment of various disease conditions, including cancer, are well established. (See, e.g., D. A. Benaron and D. K. Stevenson, *Optical time-of-flight and absorbance imaging of biologic media, Science,* 1993, 259, pp. 1463-1466; R. F. Potter (Series Editor), *Medical optical tomography: functional imaging and monitoring,* SPIE Optical Engineering Press, Bellingham, 1993; G. J. Tearney et al., *In vivo endoscopic optical biopsy with optical coherence tomography, Science,* 1997, 276, pp. 2037-2039; B. J. Tromberg et al., *Non-invasive measurements of breast tissue optical properties using frequency-domain photon migration, Phil. Trans. Royal Society London B,* 1997, 352, pp. 661-668; S. Fantini et al., *Assessment of the size, position, and optical properties of breast tumors in vivo by noninvasive optical methods, Appl. Opt.,* 1998, 37, pp. 1982-1989; A. Pelegrin et al., *Photoimmunodiagnosis with antibody-fluorescein conjugates: in vitro and in vivo preclinical studies, J. Cell Pharmacol.,* 1992, 3, pp. 141-145).

In addition to their important role in biomedical imaging and visualization, optical agents capable of absorption in the visible and NIR regions have also been extensively developed for clinical applications for phototherapy. The benefits of phototherapy using optical agents are widely acknowledged as this technique has the potential to provide efficacy comparable to radiotherapy, while entirely avoiding exposure of non-target organs and tissue to harmful ionizing radiation. Photodynamic therapy (PDT), in particular, has been used effectively for localized superficial or endoluminal malignant and premalignant conditions. The clinical efficacy of PDT has also been demonstrated for the treatment of various other diseases, injuries, and disorders, including cardiovascular disorders such as atherosclerosis and vascular restenosis, inflammatory diseases, ophthalmic diseases such as age related macular degeneration and dermatological diseases. Visudyne® and Photofrin®, for example, are two optical agents that have been developed and approved by the FDA for the treatment of macular degeneration of the eye and for ablation of several types of tumors, respectively. (See, e.g., Schmidt-Drfurth, U.; Bringruber, R.; Hasan, T. *Phototherapy in ocular vascular disease.* IEEE Journal of Selected Topics in Quantum Electronics 1996, 2, 988-996; Mlkvy, P.; Messmann, H.; Regula, J.; Conio, M.; Pauer, M.; Millson, C. E.; MacRobert, A. J.; Brown, S. G. *Phototherapy for gastrointestinal tumors using three photosensitizers—ALA induced PPIX, Photofrin, and MTHPC. A pilot study.* Neoplasma 1998, 45, 157-161; Grosjean, P.; Wagieres, G.; Fontolliet, C.; Van Den Bergh, H.; Monnier, P. *Clinical phototherapy for superficial cancer in the esophagus and the bronchi:* 514 *nm compared with* 630 *nm light irradiation after sensitization with Photofrin II.* British Journal of Cancer 1998, 77, 1989-1955; Mitton, D.; Ackroyd, R. Phototherapy of Barrett's oesophagus and oesophageal carcinoma—how I do it. Photodiagnostics and Phototherapy 2006, 3, 96-98; and Li, L.; Luo, R.; Liao, W.; Zhang, M.; Luo, Y.; Miao, J. Clinical study of photofrin phototherapy for the treatment of relapse nasopharyngeal carcinoma. Photodiagnostics and Phototherapy 2006, 3, 266-271).

Phototherapy is carried out by administration, and preferably targeted delivery, of a photosensitizer to a target tissue (e.g., tumor, lesion, organ etc.) followed by photoactivation of the photosensitizer by absorption of applied electromagnetic radiation, typically provided by a laser light source. Phototherapy targets include tumor cells, tumor microvaculature, inflammatory cells, immune host cells and neovascular endothelium cells. The applied electromagnetic radiation excites the photosensitizer, resulting in formation of reactive species capable of initiating a cascade of cellular and molecular events eventually resulting in selective target tissue destruction.

Photosensitizers may operate via two different major pathways, classified as Types 1 and 2. The Type 1 mechanism proceeds via a two-step process involving activation of the photosensitizer by applied electromagnetic radiation followed either by direct transfer of the energy from the excited state of the photosensitizer to the tissue, or though the interaction of reactive intermediates (e.g., radicals, ions, nitrene, carbene etc.) derived from the excited photosensitizer with the target tissue, resulting in tissue damage. The Type 1 mechanism can be represented by the following sequence of reactions:

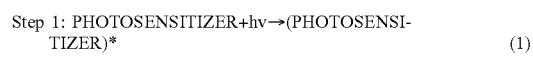
Step 1: PHOTOSENSITIZER+hv→(PHOTOSENSITIZER)*  (1)

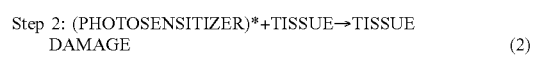
Step 2: (PHOTOSENSITIZER)*+TISSUE→TISSUE DAMAGE  (2)

wherein hv indicates applied electromagnetic radiation and (PHOTOSENSITIZER)* indicates photoactivated photosensitizer. The Type 2 mechanism proceeds via a three-step process involving activation of the photosensitizer by absorption of electromagnetic radiation followed by energy transfer from the activated photosensitizer to oxygen molecules in the environment of the target tissue. This energy transfer process generates excited state oxygen ($^1O_2$) which subsequently interacts either directly or indirectly through Reactive Oxygen Species (ROS) with the target tissue so as to cause tissue damage. The Type 2 mechanism can be represented by the following sequence of reactions:

Step 1: PHOTOSENSITIZER+hv→(PHOTOSENSITIZER)* (3)

Step 2: (PHOTOSENSITIZER)*+$^3O_2$ (Triplet Oxygen)→$^1O_2$ (Singlet Oxygen) (4)

Step 3: $^1O_2$ (Singlet Oxygen)+TISSUE→TISSUE DAMAGE (5)

wherein hv indicates applied electromagnetic radiation, (PHOTOSENSITIZER)* indicates photoactivated photosensitizer, $^3O_2$ is ground state triplet oxygen, and $^1O_2$ is excited state singlet oxygen. As shown by reactions 1 and 2, Type I photosensitizers do not require the presence of oxygen for causing tissue damage, and therefore, are expected to be more effective than Type II photosensitizers under extremely hypoxic environments often found in solid tumors.

The biological basis of tissue injury brought about by tumor phototherapy agents has been the subject of intensive study. Various biochemical mechanisms for tissue damage have been postulated, which include the following: a) cancer cells up-regulate the expression of low density lipoprotein (LDL) receptors, and phototherapy (PDT) agents bind to LDL and albumin selectively; (b) porphyrin-like substances are selectively taken up by proliferative neovasculature; (c) tumors often contain increased number of lipid bodies and are thus able to bind to hydrophobic photosensitizers; (d) a combination of "leaky" tumor vasculature and reduced lymphatic drainage causes porphyrin accumulation; (e) tumor cells may have increased capabilities for phagocytosis or pinocytosis of porphyrin aggregates; (f) tumor associated macrophages may be largely responsible for the concentration of photosensitizers in tumors; and (g) cancer cells may undergo apoptosis induced by photosensitizers. Among these mechanisms, (f) and (g) are the most general and, of these two alternatives, there is a general consensus that (f) is the most likely mechanism by which the phototherapeutic effect of porphyrin-like compounds is induced.

Not withstanding the numerous benefits of phototherapy, these techniques are not without some drawbacks. For example, local hypoxia is an inherent consequence of phototherapy under some conditions. Local hypoxia may arise directly from oxygen consumption during treatment and/or indirectly from disruption of tumor vasculature as a result of treatment. Tissue hypoxia induces a range of molecular and physiological responses including an angiogenesis response associated with gene activation. For example, hypoxia mediated gene activation is believed to proceed via stabilization of the transcription factor hypoxia-inducible factor-1α (HIF-1α), which binds to the HIF-1α response element (HRE) in the promoter of a number of genes including the vascular endothelial growth factor (VEGF) gene. Vascular endothelial growth factor is an angiogenic molecule involved with the induction and maintenance of neovasclature in solid tumors. Animal studies have documented an increase in VEGF production and accelerated angiogenesis response after phototherapeutic treatment. (Momma, T; Hamblin, M. R.; Wu, H. C.; Hasan, T; "Photodynamic Therapy of Orthotropic Prostate Cancer with Benzoporphyrin Derivative: Local Control and Distant Metastasis", Cancer Research, 58, 5425-5431, December 1998.) As a result of increased secretion and stabilization of vascular endothelial growth factor (VEGF) in response to some phototherapy procedures, unwanted tumorigenesis and metastasis processes can be initiated. Accordingly, a number of combination therapy strategies for inhibiting this endogenous angiogenic response are being pursued as means to enhance the therapeutic efficacy of phototherapy.

A number of anti-VEGF compounds have been evaluated in the context of a combination therapy for the treatment of age related macular degeneration. U.S. Patent Publication US 2003/0171320, by D. R. Gruyer and published Sep. 11, 2003, discloses methods for treating ocular neovascular disease using anti-VEGF compounds, including aptamers and antibodies, alone or in combination with photodynamic therapy or thermal laser photocoagulation. This reference discloses a number of anti-VEGF aptamers such as nucleic acid ligands having 2'-F-modified nucleotides, 2'-O-methyl nucleotides, and pegylated aptamers and generally refers to therapeutic procedures using VEGF antibodies and fragments thereof. The clinical results provided suggest that combining administration of an anti-VEGF agent with phototherapy enhances efficacy for treatment of age related macular degeneration in certain patients. U.S. Patent Publication US 2003/0026945, by Gomer et al. and published Mar. 7, 2002, discloses methods for photodynamic therapy including administration of an anti-VEGF agent to improve tumoricidal activity. This reference discloses a single chain polypeptide, EMAP-II, having anti-angiogenic activity reportedly capable of inhibiting tumor growth and a dipeptide of L-glutamyl-L-tryptophan, IM862, that reportedly inhibits angiogenesis and VEGF production in monocytic lineage cells. PCT International Publication No. WO 2009/117669, published on Sep. 24, 2009, describes treatment with opioid antagonists and mTOR inhibitors in the context of cellular proliferation and migration.

Several antibody conjugates have recently been developed including pegaptanib (Macugen®), bevacizumab and ranibizumab for antagonizing VEGF mediated angiogenesis. Bevacizumab is a full-length humanized monoclonal antibody against vascular endothelial growth factor and has been commercialized as Avastin®. Ranibizumab is a humanized anti-VEGF antibody fragment derived from bevacizumab which inhibits VEGF activity by competitive binding and has been commercialized as Lucentis®. In the context of macular degeneration treatment, Avastin® and Lucentis® have been shown to stop abnormal vessels from growing and leaking but often don't cause permanent closure, and therefore, injections of either drug have to be given repeatedly. Phototherapy on the other hand has been demonstrated as effective for permanently closing vessels but can result in vision loss under some conditions. A combination therapy has recently been developed involving phototherapy with half the amount of laser dose followed with an injection of Lucentis® or of Avastin® and optionally with administration an anti-inflammatory steroid. (Augustin, A J, Puls, S, Offerman I, "Triple Therapy for Choroidal Neovascularization due to Age-Related Macular Degeneration. Vertportfrin PDT, Bevacizumab, and Dexamethasone. RETINA 27:133-140, 2007).

One problem with Type 2 phototherapy procedure is the induction of inflammatory response due to reactive oxygen species produced by photoexcitation of oxygen by Type 2 photosensitizers. This inflammatory response causes the blood vessels to become more porous and, hence, allows cancer cells to metastasize to other regions. As will be generally recognized from the foregoing, a need currently exists for enhancing the therapeutic efficacy of phototherapy by preventing metastasis, and for the treatment of macular degeneration using agents that are capable of inhibiting inflammatory response, including, but not limited to the expression and/or activity of vascular endothelial growth factor.

SUMMARY

In an aspect, the invention relates generally to combination therapy involving Type 1 and/or Type 2 photosensitizers and anti-angiogenesis agents. In an embodiment, the invention provides a class of opioid compounds, structurally related opioid derivatives and their isomers exhibiting inhibitory activity for VEGF expression for use in phototherapy. Opioid compounds and structurally related opioid derivatives of the invention may be administered in combination with administration and activation of a phototherapy agent. Embodiments of the invention include compositions and related phototherapy methods for scavenging excess reactive oxygen species (ROS) generated in a phototherapy procedure. This aspect of the invention is useful for suppressing (or preventing) tumor metastasis induced by reactive oxygen species (ROS) produced in a phototherapy procedure, for example upon activation of a Type 1 or Type 2 photosensitizer.

Therapeutic agents of the invention include mixtures of stereoisomers and substantially purified stereoisomers of opioids and structurally related derivatives for increasing therapeutic efficacy of a phototherapy procedure by inhibiting an inflammatory response to Type 1 or Type 2 phototherapy procedure and, therefore, may be characterized as anti-inflammatory agents. Certain opioid compounds and structurally related derivatives of the present invention are also useful in combination with phototherapy or as a monotherapy for treating a range of cancers and ocular neovascular diseases such as age related macular degeneration. In an embodiment, the invention includes morphinan compounds, morphinanium n-oxide compounds and morphinanium quarternary compounds and salts thereof for use in a phototherapy procedure and/or for the treatment of an ocular neovascular disease or cancer, including purified stereoisomers of these compounds such as purified (+) enantiomers and (−) enantiomers.

In an aspect, the invention provides therapeutic agents for use in an phototherapy procedure comprising opioids and structurally related opioid derivatives. In an embodiment, for example, the invention provides a compound for use in a phototherapy procedure, the compound having the formula (FX1) or (FX2):

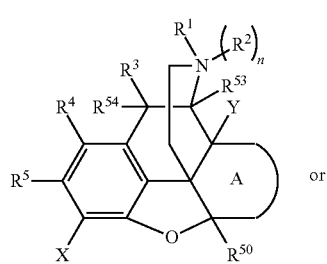

(FX1)

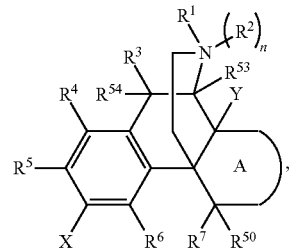

(FX2)

wherein: ring A is

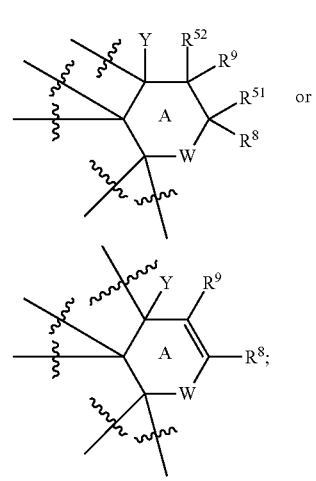

X is —OH, —OCH$_3$, or C$_2$-C$_8$ alkoxy; Y is —H or —OH; W is —(CR$^{10}$R$^{11}$)—, —(C=O)—, —(C=S)—, —(C=CR$^{12}$R$^{13}$)—, or —(CR$^{14}$NR$^{15}$R$^{16}$—); each of R$^1$ and R$^2$ is independently —H, —CH$_3$, —(O$^-$), C$_1$-C$_{10}$ alkyl, C$_3$-C$_{10}$ cycloalkyl, C$_2$-C$_{10}$ alkenyl, C$_1$-C$_{10}$ haloalkyl, C$_5$-C$_{10}$ aryl, C$_5$-C$_{10}$ heteroaryl, C$_5$-C$_{10}$ alkylaryl, C$_5$-C$_{10}$ alkylheteroaryl, C$_5$-C$_{10}$ carbonylalkenylaryl, or C$_5$-C$_{10}$ carbonylalkenylheteroaryl; each of R$^3$-R$^{16}$ and R$^{50}$-R$^{54}$ is independently —H, —OH, —OCH$_3$, C$_1$-C$_8$ alkyl, C$_3$-C$_8$ cycloalkyl, C$_2$-C$_8$ alkenyl, C$_2$-C$_8$ alkoxy, C$_5$-C$_{10}$ aryl, C$_5$-C$_{10}$ heteroaryl, C$_5$-C$_{10}$ alkylaryl, C$_5$-C$_{10}$ alkylheteroaryl, halo, nitrile, C$_1$-C$_8$ haloalkyl, C$_1$-C$_{10}$ hydroxyalkyl, or C$_5$-C$_{10}$ carbonylalkenylheteroaryl; and n is 0 or 1, wherein: when n is 1, the nitrogen to which R$^2$ is attached has a positive charge and optionally is associated with an anion; and when n is 0, R$^2$ is not present. In an embodiment, the invention provides N-oxide compounds useful as anti-VEGF therapeutic agents for phototherapeutic methods having formula (FX1) or (FX2), wherein R$^2$ is —(O$^-$), and optionally R$^1$ is C$_1$-C$_{10}$ alkyl, C$_3$-C$_{10}$ cycloalkyl, C$_5$-C$_{10}$ aryl or C$_2$-C$_{10}$ alkenyl. In an embodiment, for example, the invention provides compounds for use in a phototherapy procedure having any of formula (FX1)-(FX2), wherein each of R$^1$ and R$^2$ is a group other than H. In an embodiment, for example, the invention provides compounds for use in a phototherapy procedure having any of formula (FX1)-(FX2), wherein when n is equal to 0 then R$^1$ is a group other than H.

In an aspect, the invention provides therapeutic agents for use in the in vivo treatment of an ocular neovascular disease comprising opioids, structurally related opioid derivatives, isomers, N-oxides and salts thereof. In an embodiment, for example, the invention provides a compound for use in treatment of an ocular neovascular disease having the formula (FX1) or (FX2):

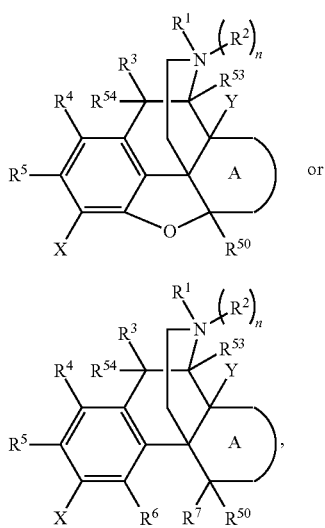

(FX1)

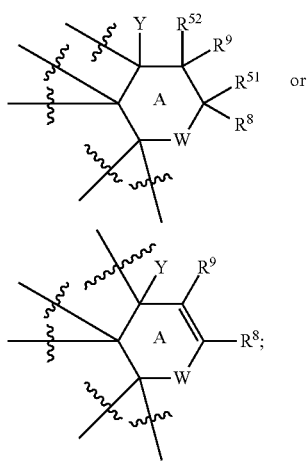

(FX2)

wherein: ring A is

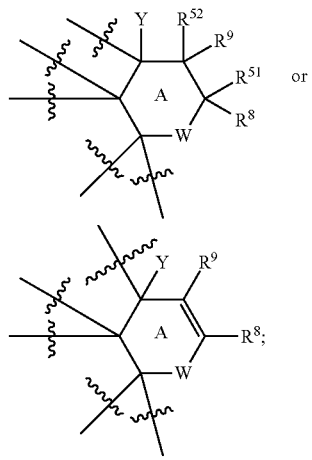

X is —OH, —OCH$_3$, or C$_2$-C$_8$ alkoxy; Y is —H or —OH; W is —(CR$^{10}$R$^{11}$)—, —(C=O)—, —(C=S)—, —(C=CR$^{12}$R$^{13}$)—, or —(CR$^{14}$NR$^{15}$R$^{16}$)—; each of R$^1$ and R$^2$ is independently —H, —CH$_3$, —(O$^-$), C$_1$-C$_{10}$ alkyl, C$_3$-C$_{10}$ cycloalkyl, C$_2$-C$_{10}$ alkenyl, C$_1$-C$_{10}$ haloalkyl, C$_5$-C$_{10}$ aryl, C$_5$-C$_{10}$ heteroaryl, C$_5$-C$_{10}$ alkylaryl, C$_5$-C$_{10}$ alkylheteroaryl, C$_5$-C$_{10}$ carbonylalkenylaryl, or C$_5$-C$_{10}$ carbonylalkenylheteroaryl; each of R$^3$-R$^{16}$ and R$^{50}$-R$^{54}$ is independently —H, —OH, —OCH$_3$, C$_1$-C$_8$ alkyl, C$_3$-C$_8$ cycloalkyl, C$_2$-C$_8$ alkenyl, C$_2$-C$_8$ alkoxy, C$_5$-C$_{10}$ aryl, C$_5$-C$_{10}$ heteroaryl, C$_5$-C$_{10}$ alkylaryl, C$_5$-C$_{10}$ alkylheteroaryl, halo, nitrile, C$_1$-C$_8$ haloalkyl, C$_1$-C$_{10}$ hydroxyalkyl, or C$_5$-C$_{10}$ carbonylalkenylheteroaryl; and n is 0 or 1, wherein: when n is 1, the nitrogen to which R$^2$ is attached has a positive charge and optionally is associated with an anion; when n is 0, R$^2$ is not present; and when in (FX1) each of X and Y is —OH, n is 1, and W is —(C=O)—, then each of R$^1$ and R$^2$ is independently a group other than cyclopropylmethyl, and each of R$^1$ and R$^2$ is independently a group other than methyl. In an embodiment, the invention provides N-oxide compounds useful as anti-VEGF therapeutic agents for phototherapeutic methods having formula (FX1) or (FX2) wherein R$^2$ is —(O$^-$), and optionally R$^1$ is C$_1$-C$_{10}$ alkyl, C$_3$-C$_{10}$ cycloalkyl, C$_5$-C$_{10}$ aryl or C$_2$-C$_{10}$ alkenyl. In an embodiment, for example, the invention provides compounds for use in treatment of an ocular neovascular disease having any of formula (FX1)-(FX2), wherein each of R$^1$ and R$^2$ is a group other than H. In an embodiment, for example, the invention provides compounds for use in treatment of an ocular neovascular disease having any of formula (FX1)-(FX2), wherein when n is equal to 0 then R$^1$ is a group other than H.

In an aspect, the invention provides therapeutic agents for use in the in vivo treatment of cancer comprising opioids, structurally related opioid derivatives, isomers, N-oxides and salts thereof. In an embodiment, for example, the invention provides a compound for the treatment of cancer, the compound having the formula (FX3) or (FX4):

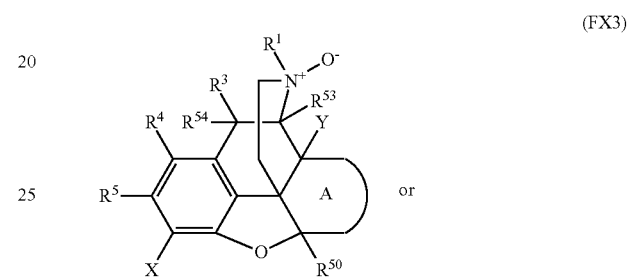

(FX3)

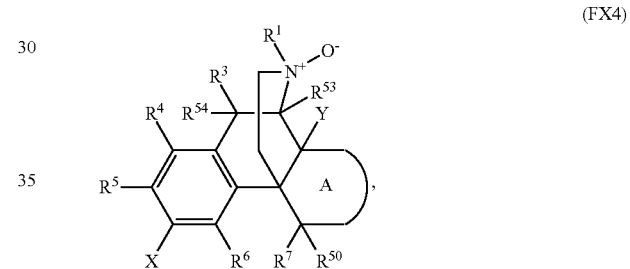

(FX4)

wherein: ring A is

X is —OH, —OCH$_3$, or C$_2$-C$_8$ alkoxy; Y is —H or —OH; W is —(CR$^{10}$R$^{11}$)—, —(C=O)—, —(C=S)—, —(C=CR$^{12}$R$^{13}$)—, or —(CR$^{14}$NR$^{15}$R$^{16}$)—; R$^1$ is —H, —CH$_3$, —(O$^-$), C$_1$-C$_{10}$ alkyl, C$_3$-C$_{10}$ cycloalkyl, C$_2$-C$_{10}$ alkenyl, C$_1$-C$_{10}$ haloalkyl, C$_5$-C$_{10}$ aryl, C$_5$-C$_{10}$ heteroaryl, C$_5$-C$_{10}$ alkylaryl, C$_5$-C$_{10}$ alkylheteroaryl, C$_5$-C$_{10}$ carbonylalkenylaryl, or $C_5$-$C_{10}$ carbonylalkenylheteroaryl; and each of $R^3$-$R^{16}$ and $R^{50}$-$R^{54}$ is independently —H, —OH, —OCH$_3$, $C_1$-$C_8$ alkyl, $C_3$-$C_8$ cycloalkyl, $C_2$-$C_8$ alkenyl, $C_2$-$C_8$ alkoxy, $C_5$-$C_{10}$ aryl, $C_5$-$C_{10}$ heteroaryl, $C_5$-$C_{10}$ alkylaryl, $C_5$-$C_{10}$ alkylheteroaryl, halo, nitrile, $C_1$-$C_8$ haloalkyl, $C_1$-$C_{10}$ hydroxyalkyl, or $C_5$-$C_{10}$ carbonylalkenylheteroaryl. In an embodiment, the invention provides N-oxide compounds useful as anti-VEGF therapeutic agents for phototherapeutic methods having formula (FX1) or (FX2) wherein $R^2$ is —(O$^-$), and optionally $R^1$ is $C_1$-$C_{10}$ alkyl, $C_3$-$C_{10}$ cycloalkyl, $C_5$-$C_{10}$ aryl, or $C_2$-$C_{10}$ alkenyl.

In an embodiment, for example, the invention provides a compound for the treatment of cancer, the compound having the formula (FX1) or (FX2):

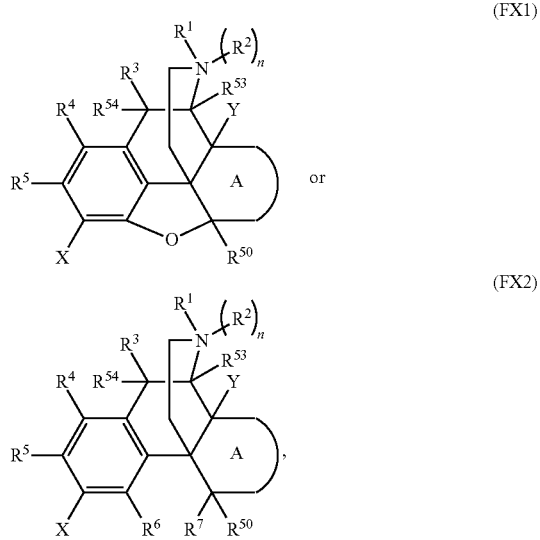

wherein: ring A is

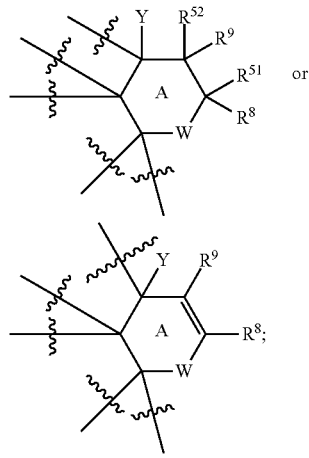

X is —OH, —OCH$_3$, or $C_2$-$C_8$ alkoxy; Y is —H or —OH; W is —(CR$^{10}$R$^{11}$)—, —(C=S)—, —(C=CR$^{12}$R$^{13}$)—, or —(CR$^{14}$NR$^{15}$R$^{16}$)—; each of $R^1$ and $R^2$ is independently —H, —CH$_3$, —(O$^-$), $C_1$-$C_{10}$ alkyl, $C_3$-$C_{10}$ cycloalkyl, $C_2$-$C_{10}$ alkenyl, $C_1$-$C_{10}$ haloalkyl, $C_5$-$C_{10}$ aryl, $C_5$-$C_{10}$ heteroaryl, $C_5$-$C_{10}$ alkylaryl, $C_5$-$C_{10}$ alkylheteroaryl, $C_5$-$C_{10}$ carbonylalkenylaryl, or $C_5$-$C_{10}$ carbonylalkenylheteroaryl; each of $R^{10}$ and $R^{11}$ is independently —OCH$_3$, $C_1$-$C_8$ alkyl, $C_3$-$C_8$ cycloalkyl, $C_2$-$C_8$ alkenyl, $C_2$-$C_8$ alkoxy, $C_5$-$C_{10}$ aryl, $C_5$-$C_{10}$ heteroaryl, $C_5$-$C_{10}$ alkylaryl, $C_5$-$C_{10}$ alkylheteroaryl, halo, nitrile, $C_1$-$C_8$ haloalkyl, $C_1$-$C_{10}$ hydroxyalkyl, or $C_5$-$C_{10}$ carbonylalkenylheteroaryl; each of $R^3$-$R^9$, $R^3$-$R^{16}$ and $R^{50}$-$R^{54}$ is independently —H, —OH, —OCH$_3$, $C_1$-$C_8$ alkyl, $C_3$-$C_8$ cycloalkyl, $C_2$-$C_8$ alkenyl, $C_2$-$C_8$ alkoxy, $C_5$-$C_{10}$ aryl, $C_5$-$C_{10}$ heteroaryl, $C_5$-$C_{10}$ alkylaryl, $C_5$-$C_{10}$ alkylheteroaryl, halo, nitrile, $C_1$-$C_8$ haloalkyl, $C_1$-$C_{10}$ hydroxyalkyl, or $C_5$-$C_{10}$ carbonylalkenylheteroaryl; and n is 0 or 1, wherein: when n is 1, the nitrogen to which $R^2$ is attached has a positive charge and optionally is associated with an anion; and when n is 0, $R^2$ is not present. In an embodiment, the invention provides N-oxide compounds useful as anti-VEGF therapeutic agents for phototherapeutic methods having formula (FX1) or (FX2) wherein $R^2$ is —(O$^-$), and optionally $R^1$ is $C_1$-$C_{10}$ alkyl, $C_3$-$C_{10}$ cycloalkyl, $C_5$-$C_{10}$ aryl or $C_2$-$C_{10}$ alkenyl. In an embodiment, for example, the invention provides compounds for use in treatment of cancer having any of formula (FX3)-(FX4), wherein each of $R^1$ and $R^2$ is a group other than H. The invention provides compounds for use in treatment of cancer having any of formula (FX3)-(FX4), wherein when n is equal to 0 then $R^1$ is a group other than H.

In an embodiment, the compound of the invention reduces an endogenous angiogenic response to the phototherapy procedure, such as an angiogenic response induced by tissue hypoxia. In an embodiment, the compound of the invention reduces or prevents migration or proliferation of endothelial cells in response to the phototherapy procedure, optionally reducing potential for tumorigenesis and metastasis processes. In an embodiment, the compound of the invention increases the therapeutic efficacy of the phototherapy procedure, for example by increasing tumorcidal activity. In an embodiment, the compound of the invention is for use in a phototherapy procedure comprising co-administration of the inhibitor agent of VEGF expression and a phototherapy agent, such as a Type 1 or Type 2 phototherapy agent, to a target tissue, such as a tumor or other lesion. In an embodiment, the compound of the invention is for use in a phototherapy procedure for the treatment of cancer or for the treatment of an ocular neovascular disease such as age related macular degeneration. In another embodiment, the compound of the invention is administered with and acts synergistically with the humanized VEGF antibody, its active humanized VEGF antibody fragment and/or an active anti-VEGF aptamer to increase the therapeutic efficacy of the phototherapy procedure. For example, coadministration of the R isomer derived from (−) naltrexone with a mirror isomer derived from the (+) naltrexone salt is synergistic in combination with VEGF antibody (Avastin) in endothelial cells. (Singleton, P. A.; Garcia, J. G. N. and Moss, J, Mol Cancer Ther 2008; 7(6) 1669-1679).

In an embodiment, the compound of the invention is not methylnaltrexone. In an embodiment of this aspect, the compound of the invention is not a (−) R isomer of methylnaltrexone. In an embodiment, the compound of the invention is not naltrexone methobromide. In an embodiment, the compound of the invention is not a (−) R isomer of naltrexone methobromide. In an embodiment, the compound of the invention is not the R isomer derived from (−) naltrexone with a mirror isomer derived from the (+) naltrexone. In an embodiment, the compound of the invention is has a formula other than formulas (FX72)-(FX75). In an embodiment of this aspect, the compound of the invention is has a formula other than formula (FX73). In an embodiment, the compound is for use in treatment of age related macular degeneration. In an embodiment, the compound of this aspect of the invention is for use in a direct monotherapy wherein the compound is administered to a target tissue to reduce or otherwise alleviate unwanted angiogenesis in connection with an ocular neovascular disease. In such embodiments, the compound is administered without co-administration of a phototherapy agent. In another embodiment, the compound of this aspect of the invention is for use in a combination therapy wherein the compound is co-administered with a suitable phototherapy agent that undergoes subsequent excitation upon exposure to electromagnetic radiation.

The compounds of the present invention include, but are not limited to, therapeutic agents comprising a class of tertiary and quarternary amines, and salts thereof, for phototherapy and/or for treatment of ocular neovascular disease or cancer. The invention provides, for example, an opioid or structurally related derivative that is a tertiary or quaternary amine for phototherapy and/or for treatment of ocular neovascular disease or cancer, the compound having the formula (FX5) to (FX8):

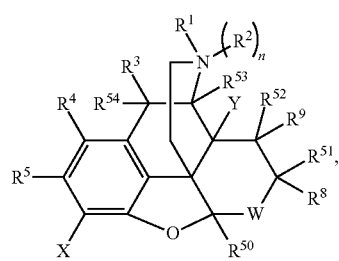
(FX5)

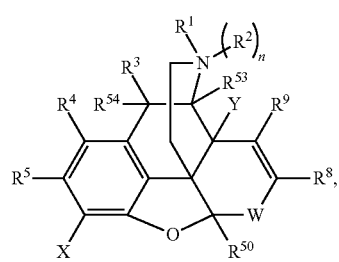
(FX6)

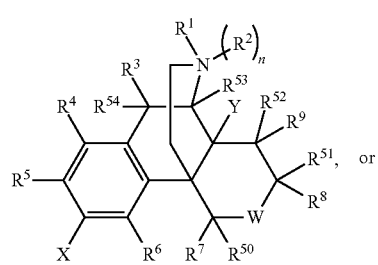
(FX7)

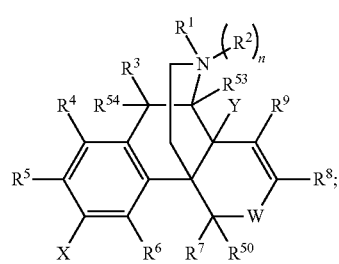
(FX8)

wherein W, X, Y, n, $R^3$-$R^{16}$ and $R^{50}$-$R^{54}$ are defined as described in connection with formulae (FX1) and (FX2). In an embodiment, the invention provides compounds useful as anti-VEGF therapeutic agents for phototherapeutic methods and/or for treatment of ocular neovascular disease or cancer having any one of formula (FX5)-(FX8), wherein X is —OH or —OCH$_3$, and wherein Y is —OH. In an embodiment, the invention provides compounds useful as anti-VEGF therapeutic agents for phototherapeutic methods and/or for treatment of ocular neovascular disease or cancer having any one of formula (FX5)-(FX8), wherein: each of $R^1$ and $R^2$ is independently allyl or

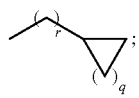

each q is independently an integer selected from 1 to 4; each r is independently an integer selected from 1 to 5, and optionally wherein $R^1$ or $R^2$ is —CH$_3$.

The invention also provides, for example, an opioid or structurally related derivative that is a tertiary amine for phototherapy and/or for treatment of ocular neovascular disease or cancer, the compound having the formula (FX9) or (FX10):

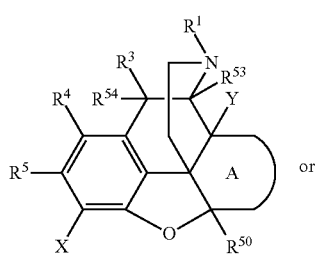
(FX9)

(FX10)

wherein X, Y, Ring A and $R^1$ and $R^3$-$R^7$, $R^{50}$, $R^{53}$, and $R^{54}$ are defined as described in connection with formulae (FX1) and (FX2). The invention provides, for example, an opioid or structurally related derivative that is a quarternary amine or salt thereof for phototherapy and/or for treatment of ocular neovascular disease or cancer, the compound having the formula (FX11) or (FX12):

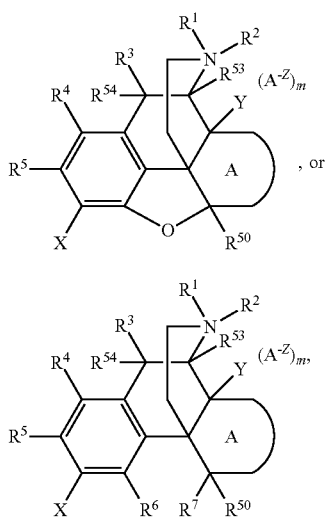

(FX11)

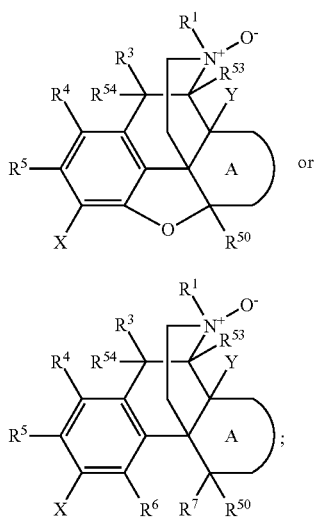

(FX12)

wherein: each $A^{-z}$ is independently an anion; each z is independently 1, 2 or 3; each m is independently 0 or 1, wherein when m is 0, $A^{-z}$ is not present; and wherein X, Y, Ring A, $R^1$-$R^7$, $R^{50}$, $R^{53}$, and $R^{54}$ are defined as described in connection with formulae (FX1) and (FX2).

The compounds of the present invention include, but are not limited to, therapeutic agents comprising a class of N-oxides, and salts thereof, for phototherapy and/or for treatment of ocular neovascular disease or cancer. The invention also provides, for example, an opioid or structurally related derivative that is a quarternary amine N-oxide, or salt thereof, for phototherapy and/or for treatment of ocular neovascular disease or cancer, the compound having the formula (FX3) or (FX4):

(FX3)

(FX4)

wherein X, Y, Ring A and $R^1$ and $R^3$-$R^7$, $R^{50}$; $R^{53}$, and $R^{54}$ are defined as described in connection with formulae (FX1) and (FX2). In an embodiment, the invention provides N-oxide compounds useful as anti-VEGF therapeutic agents for phototherapeutic methods and/or for treatment of ocular neovascular disease or cancer having formula (FX3) or (FX4), wherein X is —OH or —OCH$_3$, and wherein Y is —OH. In an embodiment, the invention provides compounds useful as anti-VEGF therapeutic agents for phototherapeutic methods and/or for treatment of ocular neovascular disease or cancer having formula (FX3) or (FX4), wherein: each of $R^1$ and $R^2$ is independently allyl or

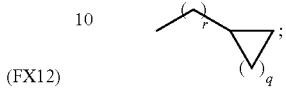

each q is independently an integer selected from 1 to 4; each r is independently an integer selected from 1 to 5; and optionally wherein $R^1$ or $R^2$ is —CH$_3$.

In an embodiment, for example, the invention provides a compound for use in a phototherapy procedure or for treatment of an ocular neovascular disease or cancer, the compound having the formula (FX13)-(FX60):

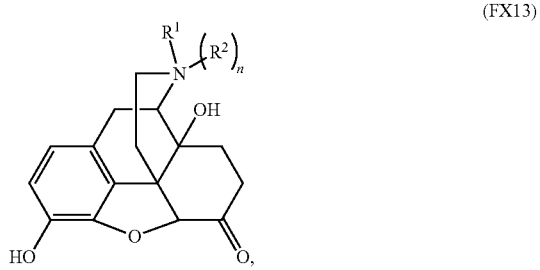

(FX13)

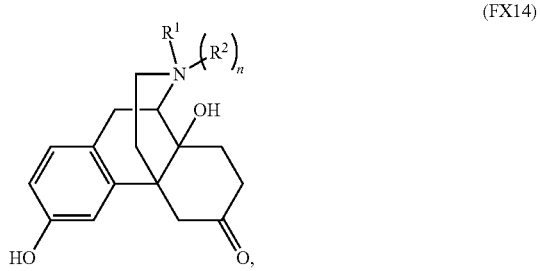

(FX14)

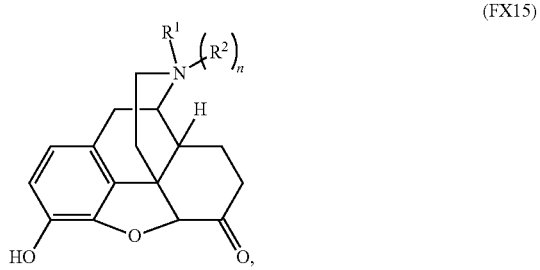

(FX15)

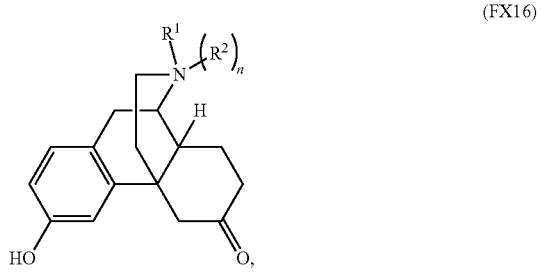

(FX16)

(FX17)
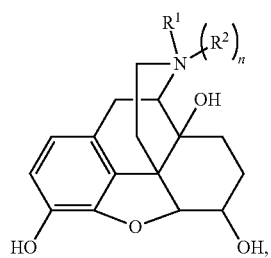
(FX18)
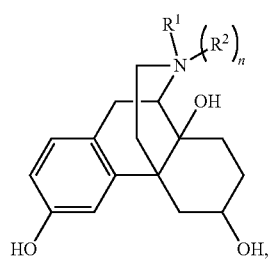
(FX19)
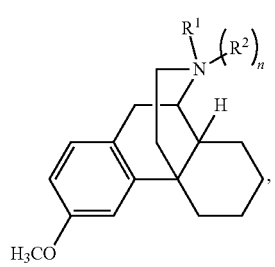
(FX20)
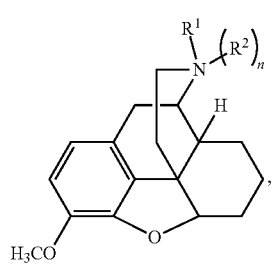
(FX21)
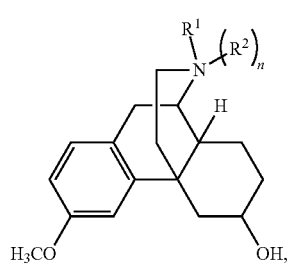
(FX22)
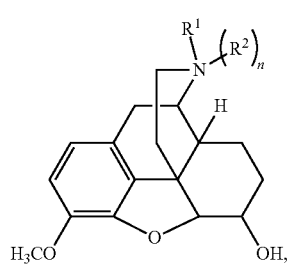
(FX23)
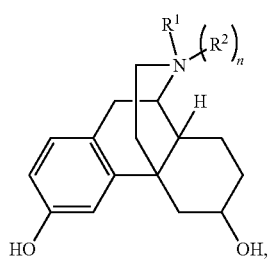
(FX24)
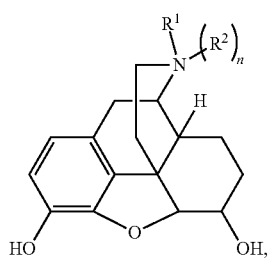
(FX25)
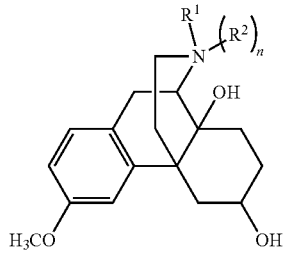
(FX26)
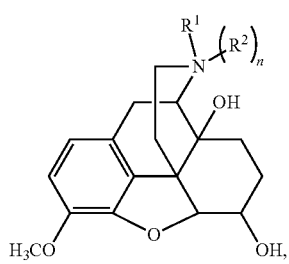
(FX27)
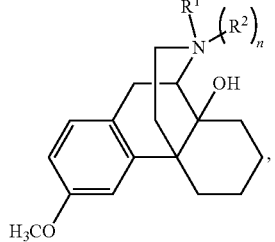
(FX28)
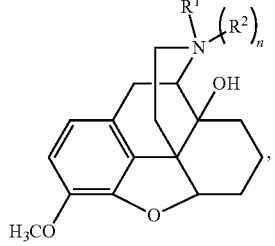

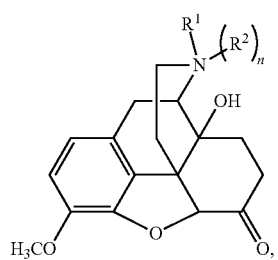
(FX29)
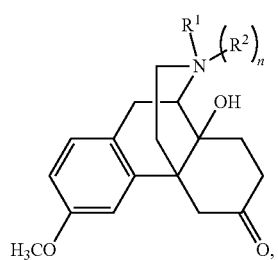
(FX30)
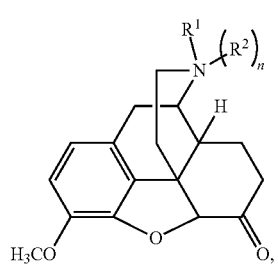
(FX31)
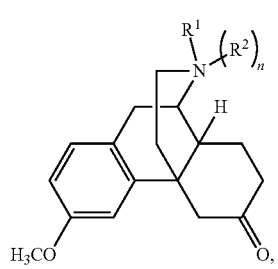
(FX32)
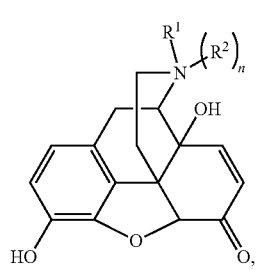
(FX33)
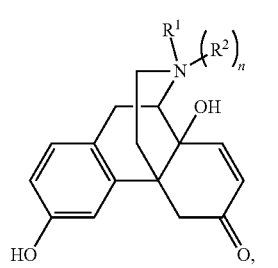
(FX34)
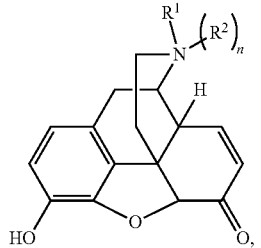
(FX35)
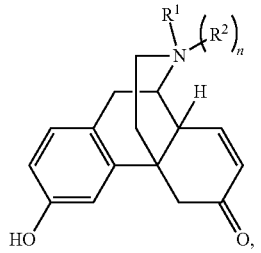
(FX36)
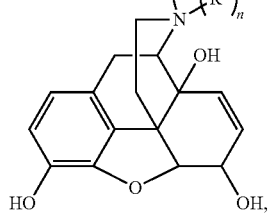
(FX37)
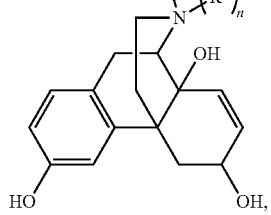
(FX38)
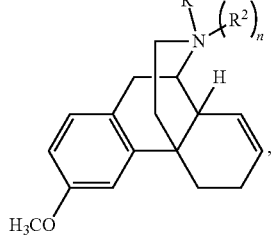
(FX39)
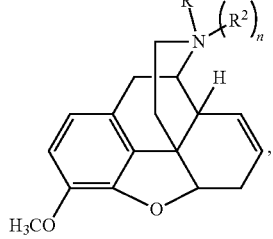
(FX40)

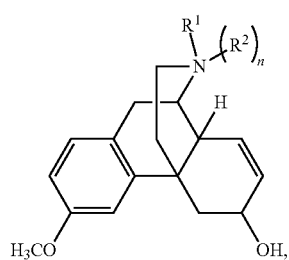
(FX41)
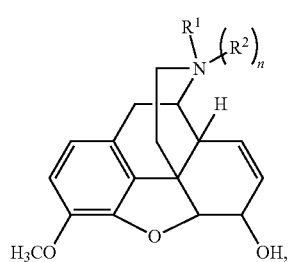
(FX42)
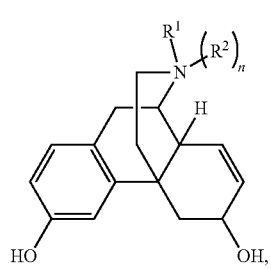
(FX43)
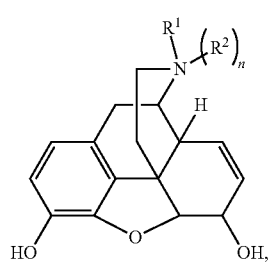
(FX44)
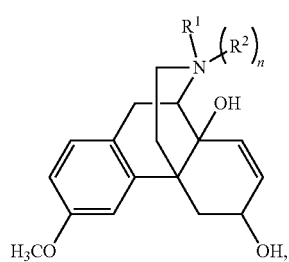
(FX45)
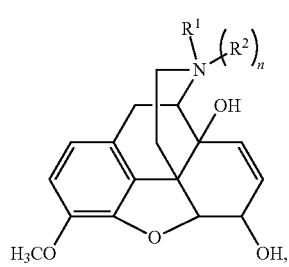
(FX46)
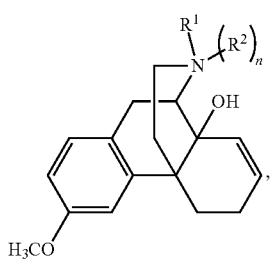
(FX47)
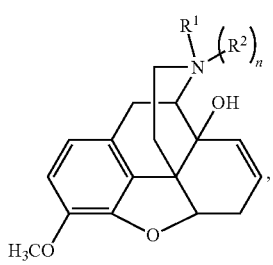
(FX48)
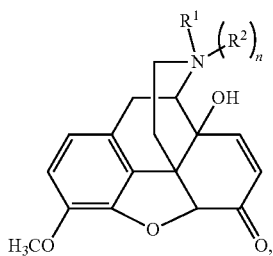
(FX49)
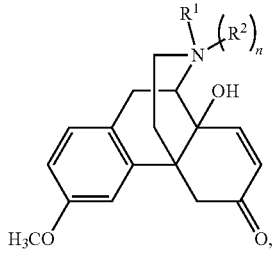
(FX50)
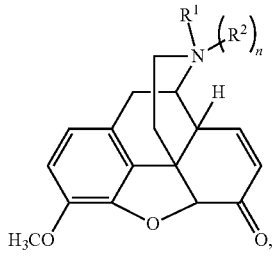
(FX51)
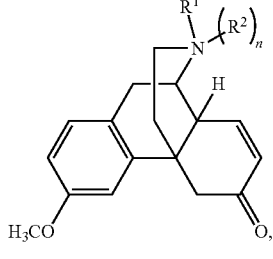
(FX52)

(FX53)
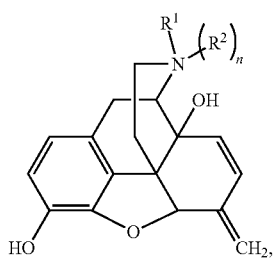

(FX54)
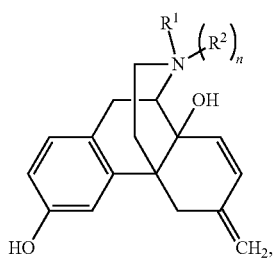

(FX55)
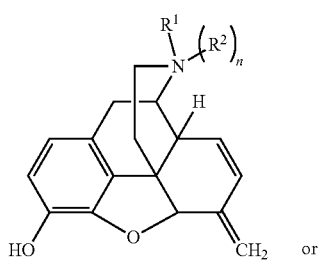 or (FX56)
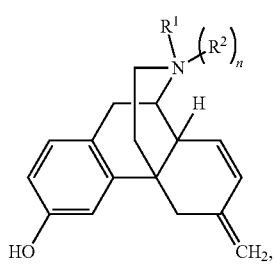

(FX57)
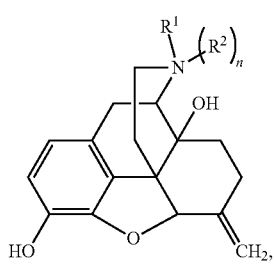

(FX58)
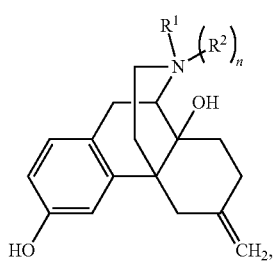

(FX59)
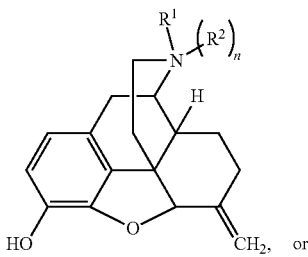, or (FX60)
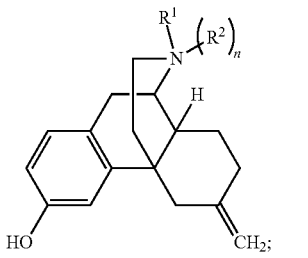;

or a pharmaceutically acceptable salt, solvate, or hydrate, clathrate or prodrug thereof; wherein n, $R^1$ and $R^2$ are defined as described in connection with formulae (FX1) and (FX2). In an embodiment, the invention provides compounds useful as anti-VEGF therapeutic agents for phototherapeutic methods or treatment of ocular neovascular disease or cancer having any one of formula (FX13)-(FX60), wherein $R^1$ or $R^2$ is allyl or:

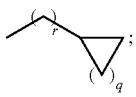

each q is independently an integer selected from 1 to 4; each r is independently an integer selected from 1 to 5, and optionally wherein $R^1$ or $R^2$ is —$CH_3$. In an embodiment, the invention provides N-oxide compounds useful as anti-VEGF therapeutic agents having formula (FX13)-(FX60) wherein $R^2$ is —($O^-$), and optionally $R^1$ is $C_1$-$C_{10}$ alkyl, $C_3$-$C_{10}$ cycloalkyl, $C_5$-$C_{10}$ aryl or $C_2$-$C_{10}$ alkenyl.

The invention of this aspect also provides purified stereoisomers of the compounds disclosed herein for use in a phototherapeutic procedure or for treatment of an ocular neovascular disease or cancer. In an embodiment, for example, the invention provides purified stereoisomer compounds for use in a phototherapeutic procedure or for treatment of an ocular neovascular disease or cancer, the compounds having any of the formula:

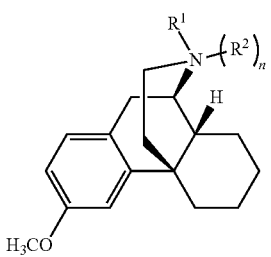

-continued
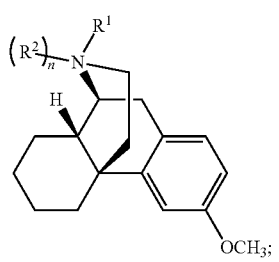
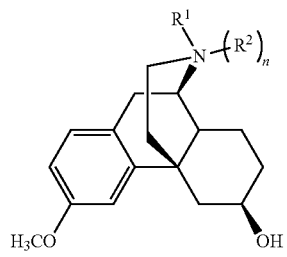
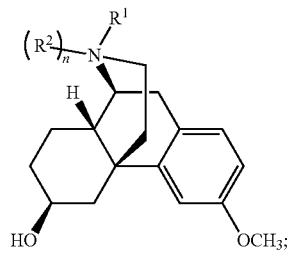
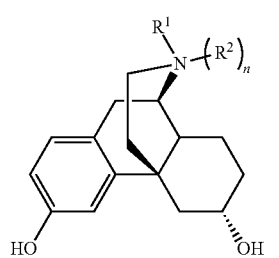
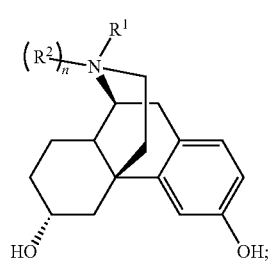
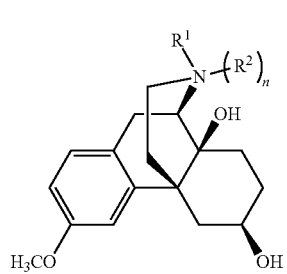
-continued
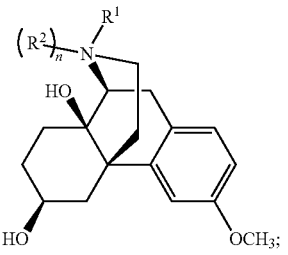
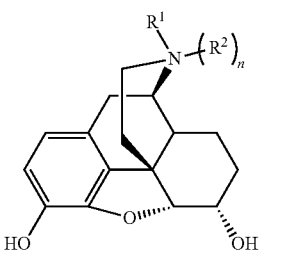
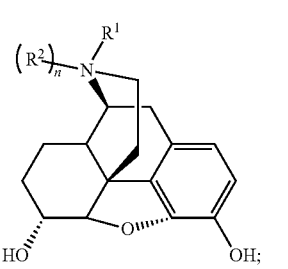
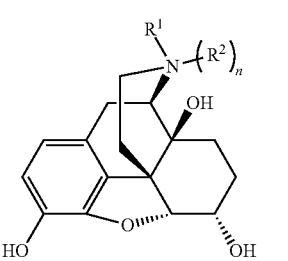
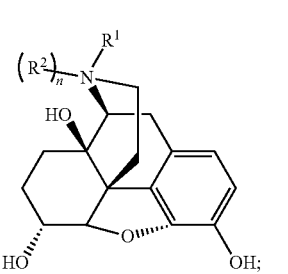
wherein $R^1$, $R^2$ and n are as described in the context of formulae (FX1) and (FX2).
In an embodiment, for example, the invention provides a compound comprising a purified stereoisomer for use in a phototherapy procedure or for treatment of an ocular neovascular disease or cancer, the compound having any of the formula (FX72) to (FX133):

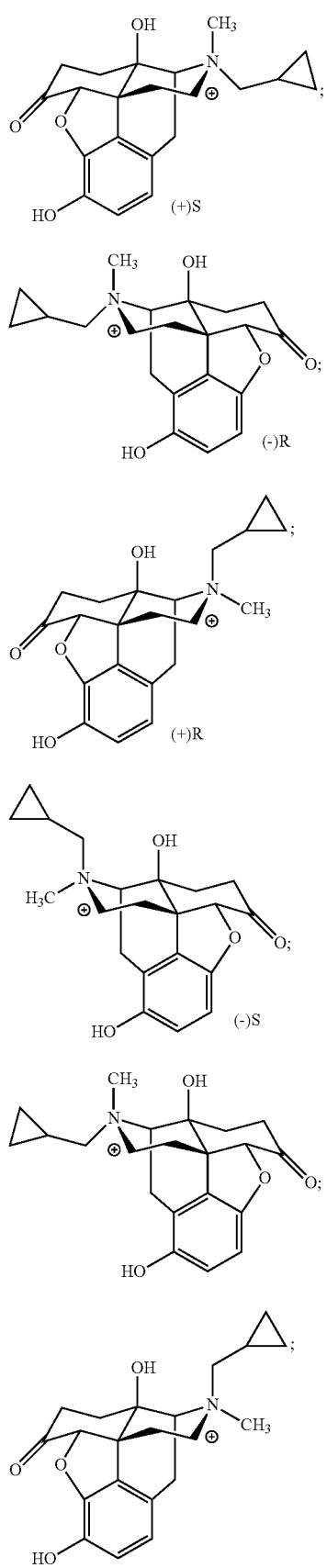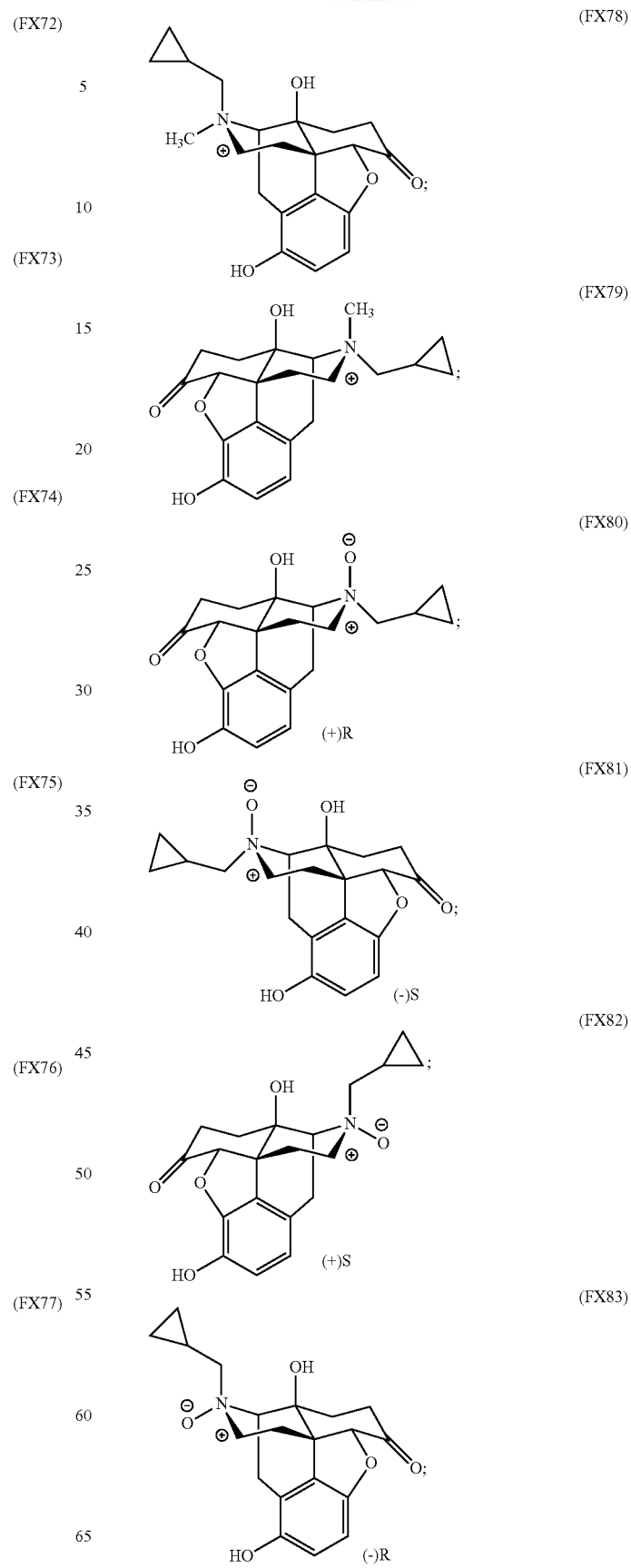

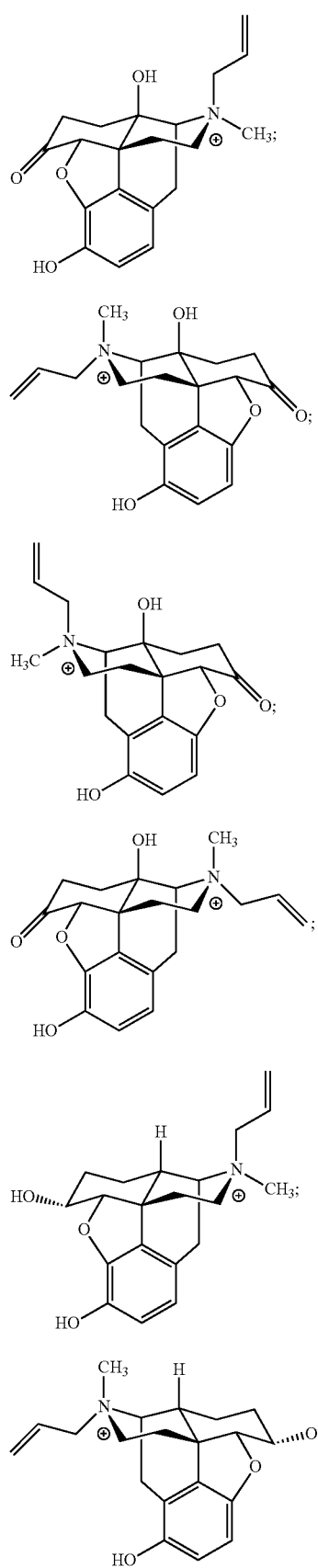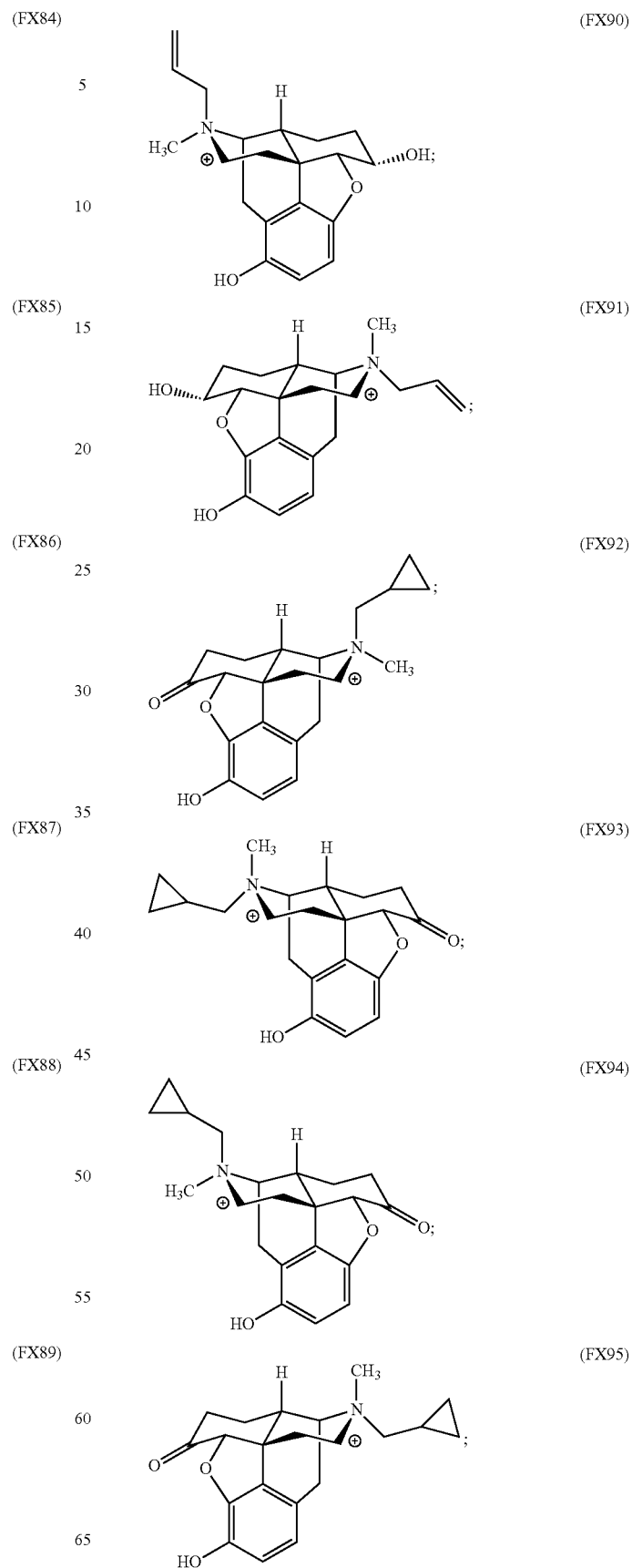

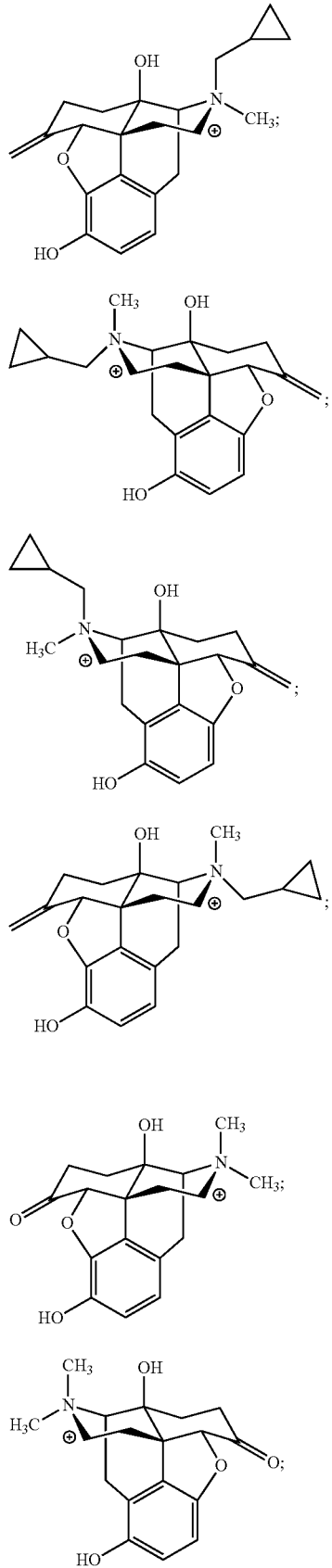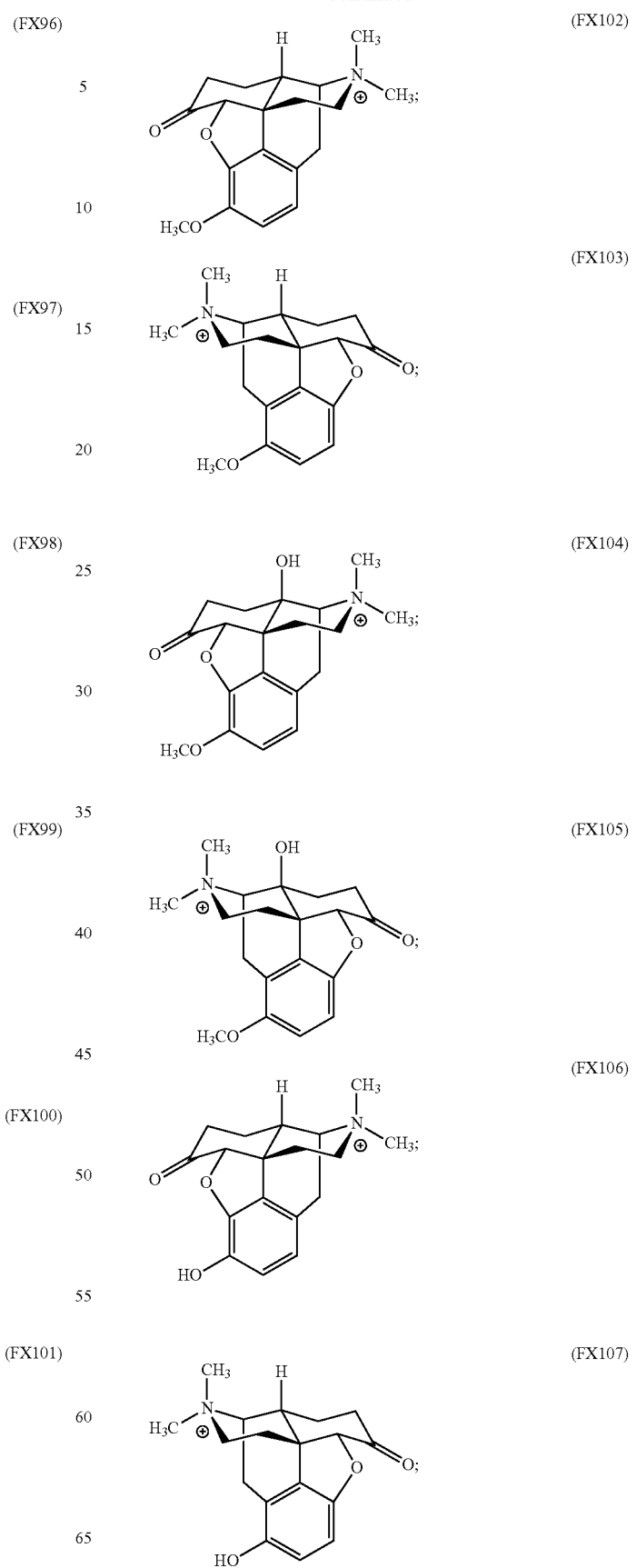

-continued
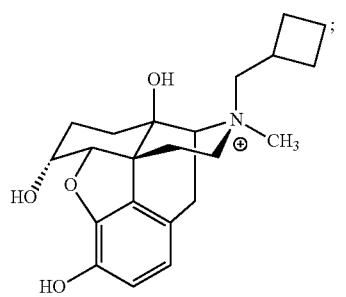
(FX108)
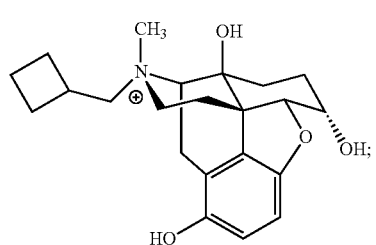
(FX109)
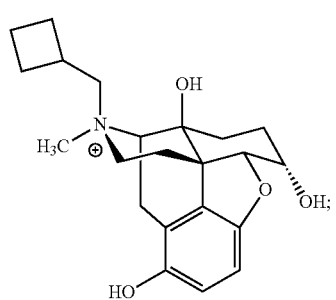
(FX110)
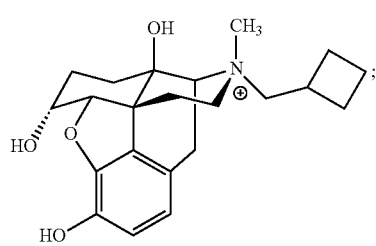
(FX111)
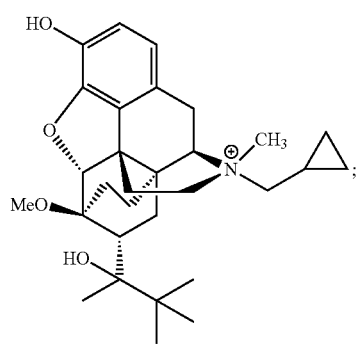
(FX112)
-continued
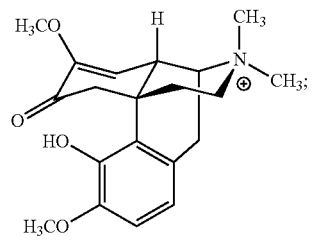
(FX113)
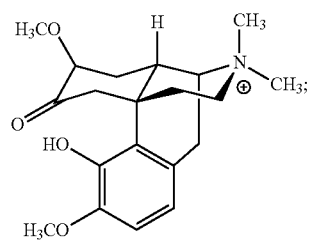
(FX114)
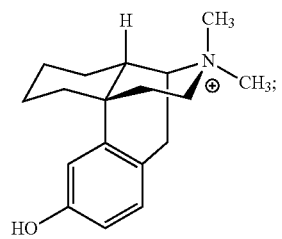
(FX115)
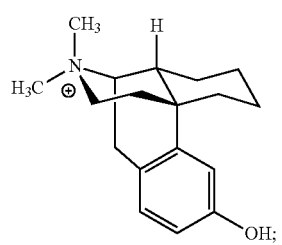
(FX116)
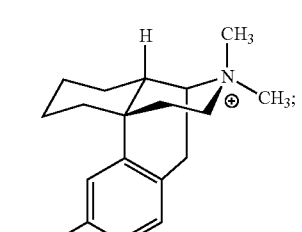
(FX117)
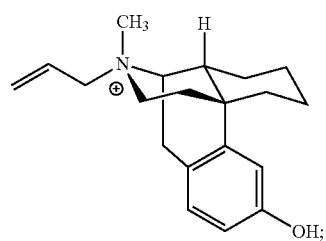
(FX118)

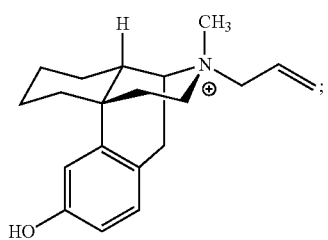 (FX119)
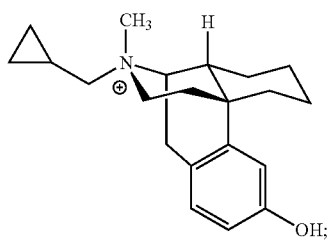 (FX120)
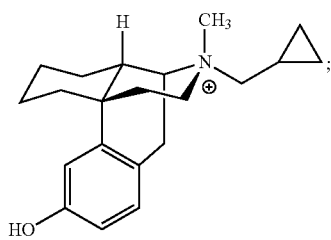 (FX121)
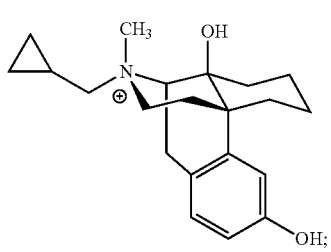 (FX122)
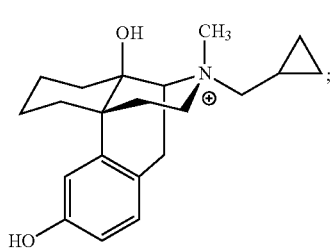 (FX123)
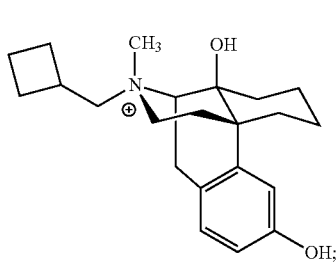 (FX124)
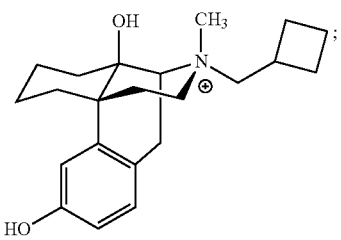 (FX125)
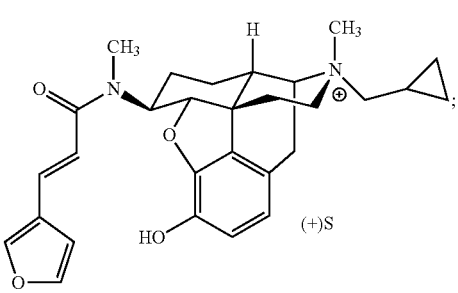 (FX126)
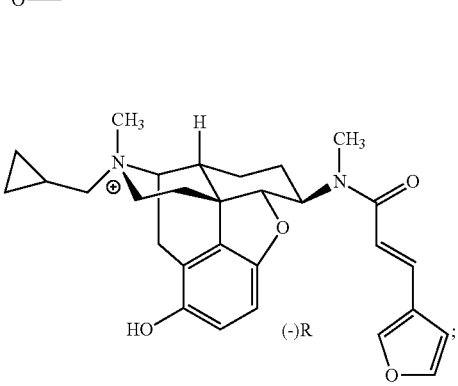 (FX127)
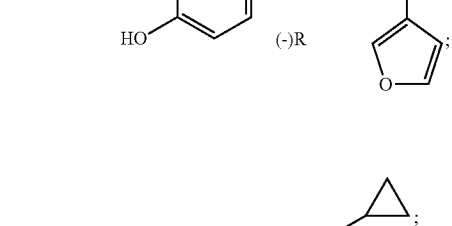 (FX128)
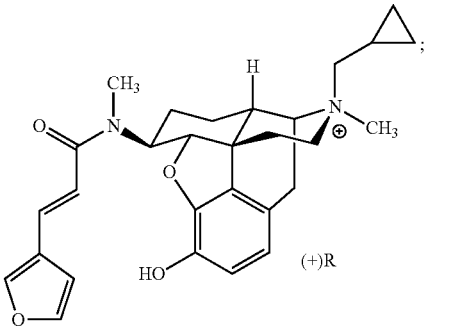 (FX129)

-continued

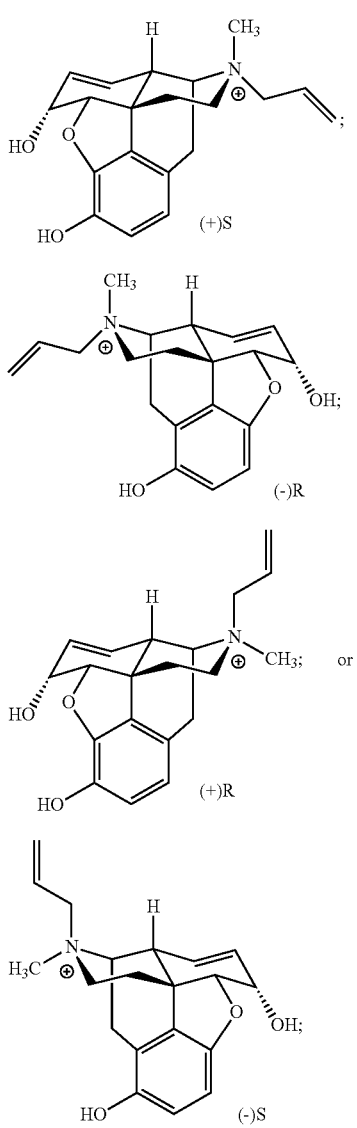

(FX130)

(+)S (FX131)

(-)R (FX132)

(+)R (FX133)

(-)S or a pharmaceutically acceptable salt, solvate, hydrate, clathrate or prodrug thereof. In an embodiment, the invention provides a compound for a phototherapy procedure or for treatment of an ocular neovascular disease or cancer having any of formula (FX72)-(FX133), provided in a substantially purified state substantially free of certain other isomers, such as a substantially purified (+) or (−) stereoisomer. In embodiments of this aspect, for example, the invention provides a compound for a phototherapy procedure or for treatment of an ocular neovascular disease or cancer having any of formula (FX72)-(FX133), provided in a substantially purified state substantially free of certain other stereoisomers, such as substantially free of other enantiomers. In an embodiment, for example, the invention provides a compound for a phototherapy procedure or for treatment of an ocular neovascular disease or cancer having any of formula (FX72)-(FX133), wherein the compound is provided as a substantially purified (+) enantiomer or a substantially purified (−) enantiomer.

In an embodiment, the invention provides a compound for use in a phototherapy procedure or for use in the treatment of an ocular neovascular disease, the compound having the formula (FX61):

(FX61)

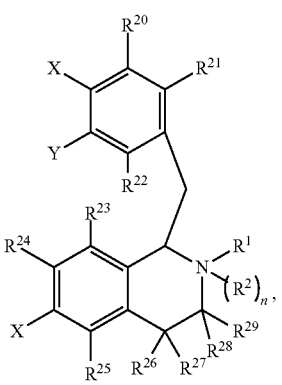

wherein: each X is independently —OH, —OCH$_3$, or C$_2$-C$_8$ alkoxy; Y is —H, or —OH;
each of R$^1$ and R$^2$ is independently —H, —CH$_3$, —(O$^-$), C$_1$-C$_{10}$ alkyl, C$_3$-C$_{10}$ cycloalkyl, C$_2$-C$_{10}$ alkenyl, C$_1$-C$_{10}$ haloalkyl, C$_5$-C$_{10}$ aryl, C$_5$-C$_{10}$ heteroaryl, C$_5$-C$_{10}$ alkylaryl, C$_5$-C$_{10}$ alkylheteroaryl, C$_5$-C$_{10}$ carbonylalkenylaryl, or C$_5$-C$_{10}$ carbonylalkenylheteroaryl; each of R$^{20}$-R$^{29}$ is independently —H, —OH, —OCH$_3$, C$_1$-C$_8$ alkyl, C$_3$-C$_8$ cycloalkyl, C$_2$-C$_8$ alkenyl, C$_1$-C$_8$ alkoxy, C$_5$-C$_{10}$ aryl, C$_5$-C$_{10}$ heteroaryl, C$_5$-C$_{10}$ alkylaryl, C$_5$-C$_{10}$ alkylheteroaryl, halo, nitrile, C$_1$-C$_8$ haloalkyl, C$_5$-C$_{10}$ carbonylalkenylheteroaryl, or C$_1$-C$_{10}$ hydroxyalkyl; and n is 0 or 1, wherein: when n is 1, the nitrogen to which R$^2$ is attached has a positive charge and optionally is associated with an anion; and when n is 0, R$^2$ is not present.

In an embodiment, the invention provides a compound for the treatment of cancer, the compound having the formula (FX61):

(FX61)

wherein: each X is independently —OH, —OCH$_3$, or C$_2$-C$_8$ alkoxy; Y is —H, or —OH; each of R$^1$ and R$^2$ is independently —H, —CH$_3$, —(O$^-$), C$_1$-C$_{10}$ alkyl, C$_3$-C$_{10}$ cycloalkyl, C$_2$-C$_{10}$ alkenyl, C$_1$-C$_{10}$ haloalkyl, C$_5$-C$_{10}$ aryl, C$_5$-C$_{10}$ heteroaryl, C$_5$-C$_{10}$ alkylaryl, C$_5$-C$_{10}$ alkylheteroaryl, C$_5$-C$_{10}$ carbonylalkenylaryl, or C$_5$-C$_{10}$ carbonylalkenylheteroaryl; each of R$^{20}$-R$^{29}$ is independently —H, —OH, —OCH$_3$, C$_1$-C$_8$ alkyl, C$_3$-C$_8$ cycloalkyl, C$_2$-C$_8$ alkenyl, C$_1$-C$_8$ alkoxy, C$_5$-C$_{10}$ aryl, C$_5$-C$_{10}$ heteroaryl, C$_5$-C$_{10}$ alkylaryl, C$_5$-C$_{10}$ alkylheteroaryl, halo, nitrile, C$_1$-C$_8$ haloalkyl, C$_5$-C$_{10}$ carbonylalkenylheteroaryl, or C$_1$-C$_{10}$ hydroxyalkyl; and n is 0 or 1, wherein: when n is 1, the nitrogen to which $R^2$ is attached has a positive charge and optionally is associated with an anion; and when n is 0, $R^2$ is not present.

In an embodiment, the invention provides a compound for the treatment of cancer, the compound having the formula (FX62):

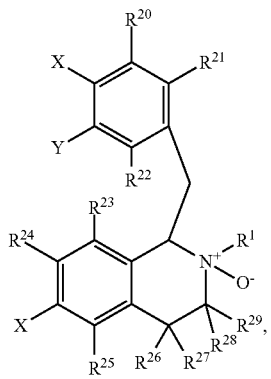
(FX62)

wherein: each X is independently —OH, —OCH$_3$, or C$_2$-C$_8$ alkoxy; Y is —H, or —OH;

$R^1$ is —H, —CH$_3$, C$_1$-C$_{10}$ alkyl, C$_3$-C$_{10}$ cycloalkyl, C$_2$-C$_{10}$ alkenyl, C$_1$-C$_{10}$ haloalkyl, C$_5$-C$_{10}$ aryl, C$_5$-C$_{10}$ heteroaryl, C$_5$-C$_{10}$ alkylaryl, C$_5$-C$_{10}$ alkylheteroaryl, C$_5$-C$_{10}$ carbonylalkenylaryl, or C$_5$-C$_{10}$ carbonylalkenylheteroaryl; and each of $R^{20}$-$R^{29}$ is independently —H, —OH, —OCH$_3$, C$_1$-C$_8$ alkyl, C$_3$-C$_8$ cycloalkyl, C$_2$-C$_8$ alkenyl, C$_1$-C$_8$ alkoxy, C$_5$-C$_{10}$ aryl, C$_5$-C$_{10}$ heteroaryl, C$_5$-C$_{10}$ alkylaryl, C$_5$-C$_{10}$ alkylheteroaryl, halo, nitrile, C$_1$-C$_8$ haloalkyl, C$_5$-C$_{10}$ carbonylalkenylheteroaryl, or C$_1$-C$_{10}$ hydroxyalkyl. In an embodiment, the invention provides a compound for the treatment of cancer, the compound having the formula (FX63):

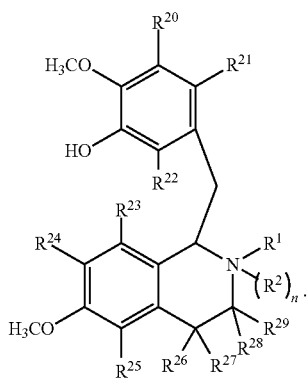
(FX63)

In an embodiment, the invention provides a compound for use in a phototherapy procedure or for use in the treatment of an ocular neovascular disease or cancer, the compound having any of formula (FX64), (FX65), (FX66), or (FX67):

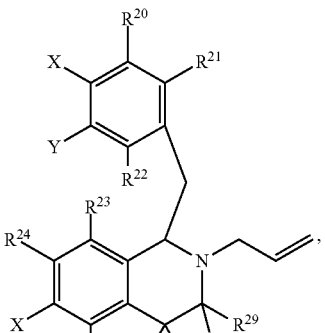
(FX64)

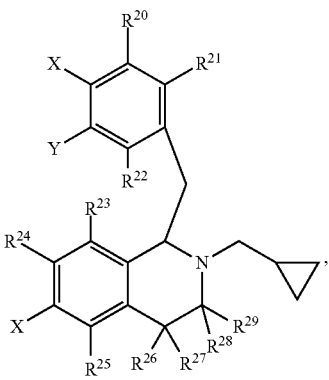
(FX65)

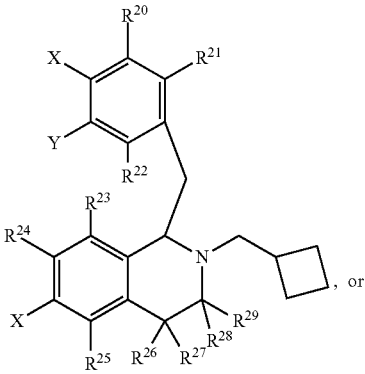
(FX66)

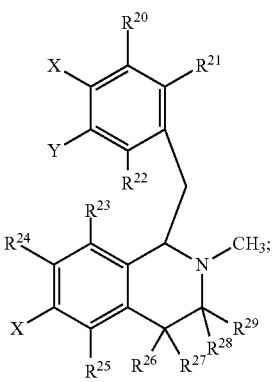
(FX67)

wherein X, Y and $R^{20}$-$R^{29}$ are as defined in the context of formula (FX61). In an embodiment, the invention provides a compound for use in a phototherapy procedure or for use in the treatment of an ocular neovascular disease or cancer, the compound having any of formula (FX68), (FX69), (FX70), or (FX71):

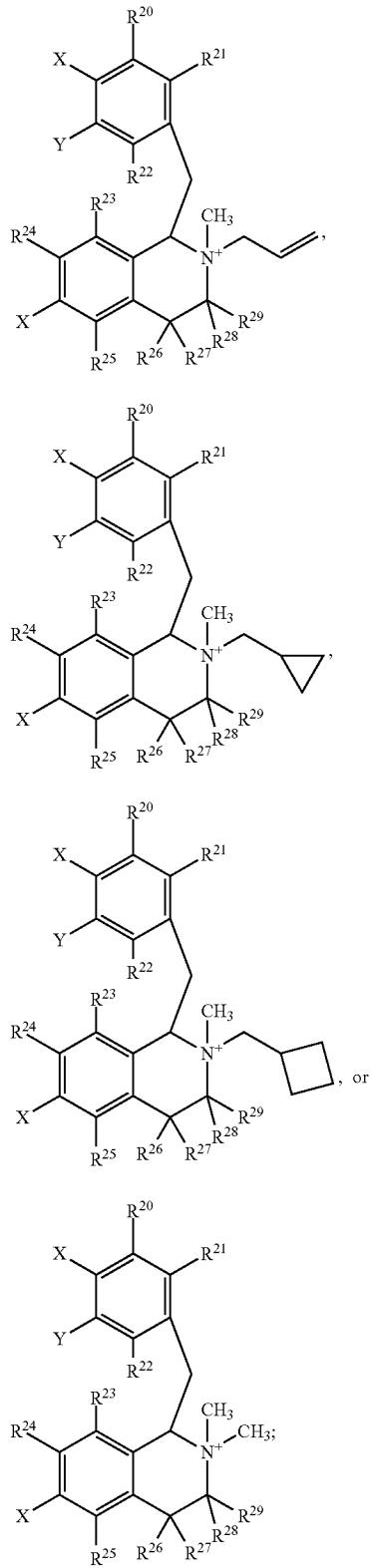

wherein X, Y and $R^{20}$-$R^{29}$ are as defined in the context of formula (FX61).

The invention of this aspect also provides purified stereoisomers of the compounds disclosed herein for use in a phototherapeutic procedure or for treatment of an ocular neovascular disease or cancer. In an embodiment, for example, the invention provides purified stereoisomer compounds for use in a phototherapeutic procedure or for treatment of an ocular neovascular disease or cancer, the compounds having any of the formula:

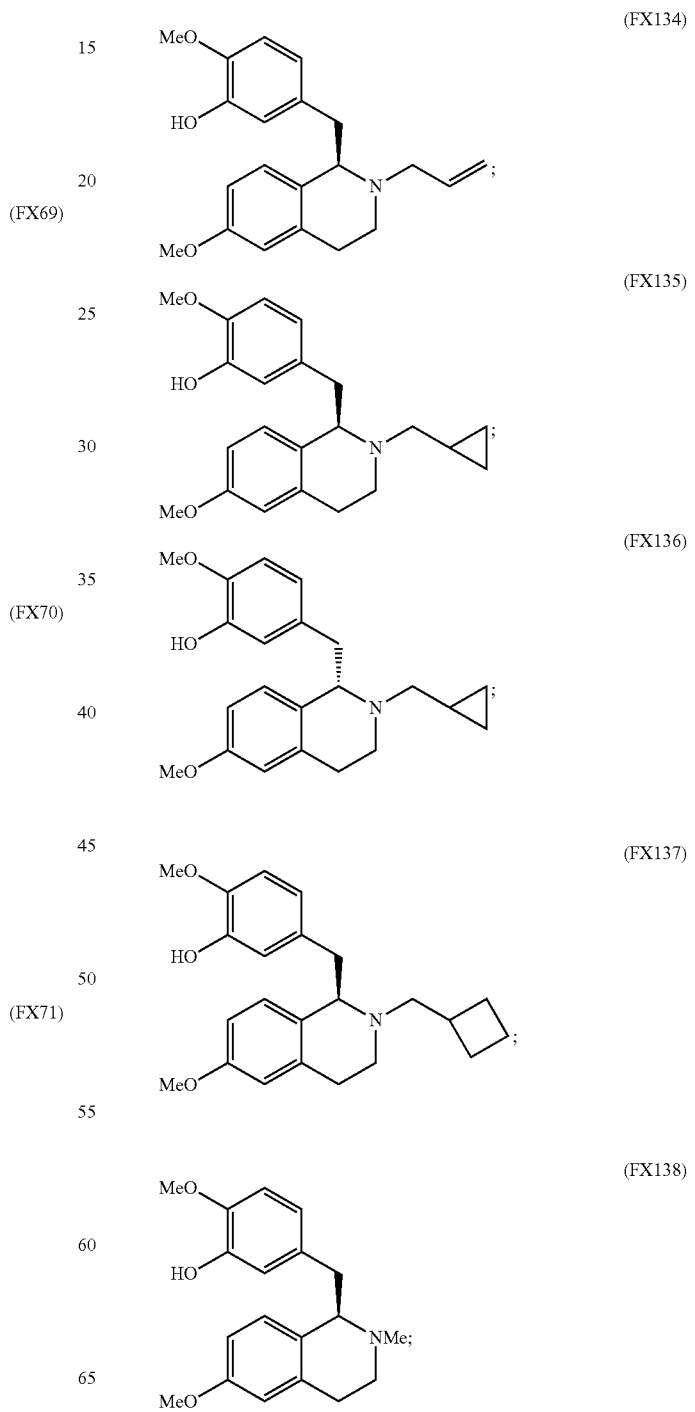

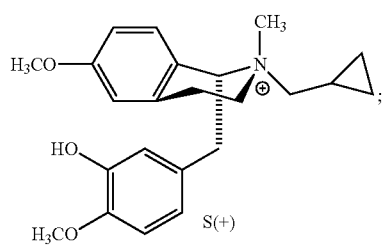
(FX139)
(FX145)
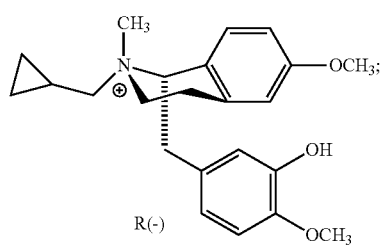
(FX140)
(FX146)
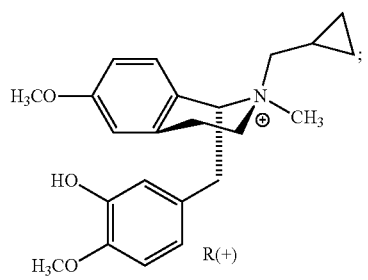
(FX141)
(FX147)
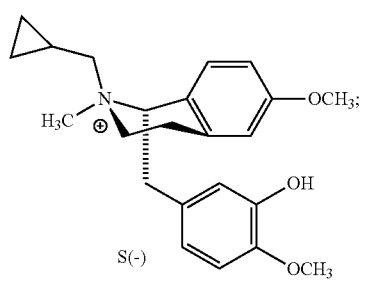
(FX142)
(FX148)
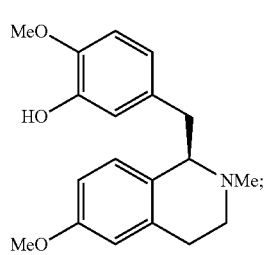
(FX143)
(FX149)
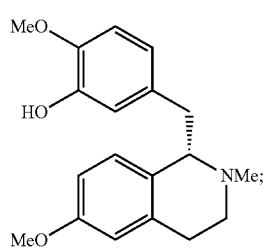
(FX144)
(FX150)

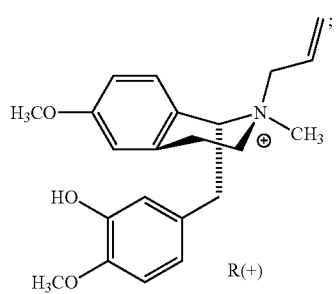
(FX151)
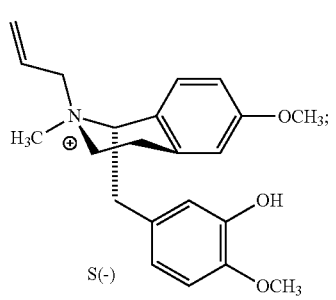
(FX152)
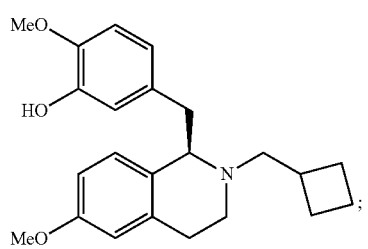
(FX153)
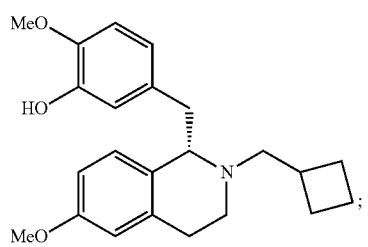
(FX154)
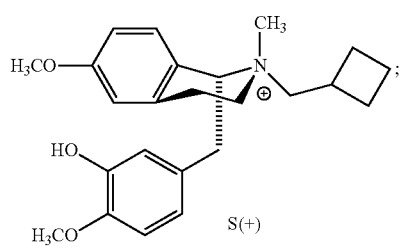
(FX155)
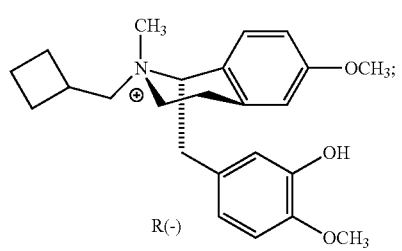
(FX156)
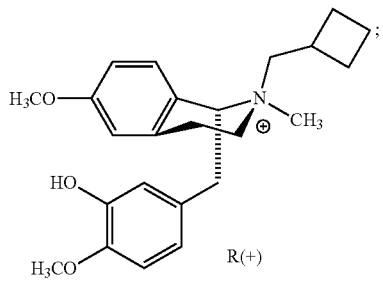
(FX157)
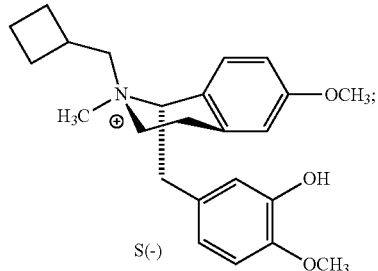
(FX158)
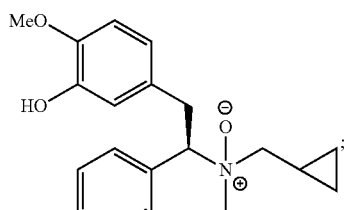
(FX159)
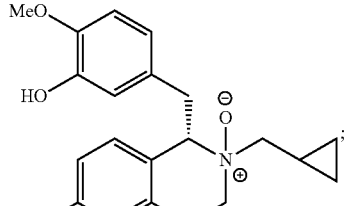
(FX160)
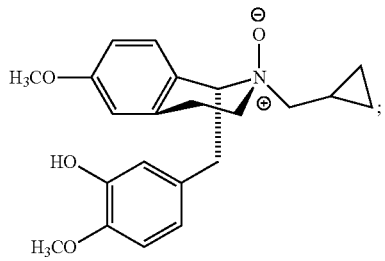
(FX161)
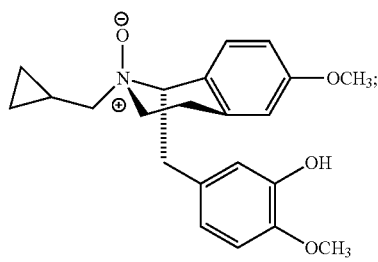
(FX162)

-continued

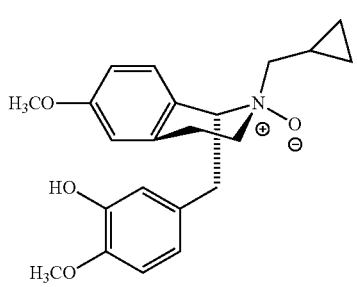
(FX163)

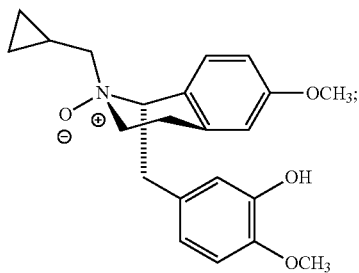
(FX164)

or a pharmaceutically acceptable salt, solvate, hydrate, clathrate or prodrug thereof. In an embodiment, the invention provides a compound for a phototherapy procedure or for treatment of an ocular neovascular disease or cancer having any of formula (FX134)-(FX164), provided in a substantially purified state substantially free of certain other isomers, such as a substantially purified (+) or (−) stereoisomer. In embodiments of this aspect, for example, the invention provides a compound for a phototherapy procedure or for treatment of an ocular neovascular disease or cancer having any of formula (FX134)-(FX164), provided in a substantially purified state substantially free of certain other stereoisomers, such as substantially free of other enantiomers. In an embodiment, for example, the invention provides a compound for a phototherapy procedure or for treatment of an ocular neovascular disease or cancer having any of formula (FX134)-(FX164), wherein the compound is provided as a substantially purified (+) enantiomer or a substantially purified (−) enantiomer.

In an embodiment, the invention provides compounds useful as anti-VEGF therapeutic agents for phototherapeutic methods having formula (FX1)-(FX164), wherein X is —OH or —OCH$_3$, and wherein Y is —OH. In an embodiment, the invention provides compounds useful as anti-VEGF therapeutic agents for phototherapeutic methods having formula (FX1)-(FX164), wherein R$^1$ or R$^2$ is allyl or

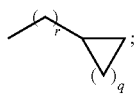

wherein each q is independently an integer selected from 1 to 4; each r is independently an integer selected from 1 to 5, and optionally wherein R$^1$ or R$^2$ is —CH$_3$ or R$^2$ is —(O$^−$).

The present invention includes therapeutic agents for phototherapy comprising purified stereoisomers (e.g., enantiomers and diastereomers), salts (including quarternary salts), N-oxides and/or ionic forms (e.g., protonated and deprotonated forms) of the compounds of formula (FX1) to (FX164), and mixtures thereof. Suitable pharmaceutically acceptable salts for compounds and compositions of the invention include, without limitation, metal salts such as aluminum, calcium, iron, magnesium, manganese and complex salts, and acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, cilexetil, citric, edetic, edisylic, estolic, esyl, esylic, formic, fumaric, gluceptic, gluconic, glutamic, glycolic, hexamic, hexylreserinoic, hydrobromic, hydrochloric, hydroiodic, hydroxynaphthoic, isethionic, lactic, lactobionic, maleic, malic, malonic, mandelic, methanesulfonic, mucic, muconic, napsylic, nitric, oxalic, p-nitromethanesulfonic, palmoic, pantothenic, phosphoric, monohydrogen phosphoric, dihydrogen phosphoric, phthalic, polygalactouronic, propionic, salicylic, stearic, succinic, sulfamic, sulfanlic, sulfonic, sulfuric, tannic, tartaric, teoclic, toluenesulfonic, polyglutamic, polyaspartic and the like.

In some embodiments, N-oxides compounds of the invention provide prodrugs of the corresponding base forms. For example, a variety of enzymes serve to reduce the N-oxide to the active morphinan. [See, e.g., U.S. Pat. No. 4,722,928 and U.S. Pat. No. 4,990,617]. 3-Hydroxy morphinan N-oxides; such as, N-oxides of naloxone, naltrexone, nalbuphine, nalmefene, pentazocine, butorphanol, buprenorphine, oxymorphone, morphine, dihydromorphine, hydromorphone, levorphanol, levallorphan, and etorphine, may exhibit significantly enhanced oral bioavailability of the corresponding reduced forms.

In an embodiment, the invention provides a compound for use in a phototherapy procedure and/or for use in the treatment of macular degeneration or cancer, the compound comprising the purified (+) enantiomers of the present opioids and/or derivatives or isomers thereof, such as (+) enantiomer morphinan compounds, (+) enantiomer morphinanium n-oxide compounds or (+) enantiomer morphinanium quarternary compounds and salts thereof. Methods of phototherapy and/or treatment of an ocular neovascular disease or cancer using a (+) enantiomer of the present opioids and/or derivatives that is substantially free of other isomers, such as the (−) enantiomers, is beneficial for some applications as the purified (+) enantiomer form of these compounds does not undergo specific binding to the opioid receptors. Use of purified (+) enantiomer compounds in the invention, therefore, enable therapeutic methods, including treatment providing effective anti-VEGF and/or anti-angiogenesis activity, with reduced peripheral and central nervous system effects as compared to use of corresponding racemic mixtures and (−) enantiomers. In an embodiment, the invention provides compounds for use in a phototherapy procedure and/or for use in the treatment of macular degeneration or cancer, the compound being the (+) enantiomer of any of the compounds having any of formula (FX1)-(FX164), wherein the compound is in a purified condition that is substantially free of other isomers, for example, substantially free of other stereoisomers such as (−) enantiomers.

In an embodiment, for example, the invention provides compounds for use in a phototherapy procedure and/or for use in the treatment of macular degeneration or cancer that are not nor-opiate compounds or salts thereof. In an embodiment, for example, the invention provides compounds for use in a phototherapy procedure and/or for use in the treatment of macular degeneration or cancer having any of formula (FX1)-(FX164), wherein R$^1$ and R$^2$ are each a group other than —H. In an embodiment, for example, the invention provides compounds for use in a phototherapy procedure and/or for use in the treatment of macular degeneration or cancer having any of formula (FX1)-(FX164), wherein when n is equal to 0 then R$^1$ is a group other than —H.

Anti-inflammatory agents of the present invention include therapeutic agents exhibiting in vivo anti-angiogenic activity and/or in vivo anti-VEGF activity. In an embodiment, for example, the invention provides an opioid or structurally related opioid derivative for use in a phototherapy procedure or in the treatment of an ocular neovascular disease or cancer that is an anti-angiogenesis agent. In an embodiment, for example, the invention provides an opioid or structurally related opioid derivative for use in a phototherapy procedure or in the treatment of an ocular neovascular disease or cancer that inhibits VEGF activity, optionally by inhibiting VEGF mediated intracellular signaling, for example by inhibiting VEGF receptor tyrosine phosphorylation and/or inhibiting VEGF mediated RhoA activation. The invention also includes opioids or structurally related opioid derivatives for use in a phototherapy procedure or in the treatment of an ocular neovascular disease or cancer that inhibit expression of VEGF or attenuates VEGF-induced VEGF receptor activation.

Anti-inflammatory agents of the present invention include a class of opioids, including opioid antagonists, opioid agonists and structurally related derivatives and isomers thereof, that exhibit anti-VEGF activity and/or anti-angiogenesis activity. In an embodiment, an opioid antagonist of the invention for a phototherapy procedure or treatment of an ocular neovascular disease or cancer is a quaternary or N-oxide derivative of (–) or (+) naltrexone, epimers of naltrexol, naloxone, nalmefene, or a quaternary derivative or a pharmaceutically acceptable salt thereof. For example, an opioid agonist of the invention for some phototherapy procedures and treatment of an ocular neovascular disease or cancer is methylnaltrexone or a salt of methylnaltrexone, such as naltrexone methobromide. In an embodiment, an opioid agonist of the invention for a phototherapy procedure or treatment of an ocular neovascular disease or cancer is a quarternary derivative or N-oxide of hydromorphone, epimers of naltrexol, nalmefene, nalorphine, nalbuphine, oxymorphone, oxycodone, hydrocodone, levorphanol, or a pharmaceutically acceptable salt thereof. In an embodiment, for example, a structurally related morphinan derivative of the invention for a phototherapy procedure or treatment of an ocular neovascular disease or cancer is a quaternary salt of dextrorphan, dextromethorphan, levorphanol, dextrallorphan, levallorphan, sinomenine, tetrahydrosinomenine, or a derivative or a pharmaceutically acceptable salt thereof.

Anti-inflammatory agents and VEGF inhibitors of the present invention may be co-administered with one or more other therapeutic agents. In an embodiment useful for the treatment of cancer, for example, an opioid compound or structurally related derivative of the present invention is co-administered with a cytotoxic agent. For example, the methylnaltrexone potentiates ~700× the cytotoxic effect of 5-fluorouracil. Combination therapy of cytotoxics with agents described herein is effective in treating cancers. (Singleton, P. A.; Garcia, J. G. N. and Moss, J, Mol Cancer Ther 2008; 7(6) 1669-1679.)

The invention also provides therapeutic agents for a phototherapy procedure or treatment of an ocular neovascular disease or cancer comprising a purified stereoisomer of an opioid or a quarternary derivative or a pharmaceutically acceptable salt thereof that is substantially free of other stereoisomers. Advantages of therapeutic agents comprising a purified stereoisomer may include increased in vivo anti-angiogenesis activity and increased in vivo anti-VEGF activity. Other advantages of therapeutic agents comprising a purified stereoisomer may include improved administration and targeted delivery performance and/or enhanced pharmacokinetic and toxicity characteristics.

In an embodiment of this aspect, for example, a composition of the invention for a phototherapy procedure or treatment of an ocular neovascular disease or cancer is a purified naltrexone stereoisomer quarternary derivative or N-oxide, or a pharmaceutically acceptable salt thereof, substantially free of other methylnaltrexone stereoisomers, wherein the purified naltrexone stereoisomer is (–)-R-methylnaltrexone, (+)-R-methylnaltrexone, (–)-S-methyl naltrexone, or (+)-S-methylnaltrexone.

In an embodiment of this aspect, for example, a compound of the invention for a phototherapy procedure or treatment of an ocular neovascular disease or cancer is a purified naloxone stereoisomer quarternary derivative or N-oxide, or a pharmaceutically acceptable salt thereof, substantially free of other naloxone stereoisomers; wherein the purified naloxone stereoisomer is (+)-R-methylnaloxone, (+)-S-methyl naloxone, (–)-S-methylnaloxone, or (–)-R-methylnaloxone.

In an embodiment of this aspect, for example, a compound of the invention for a phototherapy procedure or treatment of an ocular neovascular disease or cancer is a purified nalmefene stereoisomer quarternary derivative, or N-oxide, or a pharmaceutically acceptable salt thereof, substantially free of other nalmefene stereoisomers, wherein the nalmefene stereoisomer is (+)-R-methlylnalmefene, (+)-S-methylnalmefene, (–)-R-methylnalmefene, or (–)-S-methylnalmefene.

In an embodiment of this aspect, for example, a compound of the invention for a phototherapy procedure or treatment of an ocular neovascular disease or cancer is a purified nalbuphine stereoisomer, or a-quarternary derivative, or N-oxide thereof, or a pharmaceutically acceptable salt thereof substantially free of other nalbuphine stereoisomers, wherein the nalbuphine stereoisomer is (+)-R-methylnalbuphine, (+)-S-methylnalbuphine, (–)-R-methylnalbuphine, or (–)-S-methylnalbuphine.

In an embodiment of this aspect, for example, a compound of the invention for a phototherapy procedure or treatment of an ocular neovascular disease or cancer is a purified oxymorphone or a quarternary derivative thereof, or N-oxide thereof, substantially free of other oxymorphone stereoisomers, wherein the oxymorphone stereoisomer is (+)R- or S-N-alkyloxymorphone or (–)R- or S-N-alkyloxymorphone.

In an embodiment of this aspect, for example, a compound of the invention for a phototherapy procedure or treatment of an ocular neovascular disease or cancer is a purified hydrocodone stereoisomer or a quarternary derivative, or a N-oxide thereof, or a pharmaceutically acceptable salt thereof substantially free of other hydrocodone stereoisomers, wherein the hydrocodone stereoisomer is (+)R- or S-N-alkylhydrocodone or (–)R- or S-N-alkylhydrocodone.

In an embodiment of this aspect, for example, a compound of the invention for a phototherapy procedure or treatment of an ocular neovascular disease or cancer is a purified oxycodone stereoisomer or a quarternary derivative, or a N-oxide thereof, or a pharmaceutically acceptable salt thereof substantially free of other oxycodone stereoisomers, wherein the oxycodone stereoisomer is (+)R- or S-N-alkyloxycodone or (–)R or S-N-alkyloxycodone.

In an embodiment, for example, a compound of the invention for a phototherapy procedure or treatment of an ocular neovascular disease or cancer is a purified hydromorphone stereoisomer or a quarternary derivative, or a N-oxide thereof, or a pharmaceutically acceptable salt thereof substantially free of other hydromorphone stereoisomers, wherein the hydromorphone stereoisomer is (+)-hydromorphone or (−)-hydromorphone.

In an aspect, the invention provides a composition for use in a phototherapy procedure, wherein the composition comprises a mixture of two or more compounds having any of formulae (FX1)-(FX164) including isomers, N-oxides and salts thereof, and optionally a Type 1 or Type 2 phototherapy agent. In an aspect, the invention provides a composition for use in treatment of an ocular neovascular disease or cancer, wherein the composition comprises a mixture of two or more compounds having any of formulae (FX1)-(FX164) including isomers, N-oxides and salts thereof. In an embodiment, the invention provides a mixture or formulation for use in a phototherapy procedure or for use in treatment of an ocular neovascular disease or cancer, wherein at least one of dextrorphan, dextromethorphan, dextrallorphan, (+) cyclorphan, (+) butorphanol, tetrahydrosinomenine, or sinomenine is combined with at least one quarternary derivative or N-oxide of dextrorphan, dextromethorphan, dextrallorphan, (+) cyclorphan, (+) butorphanol, tetrahydrosinomenine, sinomenine or a pharmaceutically acceptable salt thereof. In an embodiment, the invention provides a mixture or formulation for use in a phototherapy procedure or for use in treatment of an ocular neovascular disease or cancer, wherein at least one of dextrorphan, dextromethorphan, dextrallorphan, (+) cyclorphan, (+) butorphanol, tetrahydrosinomenine, or sinomenine is combined with at least one quaternary derivative or N-oxide of either epimer of naltrexone, naloxone, naltrexol, nalbuphine, nalmefene, hydrocodone, or oxycodone. In an embodiment, the invention provides a mixture or formulation for use in a phototherapy procedure or for use in treatment of an ocular neovascular disease or cancer, wherein other stereoisomers of naltrexone, naloxone, naltrexol, nalbuphine, nalmefene, hydrocodone, oxycodone is combined with at least one quaternary derivative or N-oxide of dextrorphan, dextromethorphan, dextrallorphan, (+) cyclorphan, (+) butorphanol, tetrahydrosinomenine, or sinomenine.

The invention also provides a compound or composition described herein, or a pharmaceutical formulation thereof, for use in a medical phototherapy procedure comprising: administering to a subject in need of treatment a therapeutically effective amount of the compound or composition; administering to a subject in need of treatment a therapeutically effective amount of a phototherapy agent, and exposing the administered phototherapy agent to electromagnetic radiation. In an aspect, the phototherapy agent is a Type 1 or Type 2 phototherapy agent. The invention provides a compound or composition described herein, or a pharmaceutical formulation thereof, for use in a medical procedure for treatment of an ocular neovascular disease or cancer comprising: administering to a subject in need of treatment a therapeutically effective amount of the compound or composition described herein. In an aspect, the medical phototherapy procedure or medical procedure for treatment of an ocular neovascular disease or cancer comprises administrating to the subject a therapeutically effective amount of one or more additional therapeutic agents or diagnostic agents, wherein the one or more additional therapeutic agents or diagnostic agents is one or more alkylating agents, antimetabolites, anti-cytoskeletal agents, topoisomerase inhibitors, anti-hormonal agents, or targeted therapeutic agents. In an embodiment, the invention provides a method comprising contacting a cell expressing VEGF with a compound having any of formula (FX1)-(FX164), for example for a phototherapy procedure, for the treatment of an ocular neovascular disease (e.g., MD or AMD) or for treatment of cancer. In an embodiment, the invention provides a method comprising contacting a target tissue with a compound having any of formula (FX1)-(FX164), for example contacting a cancer cell or tumor with a compound having any of formula (FX1)-(FX164).

In an embodiment, the invention provides a method of treatment, comprising administering to a subject with a disorder characterized by unwanted migration or proliferation of endothelial cells an effective amount of any compound or composition described herein.

Without wishing to be bound by any particular theory, there can be discussion herein of beliefs or understandings of underlying principles or mechanisms relating to the invention. It is recognized that regardless of the ultimate correctness of any explanation or hypothesis, an embodiment of the invention can nonetheless be operative and useful. Various features discussed herein in relation to one or more of the exemplary embodiments may be incorporated into any of the described aspects of the present invention alone or in any combination.

Certain exemplary aspects of the invention are set forth herein. It should be understood that these aspects are presented merely to provide the reader with a brief summary of certain forms the invention might take and that these aspects are not intended to limit the scope of the invention. Indeed, the invention may encompass a variety of aspects that may not be explicitly set forth herein as would be understood by one of ordinary skill in the relevant art without undue experimentation.

BRIEF DESCRIPTION OF THE FIGURES

FIG. 6 shows tumor weight for control conditions corresponding to intraperitoneal injection of PBS and conditions for corresponding to intraperitoneal injection of MNTX1.

STATEMENTS REGARDING CHEMICAL COMPOUNDS AND NOMENCLATURE

Figure 1A:
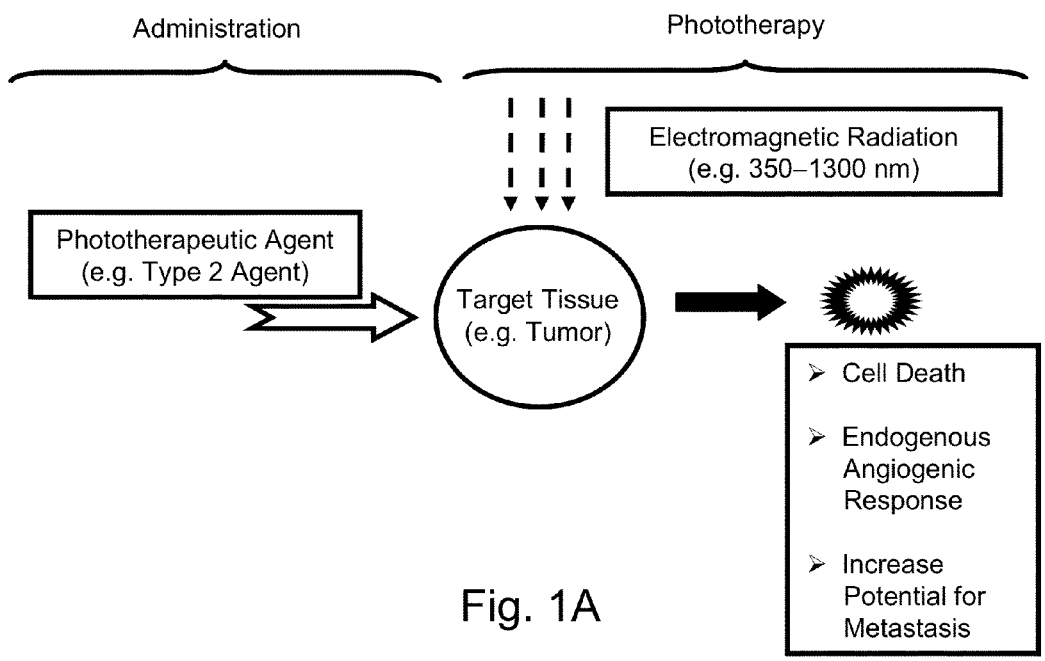
FIGS. 1A and 1B provide schematic illustrations of methods of the present invention for a phototherapy procedure involving (1A) administration of a phototherapy agent without an anti-VEGF therapeutic agent and (1B) co-administration of a phototherapy agent and an anti-VEGF therapeutic agent. Some of these compounds inhibit the expression by VEGF but are not believed to neutralize VEGF directly like an antibody of VEGF.

In an embodiment, a composition or compound of the invention is isolated or purified. In an embodiment, an isolated or purified compound can be at least partially isolated or purified as would be understood in the art. In an embodiment, the composition or compound of the invention has a chemical purity of 95%, optionally for some applications 99%, optionally for some applications 99.9%, optionally for some applications 99.99%, and optionally for some applications 99.999% pure.

Many of the molecules disclosed herein contain one or more ionizable groups. Ionizable groups are groups from which a proton can be removed (e.g., —COOH) or added (e.g., amines) or which can be quaternized (e.g., amines). All possible ionic forms of such molecules and salts thereof are intended to be included individually in the disclosure herein. With regard to salts of the compounds herein, one of ordinary skill in the art can select from among a wide variety of available counterions that are appropriate for preparation of salts of this invention for a given application. In specific applications, the selection of a given anion or cation for preparation of a salt can result in increased or decreased solubility of that salt.

The compounds of this invention can contain one or more chiral centers. Accordingly, this invention is intended to include racemic mixtures, diasteromers, enantiomers, tautomers and mixtures enriched in one or more stereoisomer. The scope of the invention as described and claimed encompasses the racemic forms of the compounds as well as the individual enantiomers and non-racemic mixtures thereof.

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to valence state. The present invention includes groups characterized as monovalent, divalent, trivalent etc. valence states.

As is customary and well known in the art, hydrogen atoms in formulas (FX1)-(FX164) are not always explicitly shown, for example, hydrogen atoms bonded to the carbon atoms of aromatic, heteroaromatic, and alicyclic rings are not always explicitly shown in formulas (FX1)-(FX164). The structures provided herein, for example in the context of the description of formulas (FX1)-(FX164), are intended to convey to one of reasonable skill in the art the chemical composition of compounds of the methods and compositions of the invention, and as will be understood by one of skill in the art, the structures provided do not indicate the specific bond angles between atoms of these compounds.

As used herein, the term "alkylene" refers to a divalent radical derived from an alkyl group as defined herein. Alkylene groups in some embodiments function as attaching and/or spacer groups in the present compositions. Compounds of the invention may have substituted and unsubstituted $C_1$-$C_{20}$ alkylene, $C_1$-$C_{10}$ alkylene and $C_1$-$C_5$ alkylene groups.

As used herein, the term "cycloalkylene" refers to a divalent radical derived from a cycloalkyl group as defined herein. Cycloalkyl groups in some embodiments function as attaching and/or spacer groups in the present compositions. Compounds of the invention may have substituted and unsubstituted $C_1$-$C_{20}$ cycloalkyl, $C_1$-$C_{10}$ cycloalkyl and $C_1$-$C_5$ cycloalkyl groups.

As used herein, the term "arylene" refers to a divalent radical derived from an aryl group as defined herein. In some embodiments, an arylene is a divalent group derived from an aryl group by removal of hydrogen atoms from two intra-ring carbon atoms of an aromatic ring of the aryl group. Arylene groups in some embodiments function as attaching and/or spacer groups in the present compositions. Arylene groups in some embodiments function as chromophore, fluorphore, aromatic antenna, dye and/or imaging groups in the present compositions. Compounds of the invention include substituted and unsubstituted $C_1$-$C_{30}$ arylene, $C_1$-$C_{20}$ arylene, $C_1$-$C_{10}$ arylene and $C_1$-$C_5$ arylene groups.

As used herein, the term "heteroarylene" refers to a divalent radical derived from a heteroaryl group as defined herein. In some embodiments, an heteroarylene is a divalent group derived from an heteroaryl group by removal of hydrogen atoms from two intra-ring carbon atoms or intra-ring nitrogen atoms of a heteroaromatic or aromatic ring of the heteroaryl group. Heteroarylene groups in some embodiments function as attaching and/or spacer groups in the present compositions. Heteroarylene groups in some embodiments function as chromophore, aromatic antenna, fluorphore, dye and/or imaging groups in the present compositions. Compounds of the invention include substituted and unsubstituted $C_1$-$C_{30}$ heteroarylene, $C_1$-$C_{20}$ heteroarylene, $C_1$-$C_{10}$ heteroarylene and $C_1$-$C_5$ heteroarylene groups.

As used herein, the term "cycloalkylene" refers to a divalent radical derived from a cycloalkyl group as defined herein. Cycloalkylene groups in some embodiments function as attaching and/or spacer groups in the present compositions. Compounds of the invention include substituted and unsubstituted $C_1$-$C_{20}$ cycloalkylene, $C_1$-$C_{10}$ cycloalkylene and $C_1$-$C_5$ cycloalkylene groups.

As used herein, the term "alkenylene" refers to a divalent radical derived from an alkenyl group as defined herein. Alkenylene groups in some embodiments function as attaching and/or spacer groups in the present compositions. Compounds of the invention include substituted and unsubstituted $C_1$-$C_{20}$ alkenylene, $C_1$-$C_{10}$ alkenylene and $C_1$-$C_5$ alkenylene groups.

As used herein, the term "cylcoalkenylene" refers to a divalent radical derived from a cylcoalkenyl group as defined herein. Cycloalkenylene groups in some embodiments function as attaching and/or spacer groups in the present compositions. Compounds of the invention include substituted and unsubstituted $C_1$-$C_{20}$ cylcoalkenylene, $C_1$-$C_{10}$ cylcoalkenylene and $C_1$-$C_5$ cylcoalkenylene groups.

As used herein, the term "alkynylene" refers to a divalent radical derived from an alkynyl group as defined herein. Alkynylene groups in some embodiments function as attaching and/or spacer groups in the present compositions. Compounds of the invention include substituted and unsubstituted $C_1$-$C_{20}$ alkynylene, $C_1$-$C_{10}$ alkynylene and $C_1$-$C_5$ alkynylene groups.

As used herein, the term "halo" refers to a halogen group such as a fluoro (—F), chloro (—Cl), bromo (—Br), or iodo (—I).

The term "heterocyclic" refers to ring structures containing at least one other kind of atom, in addition to carbon, in the ring. Examples of such atoms include nitrogen, oxygen and sulfur. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups.

The term "carbocyclic" refers to ring structures containing only carbon atoms in the ring. Carbon atoms of carbocyclic rings can be bonded to a wide range of other atoms and functional groups.

The term "alicyclic" refers to a ring that is not an aromatic ring. Alicyclic rings include both carbocyclic and heterocyclic rings.

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term "polyalkoxyalkyl" refers to a substituent of the formula alkyl-(alkoxy)$_n$-alkoxy wherein n is an integer from 1 to 10, preferably 1 to 4, and more preferably for some embodiments 1 to 3.

As used herein, the term "allyl" refers to a substituent of the formula —CH$_2$CH=CH$_2$.

Amino acids include glycine, alanine, valine, leucine, isoleucine, methionine, proline, phenylalanine, tryptophan, asparagine, glutamine, glycine, serine, threonine, serine, rhreonine, asparagine, glutamine, tyrosine, cysteine, lysine, arginine, histidine, aspartic acid and glutamic acid. As used herein, reference to "a side chain residue of a natural α-amino acid" specifically includes the side chains of the above-referenced amino acids.

Alkyl groups include straight-chain, branched and cyclic alkyl groups. Alkyl groups include those having from 1 to 30 carbon atoms. The term cycloalkyl refers to an alky group having a ring structure, such as a. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. Cyclic alkyl groups include those having one or more rings. Cycloalkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cycloalkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogen atoms replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein MeO— refers to CH$_3$O—.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms.

Aryl groups include groups having one or more 5-, 6- or 7-member aromatic and/or heterocyclic aromatic rings. The term heteroaryl specifically refers to aryl groups having at least one 5-, 6- or 7-member heterocyclic aromatic rings. Aryl groups can contain one or more fused aromatic and heteroaromatic rings or a combination of one or more aromatic or heteroaromatic rings and one or more nonaromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those which are substituted with alkyl or alkenyl groups, which groups in turn can be optionally substituted. Specific aryl groups include phenyl, biphenyl groups, pyridyl, quinolyl, isoquinolyl, pyridazinyl, pyrazinyl, indolyl, imidazolyl, oxazolyl, thiazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, oxazole, thiazole, pyrazine, benzimidazole, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic radical, including monovalent, divalent and polyvalent radicals, of the aromatic and heterocyclic aromatic groups listed herein are provided in a covalently bonded configuration in the compounds of the invention at any suitable point of attachment. In embodiments, aryl groups contain between 5 and 30 carbon atoms. In embodiments, aryl groups contain one aromatic or heteroaromatic six-membered ring and one or more additional five- or six-membered aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms.

As to any of the groups described herein which contain one or more substituents, it is understood that such groups do not contain any substitution or substitution patterns which are sterically impractical and/or synthetically non-feasible. In addition, the compounds of this invention include all stereochemical isomers arising from the substitution of these compounds. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for any alkyl, alkenyl and aryl group includes substitution with one or more of the following substituents, among others:
halogen, including fluorine, chlorine, bromine or iodine;
pseudohalides, including —CN;
—COOR where R is a hydrogen or an alkyl group or an aryl group and more specifically where R is a methyl, ethyl, propyl, butyl, or phenyl group all of which groups are optionally substituted;
—COR where R is a hydrogen or an alkyl group or an aryl group and more specifically where R is a methyl, ethyl, propyl, butyl, or phenyl group all of which groups are optionally substituted;
—CON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;
—OCON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;
—N(R)$_2$ where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring which can contain one or more double bonds and can contain one or more additional carbon atoms;
—SR, where R is hydrogen or an alkyl group or an aryl group and more specifically where R is hydrogen, methyl, ethyl, propyl, butyl, or a phenyl group, which are optionally substituted;
—SO$_2$R, or —SOR where R is an alkyl group or an aryl group and more specifically where R is a methyl, ethyl, propyl, butyl, or phenyl group, all of which are optionally substituted;
—OCOOR where R is an alkyl group or an aryl group;
—SO$_2$N(R)$_2$ where each R, independently of each other R, is a hydrogen, or an alkyl group, or an aryl group all of which are optionally substituted and wherein R and R can form a ring which can contain one or more double bonds and can contain one or more additional carbon atoms;
—OR where R is H, an alkyl group, an aryl group, or an acyl group all of which are optionally substituted. In a particular example R can be an acyl yielding —OCOR" where R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

DETAILED DESCRIPTION

Referring to the drawings, like numerals indicate like elements and the same number appearing in more than one drawing refers to the same element. In general the terms and phrases used herein have their art-recognized meaning, which can be found by reference to standard texts, journal references and contexts known to those skilled in the art. The following definitions are provided to clarify their specific use in the context of the invention.

"Optical agent" generally refers to compositions, preparations, and/or formulations that absorb, emit, or scatter electromagnetic radiation of wavelength, generally in the range of 350-1300 nanometers, within a biologically relevant environment or condition. Optical agents optionally have molecular recognition or targeting functions enabling localized delivery to a target tissue. "Optical imaging agents" or "optical contrast agents" are a class of optical agents that undergo emission via fluorescence or phosphorescence pathways when excited by electromagnetic radiation. These pathways are useful for diagnostic imaging, visualization, or organ function monitoring. "Phototherapy agents" and "photosensitizers" are used interchangeably and refer to a class of optical agents that absorb electromagnetic radiation and undergo photochemical reactions, such as photofragmentation of one or more photolabile bonds, to generate reactive intermediates for achieving a desired therapeutic result. Phototherapy agents include compounds that absorbed visible and/or near infrared radiation and generate nitrenes, carbene, free radicals, and/or ions. Phototherapy agents are useful for a wide range of phototherapy applications, for example in the treatment of tumors or other lesions and in the treatment of age related macular degeneration. Phototherapy agents include Type 1 and Type 2 phototherapy agents.

"Phototherapy procedure" refers to a therapeutic procedure involving administration of a photosensitizer to a patient followed by subsequent excitation of the phototherapy agent by exposure to applied electromagnetic radiation, such as electromagnetic radiation having wavelengths in the visible and/or near IR region of the electromagnetic spectrum, such as wavelengths in the range of 350-1300 nanometers. Phototherapy includes, but is not limited to, photodynamic therapy. As used herein phototherapy includes procedures involving administration of Type 1 and/or Type 2 phototherapy agents, optionally further including administration of one or more additional therapeutic agents, such as anti-angiogenesis agents or anti-VEGF agents.

"Opioid" refers to compounds which bind to opioid receptors. Opioid includes both opioid agonists and opioid antagonists. Opioid agonists bind to opioid receptors and alter the function of the receptor, for example by stimulating the receptor. Opioid agonist include synthetic opioid agonists and semisynthetic opioid agonists. Opioid antagonists bind to opioid receptors and do not substantially alter the function of the receptor, for example by not stimulating the receptor. Opioids of the present invention include mu opioid antagonists, mu opioid agonists, kappa opioid antagonists, and kappa opioid agonists. In some embodiments, compositions and methods of the present invention include peripheral opioids that do not tend to cross the blood brain barrier. Peripheral opioids act primarily on the physiological systems and components external to the central nervous system. In some embodiments, compositions and methods of the present invention include central-acting opioids that readily cross the blood brain barrier central and hence act on physiological systems and components of the central nervous system.

"Angiogenesis" refers molecular and physiological processes involved in the production of new blood vessels. The formation of new blood cells via angiogenesis may involve migration, proliferation and differentiation of endothelial cells. "Angiogenic agent" refers to a compound which induces or promotes angiogenesis. "Anti-angiogenic agent" refers to the capability of a compound, or pharmaceutical formulation thereof, to attenuate, inhibits or otherwise reduces angiogenesis, including in some conditions attenuation of the migration, proliferation and differentiation of endothelial cells. Anti-angiogenic agents of the present invention may reduce or terminate formation of new blood vessels in a target tissue. "Proangiogenesis effect" refers to the action of a medical procedure, such as a phototherapy procedure, which acts to cause an increase in angiogenesis.

"Target tissue" refers to tissue of a subject to which an opioid compound, structurally related opioid derivative or isomer thereof and/or phototherapy agent is administered or otherwise contacted, for example during a medical procedure such as a phototherapy procedure, treatment of an ocular neovascular disease, and/or treatment of cancer. Target tissue may be contacted with an opioid compound, structurally related opioid derivative or isomer thereof and/or phototherapy agent of the invention under in vivo conditions or ex vivo conditions. Target tissues in some methods of the invention include cancerous tissue, precancerous tissue, a tumor, a lesion, a site of inflammation, or vasculature tissue. Target tissue in some methods of the invention include a melanoma cell, a breast lesion, a prostate lesion, a lung cancer cell, a colorectal cancer cell, an atherosclerotic plaque, a brain lesion, a blood vessel lesion, a lung lesion, a heart lesion, a throat lesion, an ear lesion, a rectal lesion, a bladder lesion, a stomach lesion, an intestinal lesion, an esophagus lesion, a liver lesion, or a pancreatic lesion. Target tissue in some embodiments refers to a selected organ of the subject or component thereof, such as lung, heart, brain, stomach, liver, kidneys, gallbladder, pancreas, intestines, rectum, skin, prostate, ovaries, breast, bladder, blood vessel, throat, ear, or esophagus.

An anti-VEGF agent is a compound which attenuates, inhibits or otherwise reduces VEGF activity in a target tissue. An anti-VEGF agent may inhibit VEGF activity by affecting a range of biological agents and biological processes. In some embodiments, for example, an anti-VEGF agent inhibits expression of VEGF, or directly binds to VEGF in a manner reducing its ability to interact with biological agents in one or more biological pathways. In some embodiments, for example, an anti-VEGF agent interferes or otherwise disrupts VEGF ligand receptor binding, and/or interferes with post-receptor binding VEGF mediated cellular signaling. In an embodiment, for example, anti-VEGF agents of the invention are opioids and structurally related derivatives that attenuate VEGF activity by reducing or otherwise interfering with receptor tyrosine phosphorylation and/or VEGF mediated RhoA activation and other pathways.

As used herein, the term "substantially free of other isomers" refers to a composition or pharmaceutical formulation thereof comprising a high molar ratio of one isomer of a given molecule with respect to some or all other isomers of the given molecule. In some aspects of the present invention, for example, a purified isomer substantially free of other isomers refers to a composition characterized by a molar ratio of the purified isomer to some or all other isomers present in the composition greater than or equal 10, preferably for some embodiments greater than or equal to 20, preferably for some embodiments greater than or equal to 100, preferably for some embodiments greater than or equal to 1000, and preferably for some embodiments greater than or equal to 10000. In related aspects, the term "substantially free of other isomers" refers to a composition or pharmaceutical formulation thereof comprising a high molar ratio of one stereoisomer of a given molecule with respect to other stereoisomers of the given molecule. In further related aspects, the term "substantially free of other isomers" refers to a composition or pharmaceutical formulation thereof comprising a high molar ratio of one enantiomer of a given molecule with respect to other enantiomers of the given molecule. In an embodiment, a substantially purified (+) enantiomer has a molar ratio of the purified (+) enantiomer relative to the corresponding (−) enantiomer of greater than or equal to 10, preferably for some embodiments greater than or equal to 100, preferably for some embodiment greater than or equal to 1000, and preferably for some embodiments greater than or equal to 10000. In an embodiment, a substantially purified (−) enantiomer has a molar ratio of the purified (−) enantiomer relative to the corresponding (+) enantiomer of greater than or equal to 10, preferably for some embodiments greater than or equal to 100, preferably for some embodiment greater than or equal to 1000, and preferably for some embodiments greater than or equal to 10000.

"Administering" means that a compound or formulation thereof of the present invention, such as an opioid or structurally related opioid derivative, is provided to a patient or subject, for example in a therapeutically effective amount. The present invention includes methods for a medical phototherapy procedure comprising administering a therapeutically effective amount of a compound having any one of formulae (FX1)-(FX164) to a patient in need of treatment, for example to a patient undergoing phototherapy or treatment for a diagnosed diseased state including cancer or an ocular neovascular disease such as age related macular degeneration. "Co-administration" refers to administering two or more compounds at some time during a biomedical procedure. Co-administration refers to administration of two or more compounds at the same time, or before or after each other during the same biomedical procedure. Co-administration includes phototherapy procedures wherein an anti-angiogenesis agent and/or anti-VEGF agent is administered prior to excitation of the phototherapy agent, during excitation of the phototherapy agent and/or after excitation of the phototherapy agent. Co-administration includes phototherapy procedures wherein an anti-angiogenesis agent and/or anti-VEGF agent is administered multiple times after excitation of the phototherapy agent.

The term "inflammation" generally refers to a biological response of vascular tissues to harmful stimuli, such as pathogens, damaged cells, irritants, etc. Inflammation can be either acute or chronic. Acute inflammation is an initial response of the body to harmful stimuli and can be achieved by the increased movement of plasma and leukocytes from the blood into injured tissues. An inflammatory response can involve the local vascular system, the immune system, and/or various cells within the injured tissue. Prolonged inflammation, referred to as chronic inflammation, can lead to a progressive shift in the type of cells which are present at the site of inflammation can be characterized by simultaneous destruction and healing of the tissue from the inflammatory process.

The term "amino acid" comprises naturally occurring amino acids as well as non-naturally occurring amino acids, including amino acid analogs and derivatives. One skilled in the art will recognize that reference herein to an amino acid comprises, for example, naturally occurring proteogenic L-amino acids; D-amino acids; chemically modified amino acids such as amino acid analogs and derivatives; naturally occurring non-proteogenic amino acids, and chemically synthesized compounds having properties known in the art to be characteristic of amino acids.

The term "nucleic acid" as used herein generally refers to a molecule or strand of DNA, RNA, or derivatives or analogs thereof including one or more nucleobases. Nucleobases comprise purine or pyrimidine bases typically found in DNA or RNA (e.g., adenine, guanine, thymine, cytosine, and/or uracil). The term "nucleic acid" also comprises oligonucleotides and polynucleotides. Nucleic acids may be single-stranded molecules, or they may be double-, triple- or quadruple-stranded molecules that may comprise one or more complementary strands of a particular molecule. "Nucleic acid" includes artificial nucleic acids including peptide nucleic acids, morpholino nucleic acids, glycol nucleic acids and threose nucleic acids. Artificial nucleic acids may be capable of nucleic acid hybridization.

As used herein, "sequence" means the linear order in which monomers occur in a polymer, the order of amino acids in a polypeptide or the order of nucleotides in a polynucleotide for example.

The terms "peptide" and "polypeptide" are used synonymously in the present description, and refer to a class of compounds comprising of amino acid residues chemically bonded together by amide bonds (or peptide bonds), regardless of length, functionality, environment, or associated molecule(s). Peptides and polypeptides are polymeric compounds comprising at least two amino acid residues or modified amino acid residues. Modifications can be naturally occurring or non-naturally occurring, such as modifications generated by chemical synthesis. Modifications to amino acids in peptides include, but are not limited to, phosphorylation, glycosylation, lipidation, prenylation, sulfonation, hydroxylation, acetylation, methionine oxidation, alkylation, acylation, carbamylation, iodination and the addition of cofactors. Peptides include proteins and further include compositions generated by degradation of proteins, for example by proteolytic digestion. Peptides and polypeptides can be generated by substantially complete digestion or by partial digestion of proteins. Polypeptides comprising 2 to 100 amino acid units, optionally for some embodiments 2 to 50 amino acid units and, optionally for some embodiments 2 to 20 amino acid units can be used as polypeptide targeting ligands in the invention, for example, where the polypeptide preferentially binds to proteins, peptides or other biomolecules expressed, or otherwise generated by, a target tissue, such as a tumor, precancerous tissue, site of inflammation or other lesion. Typically, the polypeptide is at least four amino acid residues in length and can range up to a full-length protein.

"Protein" refers to a class of compounds comprising one or more polypeptide chains and/or modified polypeptide chains. Proteins can be modified by naturally occurring processes such as post-translational modifications or co-translational modifications. Exemplary post-translational modifications or co-translational modifications include, but are not limited to, phosphorylation, glycosylation, lipidation, prenylation, sulfonation, hydroxylation, acetylation, methionine oxidation, the addition of cofactors, proteolysis, and assembly of proteins into macromolecular complexes. Modification of proteins can also include non-naturally occurring derivatives, analogues and functional mimetics generated by chemical synthesis. Exemplary derivatives include chemical modifications such as alkylation, acylation, carbamylation, halogenation, iodination or any modification that derivatizes the protein.

As used herein, "polynucleotide" and "oligonucleotide" are used interchangeably and refer to a class of compounds composed of nucleic acid residues chemically bonded together. The invention provides optical agents having an oligonucleotide or polynucleotide targeting ligand which comprises a plurality of nucleic acid residues, such as DNA or RNA residues, and/or modified nucleic acid residues that preferentially binds to proteins, peptides or other biomolecules expressed, or otherwise generated by, a target tissue, such as a tumor, precancerous tissue, site of inflammation or other lesion. Modifications to nucleic acid residues can be naturally occurring or non-naturally occurring, such as modifications generated by chemical synthesis. Oligo- or poly-nucleotide targeting ligands include, for example, oligo- or poly-nucleotides comprising 1 to 100 nucleic acid units, optionally for some embodiments 1 to 50 nucleic acid units and, optionally for some embodiments 1 to 20 nucleic acid units. Polypeptide and oligonucleotide include a polymer of at least two nucleotides joined together by phosphodiester bonds and may consist of either ribonucleotides or deoxyribonucleotides.

The term "aptamer" refers to an oligo- or poly-nucleotide or polypeptide that binds to, or otherwise selectively or preferentially associates with, a specific target molecule. For example, the invention provides optical agents having an aptamer targeting ligand that preferentially binds to proteins, peptides or other biomolecules expressed, or otherwise generated by, a target tissue, such as a tumor, precancerous tissue, site of inflammation or other lesion.

"Peptidomimetic" refers to a molecule having activity, including biological activity, that resembles that of a polypeptide or is substantially the same as a polypeptide. Morphine, for example, is a peptidomimetic of endorphin peptide. In some embodiments, a peptidomimetic is a small protein-like polymer designed to mimic the functionality of a peptide. Peptidomimetics useful as targeting ligands for some compounds of the invention in the present invention include peptoids and β-peptides. The composition and biological activity of peptidomimetics and use of peptidomimetics in targeted diagnostics and therapeutics are further described in the following references: (1) A. Giannis and T. Kolter, *Peptidomimetics for Receptor Ligands—Discovery, Development, and Medical Perspectives*, Angewandte Chemie International Edition In English, vol. 32, 1993, pg. 1244-1267 and (2) Patch, J. A. et al., *Versatile oligo(N-substituted)glycines: The many roles of peptoids in drug discovery*, Pseudo-Peptides in Drug Discovery 2004, 1-31 and P. E. Nielsen.

"Optical agent" generally refers to compounds, compositions, preparations, and/or formulations that absorb, emit, or scatter electromagnetic radiation of wavelength generally in the range of 350-1300 nanometers, within a biologically relevant environment or condition. In some embodiments, optical agents of the invention, when excited by electromagnetic radiation, undergo emission via fluorescence or phosphorescence pathways. These pathways are useful for diagnostic imaging, visualization, or organ function monitoring. Compounds belonging to this class are commonly referred to as "optical imaging agents" or "optical contrast agents." In some other embodiments, optical agents of the invention absorb electromagnetic radiation and undergo photochemical reactions such as photofragmentation of one or more photolabile bonds to generate reactive species such as nitrenes, carbene, free radicals, ions, excited species, etc. This process is useful for a wide range of phototherapy applications, for example in the treatment of tumors or other lesions. Compounds belonging to this class are commonly referred to as "photosensitizers." The term "photosensitizer" refers to a phototherapy agent or a component thereof providing for photoactivation, for example, photoactivation resulting in generation of reactive species that locally kill, injure, inactivate or otherwise degrade cells (e.g., cancer cells, tumor cells, non-cancer cells, etc.). Photosensitizers of some embodiments undergo photoactivation that initiates bond cleavage reactions, such as photolysis and/or nitrogen extrusion reactions, thereby generating reactive species capable of causing localized cell death or injury. Optical agents include Type 1 and Type 2 phototherapy agents. Optical agents include, but are not limited to, phototherapy agents (Type 1 and 2), photosensitizers, imaging agents, dyes, detectable agents, photosensitizer agents, photoactivators, and photoreactive agents; and conjugates, complexes, and derivatives thereof.

Optical agents of the present invention can contain fluorophores. The term "fluorophore" generally refers to a component or moiety of a molecule or group which causes a molecule or group to be fluorescent. Fluorophores can be functional groups in a molecule which absorb electromagnetic radiation of first specific wavelengths and re-emit energy at second specific wavelengths. The amount and wavelengths of the emitted electromagnetic radiation depend on both the fluorophore and the chemical environment of the fluorophore. The term "fluorophore" is abbreviated throughout the present description as "FL". In aspects of the invention, fluorophores emit energy in the visible (e.g. 350 nm to 750 nm) and NIR regions (e.g., 750-1300 nm) of the electromagnetic spectrum.

As used herein, a "chromophore" is a compound or functional group of a compound that results in absorption of electromagnetic radiation, preferably for some applications electromagnetic radiation having wavelengths in the UV (e.g. 200 nm to 350 nm) or visible (e.g. 350 nm to 750 nm) of the electromagnetic spectrum.

As used herein, a "fluorophore" is a compound or functional group of a compound that results in absorption of electromagnetic radiation and subsequent fluorescence. Preferably for some applications incorporation of a fluorophore results in compounds of the invention that absorb electromagnetic radiation and generate fluorescence having wavelengths in the UV (e.g. 200 nm to 350 nm) or visible (e.g. 350 nm to 750 nm) of the electromagnetic spectrum. In some embodiment, incorporation of a fluorophore results in compounds having an appreciable quantum yield for fluorescence, such as a quantum yield over the range of 0.001 to 1, 0.01 to 1, optionally 0.1 to 1.

As used herein, the term "luminescence" refers to the emission of electromagnetic radiation from excited electronic states of atoms or molecules. Luminescence generally refers to electromagnetic radiation emission, such as photoluminescence, chemiluminescence, and electrochemiluminescence, among others. In photoluminescence, including fluorescence and phosphorescence, the excited electronic state is created by the absorption of electromagnetic radiation. Luminescence detection involves detection of one or more properties of the luminescence or associated luminescence process. These properties can include intensity, excitation and/or emission spectrum, polarization, lifetime, and energy transfer, among others. These properties can also include time-independent (steady-state) and/or time-dependent (time-resolved) properties of the luminescence. Representative luminescence techniques include fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), and bioluminescence resonance energy transfer (BRET), among others. By way of example, when an optical agent is used in the present invention, it is desirable that the wavelength of radiation be non-ionizing and be such that it excites the optical agent. This excitation can cause a bond of the molecule to break and can lead to creation of one or more appropriate radical(s). This excitation can also cause the molecule to emit part of the absorbed energy at a different wavelength. Such emission can be detected using fluorometric techniques as described above. One skilled in the art can readily determine the most appropriate treatment and optional detection technique based, at least in part, on the specific phototherapy agent(s) administered and/or the particular use (e.g., tissue to be treated).

"Optical condition" refers to one or more of the following: the fluorescence quantum yield, fluorescence intensity, fluorescence excitation wavelength, wavelength distribution or spectrum, emission wavelength, wavelength distribution or spectrum, Stokes shift, color, reflectance, phosphorescence, chemiluminescence, scattering, and/or other observable and/or measurable spectral property or phenomenon.

"Phototherapy procedure" refers to a therapeutic procedure involving administration of a phototherapy agent to a patient followed by subsequent excitation by exposure to applied electromagnetic radiation, such as electromagnetic radiation having wavelengths in the visible and/or near IR region of the electromagnetic spectrum. Such wavelengths can be in the range of 350-1300 nanometers, so as to generate a therapeutically effective amount of excited phototherapy agent. Phototherapy includes, but is not limited to, photodynamic therapy. As used herein, "phototherapy" includes procedures involving administration of Type 1 and/or Type 2 phototherapy agents, optionally further including administration of one or more additional therapeutic agents.

A detectable optical signal may be, for example, an observable change in absorbance, reflectance, phosphorescence, chemiluminescence, scattering, or other spectral property.

As used herein, "tumor-specific agent" refers to a compound or composition, such as an optical agent, that preferentially accumulates in a tumor at a higher level than normal tissue regardless of the particular mechanism of uptake in the tumors, for example, receptor mediated or enhanced permeability and retention (EPR). Optical agents of the invention include tumor-specific agents, including tumor specific phototherapy agents, for example having a targeting ligand providing specificity in the administration, delivery and/or binding to tumor tissue.

Methods of this invention comprise the step of administering an "effective amount" of the present diagnostic and therapeutic compositions, formulations and preparations containing the present compounds or compositions, to diagnose, image, monitor, evaluate, treat, reduce, alleviate, ameliorate or regulate a biological condition and/or disease state in a patient. The term "effective amount," as used herein, refers to the amount of the diagnostic and therapeutic formulation, that, when administered to the individual is effective to diagnose, image, monitor, evaluate, treat, reduce alleviate, ameliorate or regulate a biological condition and/or disease state. As is understood in the art, an effective amount of a given composition or formulation will depend at least in part upon the mode of administration (e.g. intravenous, oral, topical administration), any carrier or vehicle employed, and the specific individual to whom the formulation is to be administered (age, weight, condition, sex, etc.). The dosage requirements needed to achieve the "effective amount" vary with the particular formulations employed, the route of administration, and clinical objectives. Based on the results obtained in standard pharmacological test procedures, projected daily dosages of active compound or composition can be determined as is understood in the art.

In an embodiment, an effective amount of a compound or composition of the invention is a therapeutically effective amount. As used herein, the phrase "therapeutically effective" qualifies the amount of compound or composition administered in the therapy. This amount achieves the goal of ameliorating, suppressing, eradicating, preventing, reducing the risk of, or delaying the onset of a targeted condition. In an embodiment, an effective amount of a compound or composition of the invention is a diagnostically effective amount. As used herein, the phrase "diagnostically effective" qualifies the amount of compound or composition administered in diagnosis, for example of a disease state or other pathological condition. The amount achieves the goal of being detectable while avoiding adverse side effects found with higher doses. In an embodiment, an active ingredient or other component is included in a therapeutically acceptable amount. In an embodiment, an active ingredient or other component is included in a diagnostically acceptable amount.

It is contemplated that the compounds and pharmaceutically acceptable salts of the invention can be used as part of a combination. The term "combination" means the administration of two or more compounds directed to a target condition. The treatments of the combination generally can be co-administered in a simultaneous manner. Two compounds can be co-administered as, for example: (a) a single formulation (e.g., a single capsule) having a fixed ratio of active ingredients; or (b) multiple, separate formulations (e.g., multiple capsules) for each compound. The treatments of the combination can alternatively (or additionally) be administered at different times.

In certain embodiments, the invention encompasses administering optical agents useful in the invention to a patient or subject. A "patient" or "subject", used equivalently herein, refers to an animal. In particular, an animal refers to a mammal, preferably a human. The subject can either: (1) have a condition able to be monitored, diagnosed, prevented and/or treated by administration of an optical agent of the invention; or (2) is susceptible to a condition that is able to be monitored, diagnosed, prevented and/or treated by administering an optical agent of the invention.

When used herein, the terms "diagnosis", "diagnostic" and other root word derivatives are as understood in the art and are further intended to include a general monitoring, characterizing and/or identifying a state of health or disease. The term is meant to encompass the concept of prognosis. For example, the diagnosis of cancer can include an initial determination and/or one or more subsequent assessments regardless of the outcome of a previous finding. The term does not necessarily imply a defined level of certainty regarding the prediction of a particular status or outcome.

As defined herein, "administering" means that a compound or formulation thereof of the invention, such as an optical agent, is provided to a patient or subject, for example in a therapeutically effective amount. The invention includes methods for a biomedical procedure wherein a therapeutically or diagnostically effective amount of a compound having any one of formulas (FX1)-(FX164) is administered to a patient in need of treatment, for example to a patient undergoing treatment for a diagnosed diseased state including cancer and vascular diseases. Administering can be carried out by a range of techniques known in the art including parenteral administration including intravenous, intraperitoneal or subcutaneous injection or infusion, oral administration, topical or transdermal absorption through the skin, or by inhalation, for example. The chosen route of administration may depend on such factors as solubility of the compound or composition, location of targeted condition, and other factors which are within the knowledge of one having ordinary skill in the relevant art.

"Topical administration" includes the use of transdermal administration, such as transdermal patches or iontophoresis devices.

"Parenteral administration" includes subcutaneous injections, intravenous injections, intraarterial injections, intraorbital injections, intracapsular injections, intraspinal injections, intraperitoneal injections, intramuscular injections, intrasternal injections, and infusion. Dosage forms suitable for parenteral administration include solutions, suspensions, dispersions, emulsions, and any other dosage form that can be administered parenterally.

As used herein, the term "controlled-release component" refers to an agent that facilitates the controlled-release of a compound including, but not limited to, polymers, polymer matrices, gels, permeable membranes, liposomes, microspheres, or the like, or any combination thereof. Methods for producing compounds in combination with controlled-release components are known to those of skill in the art.

As used herein, the term "pharmaceutically acceptable" means approved by a regulatory agency of an appropriate federal or state government; or listed in the U.S. Pharmacopoeia or other generally recognized pharmacopoeia for use in animals, and more particularly in humans; or does not impart significant deleterious or undesirable effect on a subject to whom it is administered and in the context in which it is administered.

As will be clear to those of ordinary skill in the art, the groups and structures described herein as portions of the compounds of the invention may be defined as if they are separate valence-satisfied chemical structures. It is intended that when a group is described or shown as being a substituent of another group, that the group be viewed as having a valency to allow this binding to occur.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

Pharmaceutically acceptable salts comprise pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., $Cl^-$, $Br^-$), sulfate, acetates (e.g., acetate, trifluoroacetate), ascorbates, aspartates, benzoates, citrates, and lactate. Pharmaceutically acceptable salts include, but are not limited to, salts derived from quarternary amines, such as quarternary amine opioids and structurally related derivatives.

The compounds of this invention may contain one or more chiral centers. Accordingly, therapeutic agents, including anti-angiogenesis agents and anti-VEGF agents, include racemic mixtures of stereoisomers, and compositions comprising mixtures enriched in one or more stereoisomer and compositions comprising purified stereoisomers (e.g, diastereomers, enantiomers). The scope of the invention as described and claimed encompasses the racemic forms of the compounds as well as non-racemic mixtures thereof and purified forms of individual stereoisomers of the present compounds.

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

In certain embodiments, the invention encompasses administering compounds, such as anti-angiogenesis agents, anti-VEGF agents and phototherapy agents, useful in the invention to a patient or subject. A "patient" or "subject", used equivalently herein, refers to an animal. In particular, an animal refers to a mammal, preferably a human. The subject may either: (1) have a condition diagnosable, preventable and/or treatable by administration of an optical agent of the invention; or (2) is susceptible to a condition that is diagnosable, preventable and/or treatable by administering an optical agent of this invention.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Compositions of the invention includes formulations and preparations comprising one or more of the present optical agents provided in an aqueous solution, such as a pharmaceutically acceptable formulation or preparation. Optionally, compositions of the invention further comprise one or more pharmaceutically acceptable surfactants, buffers, electrolytes, salts, carriers, binders, coatings, preservatives and/or excipients.

In an embodiment, the invention provides a pharmaceutical formulation comprising a composition of the invention, such as a compound of any one of formulae (FX1)-(FX164). In an embodiment, the invention provides a method of synthesizing a composition of the invention or a pharmaceutical formulation thereof, such as a compound of any one of formulae (FX1)-(FX164). In an embodiment, a pharmaceutical formulation comprises one or more excipients, carriers, diluents, and/or other components as would be understood in the art. Preferably, the components meet the standards of the National Formulary ("NF"), United States Pharmacopoeia ("USP"; United States Pharmacopeial Convention Inc., Rockville, Md.), or Handbook of Pharmaceutical Manufacturing Formulations (Sarfaraz K. Niazi, all volumes, ISBN: 9780849317521, ISBN 10: 0849317525; CRC Press, 2004). See, e.g., United States Pharmacopeia and National Formulary (USP 30-NF 25), Rockville, Md.: United States Pharmacopeial Convention; 2007; and 2008, and each of any earlier editions; The Handbook of Pharmaceutical Excipients, published jointly by the American Pharmacists Association and the Pharmaceutical Press (Pharmaceutical Press (2005) (ISBN-10: 0853696187, ISBN-13: 978-0853696186); Merck Index, Merck & Co., Rahway, N.J.; and Gilman et al., (eds) (1996); Goodman and Gilman's: The Pharmacological Bases of Therapeutics, 8th Ed., Pergamon Press. In embodiments, the formulation base of the formulations of the invention comprises physiologically acceptable excipients, namely, at least one binder and optionally other physiologically acceptable excipients. Physiologically acceptable excipients are those known to be usable in the pharmaceutical technology sectors and adjacent areas, particularly, those listed in relevant pharmacopeias (e.g. DAB, Ph. Eur., BP, NF, USP), as well as other excipients whose properties do not impair a physiological use.

In an embodiment, an effective amount of a composition of the invention is a therapeutically effective amount. In an embodiment, an effective amount of a composition of the invention is a diagnostically effective amount. In an embodiment, an active ingredient or other component is included in a therapeutically acceptable amount. In an embodiment, an active ingredient or other component is included in a diagnostically acceptable amount.

Variations on compositions including salts and ester forms of compounds: Compounds of this invention and compounds useful in the methods of this invention include those of the compounds and formula (s) described herein and pharmaceutically-acceptable salts and esters of those compounds. In embodiments, salts include any salts derived from the acids of the formulas herein which acceptable for use in human or veterinary applications. In embodiments, the term esters refers to hydrolyzable esters of compounds of the names and structural formulas herein. In embodiments, salts and esters of the compounds of the formulas herein can include those which have the same or better therapeutic, diagnostic, or pharmaceutical (human or veterinary) general properties as the compounds of the formulas herein. In an embodiment, a composition of the invention is a compound or salt or ester thereof suitable for pharmaceutical formulations.

In an embodiment, the invention provides a method for treating a medical condition comprising administering to a subject (e.g. patient) in need thereof, a therapeutically effective amount of a composition of the invention, such as a compound of any one of formulae (FX1)-(FX164). In an embodiment, the medical condition is cancer, or various other diseases, injuries, and disorders, including cardiovascular disorders such as atherosclerosis and vascular restenosis, inflammatory diseases, ophthalmic diseases and dermatological diseases.

In an embodiment, the invention provides a medicament which comprises a therapeutically effective amount of one or more compositions of the invention, such as a compound of any one of formulas (FX1)-(FX164). In an embodiment, the invention provides a method for making a medicament for treatment of a condition described herein, such as the treatment of ocular neovascular disease, macular degeneration, cancer, inflammation, stenosis or a vascular disease. In an embodiment, the invention provides a method for making a medicament for diagnosis or aiding in the diagnosis of a condition described herein, such as the diagnosis of ocular neovascular disease, macular degeneration, cancer, inflammation, stenosis or a vascular disease. In an embodiment, the invention provides the use of one or more compositions set forth herein for the making of a medicament for the treatment of ocular neovascular disease, macular degeneration, cancer, inflammation, stenosis or a vascular disease. In an embodiment, the invention provides the use of one or more compositions set forth herein for the treatment of a disease. Compositions of the invention include formulations and preparations comprising one or more of the present optical agents provided in an aqueous solution, such as a pharmaceutically acceptable formulation or preparation. Optionally, compositions of the invention further comprise one or more pharmaceutically acceptable surfactants, buffers, electrolytes, salts, carriers, binders, coatings, preservatives and/or excipients.

Compounds of the invention can have prodrug forms. Prodrugs of the compounds of the invention are useful in embodiments including compositions and methods. Any compound that will be converted in vivo to provide a biologically, pharmaceutically, diagnostically, or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392). A prodrug, such as a pharmaceutically acceptable prodrug can represent prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of a compound described herein, for example, by hydrolysis in blood or by other cell, tissue, organ, or system processes. Further discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds set forth herein.

In an embodiment, a composition of the invention is isolated or purified. In an embodiment, an isolated or purified compound may be at least partially isolated or purified as would be understood in the art.

The invention is further detailed in the following Examples, which are offered by way of illustration and are not intended to limit the scope of the invention in any manner.

Example 1

Methods of Using Anti-VEGF Opioids and Structurally Related Derivatives for Phototherapy Phototherapy, such as photodynamic therapy (PDT), typically employs a combination of a nontoxic photosensitizer (PS) and visible or near infrared light to generate reactive species that kill or otherwise degrade target cells, such as tumors or other lesions. Many clinically studied photosensitizers are Type 2 phototherapy agents based on the tetrapyrrole structure of porphyrins, chlorins, and related molecules that generate cytotoxic reactive oxygen species (ROS), e.g. singlet oxygen, hydroxyl and hydroperoxyl radicals, and the like. Photodynamic therapy in conjunction with Type 2 phototherapy agents in certain tumor animal models has been shown under certain conditions to initiate tumorigenesis and metastasis through the up-regulation of vascular endothelial growth factor (VEGF) and increased permeability of damaged vasculature. Localized hypoxia and oxidative stress resulting from the phototherapy process, for example, are believed to initiate an angiogenic response. Since tumorigenesis defines the growth and invasiveness of tumors, antagonizing this endogenous angiogenic response to PDT provides a potential means to enhance the efficacy of phototherapy.

Anti-VEGF antibodies, and fragments thereof, as an inhibitor to VEGF expression, for example, has been shown to reduce angiogenesis post-PDT with Type 2 phototherapy agents and to reduce the metastatic progression. Antibodies are known to elicit anti-idiotypic response, however, that can reduce the effectiveness of immunoagents, thereby increasing the dose needed for a desired therapeutic outcome. Indeed, anti-idiotypic response is a natural "policing" by the immune system to ensure that large amounts of antibodies are not accumulated in the body that may lead to autoimmune diseases. Furthermore, because antibody production, isolation, and purification is expensive for the quantities that are needed for many therapeutic applications, there is currently a significant need for small molecular inhibitors of VEGF expression as an adjunct to phototherapy.

Figure 1B:
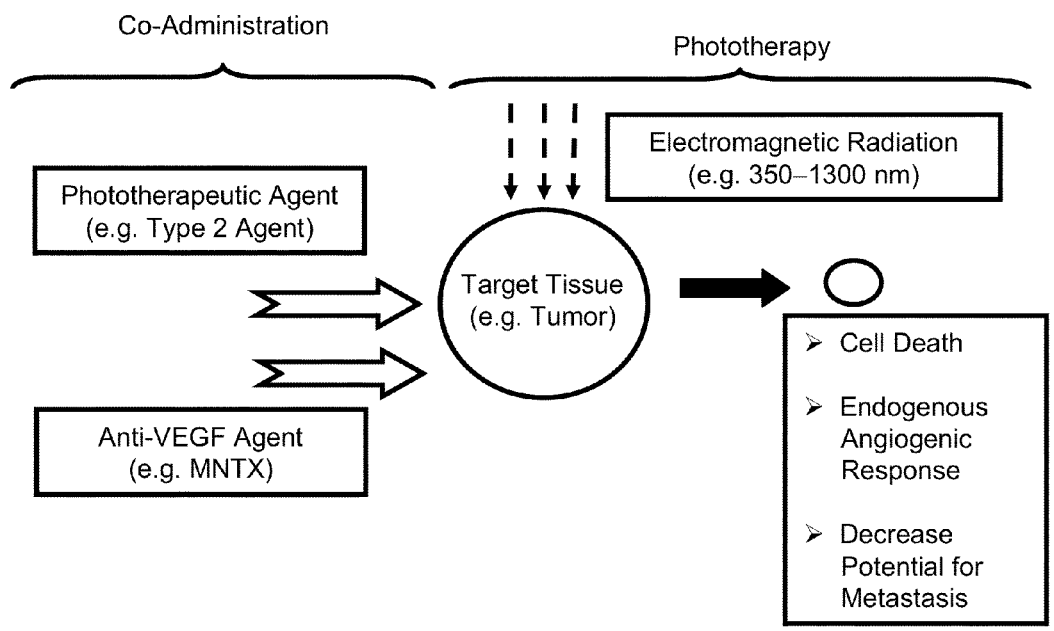
Figure 2:
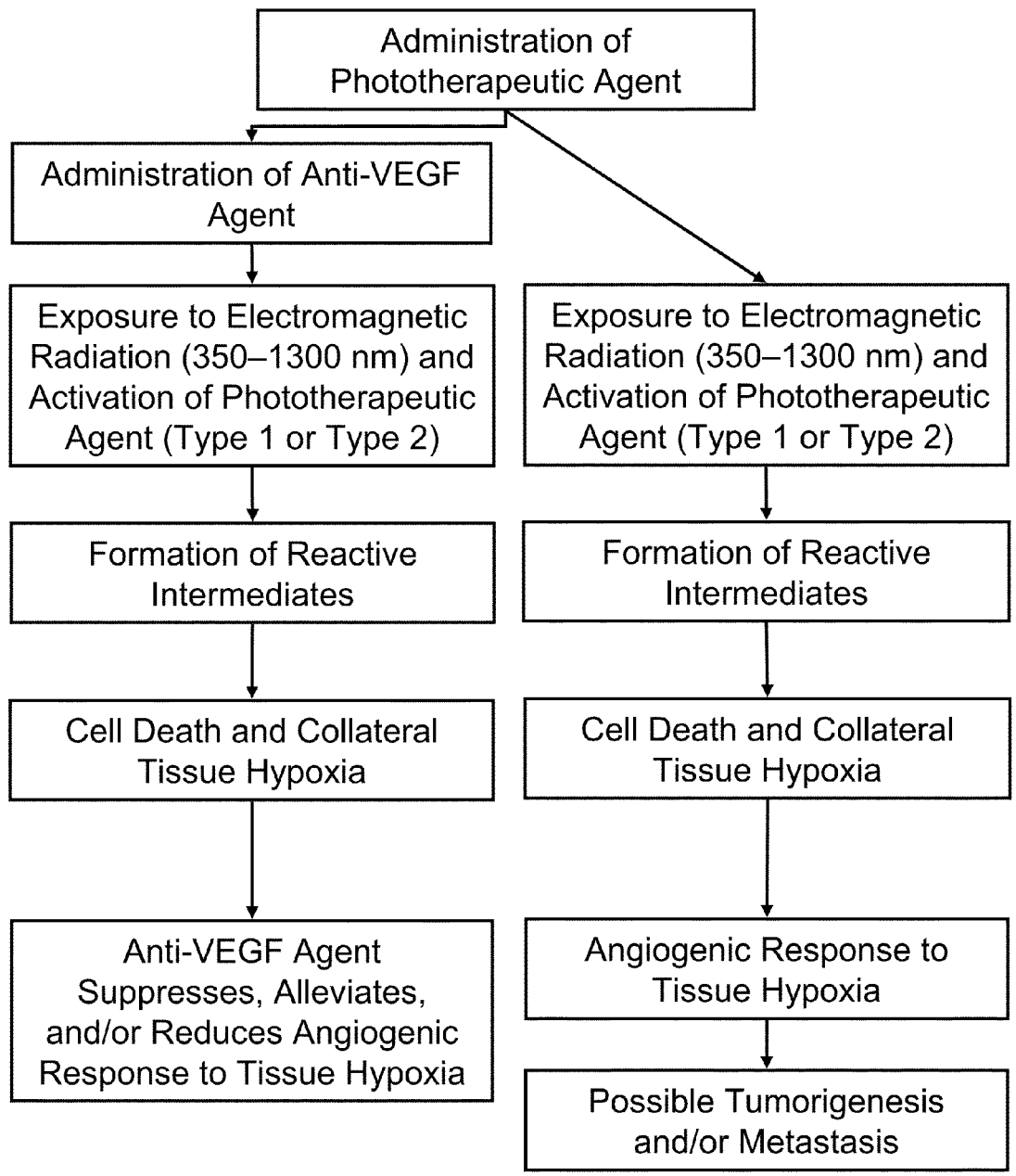
FIG. 2 provides a flow diagram comparing phototherapy procedures with and without a step of co-administration of an anti-VEGF agent.

The present invention provides opioids and structurally related derivatives useful as anti-angiogenesis agents and anti-VEGF agents for mitigating angiogenic and metastatic responses initiated by phototherapy. In some embodiments, for example, the present invention provides methods comprising in vivo co-administration of an anti-VEGF agent comprising an opioid or structurally related derivative and a Type 1 or Type 2 photosensitizer. FIG. 1A provides a schematic diagram illustrating a phototherapy procedure not including the step of administering an anti-VEGF agent. As shown in this figure, a phototherapy agent, such as a Type 2 phototherapy agent, is administered to a patient. Administration provides delivery of the phototherapy agent to a target tissue, such as a tumor or lesion. The phototherapy agent is subsequently excited by exposure to electromagnetic radiation, for example electromagnetic radiation having wavelengths selected over the range of 350 nm to 1300 nm. Excitation of the phototherapy agent generates reactive species, such as free radicals, that result in cell death. As indicated in FIG. 1A, an unwanted collateral effect of administration and excitation of the phototherapy agent under some conditions is an endogenous angiogenic response, thereby increasing the potential for metastasis. FIG. 1B provides a schematic diagram illustrating a phototherapy procedure of the present invention including the step of administering an anti-VEGF agent. As shown in this figure, a phototherapy agent, such as a Type 2 phototherapy agent, is co-administered to a patient with an anti-VEGF agent, such as an opioid (e.g. MNTX or specific (+) or (−) enantiomer thereof), or a structurally related derivative thereof. Administration provides delivery of the phototherapy agent and anti-VEGF agent to a target tissue, such as a tumor or lesion. Similar to the process outlined in FIG. 1A, the phototherapy agent is subsequently excited by exposure to electromagnetic radiation, thereby generating reactive species resulting in cell death. As shown in FIG. 1B, however, administration of the anti-VEGF agent suppress the endogenous angiogenic response, thereby decreasing the potential for metastasis. FIG. 2 provides a flow diagram comparing phototherapy procedures with and without a step of co-administration of an anti-VEGF agent.

The opioid antagonist (−)-R-Naltrexone methobromide (MNTX), is a potent inhibitor of VEGF activity that attenuates vascular permeability due to disease, injury or cancer. Therefore, in specific therapeutic methods of the present invention, MNTX serves as an adjunct to phototherapy to effectively mitigate enhancement and/or the dissemination of cancer. For example, the purified enantiomer, (+)-R-Naltrexone methobromide and, optionally purified epimers, (−)-S-Naltrexone methobromide and (+)-S-Naltrexone methobromide, provide anti-VEGF therapeutic agents for administration in combination with phototherapy. MNTX is described as an example of an anti-VEGF and anti-angiogenic agent of the invention. As will be understood by one of skill in the art, other forms of naltrexone, including other naltrexone salts and other naltrexone stereoisomers are useful in the present invention as anti-VEGF and anti-angiogenic agents. The structures of various stereoisomers of naltrexone methobromide useful in the invention, for example, are provided below in Table 1-1. The structures of various stereoisomers of naltrexone N-oxide useful in the invention, for example, are provided below in Table 1-2.

TABLE 1-1

Stereoisomers of naltrexone methobromide.

| Item No. | Name | Chemical Structure of Stereoisomers |
|---|---|---|
| 1 | naltrexone methobromide | 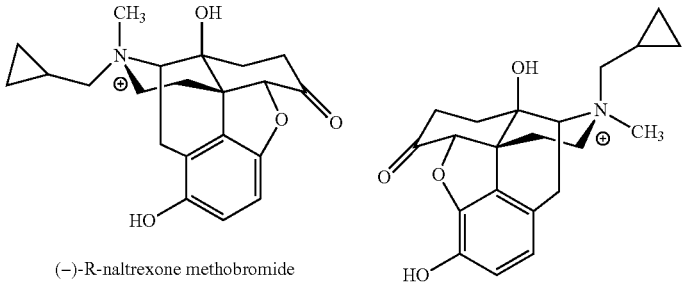 |

(−)-R-naltrexone methobromide     (+)-R-naltrexone methobromide

TABLE 1-1-continued

Stereoisomers of naltrexone methobromide.

| Item No. | Name | Chemical Structure of Stereoisomers |
|---|---|---|

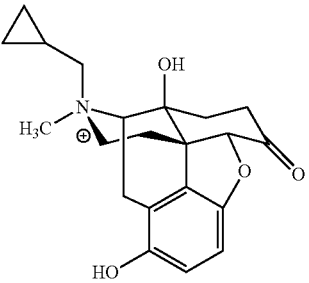

(−)-S-naltrexone methobromide (+)-S-naltrexone methobromide.

TABLE 1-2

Isomers of naltrexone N-oxide.

| Item No. | Name | Chemical Structure of N-Oxide isomers |
|---|---|---|
| 1 | naltrexone N-oxide | |

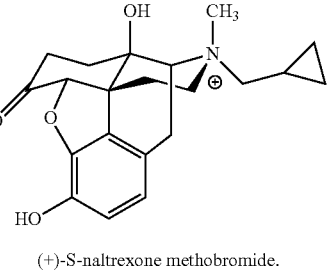

(−)-naltrexone N-oxide(axial)

(+)-naltrexone N-oxide(equatorial)

(−)-naltrexone N-oxide(equatorial)

(+)-naltrexone N-oxide(axial)

Anti-VEGF and Anti-angiogenic agents of the methods of this aspect of the invention further include other opioid antagonists, opioid agonists and structurally related derivatives thereof including, but not limited to, quaternary salts and isomeric and epimeric forms of: (+/−)R/S-Naloxone, (+/−)R/S-Nalmefene, nalbuphine, (+/−)-oxymorphone, (+/−)-hydrocodone, (+/−)-oxycodone, (+/−)-hydromorphone, tetrahydrosinomenine, dextrorphan, and dextromethorphan. These compounds provide anti-VEGF therapeutic agents for administration in combination with phototherapy. As shown in Table 1-2 the N-oxides may be characterized as either axial or equatorial.

Structures of additional examples of anti-VEGF and Anti-angiogenic agents are provided in Table 1-3.

TABLE 1-3
Specific Opioids and Related Derivatives
| Item No. | Base Name | Chemical Structure of Stereoisomers | |
|---|---|---|---|
| 1 | Naloxone | 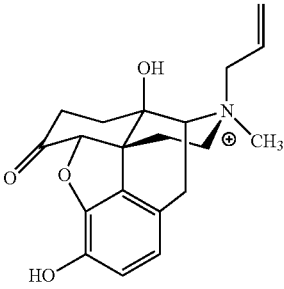<br>(+)-R-methylnaloxone | 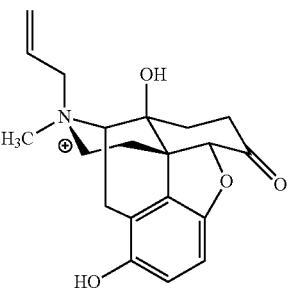<br>(−)-R-methylnaloxone |
| | | 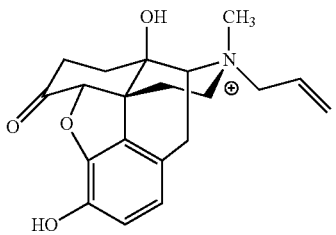<br>(−)-S-methylnaloxone | 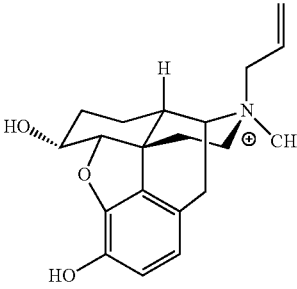<br>(+)-S-methylnaloxone |
| 2 | Nalorphine | 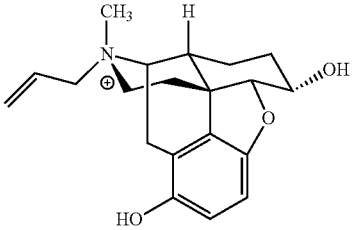<br>(+)-R-methylnalorphine | 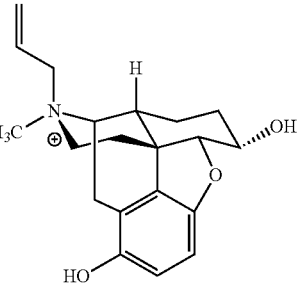<br>(−)-R-methylnalorphine |
| | | <br>(−)-S-methylnalorphine | <br>(+)-S-methylnalorphine |

TABLE 1-3-continued

Specific Opioids and Related Derivatives

| Item No. | Base Name | Chemical Structure of Stereoisomers | |
|---|---|---|---|
| 3 | 14-Deoxy-naltrexone | 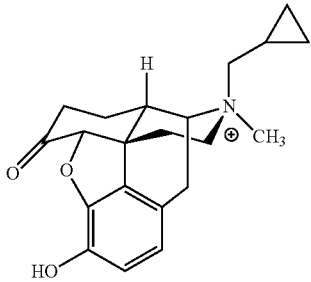<br>(+)-R-methyl-14-deoxynaltrexone | 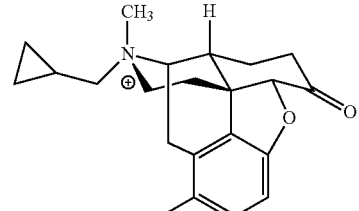<br>(−)-R-methyl-14-deoxynaltrexone |
| | | 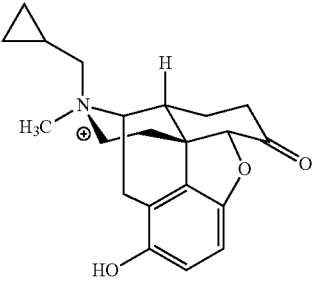<br>(−)-S-methyl-14-deoxynaltrexone | 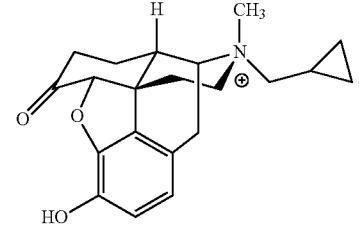<br>(+)-S-methyl-14-deoxynaltrexone |
| 4 | Nalmefene | 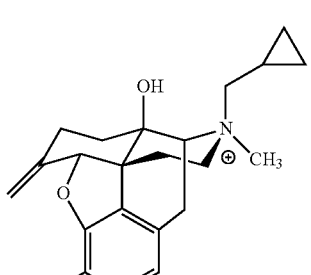<br>(+)-R-methylnalmefene | 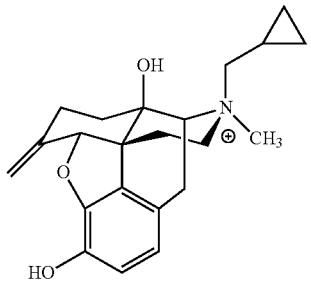<br>(−)-R-methylnalmefene |
| | | 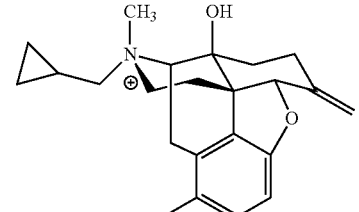<br>(−)-S-methylnalmefene | 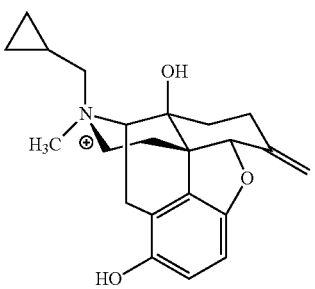<br>(+)-S-methylnalmefene |

TABLE 1-3-continued

Specific Opioids and Related Derivatives

| Item No. | Base Name | Chemical Structure of Stereoisomers | |
|---|---|---|---|
| 5 | Oxymorphone | 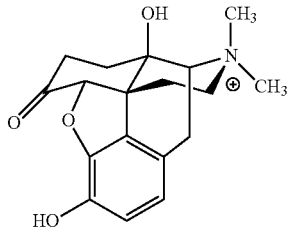<br>(+)-N-methyloxymorphone | 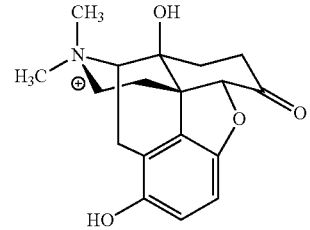<br>(−)-N-methyloxymorphone |
| 6 | Hydrocodone | 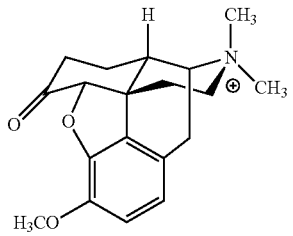<br>(+)-N-methylhydrocodone | 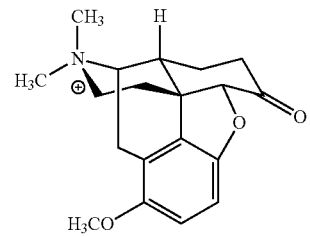<br>(−)-N-methylhydrocodone |
| 7 | Oxycodone | 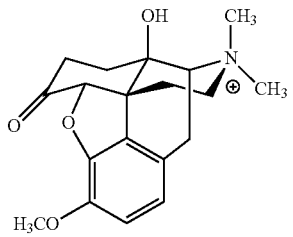<br>(+)-N-methyloxycodone | 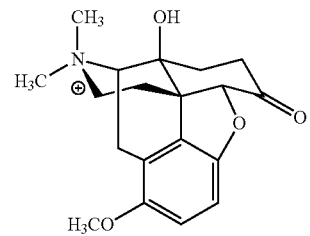<br>(−)-N-methyloxycodone |
| 8 | Hydromorphone | 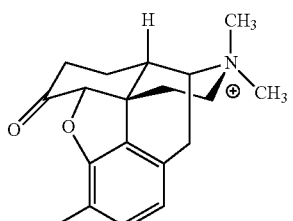<br>(+)-N-methylhydromorphone | 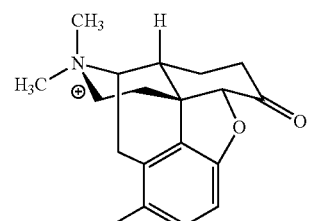<br>(−)-N-methylhydromorphone |
| 9 | Nalbuphine | 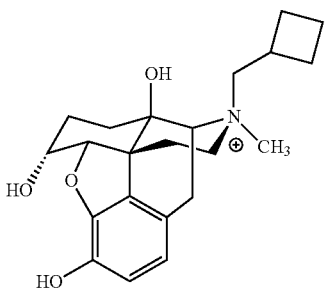<br>(+)-R-N-methylnalbuphine | 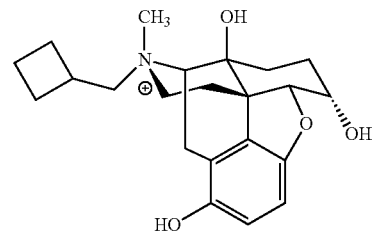<br>(−)-R-N-methylnalbuphine |

TABLE 1-3-continued
Specific Opioids and Related Derivatives
| Item No. | Base Name | Chemical Structure of Stereoisomers |
|---|---|---|
| | | 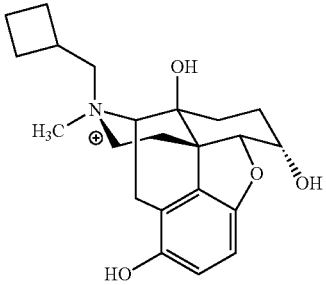 (−)-S-N-methylnalbuphine     (+)-S-N-methylnalbuphine |
| 10 | Buprenorphine | 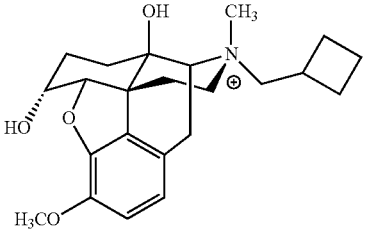 (−)-R-N-methylbuprenorphine     (+)-R-N-methylbuprenorphine 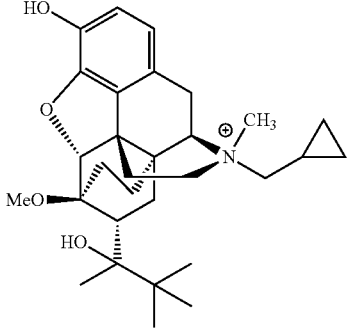 (−)-S-N-methylbuprenorphine     (−)-S-N-methylbuprenorphine |
| 11 | Sinomenine | 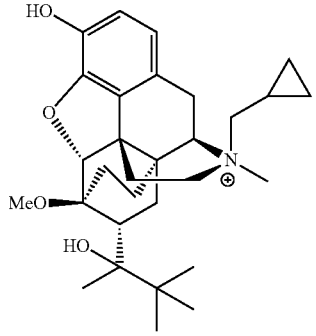 N-methylsinomenine |

TABLE 1-3-continued
Specific Opioids and Related Derivatives
| Item No. | Base Name | Chemical Structure of Stereoisomers |
|---|---|---|
| 12 | Tetrahydro-sinomenine | 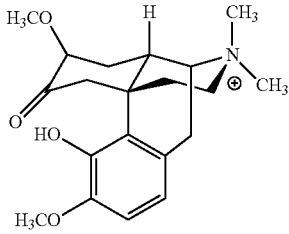<br>N-methyltetrahydrosinomenine |
| 13 | Dextrorphan | 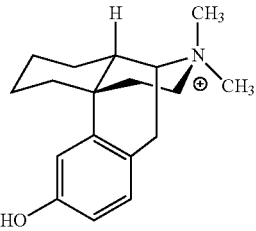<br>N-methyldextrorphan |
| 14 | Levorphanol | 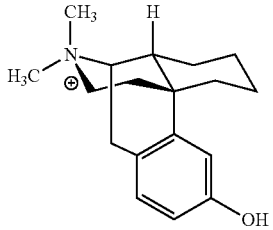<br>N-methyllevorphanol |
| 15 | Dextro-methorphan | 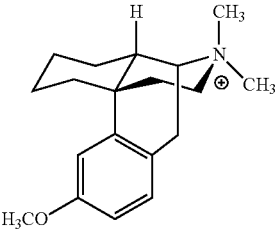<br>N-methyldextromethorphan |
| 16 | Levallorphan | 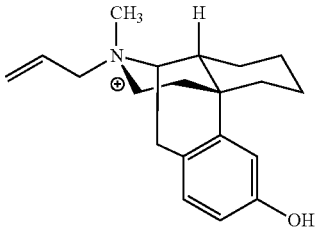<br>(−)R-N-methyllevallorphan |

TABLE 1-3-continued
Specific Opioids and Related Derivatives
| Item No. | Base Name | Chemical Structure of Stereoisomers |
|---|---|---|
| 17 | Dextrallorphan | 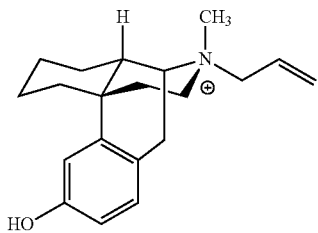<br>(+)S-N-methyldextrallorphan |
| 18 | (−)Cyclorphan | 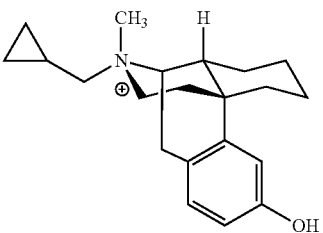<br>(−)R-N-methylcyclorphan |
| 19 | (+)Cyclorphan | 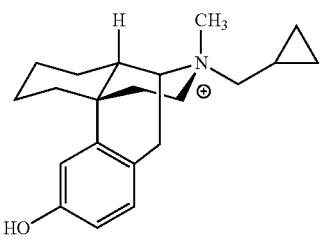<br>(+)S-N-methylcyclorphan |
| 20 | (−)Oxilorphan | 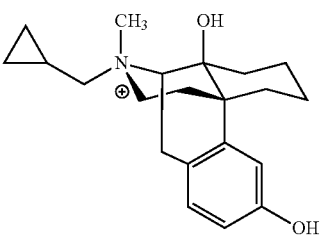<br>(−)R-N-methyloxilorphan |
| 21 | (+)Oxilorphan | 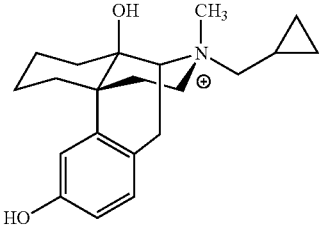<br>(+)S-N-methyloxilorphan |

TABLE 1-3-continued
Specific Opioids and Related Derivatives
| Item No. | Base Name | Chemical Structure of Stereoisomers |
|---|---|---|
| 22 | (−)Butorphanol | 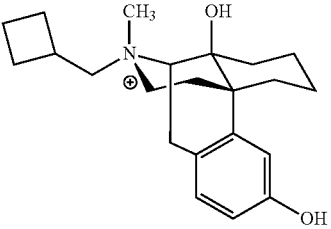<br>(−)R-N-methylbutorphanol |
| 23 | (+)Butorphanol | 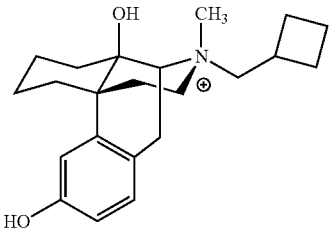<br>(+)S-N-methylbutorphanol |
| 24 | Nalfurafine | 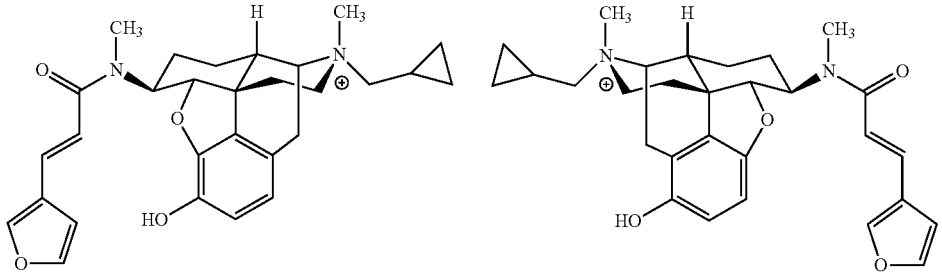<br>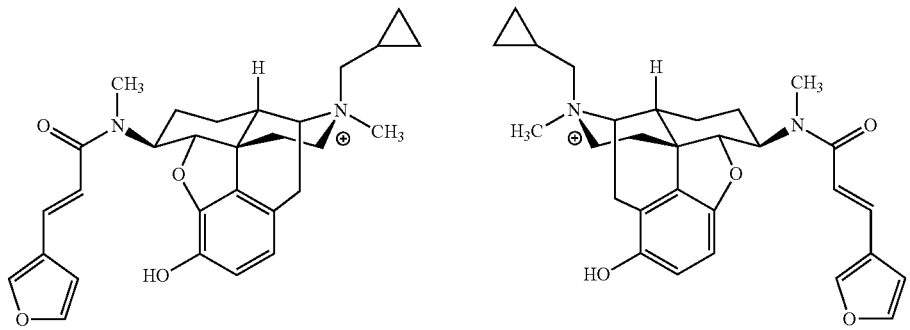 |

TABLE 1-3-continued

Specific Opioids and Related Derivatives

| Item No. | Base Name | Chemical Structure of Stereoisomers |
|---|---|---|
| 25 | Nalorphine | 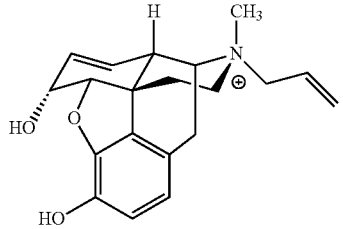 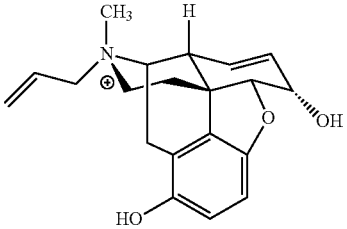 (+)S (−)R 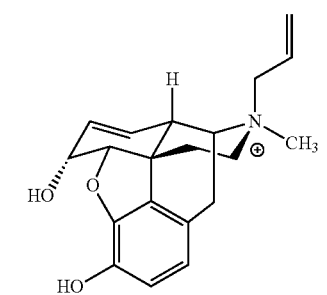 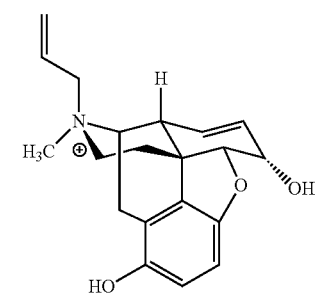 (+)R (−)S |

In the structures provided in Tables 1-1, 1-2, and 1-3, (+) and (−) denote the opposite optical isomers of the opioid compounds or structurally related derivatives. The R and S isomers created around the prochiral nitrogen atom of the quaternary derivatives have the attached groups of the nitrogen (e.g., $R^1$, $R^2$ in formulae (FX1) and (FX2)) either axial or equatorial with respect to the plane of the nitrogen containing cyclohexyl ring. Standard prioritization rules are followed. As will be understood by those having skill in the art, the N-alkyl substitution in the structures above does not have to be restricted to methyl. Therefore, the invention includes compounds having groups other than methyl attached to the nitrogen including, but not limited to, —H, —O⁻, $C_1$-$C_{10}$ alkyl, $C_2$-$C_{10}$ alkenyl, $C_1$-$C_{10}$ haloalkyl, $C_5$-$C_{10}$ aryl, or $C_5$-$C_{10}$ alkylaryl. As will be understood by those having skill in the art, the invention included N-oxides of the compounds provide in Table 1-2, wherein oxygen is in place of the methyl on the nitrogen. The (+) isomers are believe under some conditions not to bind to the opiate receptors and, thus, are preferred for some therapeutic applications. The N-oxides are usually axial although in the case of N-methyl a mixture is likely that can be separated by chromatography techniques know in the art.

The invention further includes compositions comprising mixtures of a plurality of the present opioids and structurally related derivatives exhibiting inhibitory activity for VEGF expression. In an embodiment, for example, a composition of the present invention comprises a plurality of different opioids and/or opioid derivatives for use in a phototherapy procedure or for use in treatment of an ocular neovascular disease or cancer. In an embodiment, a composition of the present invention comprises a plurality of different isomers of a particular opioid or opioid derivative of the invention. In an embodiment, a composition of the present invention includes a plurality of isomers, N-oxides and or salts of a particular opioid or opioid derivative of the invention. In an embodiment, a mixture of the invention comprises a base and an N-oxide or salt of the compounds in Tables 1-1, 1-2, and 1-3.

In an aspect, the invention provides a method for a phototherapy procedure comprising administration to a patient in need of phototherapy a therapeutic agent for scavenging reactive oxygen species (ROS) generated during phototherapy, including Type 2 phototherapy. Therapeutic agents useful in this aspect include anti-inflammatory agents and anti-angiogenesis agents, such as VEGF inhibitors. In an embodiment, for example, the invention provides a method for a phototherapy procedure, the method comprising: (i) administering to a patient in need of phototherapy an effective amount of a phototherapy agent; (ii) administering to the patient an effective amount of a compound having the formula (FX1) or (FX2):

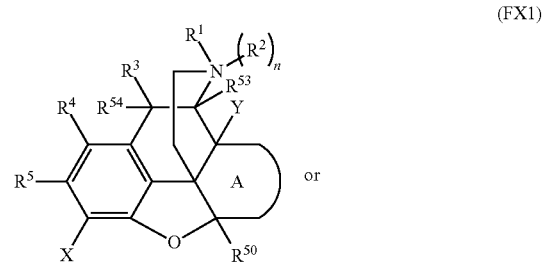

(FX1)

(FX2)

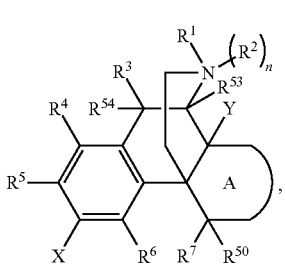

wherein: ring A is

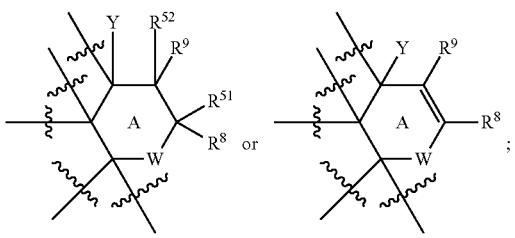

X is —OH, —OCH$_3$, or C$_2$-C$_8$ alkoxy; Y is —H or —OH; W, is —(CR$^{10}$R$^{11}$)—, —(C═O)—, —(C═S)—, —(C═CR$^{12}$R$^{13}$)—, or —(CR$^{14}$NR$^{15}$R$^{16}$)—; each of R$^1$ and R$^2$ is independently —H, —CH$_3$, —(O$^-$), C$_1$-C$_{10}$ alkyl, C$_3$-C$_{10}$ cycloalkyl, C$_2$-C$_{10}$ alkenyl, C$_1$-C$_{10}$ haloalkyl, C$_5$-C$_{10}$ aryl, C$_5$-C$_{10}$ heteroaryl, C$_5$-C$_{10}$ alkylaryl, C$_5$-C$_{10}$ alkylheteroaryl, C$_5$-C$_{10}$ carbonylalkenylaryl, or C$_5$-C$_{10}$ carbonylalkenylheteroaryl; each of R$^3$-R$^{16}$ and R$^{50}$-R$^{54}$ is independently —H, —OH, —OCH$_3$, C$_1$-C$_8$ alkyl, C$_3$-C$_8$ cycloalkyl, C$_2$-C$_8$ alkenyl, C$_2$-C$_8$ alkoxy, C$_5$-C$_{10}$ aryl, C$_5$-C$_{10}$ heteroaryl, C$_5$-C$_{10}$ alkylaryl, C$_5$-C$_{10}$ alkylheteroaryl, halo, nitrile, C$_1$-C$_8$ haloalkyl, C$_1$-C$_{10}$ hydroxyalkyl, or C$_5$-C$_{10}$ carbonylalkenylheteroaryl; and n is 0 or 1, wherein: when n is 1, the nitrogen to which R$^2$ is attached has a positive charge and optionally is associated with an anion; and when n is 0, R$^2$ is not present; and (iii) exposing the phototherapy agent administered to the patient to electromagnetic radiation.

In an embodiment, the invention provides a method for a phototherapy procedure, the method comprising: (i) administering to a patient in need of phototherapy an effective amount of a phototherapy agent; (ii) administering to the patient an effective amount of a compound having the formula (FX61):

(FX61)

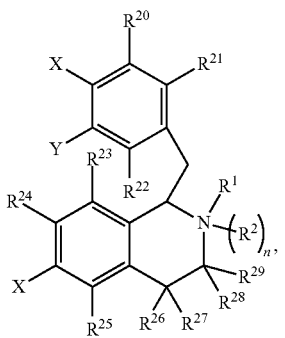

wherein: each X is independently —OH, —OCH$_3$, or C$_2$-C$_8$ alkoxy; Y is —H, or —OH; each of R$^1$ and R$^2$ is independently —H, —CH$_3$, —(O$^-$), C$_1$-C$_{10}$ alkyl, C$_3$-C$_{10}$ cycloalkyl, C$_2$-C$_{10}$ alkenyl, C$_1$-C$_{10}$ haloalkyl, C$_5$-C$_{10}$ aryl, C$_5$-C$_{10}$ heteroaryl, C$_5$-C$_{10}$ alkylaryl, C$_5$-C$_{10}$ alkylheteroaryl, C$_5$-C$_{10}$ carbonylalkenylaryl, or C$_5$-C$_{10}$ carbonylalkenylheteroaryl; each of R$^{20}$-R$^{29}$ is independently —H, —OH, —OCH$_3$, C$_1$-C$_8$ alkyl, C$_3$-C$_8$ cycloalkyl, C$_2$-C$_8$ alkenyl, C$_1$-C$_8$ alkoxy, C$_5$-C$_{10}$ aryl, C$_5$-C$_{10}$ heteroaryl, C$_5$-C$_{10}$ alkylaryl, C$_5$-C$_{10}$ alkylheteroaryl, halo, nitrile, C$_1$-C$_8$ haloalkyl, C$_5$-C$_{10}$ carbonylalkenylheteroaryl, or C$_1$-C$_{10}$ hydroxyalkyl; and n is 0 or 1, wherein: when n is 1, the nitrogen to which R$^2$ is attached has a positive charge and optionally is associated with an anion; and when n is 0, R$^2$ is not present; and (iii) exposing the phototherapy agent administered to the patient to electromagnetic radiation. In an embodiment of this aspect, the compound having the formula (FX1), (FX2) or (FX61) and the phototherapy agent are administered at the same time (e.g., co-administered). In an embodiment of this aspect, the compound having the formula (FX1), (FX2) or (FX61) is administered before, during or after administration of the phototherapy agent. In an embodiment of this aspect, the compound having the formula (FX1), (FX2) or (FX61) is administered before, during or after exposure of the phototherapy agent to electromagnetic radiation.

In an embodiment, the method of this aspect of the invention comprises administering to a patient an anti-angiogenesis agent and/or anti-VEGF agent. In an embodiment, the invention comprises administering a tertiary amine having formula (FX1), (FX2) or (FX61). In an embodiment, the invention comprises administering a quarternary amine or salt thereof having formula (FX1), (FX2) or (FX61). In an embodiment, the invention comprises administering an N-oxide or salt thereof having formula (FX1), (FX2) or (FX61). In an embodiment, the method of this aspect of the invention comprises administering to a patient a compound having any one of formulae (FX1)-(FX164), including all of the specific composition classes and compounds described herein, in combination with any of the method steps presented herein. As will be understood by one of skill in the art, the present methods expressly include administering one or more anti-VEGF agents, including the compound classes, compounds, and variations thereof described herein, including the compound classes, compounds and variations described in connection with any one of formulae (FX1)-(FX164), in combination with the steps of administering and exposing the phototherapy agent administered to the patient to electromagnetic radiation.

In an embodiment, the invention provides a method of alleviating a proangiogenesis effect of a medical therapy, the method comprising: administering to a patient undergoing a phototherapy procedure an effective amount of a compound having any one of formulae (FX1)-(FX164) or a pharmaceutically acceptable salt, solvate, hydrate, clathrate or prodrug thereof, including all of the specific compositions classes and compounds described herein. In an embodiment, the invention provides a method of inhibiting an endogenous angiogenic response to a phototherapy procedure, the method comprising: administering to a patient undergoing a phototherapy procedure an effective amount of a compound having any one of formulae (FX1)-(FX164) or a pharmaceutically acceptable salt, solvate, hydrate, clathrate or prodrug thereof. In an embodiment, the invention provides a method of increasing the therapeutic efficacy of a phototherapy procedure, the method comprising: administering to a patient undergoing the phototherapy procedure an effective amount of a compound having the any one of formulae (FX1)-(FX164) or a pharmaceutically acceptable salt, solvate, hydrate, clathrate or prodrug thereof, including all of the specific composition classes and compounds described herein.

Phototherapy methods of the invention include photodynamic therapy and thermal laser photocoagulation. Methods of the present invention may further comprise a number of additional steps. In an embodiment, for example, the method further comprises delivering a compound of any one of formulae (FX1)-(FX164) and phototherapy agent to a target tissue or organ, such as a tumor. In an embodiment, the method further comprises contacting a target tissue or organ with a compound of any one of formulae (FX1)-(FX164) and a phototherapy agent. In an embodiment, the present methods further comprise the step of administering the compound of any one of formulae (FX1)-(FX164) and the phototherapy agent into a bodily fluid of the subject. Anti-VEGF agents and phototherapy agents may be introduced into the patient by any suitable method, including intravenous, intraperitoneal or subcutaneous injection or infusion, oral administration, transdermal absorption through the skin, or by inhalation. In an embodiment, the method further comprises allowing the anti-VEGF agent and phototherapy agent to accumulate in a target tissue or organ prior to exposure of the phototherapy agent to electromagnetic radiation. In an embodiment, the anti-VEGF agent and phototherapy agent are administered to the skin, a tumor, surgical site, or a wound site. In an embodiment, for example, the anti-VEGF agent and phototherapy agent are administered and/or delivered to a blood vessel, lung, heart, throat, ear, rectum, bladder, stomach, intestine, esophagus, liver, brain, prostrate, breast or pancreas of the subject.

Dosages of the present opioids and structurally related derivatives will be variable depending on many factors, including, for example, the route of administration. If injected into the eye, for example, the dose will be very small whereas oral administration will involve a larger dosage due to transport of charged agent. A useful range for administered dose of the present therapeutic agents is 0.001 mg to 0.5 g. The formulations for treatment of macular degeneration comprise a phototherapy agent (Type I or II), and one or more VEGF inhibitors of this invention with or without additional starting base in normal saline, buffer, GRAS incipients, etc. In some embodiments for the treatment of cancers by phototherapy, the phototherapy agent with the VEGF inhibitor and a cytotoxic is administered. (−)R-naltrexone methobromide is synergistic with 5-fluorouracil in endothelial cells and is also synergistic with Avastin to inhibit VEGF expression (the agents work differently). Recited cytotoxics for cancer therapy include a broad range of known agents as combination therapy including, but not limited to, 5-Fluorouracil, floxuridine, furtulon, capecitabine, gemcitabine, taxol (all forms), doxorubicin, cisplatin, and/or in conjunction with other VEGF inhibitors like thalidomide or Avastin. The invention further includes combination therapies wherein the present opioids and structurally related derivatives are administered with one or more other therapeutic agents and/or diagnostic agents, including, but not limited to, alkylating agents, anti-metabolites, anti-cytoskeletal agents, topoisomerase inhibitors, anti-hormonal agents, targeted therapeutic agents, and the like. Examples of alkylating agents include, but are not limited to, altretamine, benzodopa, busulfan, carboplatin, carboquone, carmustine, chlorambucil, chlornaphazine, chlorophosphamide, chlorozotocin, cisplatin, cyclophosphamide, dacarbazine (DTIC), estramustine, fotemustine, ifosfamide, improsulfan, lomustine, mechlorethamine, mechlorethamine oxide hydrochloride, melphalan, meturedopa, nimustine, novembichin, phenesterine, piposulfan, prednimustine, ranimustine, temozolomide, thiotepa, triethylenemelamine, triethylenephosphoramide, triethylenethiophosphaoramide, trimethylolomelamine, trofosfamide, uracil mustard and uredopa. Suitable anti-metabolites include, but are not limited to aminopterin, ancitabine, azacitidine, 6-azauridine, capecitabine, carmofur, cytarabine or cytosine arabinoside (Ara-C), dideoxyuridine, denopterin, doxifluridine, enocitabine, floxuridine, fludarabine, 5-fluorouracil (5-FU), gemcetabine, leucovorin (folinic acid), 6-mercaptopurine, methotrexate, pemetrexed, pteropterin, thiamiprine, trimetrexate, and thioguanine. Examples of suitable anti-cytoskeletal agents include, but are not limited to, colchicines, docetaxel, macromycin, paclitaxel (taxol), vinblastine, vincristine, vindesine, and vinorelbine. Suitable topoisomerase inhibitors include, but are not limited to, amsacrine, etoposide (VP-16), irinotecan, RFS 2000, teniposide, and topotecan. Examples of suitable anti-hormonal agents include, but are not limited to, aminoglutethimide, aromatase inhibiting 4(5)-imidazoles, bicalutamide, finasteride, flutamide, goserelin, 4-hydroxytamoxifen, keoxifene, leuprolide, LY117018, mitotane, nilutamide, onapristone, raloxifene, tamoxifen, toremifene, and trilostane.—Examples of targeted therapeutic agents include, but are not limited to, a monoclonal antibodies such as alemtuzumab, bevacizumab, capecitabine, cetuximab, gemtuzumab, heregulin, rituximab, trastuzumab; tyrosine kinase inhibitors such as imatinib and mesylate; and growth inhibitory polypeptides such as erythropoietin, interleukins (e.g., IL-1, IL-2, IL-3, IL-6), leukemia inhibitory factor, interferons, thrombopoietin, TNF-α, CD30 ligand, 4-1BB ligand, and Apo-1 ligand. The (+) alkaloid bases also have potential activity as anti-inflammatory cytokine inhibitors. The combination of base with charged complement will act synergistically for an indication like macular degeneration since benefit has been shown with other combo agents that include an anti-VEGF therapeutic.

A range of phototherapy agents are useful in the present methods, including Type 1 and Type 2 phototherapy agents. Type 2 phototherapy agents for the present methods, include, but are not limited to, Photofrin®, Visudyne®, benzoporphyrins, phthalocyanines, phenothiazines, chlorins, bacteriochlorins, phthalocyanines, porphyrins, purpurins, merocyanines, pheophorbides, psoralens, aminolevulinic acid (ALA), hematoporphyrin derivatives, porphycenes, porphacyanine, and expanded porphyrin-like compounds and pro-drugs such as δ-aminolevulinic acid, which can produce drugs such as protoporphyrin. Type 1 phototherapy agents include, but are not limited to, cyanines, indocyanines, phthalocyanines, rhodamines, phenoxazines, phenothiazines, phenoselenazines, fluoresceins, squaraines, corrins, croconiums, azo dyes, methine dyes, indolenium dyes, halogens, anthracylines, azides, $C_1$-$C_{20}$ peroxyalkyls, $C_5$-$C_{20}$ peroxyaryls, $C_1$-$C_{20}$ sulfenatoalkyls, sulfenatoaryls, azo dyes, naphthalocyanines, methylene blues, and chalcogenopyrylium analogues. Specific photosensitizers useful in some embodiments of the present invention are further described in any of U.S. Pat. Nos. 7,303,926; 7,230,088; 7,198,778; 7,235,685; 7,011,817; 7,201,892; 7,128,896; 6,485,704; 5,438,071; 5,405,957; 5,198,460; 5,190,966; 5,173,504; 5,171,741; 5,166,197; 5,095,030; 5,093,349; 5,079,262; 5,028,621; 5,002,962; 4,968,715; 4,920,143; 4,883,790; 4,866,168; and 4,649,151. Photosensitizers useful in the present invention are further described in any of International Patent Publication Nos.

WO 2003/032900, WO 2005/089813, and WO 2007/103250, and U.S. Patent Application Publication No. US 2002/0169107.

In some methods for phototherapy, the target region is illuminated with electromagnetic radiation having wavelengths in the range of about 350 nm to about 1300 nm, preferably for some applications in the range of about 400 nm to about 900 nm. In an embodiment, the target region is illuminated with electromagnetic radiation having wavelengths in the range of about 300 nm to about 900 nm. In some embodiments, the wavelength of the electromagnetic radiation corresponds to a peak in the absorption spectrum of the phototherapy agent, for example is within 20 nanometers of a peak in the absorption spectrum of the phototherapy agent in the visible or NIR regions. In some phototherapy procedures the target site is exposed to electromagnetic radiation having fluence, dosage and/or power sufficient to activate the phototherapy agent so as to induce cell death, for example via necrosis or apoptosis processes. In some embodiments, electromagnetic radiation having low energy (e.g., less than 200 mW/cm$^2$ or optionally less than 100 mW/cm$^2$), power or fluence, but sufficient dosage, is provided to activate the phototherapy agent without undesirable thermal effects. If the region of interest is, for example, a lesion or tumor on the skin surface, the region can be directly illuminated. In some methods, endoscopic and/or endoluminal catheters can be employed to deliver electromagnetic radiation to the subject to provide a photodiagnostic and/or phototherapeutic effect. The intensity, power, and duration of the illumination and the wavelength of the electromagnetic radiation can vary widely depending on the body location, the lesion site, the effect to be achieved, etc. In an embodiment, the power of the applied electromagnetic radiation is preferably selected over the range of 1-500 mW/cm$^2$ and optionally for some applications is selected over the range of 1-200 mW/cm$^2$ and optionally for some applications selected over the range of 1-100 mW/cm$^2$. In an embodiment, the duration of the exposure to applied electromagnetic radiation is selected over the range of 1 second to 60 minutes, and optionally for some applications is selected over the range of 1 second to 30 minutes, and optionally for some applications is selected over the range of 1 second to 10 minutes, and optionally for some applications is selected over the range of 1 second to 1 minute.

In embodiments, subjects of the invention can be any mammal, such as a human, and optionally the subject of the present methods is a patient in need of treatment and/or diagnosis. The present methods are also useful for ex vivo and in vitro procedures, including medical therapeutic and diagnostic procedures. As will be understood by one having skill in the art, the optical conditions for exposing the optical agent administered to the patient to electromagnetic radiation will vary considerably with the (i) therapeutic and/or diagnostic objectives, and (ii) the condition of the subject (e.g., height, weight, state of health etc.). In an embodiment, the applied electromagnetic radiation has wavelengths, energy and/or fluence sufficient to achieve a desired therapeutic and/or diagnostic result. In an embodiment, the electromagnetic radiation has wavelengths, energy and/or fluence sufficient to activate the optical agent. Optionally, excitation is achieved using electromagnetic radiation substantially free (e.g., less than about 10% of total radiant energy), of ultraviolet radiation, for example, to minimize exposure of the subject to electromagnetic radiation capable of causing unwanted cell or tissue damage. Electromagnetic radiation can be provided to the optical agent using a range of optical sources and/or surgical instrumentation, including a laser, electromagnetic radiation emitting diodes, fiber optic device, endoscope, catheter, optical filters, mirrors, lenses, or any combination of these.

In an embodiment, the method further comprises contacting a target tissue of a patient in need of treatment with an effective amount of a compound of any one of formulae (FX1)-(FX164) and an effective amount of a phototherapy agent. In a specific method, the target tissue is a tumor, a region of abnormal tissue growth or region of abnormal blood vessel growth. In a specific method, the target tissue is a mammary carcinoma, an esophageal carcinoma, an endobronchial carcinoma, a bladder tumor, a cervical tumor, a brain tumor, a head and neck tumor, a lung tumor, a pituitary tumor, an intrathoracic tumor or a skin malignancy. The present methods have broad clinical utility which includes, but is not limited to, phototherapy of tumors, inflammatory processes, and impaired vasculature. In embodiments, subjects of the invention may be any mammal, such as a human, and optionally the subject of the present methods is a patient in need of treatment and/or diagnosis. The present methods include in vivo, ex vivo and in vitro procedures.

In an embodiment, a therapeutically effective amount of the anti-VEGF agent is provided to the subject. For example, parenteral administration advantageously contains a sterile aqueous solution or suspension of the anti-VEGF agent having a concentration of an active agent comprising the compound of any one of formulae (FX1)-(FX164) ranging from about 0.01 µM to about 0.5M. Preferred parenteral formulations have a concentration of an active agent comprising the compound of any one of formulae (FX1)-(FX164) selected over the range of 1 µM to 10 mM. Such solutions also may contain pharmaceutically acceptable buffers, emulsifiers, surfactants, and, optionally, electrolytes such as sodium chloride. The dose of the compound of any one of formulae (FX1)-(FX164) may vary from 0.1 to 500 mg/kg body weight, preferably from 0.5 to 2 mg/kg body weight.

In methods of the present invention, the anti-VEGF agent and/or phototherapy agent can be formulated for enteral (oral or rectal), parenteral, topical, or cutaneous administration. Topical or cutaneous delivery of the anti-VEGF agent and/or phototherapy agent may also include aerosols, creams, gels, solutions, emulsions and colloids. The compositions are administered in doses effective to achieve the desired diagnostic or therapeutic objective. Such doses may vary widely depending upon the particular complex employed, the organs or tissues to be examined or treated, the equipment employed in the clinical procedure, the efficacy of the treatment achieved, and the like. These compositions contain an effective amount of the anti-VEGF agent and phototherapy agent along with conventional pharmaceutical carriers and excipients appropriate for the type of administration contemplated. These compositions may also include stabilizing agents and skin penetration enhancing agents and also may contain pharmaceutically acceptable buffers, emulsifiers, surfactants, and, optionally, electrolytes such as sodium chloride. Formulations for enteral administration may vary widely, as is well known in the art. In general, such formulations are liquids, which include an effective amount of the complexes in aqueous solution or suspension. Such enteral compositions may optionally include buffers, surfactants, emulsifiers, thixotropic agents, and the like. Compounds for oral administration may also contain flavoring agents and other ingredients for enhancing their organoleptic qualities. Formulations for topical delivery may also contain liquid or semisolid excipients to assist in the penetration of the photosensitizer. The compounds may also be delivered in an aerosol spray.

As will be appreciated by one having skill in the art, the fluence employed during excitation of the phototherapy agent can vary depending on the type of tissue, depth of the target, composition of the phototherapy agent and the amount on composition of overlying fluid and blood. In some embodiments, the fluence employed is selected over the range of 10 to 500 Joules/cm$^{-2}$. The irradiance is typically selected from the range of 50 to 1500 mW/cm$^{-2}$, preferably of 50 to 500 mW/cm$^{-2}$. Electromagnetic radiation may be provided to the phototherapy agent using a range of optical sources and/or surgical instrumentation, including a laser, light emitting diodes, fiber optic device, endoscope, catheter, optical filters, or any combination of these.

Example 2

Methods of Using Anti-VEGF Opioids and Structurally Related Derivatives for Treatment and Management of Macular Degeneration Macular degeneration (MD) is an eye disease that destroys central vision by damaging the macula, a thin layer of nerve cells that lines most of the inside of the eye. There are two forms of MD: atrophic ("dry") and exudative ("wet"). About ninety percent of patients have the dry form; whereas, only ten percent have the "wet" form. Patients with the wet form can lose up to ninety percent of their vision rapidly. Macular degeneration is the most common cause of visual loss in individuals over the age of 60 and has destroyed the central vision of 1.7 million Americans with another 11 million at risk. 200,000 new cases of advanced, age-related macular degeneration (AMD) are identified each year in the United States. Currently, there is no known cure. Since the elderly is the fastest growing segment of the population, MD will become a major economic and social problem. Thus, there is an urgent need for effective treatments for MD, particularly AMD Wet macular degeneration develops when new blood vessels grow from the choroid underneath the macular portion of the retina. These new vessels are called choroidal neovascularizations (CNVs). These vessels leak fluid or blood, thus the term "wet" macular degeneration. Much like the dry form of macular degeneration, a breakdown in the vascular architecture activates the abnormal growth of blood vessels. Without normal perfusion of the macula, the tissue deteriorates. Laser photocoagulation was the only routine therapeutic option used for wet MD until recently and provided only modest response. Less intense phototherapy using the photoreactive dye, Verteporfin, has recently been used to treat wet MD. Verteporfin is a blood-vessel-blocking agent that is administered via injection. Activated verteporfin generates highly reactive oxygen species resulting in local damage to neovascular endothelium. This causes vessel occlusion and reduced progression of the disease. However, since verteporfin can accumulate in the retina, collateral damage to retinal structures may unfortunately result with concomitant loss of some remaining vision.

The first antiangiogenic agent, α-interferon, clinically tested for MD was ineffective and resulted in a high rate of adverse effects. A number of other antiangiogenic drugs are in development, including angiostatic steroids (e.g., anecortave acetate, Alcon) and antibodies or antibody fragments of vascular epidermal growth factor (VEGF) (e.g. Avastin-bevacizumab). Additional new drugs for the treatment of MD include EYE101 (Eyetech Pharmaceuticals), LY333531 (Eli Lilly), and RETISERT implant (Bausch & Lomb), which exudes a steroid into the eye for up to three years. The most successful currently FDA approved agent is Lucentis (ranibizumab), a humanized anti-VEGF antibody fragment that inhibits VEGF activity by competitive binding. Lucentis is derived from Avastin (bevacizumab), a full-length humanized monoclonal antibody against VEGF. About 95% patients with wet macular degeneration maintain their baseline vision after 12 months of treatment with Lucentis. Both agents are given by injection directly into the affected eye(s) every once a month for the first four months then every three months for the rest of the patient's life. The downside of Lucentis® and Avastin® treatment is that they stop the abnormal vessels from growing and leaking but often don't cause permanent closure. Therefore, injections of either drug have to be given repeatedly. PDT can close vessels permanently but often at the price of vision loss. Combination therapy is most efficacious. The most common combination now used is PDT with half the amount of laser dose followed with an injection of Lucentis® or of Avastin® and optionally with an anti-inflammatory steroid.

Figure 3:
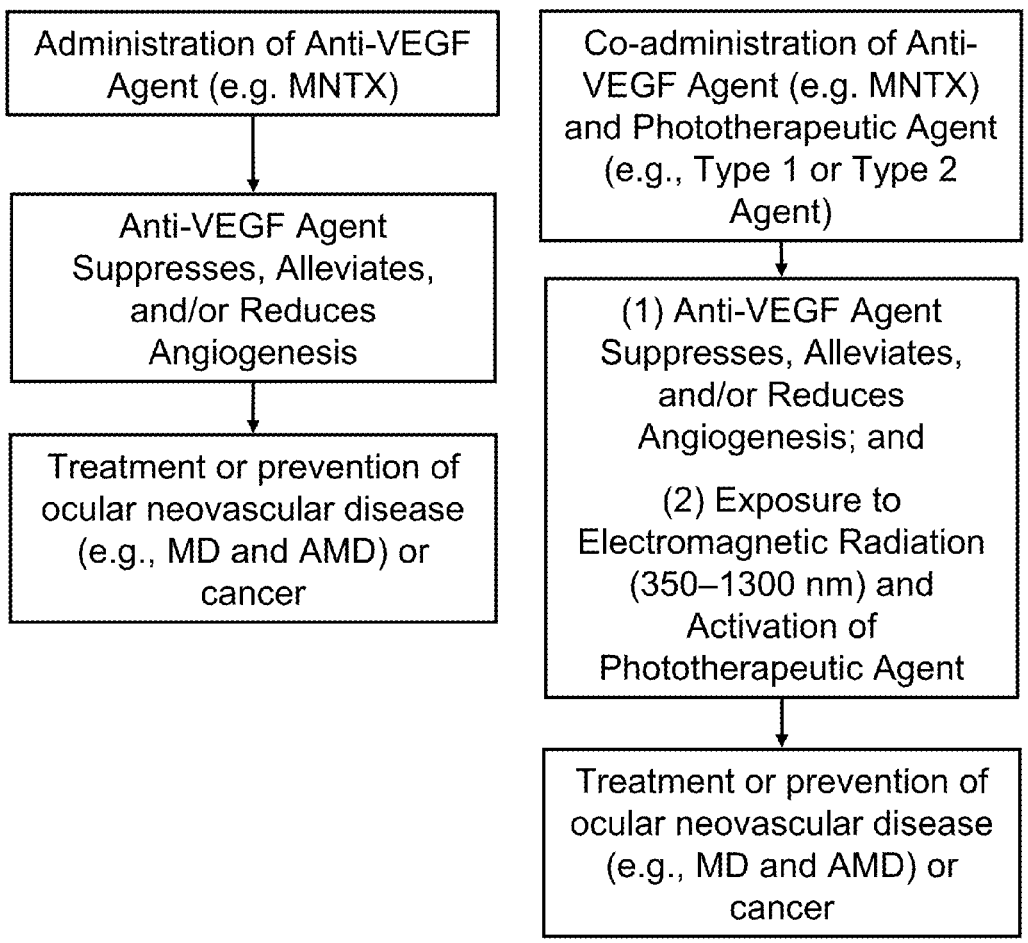
FIG. 3 provides a flow diagram diagrams illustrating methods of the present invention for the treatment of an ocular neovascular diseases including the step of administering an anti-VEGF agent. As shown in this figure the present methods and compositions for treating ocular neovascular disease encompass both monotherapies and combination therapies in conjunction with administration and excitation of a phototherapy agent.

The present invention provides opioids and structurally related derivatives useful as anti-angiogenesis agents and anti-VEGF agents for in treatment of ocular neovascular diseases, including macular degeneration such as age related macular degeneration. In some embodiments, for example, the present invention provides methods comprising in vivo administration of an anti-VEGF agent comprising an opioid or structurally related derivative to a patient in need of treatment, optionally further including administration and excitation of a phototherapy agent. FIG. 3 provides flow diagrams illustrating methods of the present invention for the treatment of ocular neovascular diseases including the step of administering an anti-VEGF agent. As shown in this figure, the present methods and compositions for treating ocular neovascular disease encompass both monotherapies and combination therapies in conjunction with administration and excitation of a phototherapy agent. In the direct monotherapy, an anti-VEGF agent is administered to a target tissue. Administration results in suppression, alleviation and/or reduction of unwanted angiogenesis, thereby resulting in treatment or prevention of an ocular neovascular disease, such as MD and AMD. In the combination therapy, an anti-VEGF agent and phototherapy agent are co-administered to a target tissue. Administration followed by activation results in treatment or prevention of ocular neovascular disease wherein the anti-VEGF agent suppresses, alleviates and/or reduces unwanted angiogenesis.

Anti-VEGF and Anti-angiogenic agents of the methods of this aspect of the invention include a large number of opioid antagonists, opioid agonists and structurally related derivatives thereof including, but not limited to, quaternary salts and isomeric and epimeric forms of (+/−)R/S-Naloxone, (+/−)R/S-Nalmefene, nalbuphine, (+/−)-oxymorphone, (+/−)-hydrocodone, (+/−)-oxycodone, (+/−)-hydromorphone, tetrahydrosinomenine, dextrorphan, and dextromethorphan. These compounds provide anti-VEGF therapeutic agents effective for treatment of ocular neovascular disease.

In an embodiment, the invention provides a method of treating an ocular neovascular disease, the method comprising administering to a patient an effective amount of a compound having the formula (FX1) or (FX2):

(FX1)

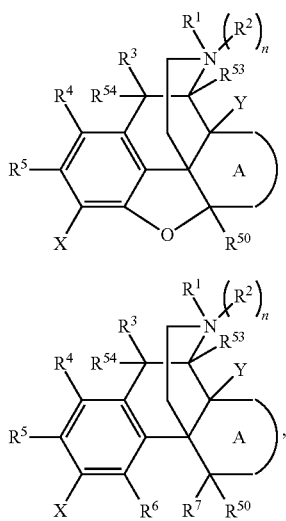

or (FX2)

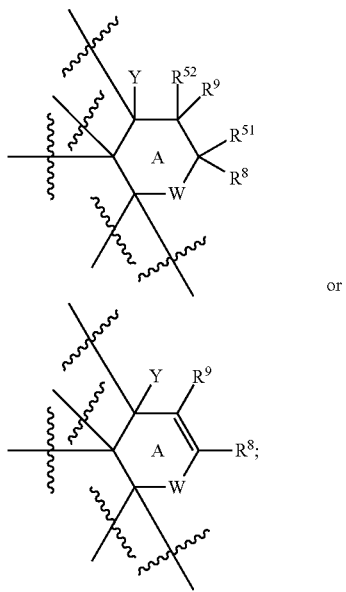

wherein: ring A is

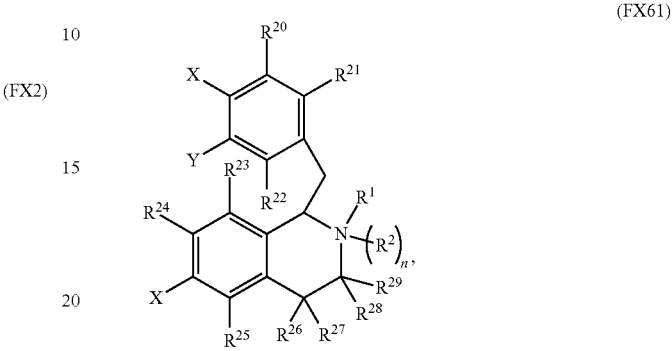

X is —OH, —OCH$_3$, or C$_2$-C$_8$ alkoxy; Y is —H or —OH; W is —(CR$^{10}$R$^{11}$)—, —(C=O)—, —(C=S)—, —(C=CR$^{12}$R$^{13}$), or —(CR$^{14}$NR$^{15}$R$^{16}$)—; each of R$^1$ and R$^2$ is independently —H, —CH$_3$, —(O$^-$), C$_1$-C$_{10}$ alkyl, C$_3$-C$_{10}$ cycloalkyl, C$_2$-C$_{10}$ alkenyl, C$_1$-C$_{10}$ haloalkyl, C$_5$-C$_{10}$ aryl, C$_5$-C$_{10}$ heteroaryl, C$_5$-C$_{10}$ alkylaryl, C$_5$-C$_{10}$ alkylheteroaryl, C$_5$-C$_{10}$ carbonylalkenylaryl, or C$_5$-C$_{10}$ carbonylalkenylheteroaryl; each of R$^3$-R$^{16}$ and R$^{50}$-R$^{54}$ is independently —H, —OH, —OCH$_3$, C$_1$-C$_8$ alkyl, C$_3$-C$_8$ cycloalkyl, C$_2$-C$_8$ alkenyl, C$_2$-C$_8$ alkoxy, C$_5$-C$_{10}$ aryl, C$_5$-C$_{10}$ heteroaryl, C$_5$-C$_{10}$ alkylaryl, C$_5$-C$_{10}$ alkylheteroaryl, halo, nitrile, C$_1$-C$_8$ haloalkyl, C$_1$-C$_{10}$ hydroxyalkyl, or C$_5$-C$_{10}$ carbonylalkenylheteroaryl; and n is 0 or 1, wherein: when n is 1, the nitrogen to which R$^2$ is attached has a positive charge and optionally is associated with an anion; when n is 0, R$^2$ is not present; and when in (FX1) each of X and Y is —OH, n is 1, and W is —(C=O)—, then each of R$^1$ and R$^2$ is independently a group other than cylcopropylmethyl, and each of R$^1$ and R$^2$ is independently a group other than methyl. In an embodiment, the invention provides a method of treating an ocular neovascular disease, the method comprising administering to a patient an effective amount of a compound having the formula (FX61):

(FX61)

wherein: each X is independently —OH, —OCH$_3$, or C$_2$-C$_8$ alkoxy; Y is —H, or —OH;

each of R$^1$ and R$^2$ is independently —H, —CH$_3$, —(O$^-$), C$_1$-C$_{10}$ alkyl, C$_3$-C$_{10}$ cycloalkyl, C$_2$-C$_{10}$ alkenyl, C$_1$-C$_{10}$ haloalkyl, C$_5$-C$_{10}$ aryl, C$_5$-C$_{10}$ heteroaryl, C$_5$-C$_{10}$ alkylaryl, C$_5$-C$_{10}$ alkylheteroaryl, C$_5$-C$_{10}$ carbonylalkenylaryl, or C$_5$-C$_{10}$ carbonylalkenylheteroaryl; each of R$^{20}$-R$^{29}$ is independently —H, —OH, —OCH$_3$, C$_1$-C$_8$ alkyl, C$_3$-C$_8$ cycloalkyl, C$_2$-C$_8$ alkenyl, C$_1$-C$_8$ alkoxy, C$_5$-C$_{10}$ aryl, C$_5$-C$_{10}$ heteroaryl, C$_5$-C$_{10}$ alkylaryl, C$_5$-C$_{10}$ alkylheteroaryl, halo, nitrile, C$_1$-C$_8$ haloalkyl, C$_5$-C$_{10}$ carbonylalkenylheteroaryl, or C$_1$-C$_{10}$ hydroxyalkyl; and n is 0 or 1, wherein: when n is 1, the nitrogen to which R$^2$ is attached has a positive charge and optionally is associated with an anion; and when n is 0, R$^2$ is not present. In an embodiment, the method of this aspect further comprises (i) administering to a patient an effective amount of a phototherapy agent and (ii) exposing the phototherapy agent administered to the patient to electromagnetic radiation. In an embodiment, the method of this aspect of the invention comprises administering to a patient a compound having any one of formulae (FX1)-(FX164), including all of the specific composition classes and compounds described herein, in combination with any of the method steps presented herein. In an embodiment, the method of this aspect of the invention comprises administering to a target tissue of a patient a compound having any one of formulae (FX1)-(FX164), including all of the specific composition classes and compounds described herein, in combination with any of the method steps presented herein. As will be understood by one of skill in the art, the present methods expressly include administering one or more anti-VEGF agents, including the compound classes, compounds, and variations thereof, described herein, including the compound classes, compounds and variations described in connection with any one of formulae (FX1)-(FX164), optionally in combination with co-administering and activating a phototherapy agent.

In an embodiment, the ocular neovascular disease is age related macular degeneration. In an embodiment, the ocular neovascular disease is ischemic retinopathy, intraocular neovascularization, neovascularization, retinal neovascularization, choroidal neovascularization, diabetic macular edema, diabetic retina ischemia, diabetic retinal edema or proliferative diabetic retinopathy. In an embodiment, a method of this aspect further includes contacting neovascular endothelium cells of a patient undergoing treatment with a compound having any one of formulae (FX1)-(FX164), and optionally contacting neovascular endothelium cells of a patient undergoing treatment with a phototherapy agent. In some embodiments, administration of a compound having any one of formulae (FX1)-(FX164) or pharmaceutical formulation thereof is delivered to an eye tissue of the patient; and optionally wherein delivery is via injection or topical delivery.

Example 3

Methods of Using Anti-VEGF Opioids and Structurally Related Derivatives for Treatment and Management of Cancer Opioids are a group of drugs that exhibit opium or morphine-like properties. They are employed primarily as moderate to strong analgesics, but have many other pharmacological effects as well, including drowsiness, respiratory depression, constipation, changes in mood, and mental clouding without a resulting loss of consciousness. Morphine and codeine are by far the most important naturally occurring opiate agonists. Substitution at the nitrogen atom of the morphinan ring of these compounds affects their pharmacologic properties. For example, morphinan derivatives having various nitrogen substituents exhibit partial agonist/antagonist activity or potent antagonist activity. Morphinan compounds comprising quaternary amines are also known. For example, some N-oxides of certain morphinans have been variously reported to be less active than the corresponding tertiary amine.

Recent research has shown that morphinans comprising opiate receptor antagonists and, in particular, their respective quaternary amines are potent inhibitors of vascular endothelial growth factor (VEGF). VEGF inhibitors are important adjuncts in the treatment of various tumors and the treatment of macular degeneration. More recent work has suggested that VEGF inhibitory activity appears to be independent of the stereochemistry of the morphinan ring system. That is, (+)-morphinan quaternary compounds appear to inhibit VEGF as well as the pharmacologically active (−)-morphinan quaternary compounds. Thus, other (+)-morphinan derivatives such as (+)-morphinanium N-oxides may be useful as improved VEGF inhibitors because they do not interact with opiate receptors.

The invention provides methods of treating cancer by administration of a therapeutically effective amount of an opioid compound, structurally related opioid derivative or isomer thereof. In an embodiment, for example, the invention provides a method of treating cancer, the method comprising administering to a patient in need of treatment an effective amount of a compound having the formula (FX1) or (FX2):

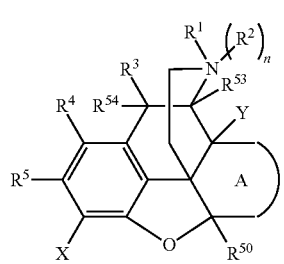

(FX1)

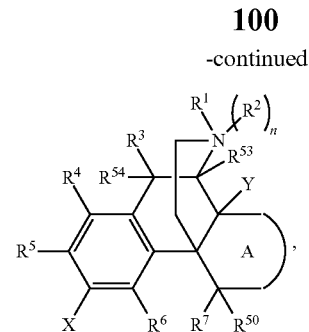

(FX2)

wherein: ring A is

[structure diagrams]

or

X is —OH, —OCH$_3$, or C$_2$-C$_8$ alkoxy;

Y is —H or —OH; W is —(CR$^{10}$R$^{11}$)—, —(C=S)—, —(C=CR$^{12}$R$^{13}$)—, or —(CR$^{14}$NR$^{15}$R$^{16}$)—; each of) R$^1$ and R$^2$ is independently —H, —CH$_3$, —(O$^{-)}$, C$_1$-C$_{10}$ alkyl, C$_3$-C$_{10}$ cycloalkyl, C$_2$-C$_{10}$ alkenyl, C$_1$-C$_{10}$ haloalkyl, C$_5$-C$_{10}$ aryl, C$_5$-C$_{10}$ heteroaryl, C$_5$-C$_{10}$ alkylaryl, C$_5$-C$_{10}$ alkylheteroaryl, C$_5$-C$_{10}$ carbonylalkenylaryl, or C$_5$-C$_{10}$ carbonylalkenylheteroaryl; each of R$^{10}$ and R$^{11}$ is independently —OCH$_3$, C$_1$-C$_8$ alkyl, C$_3$-C$_8$ cycloalkyl, C$_2$-C$_8$ alkenyl, C$_2$-C$_8$ alkoxy, C$_5$-C$_{10}$ aryl, C$_5$-C$_{10}$ heteroaryl, C$_5$-C$_{10}$ alkylaryl, C$_5$-C$_{10}$ alkylheteroaryl, halo, nitrile, C$_1$-C$_8$ haloalkyl, C$_1$-C$_{10}$ hydroxyalkyl, or C$_5$-C$_{10}$ carbonylalkenylheteroaryl; each of R$^3$-R$^9$, R$^{12}$-R$^{16}$, and R$^{50}$-R$^{54}$ is independently —H, —OH, —OCH$_3$, C$_1$-C$_8$ alkyl, C$_3$-C$_8$ cycloalkyl, C$_2$-C$_8$ alkenyl, C$_2$-C$_8$ alkoxy, C$_5$-C$_{10}$ aryl, C$_5$-C$_{10}$ heteroaryl, C$_5$-C$_{10}$ alkylaryl, C$_5$-C$_{10}$ alkylheteroaryl, halo, nitrile, C$_1$-C$_8$ haloalkyl, C$_1$-C$_{10}$ hydroxyalkyl, or C$_5$-C$_{10}$ carbonylalkenylheteroaryl; and n is 0 or 1, wherein: when n is 1, the nitrogen to which R$^2$ is attached has a positive charge and optionally is associated with an anion; and when n is 0, R$^2$ is not present. In an embodiment, for example, the invention provides a method of treating cancer, the method comprising administering to a patient in need of treatment an effective amount of a compound having the formula (FX1) or (FX2):

(FX3)

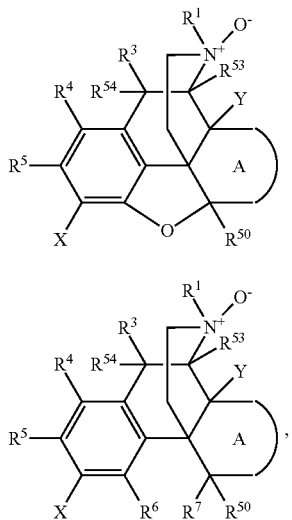

or (FX4)

wherein: ring A is

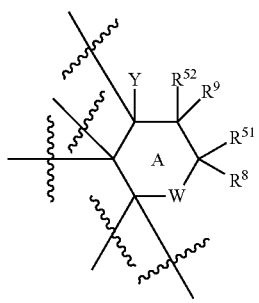

or

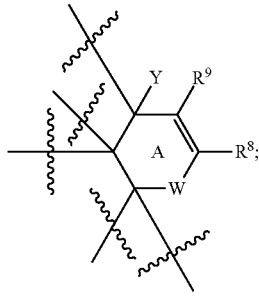

X is —OH, —OCH₃, or $C_2$-$C_8$ alkoxy; Y is —H or —OH; W, is —$(CR^{10}R^{11})$—, —(C=O)—, —(C=S)—, —$(C=CR^{12}R^{13})$—, or —$(CR^{14}NR^{15}R^{16})$—; $R^1$ is —H, —CH₃, —(O⁻), $C_1$-$C_{10}$ alkyl, $C_3$-$C_{10}$ cycloalkyl, $C_2$-$C_{10}$ alkenyl, $C_1$-$C_{10}$ haloalkyl, $C_5$-$C_{10}$ aryl, $C_5$-$C_{10}$ heteroaryl, $C_5$-$C_{10}$ alkylaryl, $C_5$-$C_{10}$ alkylheteroaryl, $C_5$-$C_{10}$ carbonylalkenylaryl, or $C_5$-$C_{10}$ carbonylalkenylheteroaryl; and each of $R^3$-$R^{16}$ and $R^{50}$-$R^{54}$ is independently —H, —OH, —OCH₃, $C_1$-$C_8$ alkyl, $C_3$-$C_8$ cycloalkyl, $C_2$-$C_8$ alkenyl, $C_2$-$C_8$ alkoxy, $C_5$-$C_{10}$ aryl, $C_5$-$C_{10}$ heteroaryl, $C_5$-$C_{10}$ alkylaryl, $C_5$-$C_{10}$ alkylheteroaryl, halo, nitrile, $C_1$-$C_8$ haloalkyl, $C_1$-$C_{10}$ hydroxyalkyl, or $C_5$-$C_{10}$ carbonylalkenylheteroaryl. In an embodiment, for example, the invention provides a method of treating cancer, the method comprising administering to a patient in need of treatment an effective amount of a compound having the formula (FX61):

(FX61)

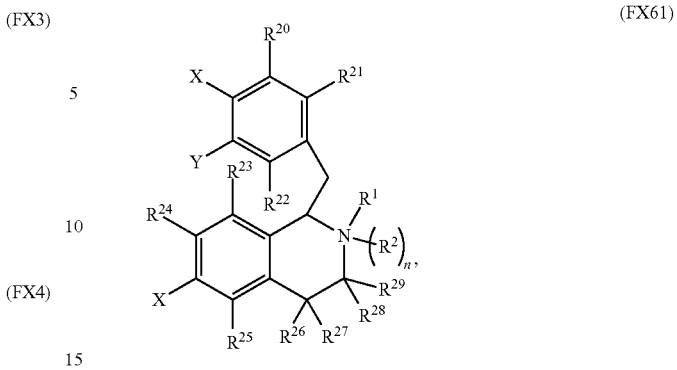

wherein: each X is independently —OH, —OCH₃, or $C_2$-$C_8$ alkoxy; Y is —H, or —OH;

each of $R^1$ and $R^2$ is independently —(O⁻), $C_1$-$C_{10}$ alkyl, $C_3$-$C_{10}$ cycloalkyl, $C_2$-$C_{10}$ alkenyl, $C_1$-$C_{10}$ haloalkyl, $C_5$-$C_{10}$ aryl, $C_5$-$C_{10}$ heteroaryl, $C_5$-$C_{10}$ alkylaryl, $C_5$-$C_{10}$ alkylheteroaryl, $C_5$-$C_{10}$ carbonylalkenylaryl, or $C_5$-$C_{10}$ carbonylalkenylheteroaryl; each of $R^{20}$-$R^{29}$ is independently —H, —OH, —OCH₃, $C_1$-$C_8$ alkyl, $C_3$-$C_8$ cycloalkyl, $C_2$-$C_8$ alkenyl, $C_1$-$C_8$ alkoxy, $C_5$-$C_{10}$ aryl, $C_5$-$C_{10}$ heteroaryl, $C_5$-$C_{10}$ alkylaryl, $C_5$-$C_{10}$ alkylheteroaryl, halo, nitrile, $C_1$-$C_8$ haloalkyl, $C_5$-$C_{10}$ carbonylalkenylheteroaryl, or $C_1$-$C_{10}$ hydroxyalkyl; and n is 0 or 1, wherein: when n is 1, the nitrogen to which $R^2$ is attached has a positive charge and optionally is associated with an anion; and when n is 0, $R^2$ is not present. In an embodiment, for example, the invention provides a method of treating cancer, the method comprising administering to a patient in need of treatment an effective amount of a compound having the formula (FX61):

(FX61)

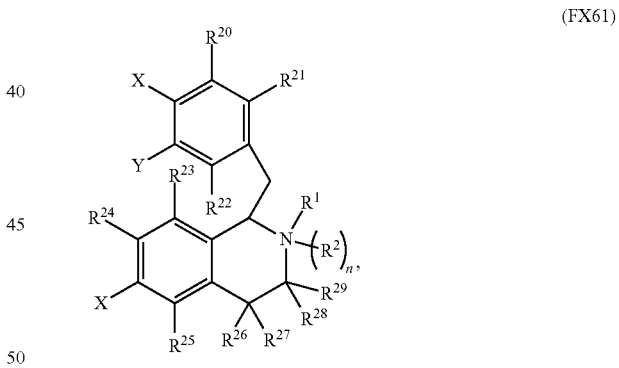

wherein: each X is independently —OH, —OCH₃, or $C_2$-$C_8$ alkoxy; Y is or —OH;

$R^1$ is —CH₃, $C_1$-$C_{10}$ alkyl, $C_3$-$C_{10}$ cycloalkyl, $C_2$-$C_{10}$ alkenyl, $C_1$-$C_{10}$ haloalkyl, $C_5$-$C_{10}$ aryl, $C_5$-$C_{10}$ heteroaryl, $C_5$-$C_{10}$ alkylaryl, $C_5$-$C_{10}$ alkylheteroaryl, $C_5$-$C_{10}$ carbonylalkenylaryl, or $C_5$-$C_{10}$ carbonylalkenylheteroaryl; and each of $R^{20}$-$R^{29}$ is independently —H, —OH, —OCH₃, $C_1$-$C_8$ alkyl, $C_3$-$C_8$ cycloalkyl, $C_2$-$C_8$ alkenyl, $C_1$-$C_8$ alkoxy, $C_5$-$C_{10}$ aryl, $C_5$-$C_{10}$ heteroaryl, $C_5$-$C_{10}$ alkylaryl, $C_5$-$C_{10}$ alkylheteroaryl, halo, nitrile, $C_1$-$C_8$ haloalkyl, $C_5$-$C_{10}$ carbonylalkenylheteroaryl, or $C_1$-$C_{10}$ hydroxyalkyl. In an embodiment, the method of treating cancer of this aspect of the invention comprises administering to a patient a compound having any one of formulae (FX1)-(FX164), including all of the specific compositions classes and compounds described herein, in combination with any of the method steps presented herein. In an embodiment, the method of treating cancer of this aspect of the invention comprises administering to a target tissue of a patient a compound having any one of formulae (FX1)-(FX164), including all of the specific composition classes and compounds described herein, in combination with any of the method steps presented herein. As will be understood by one of skill in the art, the present methods of treating cancer expressly include administering one or more anti-VEGF agents including the compound classes, compounds, and variations thereof, described herein, including the compound classes, compounds and variations described in connection with any one of formulae (FX1)-(FX164), optionally in combination with co-administering and activating a phototherapy agent.

In an aspect, the invention provides methods of attenuating migration and/or proliferation of endothelial cells of a tumor or cancer, comprising contacting the cells with a therapeutically effective amount of an opioid compound, structurally related opioid derivative or isomer thereof, such as a compound having any of formulae (FX1)-(FX164). In another aspect, the invention provides a method of treating abnormal angiogenesis associated with cancer, comprising administering to a target tissue, such as cancer tissue or a tumor, of the patient a therapeutically effective amount of an opioid compound, structurally related opioid derivative or isomer thereof, such as a compound having any of formulae (FX1)-(FX164), in an amount which is effective to at least partially attenuate abnormal angiogenesis. The invention also provides a method of treating abnormal neovascularization associated with cancer, comprising administering to a target tissue, such as cancer tissue or a tumor, of a patient in need of such treatment, a therapeutically effective amount of an opioid compound, structurally related opioid derivative or isomer thereof, such as a compound having any of formulae (FX1)-(FX164), effective to at least partially inhibit local formation of blood vessels. The invention provides a method of attenuating proliferation of hyperproliferative cells associated with cancer in a subject, comprising administering to a target tissue, such as cancer tissue or a tumor, of the subject at least one opioid compound, structurally related opioid derivative or isomer thereof, such as a compound having any of formulae (FX1)-(FX164), in an amount which is effective to attenuate proliferation of the hyperproliferative cells.

In an aspect, the invention provides methods to treat or inhibit the onset, development or recurrence of cancer. The invention provides a method of attenuating tumor progression and metastasis in animal tissues, comprising contacting a target tissue, such as tumor cells or tissues, with a therapeutically effective amount of an opioid compound, structurally related opioid derivative or isomer thereof, such as a compound having any of formulae (FX1)-(FX164). In another aspect, the invention provides a method of reducing the risk of recurrence of a cancer or tumor after medical intervention (such intervention to include, but not be limited to surgery, e.g. pulmonary surgery, surgical and endoscopic procedures, e.g. colonoscopy, gastrolaparoscopy, chemotherapy, etc.), comprising administering to a cancer patient an opioid compound, structurally related opioid derivative or isomer thereof, such as a compound having any of formulae (FX1)-(FX164). Therefore, as will be apparent to one having skill in the art, the invention contemplates, for example, a method of minimizing post-operative recurrence of cancer in a patient, comprising administering to a cancer patient an opioid compound, structurally related opioid derivative or isomer thereof, such as a compound having any of formulae (FX1)-(FX164). In an embodiment of the invention, the cancer is prostate cancer, gastrointestinal cancer, colon cancer, colorectal cancer, pancreatic cancer, breast cancer, lung cancer, throat cancer, skin cancer, stomach cancer, pancreatic cancer, brain cancer, liver cancer, prostate cancer, kidney cancer, bladder cancer, bone cancer, brain cancer, eye cancer, gallbladder cancer, head and neck cancer, Hodgkin lymphoma, mouth cancer, ovarian cancer, testicular cancer, throat cancer, esophageal cancer, small intestine cancer, pharyngeal cancer, laryngeal cancer, urethral cancer, uterine cancer, parathyroid cancer, cervical cancer, penile cancer or vaginal cancer. The compounds of the present invention may also be useful for the treatment of cancer in patients, as described above, either when used alone or in combination with one or more other anticancer agents, e.g., radiotherapy and/or other chemotherapeutic, including anti-angiogenic, treatments conventionally administered to patients for treating cancer. Several main categories and examples of such drugs are listed herein and include, but are not limited to metalloprotease inhibitors, inhibitors of endothelial cell proliferation/migration, antagonists of angiogenic growth factors, inhibitors of Integrin/Survival signaling, and chelators of copper.

The compositions and methods of the present invention may be of therapeutic value in treatment for patients who have cancers and/or tumors that develop and/or progress (e.g., grow, become invasive, metastasize, etc.), at least in part, via one or more angiogenesis processes. Cancers and tumors that develop and/or progress, at least in part, via one or more angiogenesis processes include carcinomas, sarcomas, leukemias, blastoma, myelomas, and solid tumors. Cancers and solid tumors include, but are not limited to, adrenal cortical carcinoma, tumors of the bladder: squamous cell carcinoma, urothelial carcinomas; tumors of the bone: adamantinoma, aneurysmal bone cysts, chondroblastoma, chondroma, chondromyxoid fibroma, chondrosarcoma, fibrous dysplasia of the bone, giant cell tumour, osteochondroma, osteosarcoma; breast tumors: secretory ductal carcinoma, chordoma; colon tumors: colorectal adenocarcinoma; eye tumors: posterior uveal melanoma, fibrogenesis imperfecta ossium, head and neck squamous cell carcinoma; kidney tumors: chromophobe renal cell carcinoma, clear cell renal cell carcinoma, nephroblastoma (Wilms tumor), kidney: papillary renal cell carcinoma, primary renal ASP-SCR1-TFE3 tumor, renal cell carcinoma; liver tumors: hepatoblastoma, hepatocellular carcinoma; lung tumors: non-small cell carcinoma, small cell cancer; malignant melanoma of soft parts; nervous system tumors: medulloblastoma, meningioma, neuroblastoma, astrocytic tumors, ependymomas, peripheral nerve sheath tumors, phaeochromocytoma; ovarian tumors: epithelial tumors, germ cell tumors, sex cord-stromal tumors, pericytoma; pituitary adenomas; rhabdoid tumor; skin tumors: cutaneous benign fibrous histiocytomas; smooth muscle tumors: intravenous leiomyomatosis; soft tissue tumors: liposarcoma, myxoid liposarcoma, low grade fibromyxoid sarcoma, leiomyosarcoma, alveolar soft part sarcoma, angiomatoid fibrous histiocytoma (AFH), clear cell sarcoma, desmoplastic small round cell tumor, elastofibroma, Ewing's tumors, extraskeletal myxoid chondrosarcoma, inflammatory myofibroblastic tumor, lipoblastoma, lipoma/benign lipomatous tumors, liposarcoma/malignant lipomatous tumors, malignant myoepithelioma, rhabdomyosarcoma, synovial sarcoma, squamous cell cancer; tumors of the testis: germ cell tumors, spermatocytic seminoma; thyroid tumors: anaplastic (undifferentiated) carcinoma, oncocytic tumors, papillary carcinoma; uterus tumors: carcinoma of the cervix, endometrial carcinoma, leiomyoma and the like.

The compositions and methods of the present invention may also be of therapeutic value in treatment for cancer patients who have nonangiogenic cancers and tumors, as many of these types of cancer tumors are known to undergo spontaneous transformation into an angiogeneic phenotype under some conditions. Cancers not involving angiogenesis include those that do not involve the formation of a solid tumor fed by neovasculature. Certain blood cell cancers can fall into this category, for example: leukemias, including acute lymphocytic leukemia (ALL), acute myelogenous leukemia (AML), chronic lymphocytic leukemia (CLL), chronic myelogenous leukemia (CML), and hairy cell leukemia; lymphomas (arising in the lymph nodes or lymphocytes) including Hodgkin lymphoma, Burkitt's lymphoma, cutaneous lymphoma, cutaneous T-cell lymphoma, follicular lymphoma, lymphoblastic lymphoma, MALT lymphoma, mantle cell lymphoma, Waldenstrom's macroglobulinemia, primary central nervous system lymphoma; and some cancers of the bone marrow elements including Ewing's sarcoma and osteosarcoma. Thus, in one aspect, the invention provides a method of treating cancer, wherein the cancer may be associated with an angiogenesis process or may be not associated with angiogenesis process.

Therapeutic methods for treatment of ocular neovascular disease and some forms of cancer can optionally include additional method steps, processes, variations, compositions, phototherapy agents, formulations, delivery conditions and phototherapeutic conditions as described above in connection with the phototherapy methods of the present invention.

Example 4

Quaternary Alkaloid VEGF Inhibitors as Adjuncts for the Treatment of Cancer and Macular Degeneration and in Phototherapy The invention provides compounds, such as morphinanium compounds and related derivative, salts and alkaloid forms, that inhibit metastasis induction by activation of the inflammatory response to excessive reactive oxygen species produced during photodynamic therapy (PDT) and other angiogenesis initiating therapies and disease conditions.

For example, it is believed that certain Type II Photodynamic therapy (PDT) agents initiate the up-regulation of VEGF that then promote tumorigenesis in certain vascular cancer types. Accelerated disease presents as gross metastasis. VEGF inhibitors effectively reduce the levels of VEGF post-PDT and thus mitigate side-effects and proliferation. (−)-R-Naltrexone methobromide (MNTX) may provide a potent VEGF inhibitor in some therapies. For example, MNTX may attenuate vascular permeability due to disease, injury or cancer. For example, MNTX may act synergistically with 5-fluorouracil and bevacizumab in suppressing VEGF-induced human pulmonary microvascular endothelial cell (EC) proliferation and migration, which are two key components in cancer-associated angiogenesis. For example, MNTX provides an active inhibitor of pancreatic cancer in mouse models. The synergistic effect of VEGF antibody, PDT/TypeII, Gemcitabine delivered by a non-targeted nanoparticle/liposomal methodology, significantly reduces pancreatic tumor weight relative to controls. Because the structurally unrelated quaternary alkaloid, berberine, also exhibits some inhibition of VEGF expression, opiate receptor binding may not be a necessary criteria for adjunct or therapeutic candidacy. Sufficiency for activity is also met by the (+) enantiomer and other isomers of MNTX as well as other related quaternary alkaloid salts and the nitrogen oxides of (+ or −) of morphinan alkaloids.

To evaluate the effectiveness of the present compounds in the context of therapeutic applications for the treatment of cancer and macular degeneration and for use in a phototherapy procedure, in vitro assay techniques such as cell proliferation and migration assay and VEGF ELISA methods may be used.

4.1 In Vitro Assay Techniques for Determining Anti-VEGF Activity

Angiogenesis or the formation of new blood vessels is used by neoplasm to harness nutrients for their survival and growth. Endothelia cells are activated by the nearby neoplastic cells that lead to secretion of VEGF, MMPS and other angiogenic stimuli. MMPS degrades the extracellular matrix and VEGF stimulates angiogenesis. [See, (1) Folkman, J. Angiogenesis in cancer, vascular, rheumatoid and other diseases. Nat. Med., 1: 27-33, 1995; and (2) J. Folkman, The role of angiogenesis in tumor growth, Cancer Biol., 1992, 3, 65-71]. As a result the endothelial cells invade the ECM where they migrate, proliferate and form new blood vessels, which supports neoplasm growth and survival. The angiogenic potential of neoplasm also correlates with its metastases potential. Hence by inhibiting some of these factors the angiogenesis process can be stopped suppressing the tumor growth and metastases. [See, e.g., Dvorak, H. F., Brown, L. F., Detmar, M., and Dvorak, A. M. Vascular permeability factor/vascular endothelial growth factor, microvascular hyperpermeability and angiogenesis. Am. J. Pathol., 146: 1029-1039, 1995.]

Cell Proliferation and Migration Assay

Proliferation and migration of Endothelial Cells (EC) is an important hallmark of angiogenesis. [See. e.g., Folkman, J. Angiogenesis in cancer, vascular, rheumatoid and other diseases. Nat. Med., 1: 27-33, 1995]. Hence it is important to screen compounds for their inhibitor properties on cell migration and proliferation. Human umbilical vein endothelial cells (HUVECs) and Human Pulmonary Microvascular EC (HPMEC) may be used to assess the anti-proliferative and migrating properties of the present compounds.

The cell migration assay is based on the cell migration in a modified Boyden chamber. [See, e.g., Lingen, M. W., 2002. Endothelial Cell Migration Assay: A Quantitative Assay for Prediction of In Vivo Biology. Humana Press, Inc., pp. 337-347]. The upper chamber (UC) contains cell is treated with various test compounds and the lower chamber (LC) contains the agonist/chemo attractant. At the end of the assay, typically 24 hours, a cell proliferation reagent like WSt-1 is added. After 2 hours the absorbance of the cells is read with a plate reader. Any reduction in the absorbance values by the present compounds versus that of control suggests that the compound has anti-angiogenic properties.

The cell proliferation assay measures the ability of various compounds of the invention to inhibit the growth of EC in presence VEGF or Morphine Sulfate. [See, e.g., Methylnaltrexone inhibits opiate and VEGF-induced angiogenesis: Role of receptor transactivation. P. A. Singleton et al./Microvascular Research 72 (2006) 3-11]. Briefly, cells are pretreated with the test compounds followed by VEGF incubation. Negative controls are not pretreated and VEGF is added directly. After the VEGF treatment, a cell proliferation reagent, such as WST-1, is added and the absorbance is measured. Any reduction in absorbance values observed for cells pre-treated with the present compounds versus no pre-treatment points toward the anti-angiogenic properties of the compounds tested.

VEGF ELISA

VEGF is a potent, multifunctional, and endothelial cell specific growth factor. The production of vascular endothelial growth factor (VEGF) by tumor cells plays an integral role in controlling proliferation and metastasis. [See, e.g., Dvorak, H. F., Brown, L. F., Detmar, M., and Dvorak, A. M. Vascular permeability factor/vascular endothelial growth factor, microvascular hyperpermeability and angiogenesis. Am. J. Pathol., 146: 1029-1039, 1995]. It stimulates vasodilatation and cell proliferation, increases permeability and migration, and promotes endothelial cell survival. [See, e.g., Ferrara N: Vascular endothelial growth factor as a target for anticancer therapy. Oncologist 9: 2-10, 2004]. It is upregulated in response to hypoxic conditions in the tumor [See, e.g., Pugh C W and Ratcliffe P J: Regulation of angiogenesis by hypoxia: Role of the HIF system. Nat Med 9: 677-684, 2003], chemotherapy and radiation induced stress [See, e.g., (1) Effect of chemotherapeutic stress on induction of vascular endothelial growth factor family members and receptors in human colorectal cancer cells Mol Cancer Ther 2008; 7(9):3064-70], (2) Targeting Chemotherapy-induced VEGF Up-regulation by VEGF Antisense Oligonucleotides in HNSCC Cell Lines. FRANK RIEDEL, KARL GÖTTE, ULRICH GOESSLER, HANNEN SADICK and KARL HÖRMANN. Anticancer Research Jul. 1, 2004 vol. 24 no. 4 2179-2184, (3) Z-360, a Novel Cholecystokinin-2/Gastrin Receptor Antagonist, Inhibits Gemcitabine-Induced Expression of the Vascular Endothelial Growth Factor Gene in Human Pancreatic Cancer Cells. Nobuyoshi KOBAYASHI, Koichi SETO, *Yuki ORIKAWA, Hiroki HAMANO, Koji YOSHINAGA, and Mineo TAKEI. Biol. Pharm. Bull. 33(2) 216-222 (2010)], and photodynamic therapy. [See, e.g., Effect of hypericin-mediated photodynamic therapy on the expression of vascular endothelial growth factor in human nasopharyngeal carcinoma. INTERNATIONAL JOURNAL OF MOLECULAR MEDICINE 20: 421-428, 2007].

The VEGF ELISA is an in vitro method that measures VEGF content in conditioned media, tissue lysates, cell lysates, and serum. Briefly, cells are pre-treated with compounds/drugs that induce VEGF expression and its secretion in conditioned media. The conditioned media is then collected and the secreted VEGF can be captured using a capture antibody. [See, e.g., Z-360, a Novel Cholecystokinin-2/Gastrin Receptor Antagonist, Inhibits Gemcitabine-Induced Expression of the Vascular Endothelial Growth Factor Gene in Human Pancreatic Cancer Cells. Nobuyoshi KOBAYASHI, Koichi SETO, *Yuki ORIKAWA, Hiroki HAMANO, Koji YOSHINAGA, and Mineo TAKEI. Biol. Pharm. Bull. 33(2) 216-222 (2010)]. The captured VEGF is then detected as summarized in the general ELISA protocol. (R&D Systems, Minneapolis, Minn.).

The present compounds are screened in a similar fashion for their effect on the VEGF levels in conditioned media. Cells are pretreated with the present compounds, for example for 1 hour, before actual treatment with VEGF inducing drugs/compounds. After a pre-determined treatment time, the conditioned media is collected and stored at −20 C. The cell lysate is also prepared for measuring the intracellular level of VEGF. The VEGF levels are measured using the VEGF ELISA kit from R&D Systems (Minneapolis, Minn.). The VEGF levels are then be compared for any reduction seen with pre-treatment of cells with the present compounds as compared to cells without any pre-treatment.

In vitro cell proliferation and migration assay may be carried out in connection with the compounds of the present invention. For example, such an assay approach may be carried out with respect to the four related alkaloids shown below provided in a substantially purified form with respect to other stereoisomers:

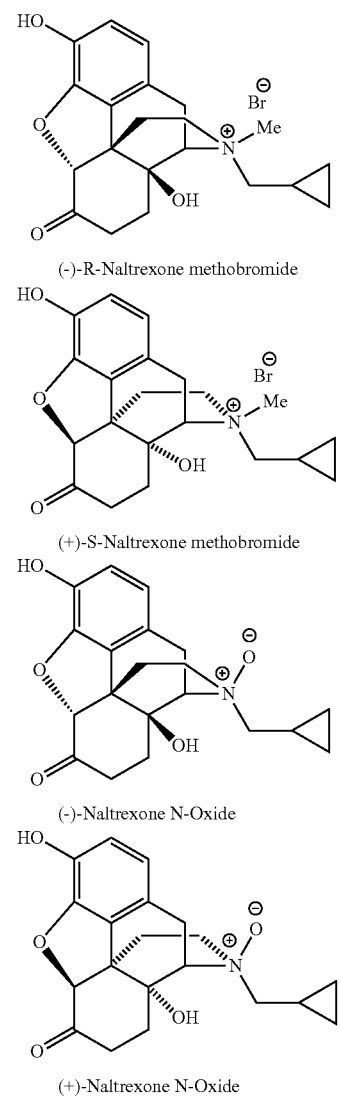

(−)-R-Naltrexone methobromide (+)-S-Naltrexone methobromide (−)-Naltrexone N-Oxide (+)-Naltrexone N-Oxide 4.2 In Vivo Techniques for with Mouse Tumor Model To demonstrate the effectiveness of the present compounds and methods for treatment of cancer and in phototherapy applications, in vivo mouse tumor model experiments were carried in connection with the compound MNTX, for example the purified stereoisomer (−)-R-naltrexone methobromide. These experiments include comparative studies and pancreatic tumor growth inhibition studies.

Comparative Studies

In these experiments nude mice weighing approximately 25 grams were used. First, the tail of the pancreas was exposed through an abdominal incision. Then $1\times10^6$ AsPC-1 cells were injected into the pancreas. The pancreas was replaced in the peritoneal cavity and the incision was closed. A 3-5 mm diameter tumor developed in 10 days.

MNTX was dissolved at 40 mg/mL in phosphate buffered saline (PBS) and then formulated to 100 uL (50 uL drug and 50 uL PBS) and injected subQ close to the pancreas. One injection per day was given for 10 days. The total dose was therefore 20 mg/mouse. For control and comparison, experiments on mice that were 1) not treated, 2) treated with light alone, 3) treated with gemcitibine alone, and 4) treated with Avastin alone using essentially the same procedure as described above were performed. The mice were sacrificed at day 24 and tumor weight was determined.

Figure 4:
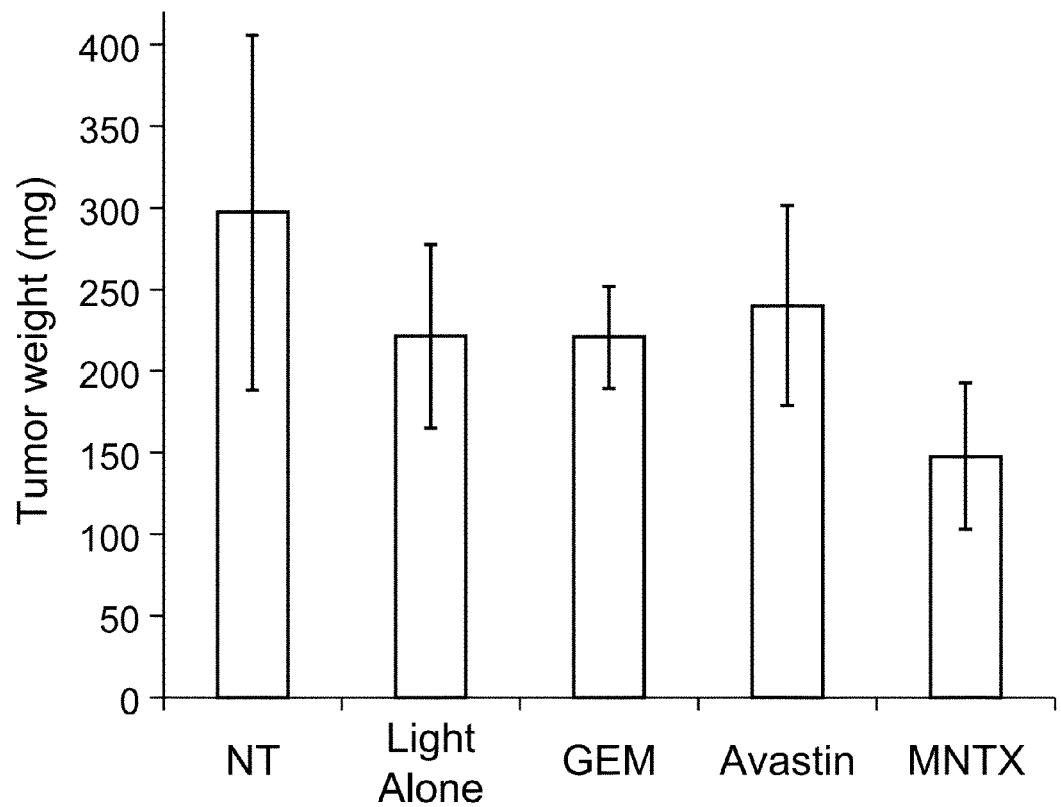
FIG. 4 provides local tumor burden experimental results for comparative studies involving administration of MNTX, Avastin and Gemcitabine anti-tumor agents. Tumor weight (mg) is shown for tumor conditions of: no treatment (NT); treatment with light alone (light alone); treatment with Gemcitabine alone (GEM); treatment with Avastin alone (Avastin) and treatment with MNTX (MNTX).

FIG. 4 provides local tumor burden experimental results for comparative studies involving administration of MNTX, Avastin and Gemcitabine anti-tumor agents. Tumor weight (mg) is shown for tumor conditions of: no treatment (NT); treatment with light alone (light alone); treatment with Gemcitabine alone (GEM); treatment with Avastin alone (Avastin) and treatment with MNTX (MNTX). FIG. 4 shows the tumor weight measured at sacrifice. As shown in FIG. 4, the treatment with MNTX was measurably superior to the control, Gemcitabine and Avastin conditions.

Pancreatic Tumor Growth Inhibition Studies

In these experiments, the effect of a purified stereoisomer of MNTX on AsPC-1 pancreatic cancer was evaluated. Specifically, the experiments demonstrate the potential application of (−)-R-naltrexone methobromide (abbreviated MNTX1) administration for treatment of pancreatic cancer.

The MNTX1 dose was established using an escalating dose study on mice. An intraperitoneal injection dose of 150 mg/kg was chosen. For a dosage of 400 mg/kg, 2 of 2 died, for a dosage of 200 mg/kg, 1 of 4 died; and for a dosage of 150 mg/kg (300 µl of 10 mg/ml), 3 of 3 survived. Therefore, a dose of 150 mg/kg (Intraperitoneal injection, I.P.) was used for each administration in the following orthotopic pancreatic tumor growth inhibition experiments.

Nude mice weighing approximately 25 grams were used. The tail of the pancreas was exposed through an abdominal incision. Then $1 \times 10^6$ AsPC-1 cells were injected into the pancreas. The pancreas was replaced in the peritoneal cavity and the incision was closed. A 3-5 mm diameter tumor developed in 10 days.

Figure 5:
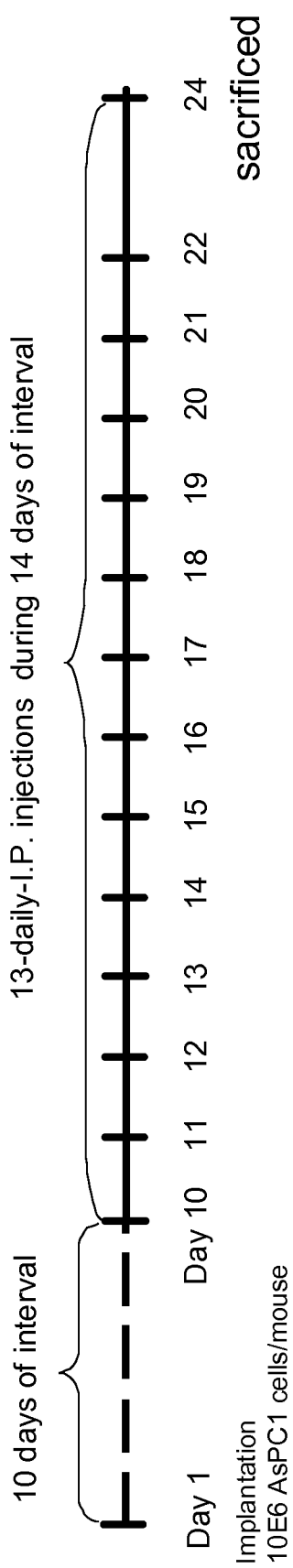
FIG. 5 provides a schematic illustrating the experimental design of the pancreatic tumor growth inhibition studies.

MNTX1 was formulated at 10 mg/mL in PBS. The 150 mg/kg dose was accomplished by a 30 uL injection of a 10 mg/mL stock solution. Injections were done daily for 13 days, and the 10 animals were subsequently sacrificed on day 24. Treatments start after 10 days of AsPC1 pancreatic tumor cell orthotopic implantation. After two more weeks, the mice are sacrificed and tumor weight is measured for the evaluation of tumor growth inhibition effects. For control, four mice were injected according to the above schedule with PBS only. They were also sacrificed on day 24. FIG. 5 provides a schematic illustrating the experimental design of the pancreatic tumor growth inhibition studies. I.P. treatments (150 mg MNTX1/kg/each injection, 300 µl of 10 mg/ml for each injection totally for 13 times, animal number=10).

Figure 6:
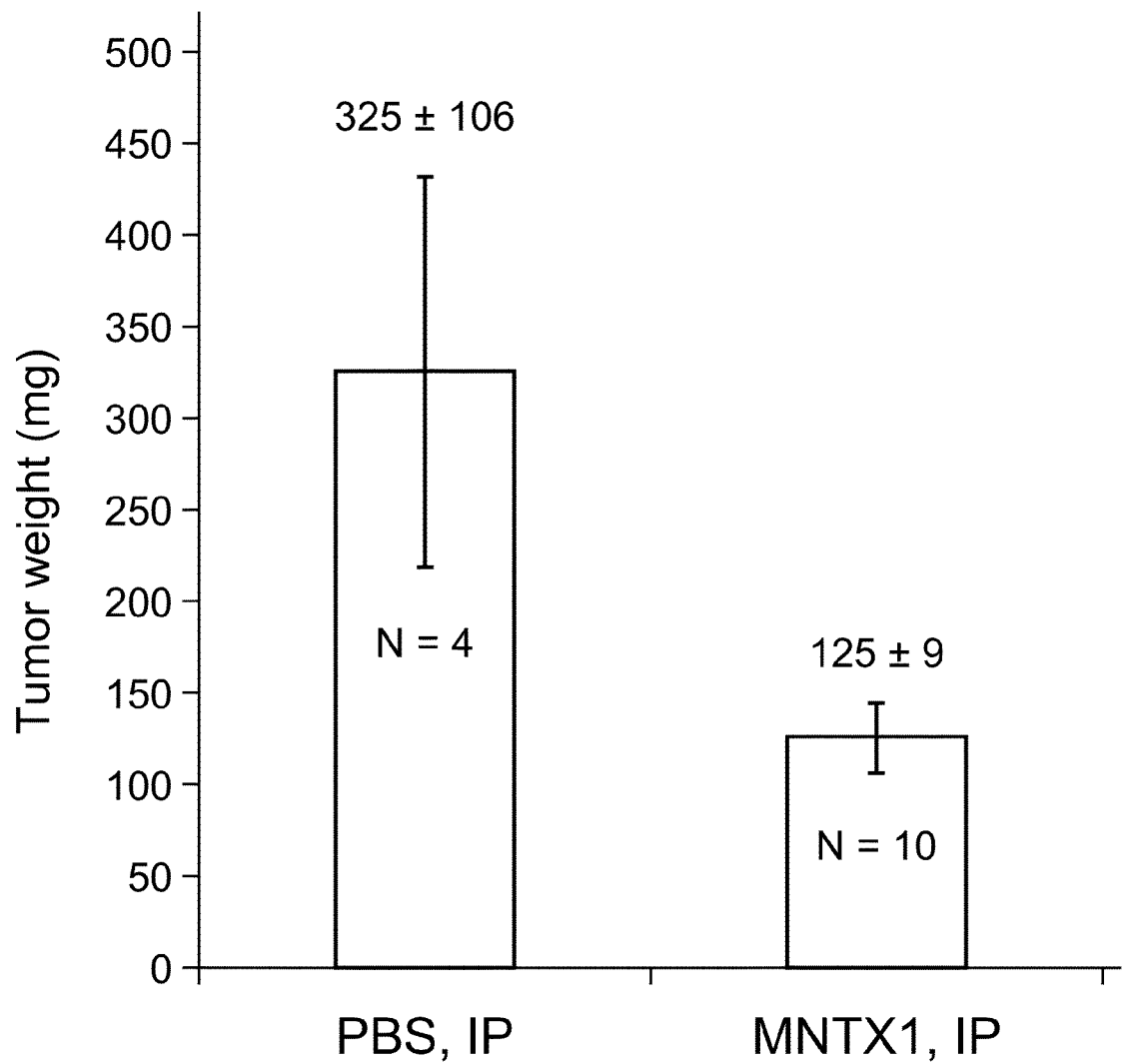
FIG. 6 provides experimental results for the pancreatic tumor growth inhibition studies showing the effects of MNTX1 on AsPC-1 pancreatic cancer.
Figure 7:
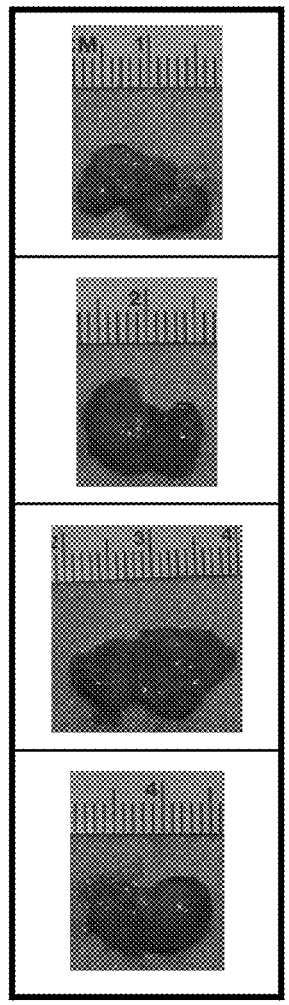
FIG. 7 provides AsPC1 pancreatic tumor size photograph records at the end point of the mouse sacrifice observed for pancreatic tumor growth inhibition studies.
Figure 7:
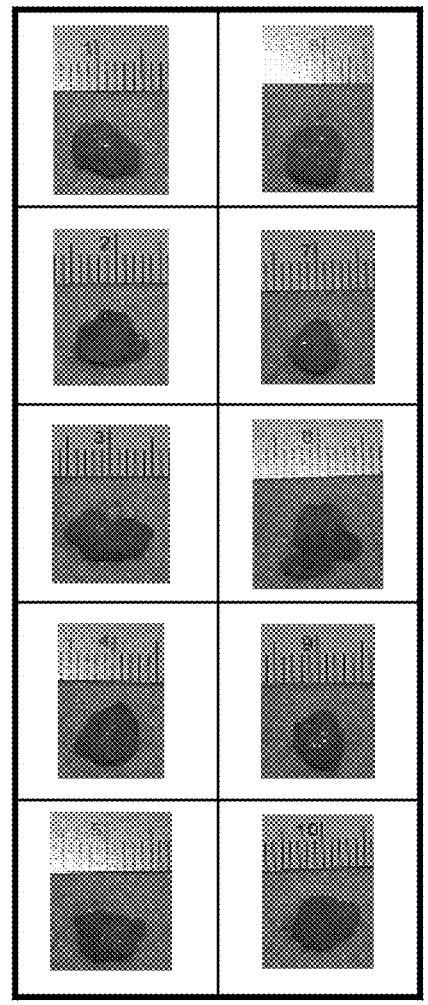

FIG. 6 provides experimental results for the pancreatic tumor growth inhibition studies showing the effects of MNTX1 on AsPC-1 pancreatic cancer. FIG. 6 shows tumor weight for control conditions corresponding to intraperitoneal injection of PBS and conditions for corresponding to intraperitoneal injection of MNTX1. The figure shows the tumor weight measured at sacrifice. The treatment with MNTX1 was measurably superior to the control. FIG. 7 provides AsPC1 pancreatic tumor size photograph records at the end point of the mouse sacrifice observed for pancreatic tumor growth inhibition studies.

Example 5

Administration and Formulation

5a: Salts and Prodrugs

The invention contemplates pharmaceutically active compounds either chemically synthesized or formed by in vivo biotransformation to compounds set forth herein.

Compounds of this invention and compounds useful in the methods of this invention include those of the compounds and formula (s) described herein and pharmaceutically-acceptable salts and esters of those compounds. In embodiments, salts include any salts derived from the acids and bases of the formulas herein which are acceptable for use in human or veterinary applications. In embodiments, the term ester refers to hydrolyzable esters of compounds of the names and formulas herein. In embodiments, salts and esters of the compounds of the formulas herein can include those which have the same or better therapeutic, diagnostic, or pharmaceutical (human or veterinary) general properties as the compounds of the formulas herein. In an embodiment, a composition of the invention is a compound or salt or ester thereof suitable for pharmaceutical formulations.

Compounds of the invention can have prodrug forms. Prodrugs of the compounds of the invention are useful in embodiments including compositions and methods. Any compound that will be converted in vivo to provide a biologically, pharmaceutically, diagnostically, or therapeutically active form of a compound of the invention is a prodrug. Various examples and forms of prodrugs are well known in the art. Examples of prodrugs are found, inter alia, in: Design of Prodrugs, edited by H. Bundgaard, (Elsevier, 1985); Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191 (1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392). A prodrug, such as a pharmaceutically acceptable prodrug, can represent prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of a compound described herein, for example, by hydrolysis in blood or by other cell, tissue, organ, or system processes. Further discussion is provided in: T. Higuchi and V. Stella, Pro-drugs as Novel Delivery Systems, V. 14 of the A.C.S. Symposium Series; and in Edward B. Roche, ed., Bioreversible Carriers in Drug Design, American Pharmaceutical Association and Pergamon Press (1987).

Optical agents of the invention can be formulated with pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include, among others, halides (e.g., $F^-$, $Cl^-$, $Br^-$, $At^-$), sulfate, acetates (e.g., acetate, trifluoroacetate), ascorbates, aspartates, benzoates, citrates, and lactate.

Pharmaceutically acceptable salts comprise pharmaceutically-acceptable anions and/or cations. As used herein, the term "pharmaceutically acceptable salt" can refer to acid addition salts or base addition salts of the compounds in the present disclosure. A pharmaceutically acceptable salt is any salt which retains at least a portion of the activity of the parent compound and does not impart significant deleterious or undesirable effect on a subject to whom it is administered and in the context in which it is administered. Pharmaceutically acceptable salts include metal complexes and salts of both inorganic and organic acids. Pharmaceutically acceptable salts include metal salts such as aluminum, calcium, iron, magnesium, manganese and complex salts. Pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, cilexetil, citric, edetic, edisylic, estolic, esyl, esylic, formic, fumaric, gluceptic, gluconic, glutamic, glycolic, hexamic, hexylreserinoic, hydrobromic, hydrochloric, hydroiodic, hydroxynaphthoic, isethionic, lactic, lactobionic, maleic, malic, malonic, mandelic, methanesulfonic, mucic, muconic, napsylic, nitric, oxalic, p-nitromethanesulfonic, palmoic, pantothenic, phosphoric, monohydrogen phosphoric, dihydrogen phosphoric, phthalic, polygalacturonic, propionic, salicylic, stearic, succinic, sulfamic, sulfanlic, sulfonic, sulfuric, tannic, tartaric, teoclic, toluenesulfonic, polyglutamic, polyaspartic and the like. Pharmaceutically acceptable salts can be derived from amino acids, including, but not limited to, cysteine. Other pharmaceutically acceptable salts can be found, for example, in Stahl et al., Handbook of Pharmaceutical Salts: Properties, Selection, and Use, Wiley-VCH, Verlag Helvetica Chimica Acta, Zurich, 2002. (ISBN 3-906390-26-8).

5b: Efficacy

Typically, a compound of the invention, or pharmaceutically acceptable salt thereof, is administered to a subject in a diagnostically or therapeutically effective amount. One skilled in the art generally can determine an appropriate dosage.

Compositions for oral administration can be, for example, prepared in a manner such that a single dose in one or more oral preparations contains at least about 20 mg of the anti-angiogenesis agent compound per square meter of subject body surface area, or at least about 50, 100, 150, 200, 300, 400, or 500 mg of the anti-angiogenesis agent compound per square meter of subject body surface area (the average body surface area for a human is, for example, 1.8 square meters). In particular, a single dose of a composition for oral administration can contain from about 20 to about 600 mg, and in certain aspects from about 20 to about 400 mg, in another aspect from about 20 to about 300 mg, and in yet another aspect from about 20 to about 200 mg of the anti-angiogenesis agent compound per square meter of subject body surface area. Compositions for parenteral administration can be prepared in a manner such that a single dose contains at least about 20 mg of the anti-angiogenesis agent compound per square meter of subject body surface area, or at least about 40, 50, 100, 150, 200, 300, 400, or 500 mg of the anti-angiogenesis agent compound per square meter of subject body surface area. In particular, a single dose in one or more parenteral preparations contains from about 20 to about 500 mg, and in certain aspects from about 20 to about 400 mg, and in another aspect from about 20 to about 450 mg, and in yet another aspect from about 20 to about 350 mg of the anti-angiogenesis agent per square meter of subject body surface area. It should be recognized that these oral and parenteral dosage ranges represent generally preferred dosage ranges, and are not intended to limit the invention. The dosage regimen actually employed can vary widely, and, therefore, can deviate from the generally preferred dosage regimen. It is contemplated that one skilled in the art will tailor these ranges to the individual subject.

Toxicity and therapeutic efficacy of such compounds and bioconjugates can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$. Compounds and bioconjugates that exhibit large therapeutic indices are preferred. While compounds and bioconjugates exhibiting toxic side effects can be used, care should be taken to design a delivery system that targets such compounds and bioconjugates to the site affected by the disease or disorder in order to minimize potential damage to unaffected cells and reduce side effects.

Data obtained from the cell culture assays and animal studies can be used in formulating a range of dosages for use in humans and other mammals. The dosage of such compounds and bioconjugates lies preferably within a range of circulating plasma or other bodily fluid concentrations that include the $ED_{50}$ and provides clinically efficacious results (i.e., reduction in disease symptoms). The dosage can vary within this range depending upon the dosage form employed and the route of administration utilized. For any compound and bioconjugate of the present invention, the therapeutically effective amount can be estimated initially from cell culture assays. A dosage can be formulated in animal models to achieve a circulating plasma concentration range that includes the $ED_{50}$ (the concentration of the test compound that achieves a half-maximal inhibition of symptoms) as determined in cell culture. Such information can be used to more accurately determine useful dosages in humans and other mammals. Compound and bioconjugate levels in plasma can be measured, for example, by high performance liquid chromatography.

An amount of a compound or bioconjugate that can be combined with a pharmaceutically acceptable carrier to produce a single dosage form will vary depending upon the patient treated and the particular mode of administration. It will be appreciated by those skilled in the art that the unit content of a compound/bioconjugate contained in an individual dose of each dosage form need not in itself constitute a therapeutically effective amount, as the necessary therapeutically effective amount could be reached by administration of a number of individual doses. The selection of dosage depends upon the dosage form utilized, the condition being treated, and the particular purpose to be achieved according to the determination of those skilled in the art.

The dosage and dosage regime for treating a disease or condition can be selected in accordance with a variety of factors, including the type, age, weight, sex, diet and/or medical condition of the patient, the route of administration, pharmacological considerations such as activity, efficacy, pharmacokinetic and/or toxicology profiles of the particular compound/bioconjugate employed, whether a compound/bioconjugate delivery system is utilized, and/or whether the compound/bioconjugate is administered as a pro-drug or part of a drug combination. Thus, the dosage regime actually employed can vary widely from subject to subject, or disease to disease and different routes of administration can be employed in different clinical settings.

The identified compounds/bioconjugates monitor, treat, inhibit, control and/or prevent, or at least partially arrest or partially prevent, diseases and conditions of interest and can be administered to a subject at therapeutically effective amounts and optionally diagnostically effective amounts. Compositions/formulations of the present invention comprise a therapeutically effective amount (which can optionally include a diagnostically effective amount) of at least one compound or bioconjugate of the present invention. Subjects receiving treatment that includes a compound/bioconjugate of the invention are preferably animals (e.g., mammals, reptiles and/or avians), more preferably humans, horses, cows, dogs, cats, sheep, pigs, and/or chickens, and most preferably humans.

5c: Administration

The preferred composition depends on the route of administration. Any route of administration can be used as long as the target of the compound or pharmaceutically acceptable salt is available via that route. Suitable routes of administration include, for example, oral, intravenous, parenteral, inhalation, rectal, nasal, topical (e.g., transdermal and intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual, and intestinal administration.

In an embodiment, the invention provides a method for treating a medical condition comprising administering to a subject (e.g. patient) in need thereof, a therapeutically effective amount of a composition of the invention, such as a compound of any one of formulas (FX1)-(FX164). In an embodiment, the invention provides a method for diagnosing or aiding in the diagnosis of a medical condition comprising administering to a subject in need thereof, a diagnostically effective amount of a composition of the invention. In an embodiment, the medical condition is cancer, or various other diseases, injuries, and disorders, including cardiovascular disorders such as atherosclerosis and vascular restenosis, inflammatory diseases, ophthalmic diseases and dermatological diseases.

The diagnostic and therapeutic formulations of this invention can be administered alone, but can be administered with a pharmaceutical carrier selected upon the basis of the chosen route of administration and standard pharmaceutical practice.

Any suitable form of administration can be employed in connection with the diagnostic and therapeutic formulations of the invention. The diagnostic and therapeutic formulations of this invention can be administered intravenously, in oral dosage forms, intraperitoneally, subcutaneously, or intramuscularly, all using dosage forms well known to those of ordinary skill in the pharmaceutical arts.

The present compositions, preparations and formulations can be formulated into diagnostic or therapeutic compositions for enteral, parenteral, topical, aerosol, inhalation, or cutaneous administration. Topical or cutaneous delivery of the compositions, preparations and formulations can also include aerosol formulation, creams, gels, solutions, etc. The present compositions, preparations and formulations are administered in doses effective to achieve the desired diagnostic and/or therapeutic effect. Such doses can vary widely depending upon the particular compositions employed in the composition, the organs or tissues to be examined, the equipment employed in the clinical procedure, the efficacy of the treatment achieved, and the like. These compositions, preparations and formulations contain an effective amount of the composition(s), along with conventional pharmaceutical carriers and excipients appropriate for the type of administration contemplated. These compositions, preparations and formulations can also optionally include stabilizing agents and skin penetration enhancing agents.

(i) Parenteral Administration

Compounds and bioconjugates of the present invention can be formulated for parenteral administration by injection (e.g., by bolus injection or continuous infusion). Formulations for injection can be presented in unit dosage form in ampoules or in multi-dose containers with an optional preservative added. The parenteral preparation can be enclosed in ampoules, disposable syringes or multiple dose vials made of glass, plastic or the like. The formulation can take such forms as suspensions, solutions or emulsions in oily or aqueous vehicles, and can contain formulatory agents such as suspending, stabilizing and/or dispersing agents.

For example, a parenteral preparation can be a sterile injectable solution or suspension in a nontoxic parenterally acceptable diluent or solvent (e.g., as a solution in 1,3-butanediol). Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid can be used in the parenteral preparation.

Alternatively, compounds and bioconjugates of the present invention can be formulated in powder form for constitution with a suitable vehicle, such as sterile pyrogen-free water, before use. For example, a compound/bioconjugate suitable for parenteral administration can include a sterile isotonic saline solution containing between 0.1 percent and 90 percent weight per volume of the compound/bioconjugate. By way of example, a solution can contain from about 5 percent to about 20 percent, more preferably from about 5 percent to about 17 percent, more preferably from about 8 to about 14 percent, and still more preferably about 10 percent weight per volume of the compound/bioconjugate. The solution or powder preparation can also include a solubilizing agent and a local anesthetic such as lignocaine to ease pain at the site of the injection. Other methods of parenteral delivery of compounds/bioconjugates will be known to the skilled artisan and are within the scope of the invention.

(ii) Oral Administration

For oral administration, a compound/bioconjugate of the invention can be formulated to take the form of tablets or capsules prepared by conventional means with one or more pharmaceutically acceptable carriers (e.g., excipients such as binding agents, fillers, lubricants and disintegrants).

(iii) Controlled-Release Administration

Controlled-release (or sustained-release) preparations can be formulated to extend the activity of a compound/bioconjugate and reduce dosage frequency. Controlled-release preparations can also be used to effect the time of onset of action or other characteristics, such as blood levels of the compound/bioconjugate, and consequently affect the occurrence of side effects.

Controlled-release preparations can be designed to initially release an amount of a compound/bioconjugate that produces the desired therapeutic effect, and gradually and continually release other amounts of the compound/bioconjugate to maintain the level of therapeutic effect over an extended period of time. In order to maintain a near-constant level of a compound/bioconjugate in the body, the compound/bioconjugate can be released from the dosage form at a rate that will replace the amount of compound/bioconjugate being metabolized and/or excreted from the body. The controlled-release of a compound/bioconjugate can be stimulated by various inducers, e.g., change in pH, change in temperature, enzymes, water, and/or other physiological conditions or molecules.

Controlled-release systems can include, for example, an infusion pump which can be used to administer the compound/bioconjugate in a manner similar to that used for delivering insulin or chemotherapy to the body generally, or to specific organs or tumors. Typically, using such a system, the compound/bioconjugate is administered in combination with a biodegradable, biocompatible polymeric implant that releases the compound/bioconjugate over a controlled period of time at a selected site. Examples of polymeric materials include polyanhydrides, polyorthoesters, polyglycolic acid, polylactic acid, polyethylene vinyl acetate, (PEG) polyethyleneglycol and copolymers and combinations thereof. In addition, a controlled release system can be placed in proximity of a therapeutic target (e.g., organ, tissue, or group of cells), thus requiring only a fraction of a systemic dosage.

Compounds/bioconjugates of the invention can be administered by other controlled-release means or delivery devices that are well known to those of ordinary skill in the art. These include, for example, hydropropylmethyl cellulose, other polymer matrices, gels, permeable membranes, osmotic systems, multilayer coatings, microparticles, liposomes, microspheres, or the like, or a combination of any of the above to provide the desired release profile in varying proportions. Other methods of controlled-release delivery of compounds/bioconjugates will be known to the skilled artisan and are within the scope of the invention.

(iv) Inhalation Administration

Compounds/bioconjugates of the invention can be administered directly to the lung of a patient/subject by inhalation. For administration by inhalation, a compound/bioconjugate can be conveniently delivered to the lung by a number of different devices. For example, a Metered Dose Inhaler ("MDI") which utilizes canisters that contain a suitable low boiling point propellant, e.g., dichlorodifluoromethane, trichlorofluoromethane, dichlorotetrafluoroethane, carbon dioxide or other suitable gas can be used to deliver a compound/bioconjugate directly to the lung. MDI devices are available from a number of suppliers such as 3M Corporation, Aventis, Boehringer Ingleheim, Forest Laboratories, GlaxoSmithKline, Merck & Co. and Vectura.

Alternatively, a Dry Powder Inhaler (DPI) device can be used to administer a compound/bioconjugate to the lung. DPI devices typically use a mechanism such as a burst of gas to create a cloud of dry powder inside a container, which can then be inhaled by the patient. DPI devices are also well known in the art and can be purchased from a number of vendors which include, for example, GlaxoSmithKline, Nektar Therapeutics, Innovate and Vectura. A popular variation is the multiple dose DPI ("MDDPI") system, which allows for the delivery of more than one therapeutic dose. MDDPI devices are available from companies such as AstraZeneca, GlaxoSmithKline, TEVA, Merck & Co., SkyePharma and Vectura. For example, capsules and cartridges of gelatin for use in an inhaler or insufflator can be formulated containing a powder mix of the compound/bioconjugate and a suitable powder base such as lactose or starch for these systems.

Another type of device that can be used to deliver a compound/bioconjugate to the lung is a liquid spray device supplied, for example, by Aradigm Corporation. Liquid spray systems use extremely small nozzle holes to aerosolize liquid compound/bioconjugate formulations that can then be directly inhaled into the lung. For example, a nebulizer device can be used to deliver a compound/bioconjugate to the lung. Nebulizers create aerosols from liquid compound/bioconjugate formulations by using, for example, ultrasonic energy to form fine particles that can be readily inhaled. Examples of nebulizers include devices supplied by Aventis and Battelle.

In another example, an electrohydrodynamic ("EHD") aerosol device can be used to deliver a compound/bioconjugate to the lung. EHD aerosol devices use electrical energy to aerosolize liquid compound/bioconjugate solutions or suspensions. The electrochemical properties of the compound/bioconjugate formulation are important parameters to optimize when delivering this compound/bioconjugate to the lung with an EHD aerosol device. Such optimization is routinely performed by one of skill in the art. Other methods of intra-pulmonary delivery of compounds/bioconjugates will be known to the skilled artisan and are within the scope of the invention.

Liquid compound/bioconjugate formulations suitable for use with nebulizers and liquid spray devices and EHD aerosol devices will typically include the compound/bioconjugate with a pharmaceutically acceptable carrier. In one exemplary embodiment, the pharmaceutically acceptable carrier is a liquid such as alcohol, water, polyethylene glycol or a perfluorocarbon. Optionally, another material can be added to alter the aerosol properties of the solution or suspension of the compound/bioconjugate. For example, this material can be a liquid such as an alcohol, glycol, polyglycol or a fatty acid. Other methods of formulating liquid compound/bioconjugate solutions or suspensions suitable for use in aerosol devices are known to those of skill in the art.

(v) Depot Administration

A compound/bioconjugate of the invention can be formulated as a depot preparation. Such long-acting formulations can be administered by implantation (e.g., subcutaneously or intramuscularly) or by intramuscular injection. Accordingly, the compound/bioconjugate can be formulated with suitable polymeric or hydrophobic materials such as an emulsion in an acceptable oil or ion exchange resin, or as sparingly soluble derivatives such as a sparingly soluble salt. Other methods of depot delivery of compounds/bioconjugates will be known to the skilled artisan and are within the scope of the invention.

(vi) Topical Administration

For topical application, a compound/bioconjugate can be combined with a pharmaceutically acceptable carrier so that an effective dosage is delivered, based on the desired activity ranging from an effective dosage, for example, of 1.0 µM to 1.0 mM. In one aspect of the invention, a topical formulation of a compound/bioconjugate can be applied to the skin. The pharmaceutically acceptable carrier can be in the form of, for example, and not by way of limitation, an ointment, cream, gel, paste, foam, aerosol, suppository, pad or gelled stick.

A topical formulation can include a therapeutically effective amount of a compound/bioconjugate in an ophthalmologically acceptable excipient such as buffered saline, mineral oil, vegetable oils such as corn or arachis oil, petroleum jelly, Miglyol 182, alcohol solutions, or liposomes or liposome-like products. Any of these formulations of such compounds/bioconjugates can include preservatives, antioxidants, antibiotics, immunosuppressants, and other biologically or pharmaceutically effective agents that do not exert a significant detrimental effect on the compound/bioconjugate. Other methods of topical delivery of compounds/bioconjugates will be known to the skilled artisan and are within the scope of the invention.

(vii) Rectal Administration

Compounds/bioconjugates of the invention can be formulated in rectal formulations such as suppositories or retention enemas that include conventional suppository bases such as cocoa butter or other glycerides and/or binders and/or carriers such as triglycerides, microcrystalline cellulose, gum tragacanth or gelatin. Rectal formulations can contain a compound/bioconjugate in the range of 0.5% to 10% by weight, for example. Other methods of rectal delivery of compounds/bioconjugates will be known to the skilled artisan and are within the scope of the invention.

(viii) Other Systems of Administration

Various other delivery systems are known in the art and can be used to administer the compounds/bioconjugates of the invention. Moreover, these and other delivery systems can be combined and/or modified to promote optimization of the administration of compounds/bioconjugates of the present invention. Exemplary formulations that include compounds/bioconjugates of the present invention are described elsewhere herein (the compounds/bioconjugates of the present invention are indicated as the active ingredient, but those of skill in the art will recognize that pro-drugs and compound combinations are also meant to be encompassed by this term).

5d: Formulation

In an embodiment, the invention provides a medicament which comprises a therapeutically effective amount of one or more compositions of the invention, such as a compound of any one of formulas (FX1)-(FX164). In an embodiment, the invention provides a medicament which comprises a diagnostically effective amount of one or more compositions of the invention. In an embodiment, the invention provides a method for making a medicament for treatment of a condition described herein. In an embodiment, the invention provides a method for making a medicament for diagnosis or aiding in the diagnosis of a condition described herein. In an embodiment, the invention provides the use of one or more compositions set forth herein for the making of a medicament. In an embodiment, the invention provides the use of one or more compositions set forth herein for the treatment of a disease. In an embodiment, the invention provides the use of one or more compositions set forth herein for the diagnosis of a disease. Compositions of the invention include formulations and preparations comprising one or more of the present optical agents provided in an aqueous solution, such as a pharmaceutically acceptable formulation or preparation. Optionally, compositions of the invention further comprise one or more pharmaceutically acceptable surfactants, buffers, electrolytes, salts, carriers, binders, coatings, preservatives and/or excipients.

In an embodiment, the invention provides a pharmaceutical formulation having an active ingredient comprising a composition of the invention, such as a compound of any one of formulas (FX1)-(FX164). In an embodiment, the invention provides a method of synthesizing a composition of the invention or a pharmaceutical formulation thereof, such as a compound of any one of formulas (FX1)-(FX164). In an embodiment, a pharmaceutical formulation comprises one or more excipients, carriers, diluents, and/or other components as would be understood in the art. Preferably, the components meet the standards of the National Formulary ("NF"), United States Pharmacopoeia ("USP"; United States Pharmacopeial Convention Inc., Rockville, Md.), or Handbook of Pharmaceutical Manufacturing Formulations (Sarfaraz K. Niazi, all volumes, ISBN: 9780849317521, ISBN 10: 0849317525; CRC Press, 2004). See, e.g., United States Pharmacopeia and National Formulary (USP 30-NF 25), Rockville, Md.: United States Pharmacopeial Convention (2007 and 2008), and each of any earlier editions; The Handbook of Pharmaceutical Excipients, published jointly by the American Pharmacists Association and the Pharmaceutical Press (Pharmaceutical Press (2005) (ISBN-10: 0853696187, ISBN-13: 978-0853696186)); Merck Index, Merck & Co., Rahway, N.J.; and Gilman et al., (eds) (1996); Goodman and Gilman's: The Pharmacological Bases of Therapeutics, 8th Ed., Pergamon Press. In embodiments, the formulation base of the formulations of the invention comprises physiologically acceptable excipients, namely, at least one binder and optionally other physiologically acceptable excipients. Physiologically acceptable excipients are those known to be usable in the pharmaceutical technology sectors and adjacent areas, particularly, those listed in relevant pharmacopeias (e.g. DAB, Ph. Eur., BP, NF, USP), as well as other excipients whose properties do not impair a physiological use.

This invention also is directed, in part, to pharmaceutical compositions including a therapeutically effective amount of a compound or salt of this invention, as well as processes for making such compositions. Such compositions generally include one or more pharmaceutically acceptable carriers (e.g., excipients, vehicles, auxiliaries, adjuvants, diluents) and can include other active ingredients. Formulation of these compositions can be achieved by various methods known in the art. A general discussion of these methods can be found in, for example, Hoover, John E., Remington's Pharmaceutical Sciences (Mack Publishing Co., Easton, Pa.: 1975). See also, Lachman, L., eds., Pharmaceutical Dosage Forms (Marcel Decker, New York, N.Y., 1980).

The diagnostic and therapeutic formulations of this invention and medicaments of this invention can further comprise one or more pharmaceutically acceptable carriers, excipients, buffers, emulsifiers, surfactants, electrolytes or diluents. Such compositions and medicaments are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985).

Compositions of the invention include formulations and preparations comprising one or more of the present compounds provided in an aqueous solution, such as a pharmaceutically acceptable formulation or preparation. Optionally, compositions of the invention further comprise one or more pharmaceutically acceptable surfactants, buffers, electrolytes, salts, carriers, binders, coatings, preservatives and/or excipients.

Compounds and bioconjugates of the present invention can be formulated by known methods for administration to a subject using several routes which include, but are not limited to, parenteral, oral, topical, intradermal, intramuscular, intraperitoneal, intravenous, subcutaneous, intranasal, epidural, and ophthalmic routes. An individual compound/bioconjugate can be administered in combination with one or more additional compounds/bioconjugates of the present invention and/or together with other biologically active or biologically inert agents. Such biologically active or inert agents can be in fluid or mechanical communication with the compound(s)/bioconjugate(s) or attached to the compound(s)/bioconjugate(s) by ionic, covalent, Van der Waals, hydrophobic, hydrophilic or other physical forces. It is preferred that administration is localized in a subject, but administration can also be systemic.

Compounds and bioconjugates of the present invention can be formulated by any conventional manner using one or more pharmaceutically acceptable carriers. Thus, the compound(s)/bioconjugate(s) and their pharmaceutically acceptable salts and solvates can be specifically formulated for administration, e.g., by inhalation or insufflation (either through the mouth or the nose) or oral, buccal, parenteral or rectal administration. The compounds/bioconjugates can take the form of charged, neutral and/or other pharmaceutically acceptable salt forms. Examples of pharmaceutically acceptable carriers include, but are not limited to, those described in REMINGTON'S PHARMACEUTICAL SCIENCES (A. R. Gennaro, Ed.), 20th edition, Williams & Wilkins PA, USA (2000).

Compounds and bioconjugates of the present invention can be formulated in the form of solutions, suspensions, emulsions, tablets, pills, capsules, powders, controlled- or sustained-release formulations and the like. Such formulations will contain a therapeutically effective amount of the compound/bioconjugate, preferably in purified form, together with a suitable amount of carrier so as to provide the form for proper administration to the patient. The formulation should suit the mode of administration.

Pharmaceutically acceptable carriers that can be used in conjunction with the compounds of the invention are well known to those of ordinary skill in the art. Carriers can be selected based on a number of factors including, for example, the particular anti-angiogenesis agent compound(s) or pharmaceutically acceptable salt(s) used; the compound's concentration, stability, and intended bioavailability; the condition being treated; the subject's age, size, and general condition; the route of administration; etc. A general discussion related to carriers can be found in, for example, J. G. Nairn, Remington's Pharmaceutical Science, pp. 1492-1517 (A. Gennaro, ed., Mack Publishing Co., Easton, Pa. (1985)).

Solid dosage forms for oral administration include, for example, capsules, tablets, gelcaps, pills, dragees, troches, powders, granules, and lozenges. In such solid dosage forms, the compounds or pharmaceutically acceptable salts thereof can be combined with one or more pharmaceutically acceptable carriers. The compounds and pharmaceutically acceptable salts thereof can be mixed with carriers including, but not limited to, lactose, sucrose, starch powder, corn starch, potato starch, magnesium carbonate, microcrystalline cellulose, cellulose esters of alkanoic acids, cellulose alkyl esters, talc, stearic acid, magnesium stearate, magnesium oxide, sodium and calcium salts of phosphoric and sulfuric acids, sodium carbonate, agar, mannitol, sorbitol, sodium saccharin, gelatin, acacia gum, alginic acid, sodium alginate, tragacanth, colloidal silicon dioxide, croscarmellose sodium, polyvinylpyrrolidone, and/or polyvinyl alcohol, and then tableted or encapsulated for convenient administration. Such capsules or tablets can contain a controlled-release formulation, as can be provided in a dispersion of the compound or salt in hydroxypropylmethyl cellulose. In the case of capsules, tablets, and pills, the dosage forms also can include buffering agents, such as sodium citrate, or magnesium or calcium carbonate or bicarbonate. Tablets and pills additionally can, for example, include a coating (e.g., an enteric coating) to delay disintegration and absorption. The concentration of the anti-angiogenesis agent compound in a solid oral dosage form can be from about 5 to about 50% for example, and in certain aspects from about 8 to about 40%, and in another aspect from about 10 to about 30% by weight based on the total weight of the composition.

Liquid dosage forms of the compounds of the invention for oral administration include, for example, pharmaceutically acceptable emulsions, solutions, suspensions, syrups, and elixirs containing inert diluents commonly used in the art (e.g., water). Such compositions also can include adjuvants, such as wetting, emulsifying, suspending, flavoring (e.g., sweetening), and/or perfuming agents. The concentration of the anti-angiogenesis agent compound in the liquid dosage form can be from about 0.01 to about 5 mg, and in certain aspects from about 0.01 to about 1 mg, and in another aspect from about 0.01 to about 0.5 mg per ml of the composition. Low concentrations of the compounds of the invention in liquid dosage form can be prepared in the case that the anti-angiogenesis agent compound is more soluble at low concentrations. Techniques for making oral dosage forms useful in the invention are generally described in, for example, Modern Pharmaceutics, Chapters 9 and 10 (Banker & Rhodes, Editors (1979)). See also, Lieberman et al., Pharmaceutical Dosage Forms: Tablets (1981). See also, Ansel, Introduction to Pharmaceutical Dosage Forms (2nd Edition (1976)).

In some aspects of the invention, tablets or powders for oral administration can be prepared by dissolving the anti-angiogenesis agent compound in a pharmaceutically acceptable solvent capable of dissolving the compound to form a solution and then evaporating when the solution is dried under vacuum. A carrier can also be added to the solution before drying. The resulting solution can be dried under vacuum to form a glass. The glass can then be mixed with a binder to form a powder. This powder can be mixed with fillers or other conventional tableting agents, and then processed to form a tablet. Alternatively, the powder can be added to a liquid carrier to form a solution, emulsion, suspension, or the like.

In some aspects, solutions for oral administration are prepared by dissolving the anti-angiogenesis agent compound in a pharmaceutically acceptable solvent capable of dissolving the compound to form a solution. An appropriate volume of a carrier is added to the solution while stirring to form a pharmaceutically acceptable solution for oral administration.

In some embodiments, a liposome or micelle can be utilized as a carrier or vehicle for the composition. For example, in some embodiments, the anti-angiogenesis agent compound can be a part of the lipophilic bilayers or micelle, and the targeting ligand, if present, can be on the external surface of the liposome or micelle. As another example, a targeting ligand can be externally attached to the liposome or micelle after formulation for targeting the liposome or micelle (which contains the anti-angiogenesis agent optical agents) to the desired tissue, organ, or other site in the body.

Injectable preparations (e.g., sterile injectable aqueous or oleaginous suspensions) can be formulated according to the known art using suitable dispersing, wetting agents, and/or suspending agents. Acceptable vehicles for parenteral use include both aqueous and nonaqueous pharmaceutically-acceptable solvents. Suitable pharmaceutically acceptable aqueous solvents include, for example, water, saline solutions, dextrose solutions (such as DW5), electrolyte solutions, etc.

In one embodiment, the present anti-angiogenesis agent compounds are formulated as nanoparticles or microparticles. Use of such nanoparticle or microparticle formulations can be beneficial for some applications to enhance delivery, localization, target specificity, administration, etc. of the anti-angiogenesis agent compound. Potentially useful nanoparticles and microparticles include, but are not limited to, micelles, liposomes, microemulsions, nanoemulsions, vesicles, tubular micelles, cylindrical micelles, bilayers, folded sheets structures, globular aggregates, swollen micelles, inclusion complex, encapsulated droplets, microcapsules, nanocapsules or the like. As will be understood by those having skill in the art, the present anti-angiogenesis agent compounds can be located inside the nanoparticle or microparticle, within a membrane or wall of the nanoparticle or microparticle, or outside of (but bonded to or otherwise associated with) the nanoparticle or microparticle. The agent formulated in nanoparticles or microparticles can be administered by any of the routes previously described. In a formulation applied topically, the anti-angiogenesis agent compound is slowly released over time. In an injectable formulation, the liposome, micelle, capsule, etc., circulates in the bloodstream and is delivered to the desired site (e.g., target tissue).

Preparation and loading of nanoparticles and microparticles are well known in the art. As one example, liposomes can be prepared from dipalmitoyl phosphatidylcholine (DPPC) or egg phosphatidylcholine (PC) because this lipid has a low heat transition. Liposomes are made using standard procedures as known to one skilled in the art (e.g., Braun-Falco et al., (Eds.), Griesbach Conference, Liposome Dermatics, Springer-Verlag, Berlin (1992), pp. 69 81; 91 117. Polycaprolactone, poly(glycolic) acid, poly(lactic) acid, polyanhydride or lipids can be formulated as microspheres. As an illustrative example, the present anti-angiogenesis agent compounds can be mixed with polyvinyl alcohol (PVA), the mixture then dried and coated with ethylene vinyl acetate, then cooled again with PVA. In a liposome, the present anti-angiogenesis agent compounds can be within one or both lipid bilayers, in the aqueous between the bilayers, or within the center or core. Liposomes can be modified with other molecules and lipids to form a cationic liposome. Liposomes can also be modified with lipids to render their surface more hydrophilic which increases their circulation time in the bloodstream. The thus-modified liposome has been termed a "stealth" liposome, or a long-lived liposome, as described in U.S. Pat. No. 6,258,378, and in Stealth Liposomes, Lasic and Martin (Eds.) 1995 CRC Press, London. Encapsulation methods include detergent dialysis, freeze drying, film forming, injection, as known to one skilled in the art and disclosed in, for example, U.S. Pat. No. 6,406,713. Optionally, the present compositions and methods include a micelle delivery system, for example, involving one or more PEG-based amphiphilic polymers developed for drug delivery including: PEG-poly(ε-caprolactone), PEG-poly(amino acid), PEG-polylactide or PEG-phospholipid constructs; a cross linked poly(acrylic acid) polymer system, a phospholipid-based system and/or block copolymer systems comprising one or more of the following polymer blocks: a poly(lactic acid) polymer block; a poly(propylene glycol) polymer block; a poly(amino acid) polymer block; a poly(ester) polymer block; a poly(ε-caprolactone) polymer block; a poly(ethylene glycol) block, a poly(acrylic acid) block; a polylactide block; a polyester block; a polyamide block; a polyanhydride block; a polyurethane block; a polyimine block; a polyurea block; a polyacetal block; a polysaccharide block; and a polysiloxane block.

Suitable pharmaceutically-acceptable nonaqueous solvents include, but are not limited to, the following (as well as mixtures thereof):

(i) Alcohols (these include, for example, σ-glycerol formal, β-glycerol formal, 1,3-butyleneglycol, aliphatic or aromatic alcohols having from 2 to about 30 carbons (e.g., methanol, ethanol, propanol, isopropanol, butanol, t-butanol, hexanol, octanol, amylene hydrate, benzyl alcohol, glycerin (glycerol), glycol, hexylene, glycol, tetrahydrofuranyl alcohol, cetyl alcohol, and stearyl alcohol), fatty acid esters of fatty alcohols (e.g., polyalkylene glycols, such as polypropylene glycol and polyethylene glycol), sorbitan, sucrose, and cholesterol);

(ii) Amides, which include, for example, dimethylacetamide (DMA), benzyl benzoate DMA, dimethylformamide, N-hydroxyethyO-lactamide, N,N-dimethylacetamide-amides, 2-pyrrolidinone, 1-methyl-2-pyrrolidinone, and polyvinylpyrrolidone;

(iii) Esters, which include, for example, acetate esters (e.g., monoacetin, diacetin, and triacetin), aliphatic and aromatic esters (e.g., ethyl caprylate or octanoate, alkyl oleate, benzyl benzoate, or benzyl acetate), dimethylsulfoxide (DMSO), esters of glycerin (e.g., mono, di, and triglyceryl citrates and tartrates), ethyl benzoate, ethyl acetate, ethyl carbonate, ethyl lactate, ethyl oleate, fatty acid esters of sorbitan, glyceryl monostearate, glyceride esters (e.g., mono, di, or triglycerides), fatty acid esters (e.g., isopropyl myristrate), fatty acid derived PEG esters (e.g., PEG-hydroxyoleate and PEG-hydroxystearate), N-methylpyrrolidinone, pluronic 60, polyoxyethylene sorbitol oleic polyesters (e.g., poly(ethoxylated)$_{30-60}$ sorbitol poly(oleate)$_{2-4}$, poly(oxyethylene)$_{15-20}$ monooleate, poly(oxyethylene)$_{15-20}$ mono 12-hydroxystearate, and poly(oxyethylene)$_{15-20}$ mono ricinoleate), polyoxyethylene sorbitan esters (e.g., polyoxyethylene-sorbitan monooleate, polyoxyethylene-sorbitan monopalmitate, polyoxyethylene-sorbitan monolaurate, polyoxyethylene-sorbitan monostearate, and POLYSORBATE 20, 40, 60, and 80 (from ICI Americas, Wilmington, Del.)), polyvinylpyrrolidone, alkyleneoxy modified fatty acid esters (e.g., polyoxyl 40 hydrogenated castor oil and polyoxyethylated castor oils, such as CREMOPHOR EL solution or CREMOPHOR RH 40 solution), saccharide fatty acid esters (i.e., the condensation product of a monosaccharide (e.g., pentoses, such as, ribose, ribulose, arabinose, xylose, lyxose, and xylulose; hexoses, such as glucose, fructose, galactose, mannose, and sorbose; trioses; tetroses; heptoses; and octoses), disaccharide (e.g., sucrose, maltose, lactose, and trehalose), oligosaccharide, or a mixture thereof with one or more $C_4$-$C_{22}$ fatty acids (e.g., saturated fatty acids, such as caprylic acid, capric acid, lauric acid, myristic acid, palmitic acid, and stearic acid; and unsaturated fatty acids, such as palmitoleic acid, oleic acid, elaidic acid, erucic acid, and linoleic acid), and steroidal esters;

(iv) Ethers, for example, alkyl, aryl, and cyclic ethers having from 2 to about 30 carbons. Examples include diethyl ether, tetrahydrofuran, dimethyl isosorbide, diethylene glycol monoethyl ether), and glycofurol (tetrahydrofurfuranyl alcohol polyethylene glycol ether);

(v) Ketones which typically have from about 3 to about 30 carbons. Examples include acetone, methyl ethyl ketone, and methyl isobutyl ketone;

(vi) Hydrocarbons which are typically aliphatic, cycloaliphatic, or aromatic hydrocarbons having from about 4 to about 30 carbons. Examples include benzene, cyclohexane, dichloromethane, dioxolanes, hexane, n-decane, n-dodecane, n-hexane, sulfolane, tetramethylenesulfone, tetramethylenesulfoxide, toluene, dimethylsulfoxide (DMSO); and tetramethylene sulfoxide;

(vii) Oils which include, for example, oils of mineral, vegetable, animal, essential, or synthetic origin. These include: mineral oils, such as aliphatic and wax-based hydrocarbons, aromatic hydrocarbons, mixed aliphatic and aromatic based hydrocarbons, and refined paraffin oil; vegetable oils, such as linseed, tung, safflower, soybean, castor, cottonseed, groundnut, rapeseed, coconut, palm, olive, corn, corn germ, sesame, persic, and peanut oil; glycerides, such as mono-, di-, and triglycerides; animal oils, such as fish, marine, sperm, cod-liver, haliver, squalene, squalane, and shark liver oil; oleic oils; and polyoxyethylated castor oil;

(viii) Alkyl, alkenyl, or aryl halides which include, for example, alkyl or aryl halides having from 1 to about 30 carbons and one or more halogen substituents. Examples include: methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (SOLUTOL HS-15, from BASF, Ludwigshafen, Germany); polyoxyethylene glycerol; sodium laurate; sodium oleate; and sorbitan monooleate.

Other pharmaceutically acceptable solvents for use in the invention are well known to those of ordinary skill in the art. General discussion relating to such solvents can be found in, for example, The Chemotherapy Source Book (Williams & Wilkens Publishing), The Handbook of Pharmaceutical Excipients, (American Pharmaceutical Association, Washington, D.C., and The Pharmaceutical Society of Great Britain, London, England, 1968), Modern Pharmaceutics 3d ed., (G. Banker et. al., eds., Marcel Dekker, Inc., New York, N.Y. (1995)), The Pharmacological Basis of Therapeutics, (Goodman & Gilman, McGraw Hill Publishing), Pharmaceutical Dosage Forms, (H. Lieberman et. al., eds., Marcel Dekker, Inc., New York, N.Y. (1980)), Remington's Pharmaceutical Sciences, 19th ed., (A. Gennaro, ed., Mack Publishing, Easton, Pa., (1995)), The United States Pharmacopeia 24, The National Formulary 19, (National Publishing, Philadelphia, Pa. (2000)); Spiegel, A. J., et al., "Use of Nonaqueous Solvents in Parenteral Products," J. Pharma. Sciences, Vol. 52, No. 10, pp. 917-927 (1963).

Solvents useful in the invention include, but are not limited to, those known to stabilize anti-angiogenesis agent compounds or pharmaceutically acceptable salts thereof. These can include, for example, oils rich in triglycerides, such as safflower oil, soybean oil, and mixtures thereof; and alkyleneoxy-modified fatty acid esters, such as polyoxyl 40 hydrogenated castor oil and polyoxyethylated castor oils (e.g., CREMOPHOR EL solution or CREMOPHOR RH 40 solution). Commercially available triglycerides include INTRALIPID emulsified soybean oil (Kabi-Pharmacia Inc., Stockholm, Sweden), NUTRALIPID emulsion (McGaw, Irvine, Calif.), LIPOSYN II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), LIPOSYN III 2% emulsion (a 2% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels of from about 25 to about 100% (by weight based on the total fatty acid content) (DHASCO from Martek Biosciences Corp., Columbia, Md.; DHA MAGURO from Daito Enterprises, Los Angeles, Calif.; SOYACAL; and TRAVEMULSION). Ethanol in particular is a useful solvent for dissolving a anti-angiogenesis agent compound or pharmaceutically acceptable salt thereof to form solutions, emulsions, and the like.

Additional components can be included in the compositions of this invention for various purposes generally known in the pharmaceutical industry. These components tend to impart properties that, for example, enhance retention of the anti-angiogenesis agent compound or salt at the site of administration, protect the stability of the composition, control the pH, and facilitate processing of the anti-angiogenesis agent compound or salt into pharmaceutical formulations, and the like. Specific examples of such components include cryoprotective agents; agents for preventing reprecipitation of the anti-angiogenesis agent compound or salt surface; active, wetting, or emulsifying agents (e.g., lecithin, polysorbate-80, TWEEN 80, pluronic 60, and polyoxyethylene stearate); preservatives (e.g., ethyl-p-hydroxybenzoate); microbial preservatives (e.g., benzyl alcohol, phenol, m-cresol, chlorobutanol, sorbic acid, thimerosal, and paraben); agents for adjusting pH or buffering agents (e.g., acids, bases, sodium acetate, sorbitan monolaurate, etc.); agents for adjusting osmolarity (e.g., glycerin); thickeners (e.g., aluminum monostearate, stearic acid, cetyl alcohol, stearyl alcohol, guar gum, methyl cellulose, hydroxypropylcellulose, tristearin, cetyl wax esters, polyethylene glycol, etc.); colorants; dyes; flow aids; non-volatile silicones (e.g., cyclomethicone); clays (e.g., bentonites); adhesives; bulking agents; flavorings; sweeteners; adsorbents; fillers (e.g., sugars such as lactose, sucrose, mannitol, sorbitol, cellulose, calcium phosphate, etc.); diluents (e.g., water, saline, electrolyte solutions, etc.); binders (e.g., gelatin; gum tragacanth; methyl cellulose; hydroxypropyl methylcellulose; sodium carboxymethyl cellulose; polyvinylpyrrolidone; sugars; polymers; acacia; starches, such as maize starch, wheat starch, rice starch, and potato starch; etc.); disintegrating agents (e.g., starches, such as maize starch, wheat starch, rice starch, potato starch, and carboxymethyl starch; cross-linked polyvinyl pyrrolidone; agar; alginic acid or a salt thereof, such as sodium alginate; croscarmellose sodium; crospovidone; etc); lubricants (e.g., silica; talc; stearic acid and salts thereof, such as magnesium stearate; polyethylene glycol; etc.); coating agents (e.g., concentrated sugar solutions including gum arabic, talc, polyvinyl pyrrolidone, carbopol gel, polyethylene glycol, titanium dioxide, etc.); and antioxidants (e.g., sodium metabisulfite, sodium bisulfite, sodium sulfite, dextrose, phenols, thiophenols, etc.).

Techniques and compositions for making parenteral dosage forms are generally known in the art. Formulations for parenteral administration can be prepared from one or more sterile powders and/or granules having a compound or salt of this invention and one or more of the carriers or diluents mentioned for use in the formulations for oral administration. The powder or granule typically is added to an appropriate volume of a solvent (typically while agitating (e.g., stirring) the solvent) that is capable of dissolving the powder or granule. Particular solvents useful in the invention include, for example, water, polyethylene glycol, propylene glycol, ethanol, corn oil, cottonseed oil, peanut oil, sesame oil, benzyl alcohol, sodium chloride, and/or various buffers.

Emulsions for parenteral administration can be prepared by, for example, dissolving a compound or salt of this invention in any pharmaceutically acceptable solvent capable of dissolving the compound to form a solution; and adding an appropriate volume of a carrier to the solution while stirring to form the emulsion. Solutions for parenteral administration can be prepared by, for example, dissolving a compound or salt of this invention in any pharmaceutically acceptable solvent capable of dissolving the compound to form a solution; and adding an appropriate volume of a carrier to the solution while stirring to form the solution.

Suppositories for rectal administration can be prepared by, for example, mixing the drug with a suitable nonirritating excipient that is solid at ordinary temperatures, but liquid at the rectal temperature and will therefore melt in the rectum to release the drug. Suitable excipients include, for example, cocoa butter; synthetic mono-, di-, or triglycerides; fatty acids; and/or polyethylene glycols.

Every formulation or combination of components described or exemplified herein can be used to practice the invention, unless otherwise stated.

(i) Binding Agents

Binding agents include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof. Suitable forms of microcrystalline cellulose include, for example, the materials sold as AVICEL-PH-101, AVICEL-PH-103 and AVICEL-PH-105 (available from FMC Corporation, American Viscose Division, Avicel Sales, Marcus Hook, Pa., USA). An exemplary suitable binder is a mixture of microcrystalline cellulose and sodium carboxymethyl cellulose sold as AVICEL RC-581 by FMC Corporation.

(ii) Fillers

Fillers include, but are not limited to, talc, calcium carbonate (e.g., granules or powder), lactose, microcrystalline cellulose, powdered cellulose, dextrates, kaolin, mannitol, silicic acid, sorbitol, starch, pre-gelatinized starch, and mixtures thereof.

(iii) Lubricants

Lubricants include, but are not limited to, calcium stearate, magnesium stearate, mineral oil, electromagnetic radiation mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, and mixtures thereof. Additional lubricants include, for example, a syloid silica gel (AEROSIL 200, manufactured by W.R. Grace Co. of Baltimore, Md., USA), a coagulated aerosol of synthetic silica (marketed by Deaussa Co. of Plano, Tex., USA), CAB-O-SIL (a pyrogenic silicon dioxide product sold by Cabot Co. of Boston, Mass., USA), and mixtures thereof.

(iv) Disintegrants

Disintegrants include, but are not limited to, agar-agar, alginic acid, calcium carbonate, microcrystalline cellulose, croscarmellose sodium, crospovidone, polyacrilin potassium, sodium starch glycolate, potato or tapioca starch, other starches, pre-gelatinized starch, other starches, clays, other algins, other celluloses, gums, and mixtures thereof.

Tablets or capsules can optionally be coated by methods well known in the art. If binders and/or fillers are used with a compound/bioconjugate of the invention, they are typically formulated as about 50 to about 99 weight percent of the compound/bioconjugate. In one aspect, about 0.5 to about 15 weight percent of disintegrant, and particularly about 1 to about 5 weight percent of disintegrant, can be used in combination with the compound. A lubricant can optionally be added, typically in an amount of less than about 1 weight percent of the compound/bioconjugate. Techniques and pharmaceutically acceptable additives for making solid oral dosage forms are described in Marshall, SOLID ORAL DOSAGE FORMS, Modern Pharmaceutics (Banker and Rhodes, Eds.), 7:359-427 (1979). Other formulations are known in the art.

Liquid preparations for oral administration can take the form of solutions, syrups or suspensions. Alternatively, the liquid preparations can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and/or preservatives (e.g., methyl or propyl-p-hydroxybenzoates or sorbic acid). The preparations can also contain buffer salts, flavoring, coloring, perfuming and sweetening agents as appropriate. Preparations for oral administration can also be formulated to achieve controlled release of the compound/bioconjugate. Oral formulations preferably contain 10% to 95% compound/bioconjugate. In addition, a compound/bioconjugate of the present invention can be formulated for buccal administration in the form of tablets or lozenges formulated in a conventional manner. Other methods of oral delivery of compounds/bioconjugates of the invention will be known to the skilled artisan and are within the scope of the invention.

Formulation 1

Hard gelatin capsules are prepared using the following ingredients:

TABLE F1

| Ingredients | (mg/capsule) |
| --- | --- |
| Active Ingredient | 250.0 |
| Starch | 305.0 |
| Magnesium stearate | 5.0 |

The above ingredients are mixed and filled into hard gelatin capsules in 560 mg quantities.

Formulation 2

A tablet formula is prepared using the following ingredients:

TABLE F2

| Ingredients | (mg/tablet) |
| --- | --- |
| Active Ingredient | 250.0 |
| Cellulose, microcrystalline | 400.0 |
| Colloidal silicon dioxide | 10.0 |
| Stearic acid | 5.0 |

The components are blended and compressed to form tablets, each weighing 665 mg.

Formulation 3

A dry powder inhaler formulation is prepared containing the following components:

TABLE F3

| Ingredients | Weight % |
| --- | --- |
| Active ingredient | 5 |
| Lactose | 95 |

The active ingredient is mixed with the lactose and the mixture is added to a dry powder inhaling appliance.

Formulation 4

Tablets, each containing 60 mg of active ingredient, are prepared as follows:

TABLE F4

| Ingredients | milligrams |
| --- | --- |
| Active ingredient | 60.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |
| Total | 150.0 |

The active ingredient, starch and cellulose are passed through a No. 20 mesh U.S. sieve and mixed thoroughly. The solution of polyvinylpyrrolidone is mixed with the resultant powders which are then passed through a 16 mesh U.S. sieve. The granules as produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation 5

Capsules, each containing 80 mg of active ingredient are made as follows:

TABLE F5

| Ingredients | milligrams |
| --- | --- |
| Active ingredient | 80.0 |
| Starch | 109.0 |
| Magnesium stearate | 1.0 |
| Total | 190.0 |

The active ingredient, cellulose, starch, and magnesium stearate are blended, passed through a No. 20 mesh U.S. sieve, and filled into hard gelatin capsules in 190 mg quantities.

Formulation 6

Suppositories, each containing 225 mg of active ingredient, are made as follows:

TABLE F6

| Ingredients | milligrams |
| --- | --- |
| Active Ingredient | 225 |
| Saturated fatty acid glycerides to | 2000 |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation 7

Suspensions, each containing 50 mg of active ingredient per 5.0 ml dose are made as follows:

TABLE F7

| Ingredients | milligrams |
| --- | --- |
| Active ingredient | 50.0 mg |
| Xanthan gum | 4.0 mg |
| Sodium carboxymethyl cellulose | (11%) |
| Microcrystalline cellulose | (89%) 50.0 mg |
| Sucrose | 1.75 g |
| Sodium benzoate | 10.0 mg |
| Flavor | q.v. |
| Color | q.v. |
| Purified water to | 5.0 ml |

The active ingredient, sucrose and xantham gum are blended, passed through a No. 10 mesh U.S. sieve, and mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation 8

Capsules, each containing 150 mg of active ingredient, are made as follows:

TABLE F8

| Ingredients | milligrams |
| --- | --- |
| Active ingredient | 150.0 |
| Starch | 407.0 |
| Magnesium stearate | 3.0 |
| Total | 560.0 |

The active ingredient, cellulose, starch, and magnesium stearate are blended, passed through a No. 20 mesh U.S. sieve, and filled into hard gelatin capsules in 560 mg quantities.

5f: Kits

Various embodiments of the present invention include kits. Such kits can include a compound/bioconjugate of the present invention, optionally one or more ingredients for preparing a pharmaceutically acceptable formulation of the compound/bioconjugate, and instructions for use (e.g., administration). When supplied as a kit, different components of a compound/bioconjugate formulation can be packaged in separate containers and admixed immediately before use. Such packaging of the components separately can, if desired, be presented in a pack or dispenser device which can contain one or more unit dosage forms containing the compound/bioconjugate. The pack can, for example, comprise metal or plastic foil such as a blister pack. Such packaging of the components separately can also, in certain instances, permit long-term storage without losing activity of the components. In addition, if more than one route of administration is intended or more than one schedule for administration is intended, the different components can be packaged separately and not mixed prior to use. In various embodiments, the different components can be packaged in one combination for administration together.

It is further contemplated that the anti-angiogenesis agent compounds and salts of this invention can be used in the form of a kit that is suitable for use in performing the methods described herein, packaged in a container. The kit can contain the anti-angiogenesis agent compound or compounds and, optionally, appropriate diluents, devices or device components suitable for administration and instructions for use in accordance with the methods of the invention. The devices can include parenteral injection devices, such as syringes or transdermal patch or the like. Device components can include cartridges for use in injection devices and the like. In one aspect, the kit includes a first dosage form including a anti-angiogenesis agent compound or salt of this invention and a second dosage form including another active ingredient in quantities sufficient to carry out the methods of the invention. The first dosage form and the second dosage form together can include a therapeutically effective amount of the compounds for treating the targeted condition(s).

In certain embodiments, kits can be supplied with instructional materials. Instructions can be printed on paper or other substrate, and/or can be supplied as an electronic-readable medium, such as a floppy disc, mini-CD-ROM, CD-ROM, DVD-ROM, Zip disc, videotape, audio tape, and the like. Detailed instructions cannot be physically associated with the kit; instead, a user can be directed to an Internet web site specified by the manufacturer or distributor of the kit, or supplied as electronic mail.

If desired, the emulsions or solutions described above for oral or parenteral administration can be packaged in IV bags, vials, or other conventional containers in concentrated form, and then diluted with a pharmaceutically acceptable liquid (e.g., saline) to form an acceptable anti-angiogenesis agent compound concentration before use.

Kits can include reagents in separate containers such as, for example, sterile water or saline to be added to a lyophilized active component packaged separately. For example, sealed glass ampules can contain lyophilized superoxide dismutase mimetics and in a separate ampule, sterile water, sterile saline or sterile each of which has been packaged under a neutral non-reacting gas, such as nitrogen. Ampules can consist of any suitable material, such as glass, organic polymers, such as polycarbonate, polystyrene, ceramic, metal or any other material typically employed to hold reagents. Other examples of suitable containers include bottles that can be fabricated from similar substances as ampules, and envelopes that can consist of foil-lined interiors, such as aluminum or an alloy. Other containers include test tubes, vials, flasks, bottles, syringes, and the like. Containers can have a sterile access port, such as a bottle having a stopper that can be pierced by a hypodermic injection needle. Other containers can have two compartments that are separated by a readily removable membrane that upon removal permits the components to mix. Removable membranes can be glass, plastic, rubber, and the like.

Example 6

Synthesis of Quaternary Amine Compounds

Another aspect of the invention provides processes for the synthesis of quaternary salt derivatives of the compounds described herein. The processes comprise contacting a tertiary N-substituted compound with $R^2$-(Leaving Group), wherein $R^2$ is as described in the context of (FX1) and (FX2), and X is a leaving group, to form a quaternary N-substituted salt.

(a) Synthesis of Compounds Comprising Formula (FX11) and (FX12)

In one embodiment, a quaternary salt compound comprising Formula (FX11) or (FX12) is synthesized from a compound comprising Formula (FX9) or (FX10). For purposes of illustration, Reaction Scheme 6-1 depicts production of a compound comprising Formula (FX11) in accordance with one aspect of the invention:

Reaction Scheme 6-1:

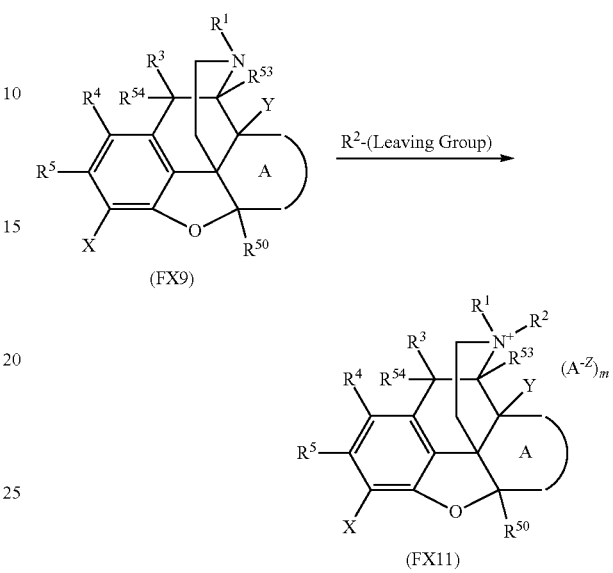

For purposes of illustration, Reaction Scheme 6-2 depicts production of a compound comprising Formula (FX12) in accordance with one aspect of the invention:

Reaction Scheme 6-2:

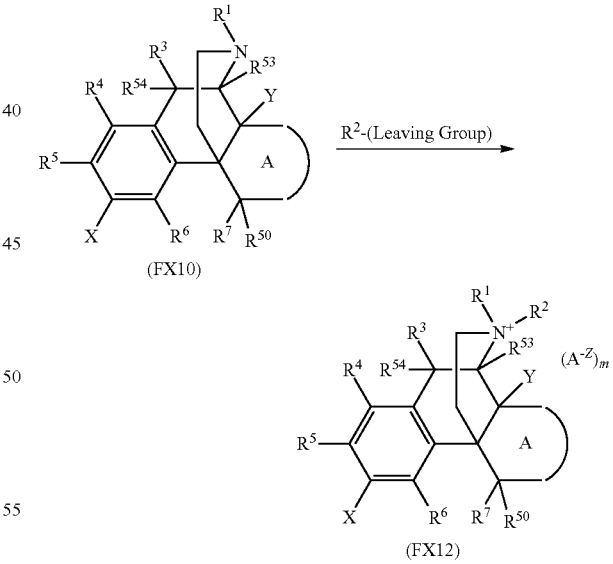

(b) Reaction Mixture

Synthesis commences with formation of a reaction mixture by combining a compound comprising Formulas (FX1) or (FX2) with $R^2$-(Leaving Group). Thus, for example, $R^2$-(Leaving Group) may be a methyl, ethyl, propyl, allyl, cyclopropyl, cyclopropylmethyl, propargyl, or benzyl halide or another leaving group. Non-limiting examples of $R^2$-(Leaving Group) include methyl bromide, methyl chloride, allyl iodide, cyclopropylmethyl bromide, dimethyl sulfate, diethyl sulfate, di(cyclopropylmethyl) sulfate, methyl fluorosulfonate, trimethyloxonium fluoroborate, triethyloxonium fluoroborate, trimethyloxonium hexachloroantimonate, n propyl or n-octyl trifluoromethane sulfonate, trimethyloxonium hexafluorophosphate, methyl trifluoromethane sulfonate, methyl iodide, and allyl trifluoromethanesulfonate. In a preferred embodiment, $R^2$-(Leaving Group) is methyl bromide.

The mole-to-mole ratio of the compound comprising Formulas (FX1) or (FX2) to $R^2$-(Leaving Group) can vary. In general, the mole-to-mole ratio of the compound comprising Formulas (FX1) or (FX2) to $R^2$-(Leaving Group) may range from about 1:1 to about 1:2. In some embodiments, the mole-to-mole ratio of the compound comprising Formulas (FX1) or (FX2) to $R^2$-(Leaving Group) may be about 1:1, 1:1.1, 1:1.2, 1:1.3, 1:1.4, 1:1.5, 1:1.6, 1:1.7, 1:1.8, 1:1.9, or 1:2. In preferred embodiments the mole-to-mole ratio of the compound comprising Formulas (FX1) or (FX2) to $R^2$-(Leaving Group) may range from about 1:1 to about 1:1.5. Furthermore, the rate of addition of $R^2$-(Leaving Group) to the compound comprising Formulas (FX1) or (FX2) may vary. Typically, the rate of addition of $R^2$-(Leaving Group) may range from 0.002 to about 0.02 equivalents of $R^2$-(Leaving Group) per minute per equivalent of the compound comprising Formulas (FX1) or (FX2) in the reaction mixture.

The reaction mixture, as detailed herein, also comprises a solvent system. In general, the solvent system is anhydrous. That is, the solvent system comprises less than about 0.5% of water by weight, typically less than about 0.2% of water by weight, and in some embodiments, less than about 0.05% of water by weight. The solvent system typically comprises an aprotic solvent. Non-limiting examples of suitable aprotic solvents include acetonitrile, 1,4-dioxane, N,N-dimethylacetamide (DMAC), N,N-dimethylformamide (DMF), N-methyl-2-pyrrolidinone (NMP), hexamethylphosphoramide, (HMPA), and combinations thereof. In a preferred embodiment, the aprotic solvent is N-methyl-2-pyrrolidinone (NMP). The solvent system may additionally comprise an organic solvent such as ether, hydrocarbon, toluene, benzene, halobenzene, xylenes, or combinations thereof. In general, the solvent system comprises at least about 50% of the aprotic solvent by weight, at least about 75% of the aprotic solvent by weight, or at least about 90% of the aprotic solvent by weight.

The amount of solvent system in the reaction mixture may vary. Typically, the weight-to-weight ratio of solvent system to the compound comprising Formulas (FX1) or (FX2) may range from about 1.5:1 to about 2.0:1. In some embodiments, the weight-to-weight ratio of solvent system to the compound comprising Formulas (FX1) or (FX2) may be about 1.5:1. 1.55:1, 1.6:1, 1.65:1, 1.7:1, 1.75:1, 1.8:1, 1.85:1, 1.9:1, 1.95:1, or 2.0:1.

In some embodiments, X is a hydroxy group in the compound comprising Formula (FX1) or (FX2), wherein reaction with $R^2$-(Leaving Group) may yield undesirable alkyloxymorphinan compounds. To prevent such side reactions, an acid may be added to the reaction mixture to suppress ionization of the hydroxy group. Suitable acids include strong mineral or organic acids. For example, the acid may be a carboxylic acid, a phosphonic acid, a sulfonic acid, or a mixture thereof. Alternatively, a small amount of a preformed alkaloid acid salt may be added to its alkaloid base in order to suppress ionization of the alkaloid base; for example, naltrexone hydrobromide may be added to naltrexone base. By way of further example, the acid may be HBr, HCl, $H_2SO_4$, $NaHSO_4$, $NaH_2PO_4$, or $Na_2HPO_4$. In preferred embodiments, the acid may be HBr gas or HCl gas. Preferably, the acid is also anhydrous. That is, the acid may comprise less that about 0.5% of water by weight, less than about 0.2% of water by weight, or more preferably, less than about 0.05% of water by weight. Those of skill in the art will also appreciate that the 3-hydroxy of the compound comprising Formulas (FX1) or (FX2) may be protected with a hydroxy protecting group prior to the reaction of the invention.

(c) Reaction Conditions

The quaternization reaction may be carried out over a wide range of temperatures and pressures. Typically, the reaction will be carried out at a temperature that ranges from about room temperature (i.e., about 25° C.) to about 90° C. In preferred embodiments, the temperature of the reaction may range from about 55° C. to about 85° C. In some embodiments, the temperature of the reaction may be about 55°, 60°, 65°, 70°, 75°, 80°, or about 85° C. In general, the reaction will be conducted at a pressure of no more than about 4 atmospheres. In preferred embodiments, the pressure of the reaction may range from about 1 to about 2 atmospheres. In other embodiment, the reaction may occur at atmospheric pressure.

The duration of the reaction can and will vary. For example, the reaction may be allowed to proceed from about several hours to about several days. Typically, however, the reaction is allowed to proceed for a sufficient period of time until the reaction is complete, as determined by means well known to those of skill in the art. In this context, a "completed reaction" generally means that the final reaction mixture contains a significantly diminished amount of the reactants and a significantly increased amount of the products of Reaction Schemes 1 and 2 compared to the amounts of each present at the beginning of the reaction. Typically, the amount of the reactant remaining in the final reaction mixture may be less than about 5%, and preferably less than about 1%.

When the reaction is completed, the reaction mixture is generally cooled to at least about room temperature, such that the reaction product may be isolated. In some embodiments, a solvent of lower polarity in which the reaction product is not soluble may be added to the cooled reaction mixture to facilitate precipitation of the quaternary reaction product while leaving the unreacted tertiary substrate in solution. Examples of suitable solvents include, but are not limited to acetone, chloroform, dichloromethane, ethyl acetate, propyl acetate, methyl ethyl ketone, methyl butyl ketone, ether, t-butylmethylether, 2-methyltetrahydrofuran, hydrocarbon, toluene, benzene, chlorobenzene, bromobenzene, and mixtures thereof. The reaction mixture may be optionally cooled further to about 0° C. to about 5° C. The precipitated product generally is separated from the remaining reaction mixture by filtration, and is washed and dried to produce the final product. The yield of the final product typically will range form about 50% to about 99%. In some embodiments, the yield of the final product may be at least about 50, 55, 60, 65, 70, 75, 80, 85, 90, or 95%.

In embodiments in which the Leaving Group is a halide, the final product comprises a halide anion. This anion may be exchanged by treating the compound with a protic acid, thereby replacing the halide ion with another anion such as nitrate, sulfate, phosphate, or another halide ion.

(d) Synthesis of R-3-Acetoxy-(+)-Naltrexone Methobromide

The following reaction scheme depicts the synthesis of 3-acetoxy-(+)-naltrexone methobromide:

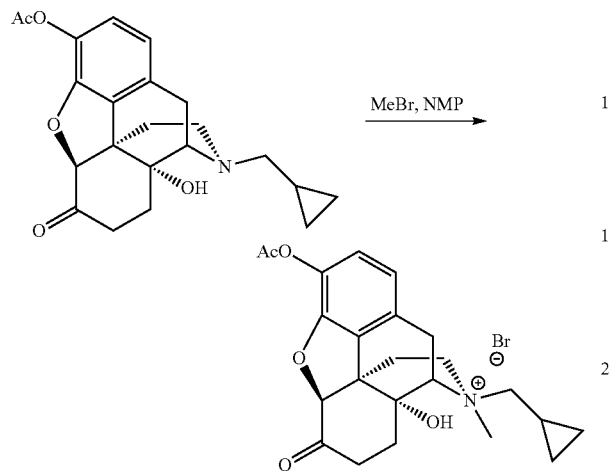

A solution of 3-acetoxy-(+)-naltrexone in 1-methyl-3-pyrrollidinone (NMP) (732.2 g of 30% wt/wt solution, 0.57 moles) may be added to a 1-L, 5-neck, jacketed pressure reactor equipped with a polished glass stirring shaft, mechanical stirrer, reflux condenser, pressure manifold, thermowell, and ⅛" (id) addition line. Methyl bromide (MeBr, 107.9 g, 1.14 moles) then may be added subsurface through the addition line with vigorous stirring of the solution over a 1-hour period. The amount of MeBr is determined by a difference in the initial and final weights of a MeBr lecture bottle. During the addition, the temperature of the reaction mixture may increase to about 33° C. (yellow solution) with a maximum pressure of 3-4 psi. After the appropriate amount of MeBr is added, the reactor headspace may be evacuated and re-pressurized with MeBr (to about 2 psi) twice before heating to 60° C. At 60° C., a pressure of 2-4 psi may be observed. The reaction mixture may be stirred overnight (15 hours) with no pressure remaining over the yellow solution. Aqueous hydrogen bromide (HBr, 1.0 equiv, 0.57 moles, 96.58 g of 48 wt. %) may be added slowly at 60° C. over a 30-minute period. The reactor may be vented into NMP in order to trap gaseous methyl bromide that is generated during the HBr addition. During the addition, the reaction temperature may increase to about 64° C. The reaction temperature then may be increased to 80° C. over a 1.5-hour period, wherein evolution of methyl bromide ceases. The mixture may be stirred at 80° C. for 2 hours, wherein precipitation occurs. After 5 hours at 80° C., the slurry may be analyzed by HPLC. Preferably, only a minor amount of 3-acetoxy-(+)-naltrexone methobromide remains in the slurry (<0.5% by area). The mixture then may be transferred to a 2-L three-neck round-bottomed flask equipped with a glass stirring shaft, mechanical stirrer, reflux condenser, and thermocouple under a nitrogen atmosphere. The mixture may be cooled to about 56° C. and methanol (512.5 g, 1.0 wt equiv. based on the amount of NMP charged) may be added quickly to facilitate crystallization of methobromide salts. The slurry then may be cooled to about 20° C. over a 30-minute period and then to about 5-10° C. in an ice bath. The slurry may be stirred for 1 hour at 5-10° C., filtered, and the product washed with cold methanol (319 mL, 1.45 mL/g of starting material to afford product as a white solid (e.g., about 236.1 g of product; 87.2%). The crude product may be analyzed by HPLC (e.g., it may contain 88.54% R and 1.47% S diastereomers).

(e) Synthesis of R-(+)-Naltrexone Methobromide

The following reaction scheme depicts the synthesis of (+)-naltrexone methobromide:

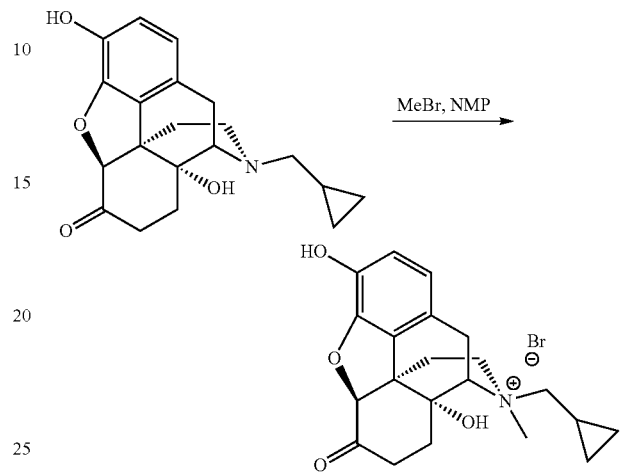

Fresh anhydrous 1-methyl-2-pyrrolidinone (50 mL) may be added to a 3-necked 250 mL flask fitted with a thermocouple, addition funnel, condenser, and a mechanical stirrer under a sweep of dry nitrogen. The solution may be heated to 55° C. The addition funnel may be replaced with a powder funnel and anhydrous (+) naltrexone base (39.5 grams) added with stirring. After the funnel is "washed down" with 10 mL of additional 1-methyl-2-pyrrolidinone, the temperature may be is adjusted to 55-58° C. and the addition funnel replaced on the flask. Separately, 10 mL of anhydrous 1-methyl-2-pyrrolidinone may be cooled in a graduated cylinder, and methyl bromide gas may be condensed in a lecture bottle using an ice bath and 10 mL measured out as a liquid into another cold graduated cylinder. The cold methyl bromide liquid and 1-methyl-2-pyrrolidinone may be combined and mixed. The methyl bromide solution may be poured into the addition funnel and added dropwise to the (+) naltrexone solution under a slow sweep of dry nitrogen. The temperature of the solution may increase to about 66° C. The reaction temperature and time may be set at 62.5° C. for nine hours. After an hour, a fine white suspension of R-(+)-naltrexone methobromide may begin to form. At the end of nine hours the heating may be discontinued and the mixture may be allowed to cool to room temperature with stirring overnight. Acetone (75 mL) may be poured into the suspension to facilitate the precipitation of product. The slurry may be cooled to ice bath temperature and stirred. The product may be recovered by vacuum filtration and washed with 25 mL of additional acetone. The product may be dried to a constant weight in a vacuum oven set at 60° C. The yield of the unpurified salts may be about 31.8 g.

(f) Synthesis of R-(+)-Naloxone Methobromide

Anhydrous 1-methyl-2-pyrrolidinone (5 mL) may be added to a 25 mL flask fitted with a condenser and stirring bar under a sweep of dry nitrogen. Anhydrous (+) naloxone base (4.11 grams) may be added with stirring. Methyl bromide gas may be condensed in a lecture bottle using an ice bath and 0.5 mL measured out as a liquid in another cold graduated cylinder. The methyl bromide may be poured into the naltrexone base suspension under a slow sweep of dry nitrogen. The reaction temperature and time may be set at 60° C. for ten hours. At the end of ten hours the heating may be discontinued and the mixture allowed to cool to room temperature with stirring overnight (or longer). Acetone (10 mL) may be added to the suspension to facilitate the precipitation of the product. The slurry may be cooled to ice bath temperature with stirring. The product may be recovered by vacuum filtration and washed with additional acetone. The product may be dried in a vacuum oven set at 60° C. for two hours. For example, 2.89 grams of the crude product may be recovered. Recrystallization from methanol/water (20 30 mL, 8:2) may yield 2.43 grams of a white crystalline salt.

(g) Synthesis of R-(+)-Nalfurafine Methoiodide (+)-Nalfurafine (2.0 g, 4.3 mmol), ethyl acetate (60 mL), methanol (6 mL), and methyl iodide (1.3 mL) may be placed together in a sealed reactor. The reactor contents may be stirred at 100° C. for about four days. Methanol (60 mL) may be added to the reaction solution to facilitate precipitation of the product. The precipitated solid may be dissolved and concentrated. Distilled water (400 mL) may be added to the resulting residue. This aqueous solution may be washed with chloroform (7×100 mL). The water phase may be concentrated. The resulting residue may be recrystallized from ethyl acetate-methanol. The resulting crystal may be dissolved in distilled water (500 mL). This aqueous solution may be washed with chloroform (3×100 mL). The water phase may be concentrated. The resulting residue may be recrystallized three times from methanol. As an example, 102 mg of the product, R-(+)-nalfurafine methoiodide, may be obtained.

(h) Synthesis of R-(+)-Oxycodone Cyclopropylmethobromide

The following reaction scheme depicts the synthesis of (+)-oxycodone cyclopropylmethobromide:

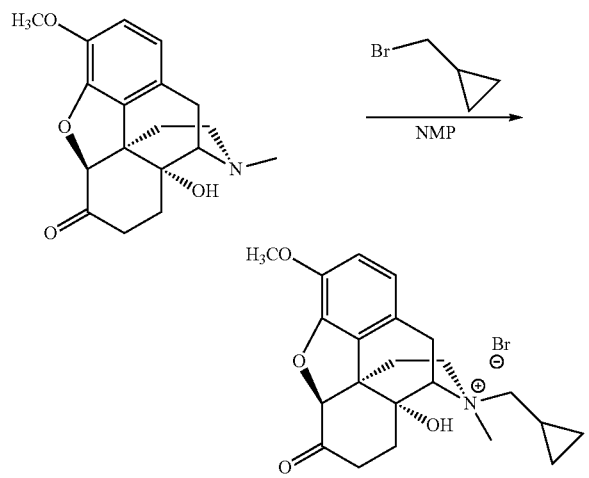

A reactor was charged with (+)-oxycodone (0.5 g, 1.595 mmol) and 2 mL of 1-methyl-3-pyrrollidinone (NMP). The reactor was flushed with nitrogen and the mixture was kept under nitrogen throughout the reaction. Cyclopropylmethylbromide (0.2 mL, 1.3 eq) was added and the reaction mixture was heated to 68° C. for 3 h. Samples were removed at 1 h, 2 h, and 3 h for analysis; the reaction was complete after 2 h. The reaction mixture was cooled to room temperature. Acetone (4 mL) was added and the mixture was stirred at 20° C. for 1 h. The solids were filtered and washed with acetone (3×2 mL); 0.2 g of solid was recovered. The filtrate and acetone wash were pumped down (and washed with water) to give another 0.22 g of solid. The solids were combined, charged with water (5 mL, stirred at rt for 2 h), and filtered. The solid was washed with water (3×2 mL), dried in a vacuum oven at 65° C. for 18 h to give 0.36 g of white solid.

Example 7

Synthesis of N-Oxide Compounds

Another aspect of the invention provides processes for the synthesis of N-oxide derivatives of the compounds described herein. The processes comprise contacting a tertiary N-substituted compound with an oxidizing agent, to form a quaternary N-oxide.

(a) Synthesis of Compounds Comprising Formula (FX3) and (FX4)

In one embodiment, a quaternary salt compound comprising Formula (FX3) or (FX4) is synthesized from a compound comprising Formula (FX9) or (FX10). For purposes of illustration, Reaction Scheme 7-1 depicts production of a compound comprising Formula (FX3) in accordance with one aspect of the invention:

Reaction Scheme 7-1:

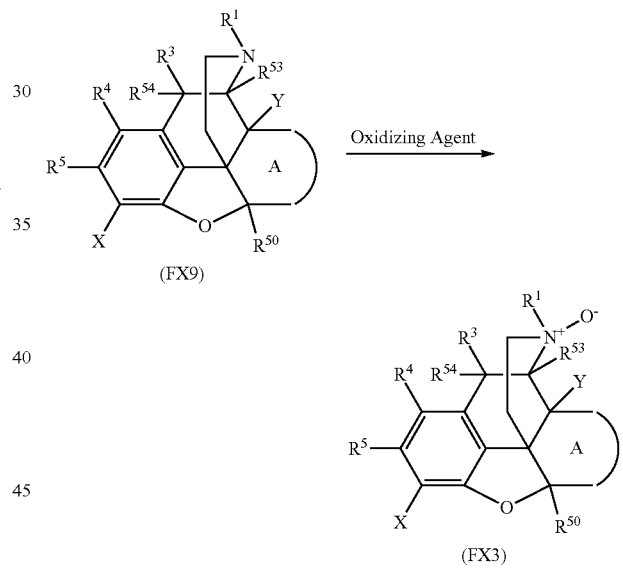

For purposes of illustration, Reaction Scheme 7-2 depicts production of a compound comprising Formula (FX4) in accordance with one aspect of the invention:

Reaction Scheme 7-2:

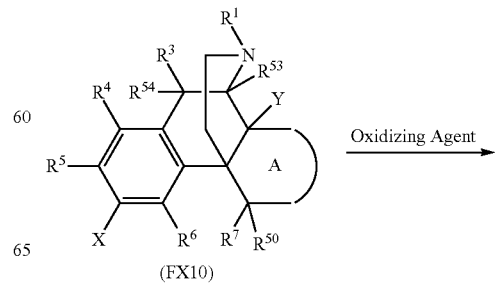

-continued

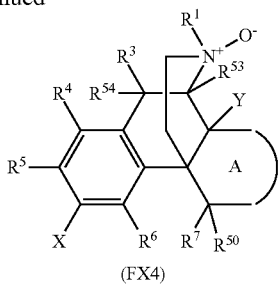

(FX4)

(b) Reaction Mixture

The process of the invention commences with formation of a reaction mixture by combining a compound comprising Formulas (FX1) or (FX2) with an oxidizing agent. A variety of oxidizing agents are suitable for use in the process of the invention. Examples of oxidizing agents that may be used include, but are not limited to tungsten(VI) oxide, chromium oxide, dichromate, copper oxide, nickel oxide, cobalt oxide, silver oxide, oxides of mercury, oxides of lead, selenium oxide, ruthenium oxide, hydrogen peroxide, peroxysulfate, peroxyacetic acid, 3-chloroperoxybenzoic acid, $RCO_3H$, wherein R is selected from the group consisting of hydrogen, an alkyl, a substituted alkyl, an aryl, a substituted aryl, dichromates (e.g., ammonium dichromate, potassium dichromate, sodium dichromate, and the like); bromates (e.g., barium bromate, magnesium bromate, potassium bromate, sodium bromate, and the like); chlorates (e.g., ammonium chlorate, barium chlorate, calcium chlorate, potassium chlorate, sodium chlorate, and the like); chlorites (e.g., copper chlorite, lead chlorite, potassium chlorite, sodium chlorite, and the like); chloroisocyanuric acids (e.g., trichloroisocyanuric acid, and the like); chromates (e.g., potassium chromate, and the like); chromium oxides (e.g., chromic anhydride (chromium trioxide)); dichromates (e.g., sodium dichromate, potassium dichromate, and the like); hydrogen peroxide; hypobromites (e.g., sodium hypobromite, and the like); hypochlorites (e.g., calcium hypochlorite, potassium hypochlorite, sodium hypochlorite, and the like); hypoiodites (e.g., sodium hypoiodite, potassium hypoiodite, and the like); inorganic peroxides (e.g., barium peroxide, calcium peroxide, cesium peroxide, lithium peroxide, magnesium peroxide, potassium peroxide, rubidium peroxide, sodium peroxide, strontium peroxide, and the like); iodates (e.g., calcium iodate, potassium iodate, sodium iodate, zinc iodate, and the like); iodine oxides (e.g., diiodine pentaoxide, and the like); lead oxides (e.g., lead dioxide, and the like); manganese dioxide; nitrates (e.g., ammonium nitrate, ammonium cerium nitrate, barium nitrate, potassium nitrate, silver nitrate, sodium nitrate, and the like); nitric acid; nitrites (e.g., potassium nitrite, sodium nitrite, and the like); perchlorates (e.g., ammonium perchlorate, potassium perchlorate, sodium perchlorate, and the like); periodates (e.g., potassium periodate, sodium periodate, and the like); periodic acids (e.g., metaperiodic acid, and the like); permanganates (e.g., ammonium permanganate, magnesium permanganate, potassium permanganate, sodium permanganate, and the like); peroxoborates (e.g., ammonium peroxoborate, and the like); perchloric acid; peroxodisulfates (e.g., ammonium peroxodisulfates, potassium peroxydisulfate, and the like); peroxyacids (e.g., peroxyacetic acid, peroxybenzoic acid, peroxyformic acid, trifluoroperacetic acid, and the like); organic peroxides (e.g., benzoyl peroxide, and the like); tetroxides (e.g., osmium tetroxide, ruthenium tetroxide, and the like); dimethyldioxirane; and oxygen. As the oxygen source, air may also be used. In an exemplary embodiment the oxidizing agent is hydrogen peroxide.

The mole-to-mole ratio of the compound comprising Formulas (FX1) or (FX2) to oxidizing agent can vary. In general, the mole-to-mole ratio of the compound comprising Formulas (FX1) or (FX2) to oxidizing agent may range from about 1:1 to about 1:20. In some embodiments, the mole-to-mole ratio of the compound comprising Formulas (FX1) or (FX2) to oxidizing agent may be about 1:1, 1:1.1, 1:1.5, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20. In preferred embodiments the mole-to-mole ratio of the compound comprising Formulas (FX1) or (FX2) to oxidizing agent may range from about 1:10 to about 1:15.

The reaction mixture, as detailed herein, generally also comprises a solvent. Those of skill in the art will appreciate that they solvent utilized will depend upon a variety of factors, including the chemical nature of the starting compound. In some embodiments, the solvent may be a protic solvent. Non-limiting suitable examples of protic solvents include, but are not limited to, methanol, ethanol, isopropanol, n-propanol, isobutanol, n-butanol, s-butanol, t-butanol, formic acid, acetic acid, water, and combinations thereof. In an exemplary embodiment, the protic solvent is methanol. In other embodiments, the solvent may be an aprotic solvent. Non-limiting examples of suitable aprotic solvents include acetone, acetonitrile, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), N,N-dimethylacetamide (DMAC), N-methyl-2-pyrrolidinone (NMP), ethyl acetate, ethyl formate, ethyl methyl ketone, formamide, hexachloroacetone, hexamethylphosphoramide, methyl acetate, N-methylacetamide, N-methylformamide, methylene chloride, nitrobenzene, nitromethane, propionitrile, sulfolane, tetramethylurea, toluene, trichloromethane, xylenes, and combinations thereof. In still other embodiments, the solvent may be an organic solvent. Suitable organic solvents include, but are not limited to, alkane and substituted alkane solvents (including cycloalkanes), aromatic hydrocarbons, esters, ethers, combinations thereof, and the like. Specific organic solvents that may be employed, include, for example, acetonitrile, benzene, butyl acetate, t-butyl methylether, chlorobenzene, chloroform, chloromethane, cyclohexane, dichloromethane, dichloroethane, ethyl acetate, diethylene glycol, fluorobenzene, heptane, hexane, isopropyl acetate, pentyl acetate, n-propyl acetate, tetrahydrofuran, toluene, and combinations thereof. In additional embodiments, the solvent may comprise a mixture of protic, aprotic, and/or organic solvents as delineated above.

The amount of solvent in the reaction mixture may vary. Typically, the weight-to-weight ratio of solvent to the compound comprising Formulas (FX1) or (FX2) may range from about 2:1 to about 100:1, preferably from about 3:1 to about 30:1, or more preferably from about 5:1 to about 15:1. In some embodiments, the weight-to-weight ratio of solvent to the compound comprising Formulas (FX1) or (FX2) may be about 1:5, 1:6, 1:7, 1:8, 1:9, 1:10, 1:11, 1:12, 1:13, 1:14, or 1:15.

(c) Reaction Conditions

In general, the oxidation reaction may be conducted at a temperature that ranges from about −10° C. to about 120° C. for a period of time that is sufficient to convert a substantial portion of the reactants to products. In one embodiment, the temperature of the reaction may range from about −10° C. to about 80° C. In another embodiment, the temperature may range from about −10° C. to about 50° C. In still another embodiment, the temperature of the reaction may range from about −5'C to about 30° C. In a further embodiment, the temperature of the reaction may be about room temperature (~25° C.). The reaction is preferably performed under ambient pressures and preferably in an inert atmosphere (e.g., nitrogen or argon).

Typically, the reaction is allowed to proceed for a sufficient period of time until the reaction is complete, as determined by chromatography (e.g., TLC or HPLC). In this context, a "completed reaction" generally means that the reaction mixture contains a significantly diminished amount of reactants and a significantly increased amount of products compared to the amounts of each present at the beginning of the reaction. Typically, the amount of reactants remaining in the reaction mixture may be less than about 5%, and preferably less than about 1%.

Upon completion of the reaction, the reaction mixture may be cooled to about 4'C or less. Once the solution has cooled, filtration may be performed (for example by use of a celite plug) to remove impurities. The product may be isolated by phase extraction, liquid chromatography, crystallization, or other means familiar to those of skill in the art. The final product may washed and dried, and analyzed by HPLC, UPLC, MS, NMR, IR, or TGA. The yield of the compound comprising Formula (II) or Formula (IV) may vary. Typically, the yield of the compound may range from about 60% to about 99%, and more specifically from about 70% to about 80%.

(d) Synthesis of (+)-Hydrocodone N-Oxide

The following scheme depicts the synthesis of (+)-hydrocodone N-oxide from (+)-hydrocodone.

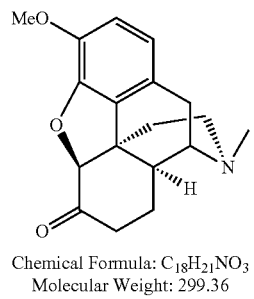

Chemical Formula: $C_{18}H_{21}NO_3$
Molecular Weight: 299.36

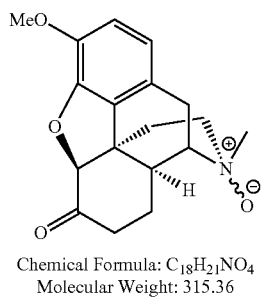

Chemical Formula: $C_{18}H_{21}NO_4$
Molecular Weight: 315.36

Hydrogen peroxide (2.5 mL, 50% w/v, 36.8 mmol, 11 eq.) was added drop-wise to a cooled solution of (+)-hydrocodone (1.0 g, 3.34 mmol, 1.0 eq.) in 10 mL of methanol (MeOH) in an ice bath. The reaction mixture was gradually warmed to room temperature overnight. High phase liquid chromatography (HPLC) analysis indicated the reaction was done. Approximately 50 mg $MnO_2$ was added to the reaction to decompose the excess hydrogen peroxide. Bubbling was observed after adding $MnO_2$. After the bubbling stopped, the reaction was filtered through celite and the solid residue was washed with methanol (3 mL×3). After removal of the volatiles from the combined filtrates on a rotoevaporator unit, a grey solid remained. The grey solid was added to 30 mL brine, the resulting suspension was cooled to approximately 0° C. in an ice bath, and the pH was adjusted to 1 with 6 N HCl. The product was extracted with dichloromethane (3×20 mL) and the combined organic phases were dried over anhydrous magnesium sulfate. After removing volatiles of the dried organic phase by means of the rotoevaporator, a white solid was left, 0.78 g, a yield of 74%, with purity=98.7%. Two peaks were observed on ultra pressure liquid chromatography (UPLC) analysis, the smaller peak had 5.17% ratio and the bigger peak had 94.83% ratio. Both peaks had M+1=316.3 and fragmentation pattern on LC-MS analysis.

(e) Synthesis of (+)-Hydrocodone N-Oxide and Isolation of Isomers

The following reaction scheme depicts the oxidation of (+)-hydrocodone to form (+)-hydrocodone N-oxide.

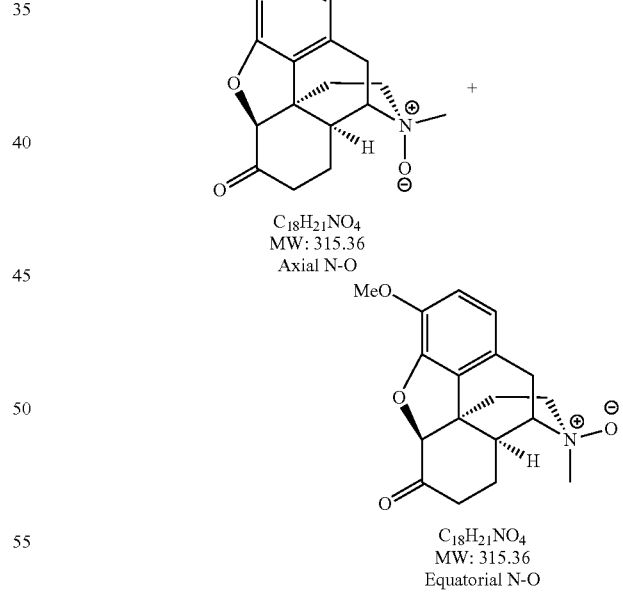

(+)-Hydrocodone N-oxide may be prepared in high yield by N-oxidation of (+)-hydrocodone base with hydrogen peroxide in the presence of a protic solvent. Accordingly, a suspension of 4.348 g (+)-hydrocodone base (14.52 mmol) in 50 mL of methanol may be slowly mixed with 19 mL of 30% hydrogen peroxide ($H_2O_2$) (186 mmol, 12.8 eq.) at room temperature. The suspension may be stirred overnight at room temperature under nitrogen. The completeness of the reaction may be monitored by TLC analysis (e.g., CHCl$_3$:MeOH:NH$_4$OH, 80:20:1). The starting material should be consumed and two products may be detected (major product, R$_f$ 0.44, and minor product, R$_f$ 0.25). The reaction mixture may be was cooled in an ice-water bath and the quenched with manganese dioxide (MnO$_2$). After filtration though a plug of celite followed by concentration, the crude reaction mixture may be subjected to flash column chromatography (CHCl$_3$:MeOH:NH$_4$OH gradient, from 100:0:1 to 95:5:1) such that both products are isolated. By mass spectroscopy (MS) analysis, both major (3.7 g) and minor (230 mg) products have the same molecular weight and similar fragmentation patterns consistent for the N-oxide isomers. HPLC may be use to determine that both peaks (major at 6.65 min, minor at 4.37 min) are chromatographically pure. Nuclear magnetic resonance (NMR) may be used to show that the minor product could be a mixture of two or three compounds. NMR analysis may show that the major product is the (+) hydrocodone N-oxide with an axial N—O bond. The major isomer may be purified by flash column chromatography (CHCl$_3$:MeOH:NH$_4$OH gradient, from 100:0:1 to 95:5:1) with four fractions being collected (F1, 97.55% area; F2, 98.05% area; F3, 97.51% area and F4, 98.19% area). Fractions 2 and 4 may be combined, and after removal of the solvent, 1.45 g of the major product may be obtained (C1, 98.36% area) as an off-white foam. Fractions 1 and 3 may be combined, and after solvent removal, 1.26 g of product may be obtained (C2) as an off-white foam. C1 may be further analyzed and verified by infrared spectroscopy (IR), thermogravimetric analysis (TGA), NMR, HPLC, and MS methods.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

U.S. patent application Ser. No. 12/710,383, filed on Feb. 23, 2010, U.S. patent application Ser. No. 12/710,379, filed on Feb. 23, 2010, PCT International Application No. PCT/US10/24963, filed on Feb. 23, 2010, and PCT International Application No. PCT.US10/24961, filed on Feb. 23, 2010, are each hereby incorporated by reference in its entirety and generally relate to methods of synthesizing and derivatizing morphinanium n-oxides, morphinanium quaternary salts and stereoisomers thereof.

U.S. Provisional Patent Application No. 61/226,015, filed on Jul. 16, 2009, and U.S. Provisional Patent Application No. 61/286,877, filed on Dec. 16, 2009, are each hereby incorporated by reference in its entirety and generally relate to (+) morphinan compounds and related methods of synthesizing and using (+) morphinan compounds, for example in therapeutic methods.

PCT International Application No. PCT/US2007/025263, filed on Dec. 10, 2007 and published on Jun. 19, 2008 as International Publication No. WO/2008/073390; PCT International Application No. PCT/US2007/025262, filed on Dec. 10, 2007 and published on Jun. 19, 2008 as International Publication No. WO/2008/073389; and PCT International Application No. PCT/US2005/038140, filed on Oct. 21, 2005 and published on May 18, 2006 as International Publication No. WO/2006/052430 are each hereby incorporated by reference in its entirety and generally relate to the synthesis and derivatization of isoquinolines, for example by total opiate synthesis and chiral reduction techniques.

U.S. patent application Ser. No. 12/316,862, filed on Dec. 17, 2008 and published on Jun. 18, 2009 as U.S. Patent Publication No. 2009/0156,818; and U.S. patent application Ser. No. 12/316,846, filed on Dec. 17, 2008 and published on Jun. 18, 2009 as U.S. Patent Publication No. 2009/0156,816 are each hereby incorporated by reference in its entirety and generally relate to the synthesis and derivatization of (+) morphinan compounds, for example using the natural product Sinomenine.

U.S. patent application Ser. No. 12/485,200, filed on Jun. 16, 2009 and published on Dec. 17, 2009 as U.S. Patent Publication No. 2009/0312,552; is hereby incorporated by reference in its entirety and generally relates to a chemical process to make a beta epimer for b-naltrexol preparation.

U.S. patent application Ser. No. 12/316,861, filed on Dec. 17, 2008 and published on Jun. 18, 2009 as U.S. Patent Publication No. 2009/0156,817; is hereby incorporated by reference in its entirety and generally relates to process chemistry to make bases such as, the (+) buprenorphine base, which may be further derivatized (e.g., oxidize or alkylate) using processes disclosed herein and known in the art.

PCT International Application No. PCT/US2008/068103, filed on Jun. 25, 2008 and published on Jan. 15, 2009 as International Publication No. WO/2009/009292; is hereby incorporated by reference in its entirety and generally relates to the preparation of naltrexone methobromide, for example of morphic crystalline forms of naltrexone methobromide.

PCT International Application No. PCT/US2008/062413, filed on May 2, 2008 and published on Nov. 13, 2008 as International Publication No. WO/2008/137672; is hereby incorporated by reference in its entirety and generally relates to preparation of a 6-alpha epimer hydroxymorphinan and synthesis of nalbuphine.

PCT International Application No. PCT/US07/019,489, filed on Sep. 6, 2007 and published on Mar. 27, 2008 as International Publication No. WO/2008/036172; is hereby incorporated by reference in its entirety and generally relates to chemistry and synthetic processes that bridge intermediates from benzyl isoquinolines to a primary morphinan structure, including description of derivatization and transformation of the morphinan structure to product opiates or their mirror isomers.

PCT International Application No. PCT/US06/006285, filed on Feb. 23, 2006 and published on Sep. 21, 2006 as International Publication No. WO/2006/098855 is hereby incorporated by reference in its entirety and generally relates to processes for making and derivatizing primary morphinan compounds.

PCT International Application No. PCT/US03/035463, filed on Nov. 5, 2003 and published on May 27, 2004 as International Publication No. WO/2004/043964; and PCT International Application No. PCT/US08/003,070, filed on Mar. 6, 2008 and published on Sep. 12, 2008 as International Publication No. WO/2008/109156; are each hereby incorporated by reference in its entirety and generally processes and synthetic approaches for preparing quaternary alkaloids salts.

PCT International Application No. PCT/US05/029437, filed on Aug. 17, 2005 and published on Mar. 2, 2006 as International Publication No. WO/2006/023669 is hereby incorporated by reference in its entirety and generally relates to processes and synthetic approaches for making and derivatizing levorphanol.

U.S. Pat. No. 4,521,601 issued on Jun. 4, 1985 is hereby incorporated by reference in its entirety and generally relates to methods of making and derivatizing (+) morphinan alkaloid compounds.

Each of the following references are hereby incorporated by reference its entirety and relates generally to differences in binding to the opiate receptor of the opiate isomers:
(1) Studies in the (+)-morphinan series. 5. Synthesis and biological properties of (+)-naloxone. Iijima, Ikuo; Minamikawa, Junichi; Jacobson, Arthur E.; Brossi, Arnold; Rice, Kenner C.; Klee, Werner A. Lab. Chem., Natl. Inst. Arthritis, Metab. Dig. Dis., Bethesda, Md., USA. Journal of Medicinal Chemistry (1978), 21(4), 398-400;
(2) "Unnatural alkaloids". Brossi, Arnold. Natl. Inst. Arthritis Metab. Dig. Dis., Natl. Inst. Health, Bethesda, Md., USA. Pure and Applied Chemistry (1979), 51(4), 681-8;
(3) Efficient syntheses and biological evaluation of novel (+)-morphinans. Brossi, Arnold; Kerekes, Peter; Chishen, Chang. Lab. Chem., Med. Chem. Sect., Natl. Inst. Arthritis, Diabetes Digest. Kidney Dis., Bethesda, Md., USA. Studies in Organic Chemistry (Amsterdam) (1985), 20(Nat. Prod. Chem.), 15-24; and
(4) Stereospecific and nonstereospecific effects of (+)- and (−)-morphine: Evidence for a new class of receptors? Jacquet, Yasuko F.; Klee, Werner A.; Rice, Kenner C.; Iijima, Ikuo; Minamikawa, Junichi. New York State Res. Inst. Neurochem. Drug Addict., Ward's Island, N.Y., USA. Science (Washington, D.C., United States) (1977), 198(4319), 842-5.

PCT International Application No. PCT/US08/064,412, filed on May 21, 2008 and published on May 28, 2009 as International Publication No. WO/2009/067275; PCT International Application No. PCT/US07/85458, filed on Nov. 21, 2007 and published on May 29, 2008 as International Publication No. WO/2008/064351; and U.S. patent application Ser. No. 11/944,242, filed on Nov. 21, 2007 and published on Aug. 28, 2008 as U.S. Publication No. 20080207669 are each hereby incorporated by reference in its entirety and generally relate to morphinanium oxide compounds, including (−) enantiomers or naturally derived morphinanium oxide compounds.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments, exemplary embodiments and optional features, modification and variation of the concepts herein disclosed can be resorted to by those skilled in the art, and that such modifications and variations are considered to be within the scope of this invention as defined by the appended claims. The specific embodiments provided herein are examples of useful embodiments of the invention and it will be apparent to one skilled in the art that the invention can be carried out using a large number of variations of the devices, device components, methods steps set forth in the present description. As will be apparent to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous and can be used interchangeably with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms. The invention illustratively described herein suitably can be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed can be resorted to by those skilled in the art, and that such modifications and variations are considered to be within the scope of this invention as defined by the appended claims.

REFERENCES (1) Momma, T; Hamblin, M. R.; Wu, N. C.; Hasan, T; "Photodynamic Therapy of Orthotropic Prostate Cancer with Benzoporphyrin Derivative: Local Control and Distant Metastasis", Cancer Research, 58, 5425-5431 (December 1998).
(2) A mechanism-based combination therapy reduces local tumor growth and metastasis in an orthotopic model of prostate cancer. Kosharskyy, Boleslav; Solban, Nicolas; Chang, Sung K.; Rizvi, Imran; Chang, Yuchiao; Hasan, Tayyaba. Department of Anesthesiology, Mount Sinai Hospital, New York, N.Y., USA. Cancer Research (2006), 66(22), 10953-10958.
(3) Mechanistic Investigation and Implications of Photodynamic Therapy Induction of Vascular Endothelial Growth Factor in Prostate Cancer. Solban, Nicolas; Pal, Selbo K.; Alok, Sinha K.; Sung, Chang K.; Hasan, Tayyaba. Wellman Center for Photomedicine, Massachusetts General Hospital, Harvard Medical School, Boston, Mass., USA. Cancer Research (2006), 66(11), 5633-5640.
(4) Ferrario A, Gomer C J. Avastin enhances photodynamic therapy treatment of Kaposi's sarcoma in a mouse tumor model. J Environ Pathol Toxicol Oncol 2006; 25:251-60.
(5) Singleton, P. A.; Lingen, M. W.; Fekete, M. J.; Garcia, J. G. N.; Moss, J. Methylnaltrexone inhibits opiate and VEGF-induced angiogenesis: role of receptor transactivation. Microvascular Research (2006), 72(1-2), 3-11.
(6) Moss, Jonathan; Lingen, Mark; Singleton, Patrick A.; Garcia, Joe G. N.; Yuan, Chun-Su. Use of opioid antagonists to attenuate endothelial cell proliferation and migration. U.S. Pat. Appl. Publ. (2006), 50 pp., Cont.-in-part of Appl. No. PCT/US06/07892. CODEN: USXXCO US 2006258696 A1 20061116.
(7) Singleton, Patrick A.; Moreno-Vinasco, Liliana; Sammani, Saad; Wanderling, Sherry L.; Moss, Jonathan; Garcia, Joe G. N. Attenuation of vascular permeability by methylnaltrexone: role of mOP-R and S1P3 transactivation. American Journal of Respiratory Cell and Molecular Biology (2007), 37(2), 222-231. CODEN: AJRBEL ISSN:1044-1549.
(8) Synergistic effects of methylnaltrexone with 5-fluorouracil and bevacizumab on inhibition of vascular endothelial growth factor-induced angiogenesis. Singleton, Patrick A.; Garcia, Joe G. N.; Moss, Jonathan. Departments of Medicine and Anesthesia and Critical Care, University of Chicago, Chicago, Ill., USA. Molecular Cancer Therapeutics (2008), 7(6), 1669-1679. Publisher: American Association for Cancer Research.
(9) Lin, Shankung; Tsai, Shiow-Chwen; Lee, Chun-Chung; Wang, Bao-Wei; Liou, Jer-Young; Shyu, Kou-Gi. Berberine inhibits HIF-1α expression via enhanced proteolysis. Molecular Pharmacology (2004), 66(3), 612-619.
(10) Augustin, A J; Puls, S; Offerman I. Triple Therapy for Choroidal Neovascularization due to Age-Related Macular Degeneration. Vertportfrin PDT, Bevacizumab, and Dexamethasone. RETINA 27:133-140, 2007.

What is claimed is:
1. A method for treating cancer, the method comprising: administering to a patient in need of treatment an effective amount of a purified (+) enantiomer compound substantially free of a corresponding (−) enantiomer, the (+) enantiomer compound having the formula (FX2):

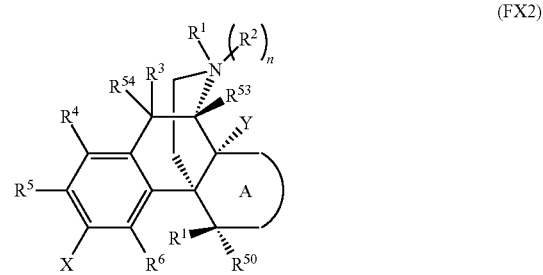

(FX2)

wherein:
ring A is

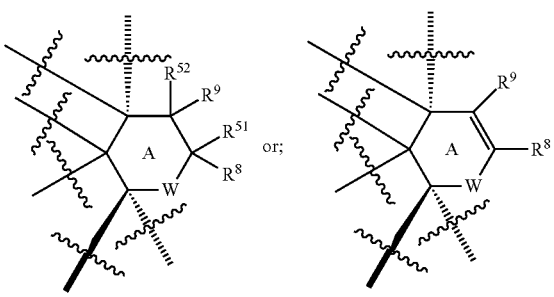

X is —OH, —OCH$_3$, or C$_2$-C$_8$ alkoxy;
Y is —H or —OH;
W is —(CR$^{10}$R$^{11}$)—, —(C=O)—, —(C=S)—, —(C=CR$^{12}$R$^{13}$)—, or —(CR$^{14}$NR$^{15}$R$^{16}$—);
each of R$^1$ and R$^2$ is independently —H, —CH$_3$, —(O$^-$), C$_1$-C$_{10}$ alkyl, C$_3$-C$_{10}$ cycloalkyl, C$_2$-C$_{10}$ alkenyl, C$_1$-C$_{10}$ haloalkyl, C$_5$-C$_{10}$ aryl, C$_5$-C$_{10}$ heteroaryl, $C_5$-$C_{10}$ alkylaryl, $C_5$-$C_{10}$ alkylheteroaryl, $C_5$-$C_{10}$ carbonylalkenylaryl, or $C_5$-$C_{10}$ carbonylalkenylheteroaryl;

each of $R^3$-$R^{16}$ and $R^{50}$-$R^{54}$ is independently —H, —OH, —OCH$_3$, $C_1$-$C_8$ alkyl, $C_3$-$C_8$ cycloalkyl, $C_2$-$C_8$ alkenyl, $C_2$-$C_8$ alkoxy, $C_5$-$C_{10}$ aryl, $C_5$-$C_{10}$ heteroaryl, $C_5$-$C_{10}$ alkylaryl, $C_5$-$C_{10}$ alkylheteroaryl, halo, nitrile, $C_1$-$C_8$ haloalkyl, $C_1$-$C_{10}$ hydroxyalkyl, or $C_5$-$C_{10}$ carbonylalkenylheteroaryl; and when n is 1, and the nitrogen to which $R^2$ is attached has a positive charge and optionally is associated with an anion.

2. The method of claim 1 wherein said (+) enantiomer compound has the formula (FX12):

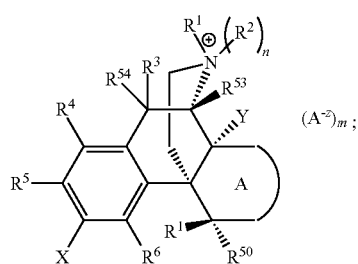

(FX12)

wherein:

$A^{-z}$ is independently an anion;

z is independently 1, 2 or 3; and m is independently 0 or 1, wherein when m is 0, $A^{-z}$ is not present.

3. The method of claim 1 wherein said (+) enantiomer compound has the formula:

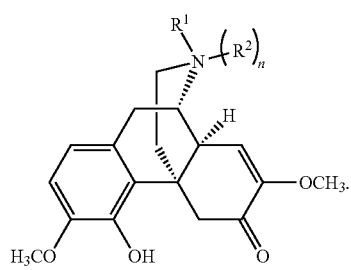

4. The method of claim 1 wherein said (+) enantiomer compound has the formula:

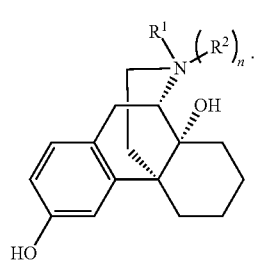

5. The method of claim 1 wherein said (+) enantiomer compound has the formula:

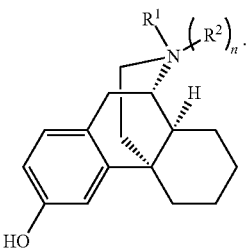

6. The method of claim 1 wherein said (+) enantiomer compound has the formula (FX14):

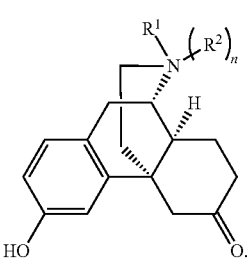

(FX14)

7. The method of claim 1 wherein said (+) enantiomer compound has the formula (FX16):

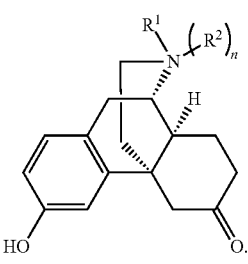

(FX16)

8. The method of claim 1 wherein said (+) enantiomer compound has the formula (FX18):

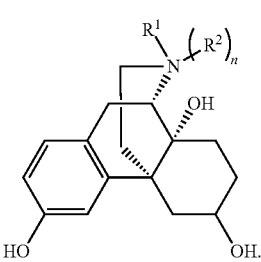

(FX18)

9. The method of claim 1 wherein said (+) enantiomer compound has the formula (FX19):

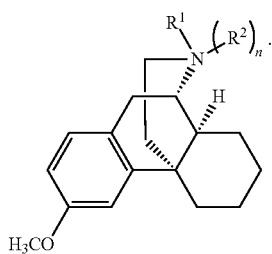

(FX19)

10. The method of claim 1 wherein said (+) enantiomer compound has the formula (FX21):

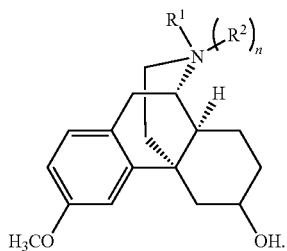

(FX21)

11. The method of claim 1 wherein said (+) enantiomer compound has the formula (FX23):

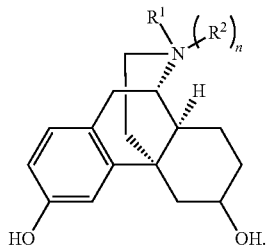

(FX23)

12. The method of claim 1 wherein said (+) enantiomer compound has the formula (FX25):

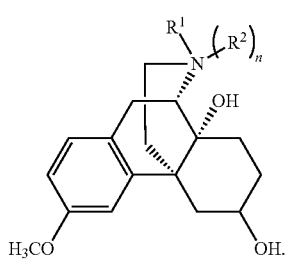

(FX25)

13. The method of claim 1 wherein said (+) enantiomer compound has the formula (FX27):

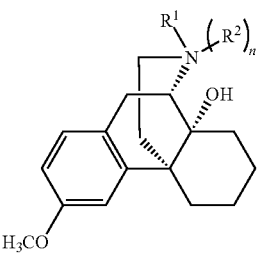

(FX27)

14. The method of claim 1 wherein said (+) enantiomer compound has the formula (FX30):

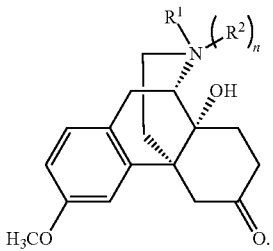

(FX30)

15. The method of claim 1 wherein said (+) enantiomer compound has the formula (FX32):

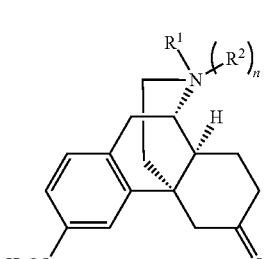

(FX32)

16. The method of claim 1 wherein said (+) enantiomer compound has the formula (FX34):

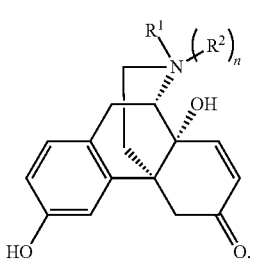

(FX34)

17. The method of claim 1 wherein said (+) enantiomer compound has the formula (FX36):

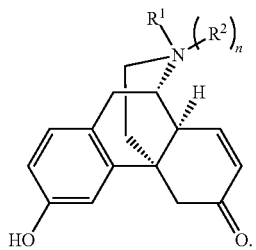

(FX36)

18. The method of claim 1 wherein said (+) enantiomer compound has the formula (FX38):

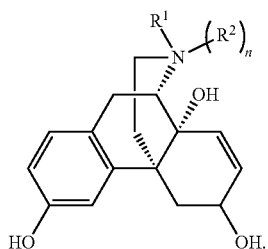

(FX38)

19. The method of claim 1 wherein said (+) enantiomer compound has the formula (FX39):

(FX41)

20. The method of claim 1 wherein said (+) enantiomer compound has the formula (FX41):

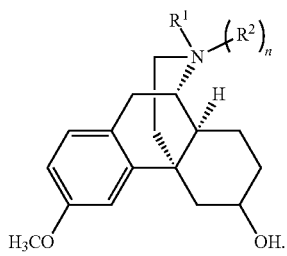

(FX39)

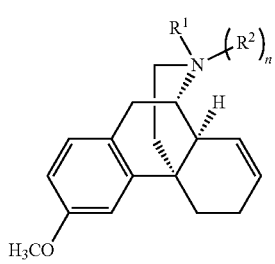

21. The method of claim 1 wherein said (+) enantiomer compound has the formula (FX43):

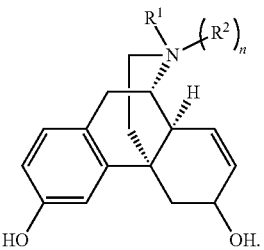

(FX43)

22. The method of claim 1 wherein said (+) enantiomer compound has the formula (FX45).

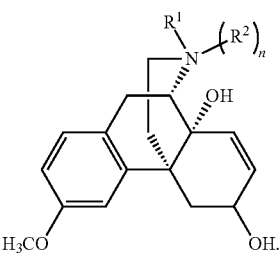

(FX45)

23. The method of claim 1 wherein said (+) enantiomer compound has the formula (FX47):

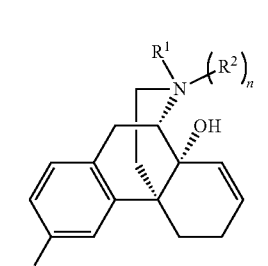

(FX47)

24. The method of claim 1 wherein said (+) enantiomer compound has the formula (FX50):

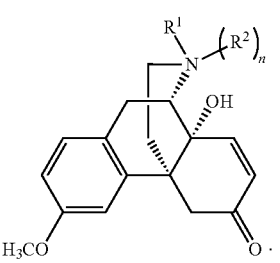

(FX50)

25. The method of claim 1 wherein said (+) enantiomer compound has the formula (FX52):

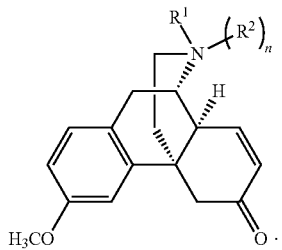

(FX52)

26. The method of claim 1 wherein said (+) enantiomer compound has the formula (FX54):

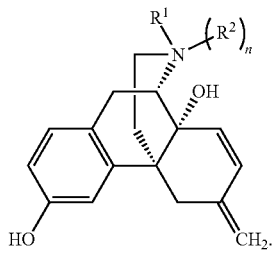

(FX54)

27. The method of claim 1 wherein said (+) enantiomer compound has the formula (FX56):

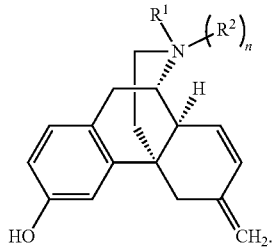

(FX56)

28. The method of claim 1 wherein said (+) enantiomer compound has the formula (FX58):

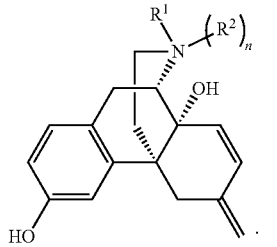

(FX58)

29. The method of claim 1 wherein said (+) enantiomer compound has the formula (FX60):

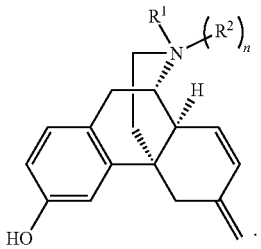

(FX60)

30. The method for treating cancer of claim 1, further comprising administering to said patient a mixture of two or more purified (+) enantiomer compounds each independently having a formula (FX2).

31. The method of claim 1, comprising a method for treating pancreatic cancer.

32. The method of claim 1, comprising a method of suppressing tumor growth or tumor metastasis.

33. The method of claim 1, further comprising administering to said patient one or more chemotherapeutic agents.

34. The method of claim 1, further comprising administering to said patient one or more VEGF inhibitors.

35. The method of claim 1, further comprising administering to said patient 5-fluorouracil, floxuridine, furtulon, capecitabine, gemcitabine, taxol, doxorubicin, cisplatin, thalidomide, paclitaxel, docetaxel or bevacizumab.

36. A method for treating cancer, the method comprising:
administering to a patient in need of treatment an effective amount of a purified (+) enantiomer compound substantially free of a corresponding (−) enantiomer, the (+) enantiomer compound having the formula:

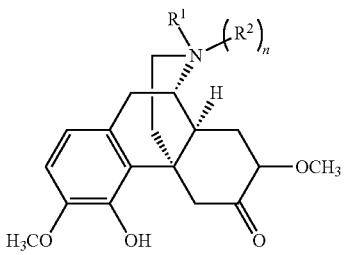

wherein:
each of $R^1$ and $R^2$ is independently —H, —CH$_3$, —(O$^−$), $C_1$-$C_{10}$ alkyl, $C_3$-$C_{10}$ cycloalkyl, $C_2$-$C_{10}$ alkenyl, $C_1$-$C_{10}$ haloalkyl, $C_5$-$C_{10}$ aryl, $C_5$-$C_{10}$ heteroaryl, $C_5$-$C_{10}$ alkylaryl, $C_5$-$C_{10}$ alkylheteroaryl, $C_5$-$C_{10}$ carbonylalkenylaryl, or $C_5$-$C_{10}$ carbonylalkenylheteroaryl; and n is 1, and the nitrogen to which $R^2$ is attached has a positive charge and optionally is associated with an anion.

37. The method for treating cancer of claim 36, further comprising administering to said patient a mixture of two or more purified (+) enantiomer compounds each independently having a formula:

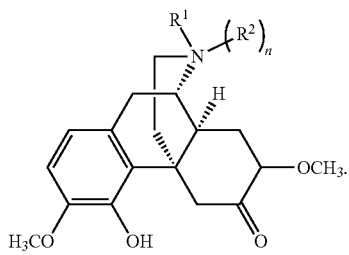

38. The method of claim 36, comprising a method for treating pancreatic cancer.

39. The method of claim 36, comprising a method of suppressing tumor growth or tumor metastasis.

40. The method of claim 36, further comprising administering to said patient one or more chemotherapeutic agents.

41. The method of claim 36, further comprising administering to said patient one or more VEGF inhibitors.

42. The method of claim 36, further comprising administering to said patient 5-fluorouracil, floxuridine, furtulon, capecitabine, gemcitabine, taxol, doxorubicin, cisplatin, thalidomide, paclitaxel, docetaxel or bevacizumab.

43. A method for treating cancer, the method comprising:
administering to a patient in need of treatment an effective amount of a purified (+) enantiomer compound substantially free of a corresponding (−) enantiomer, the (+) enantiomer compound having the formula (FX14):

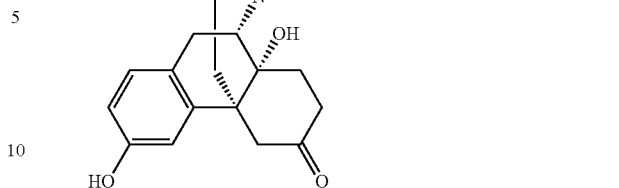

wherein:
each of $R^1$ and $R^2$ is independently —H, —CH$_3$, —(O$^-$), $C_1$-$C_{10}$ alkyl, $C_3$-$C_{10}$ cycloalkyl, $C_2$-$C_{10}$ alkenyl, $C_1$-$C_{10}$ haloalkyl, $C_5$-$C_{10}$ aryl, $C_5$-$C_{10}$ heteroaryl, $C_5$-$C_{10}$ alkylaryl, $C_5$-$C_{10}$ alkylheteroaryl, $C_5$-$C_{10}$ carbonylalkenylaryl, or $C_5$-$C_{10}$ carbonylalkenylheteroaryl; and n is 1, and the nitrogen to which $R^2$ is attached has a positive charge and optionally is associated with an anion.

44. The method for treating cancer of claim 43, further comprising administering to said patient a mixture of two or more purified (+) enantiomer compounds each independently having a formula (FX14).

45. The method of claim 43, comprising a method for treating pancreatic cancer.

46. The method of claim 43, comprising a method of suppressing tumor growth or tumor metastasis.

47. The method of claim 43, further comprising administering to said patient one or more chemotherapeutic agents.

48. The method of claim 43, further comprising administering to said patient one or more VEGF inhibitors.

49. The method of claim 43, further comprising administering to said patient 5-fluorouracil, floxuridine, furtulon, capecitabine, gemcitabine, taxol, doxorubicin, cisplatin, thalidomide, paclitaxel, docetaxel or bevacizumab.

* * * * *